United States Patent
Grant et al.

(10) Patent No.: US 12,075,975 B2
(45) Date of Patent: *Sep. 3, 2024

(54) ENDOSCOPE WITH PANNABLE CAMERA

(71) Applicant: DEKA Products Limited Partnership, Manchester, NH (US)

(72) Inventors: Kevin L. Grant, Litchfield, NH (US); Jason A. Demers, Manchester, NH (US); Peter K. Vondras, Somerville, MA (US); Stephen L. Fichera, Salem, NH (US); Timothy D. Moreau, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 852 days.

This patent is subject to a terminal disclaimer.

(21) Appl. No.: 17/120,614

(22) Filed: Dec. 14, 2020

(65) Prior Publication Data
US 2021/0093171 A1   Apr. 1, 2021

Related U.S. Application Data

(63) Continuation of application No. 16/460,545, filed on Jul. 2, 2019, now Pat. No. 10,863,888, which is a (Continued)

(51) Int. Cl.
*A61B 1/00* (2006.01)
*A61B 1/015* (2006.01)
(Continued)

(52) U.S. Cl.
CPC ...... *A61B 1/00183* (2013.01); *A61B 1/00096* (2013.01); *A61B 1/00103* (2013.01);
(Continued)

(58) Field of Classification Search
CPC .................................................. A61B 1/00105
See application file for complete search history.

(56) References Cited

U.S. PATENT DOCUMENTS

| | | |
|---|---|---|
| 4,838,247 A | 6/1989 | Forkner et al. |
| 4,846,154 A | 7/1989 | MacAnally et al. |

(Continued)

FOREIGN PATENT DOCUMENTS

| | | |
|---|---|---|
| DE | 102008057734 | 5/2010 |
| JP | 2004-537362 A2 | 12/2004 |

(Continued)

OTHER PUBLICATIONS

International Preliminary Report on Patentability and Written Opinion, dated Mar. 6, 2018, received in International patent application No. PCT/US2016/049743, 9 pgs.

(Continued)

*Primary Examiner* — Timothy J Neal
(74) *Attorney, Agent, or Firm* — Michael George Norris

(57) ABSTRACT

An endoscope has a pannable camera at the distal end of its insertion shaft, the pannable camera assembly being pivotable to provide a range of a field of view that can be equal to or greater than 180 degrees. A terminal light emitting element may be mounted to the camera assembly in order to illuminate the immediate field of view of the camera sensor regardless of the rotational position of the camera assembly. A fluid-carrying conduit of the insertion section may also be used to house functional components, including the camera assembly, actuation cables, a communications cable connected to the camera sensor, and/or a fiberoptic cable providing light to the light emitting element. A distal section of the endoscope handle may be rotatable relative to a proximal handheld section of the endo scope handle, a rotary encoder being provided to convert the rotational position of the insertion shaft relative to the handle into a signal for the (Continued)

purpose of image orientation correction by an electronic processor.

9 Claims, 63 Drawing Sheets

Related U.S. Application Data continuation of application No. 15/910,495, filed on Mar. 2, 2018, now Pat. No. 10,362,927, which is a continuation of application No. 14/170,080, filed on Jan. 31, 2014, now Pat. No. 9,907,457.

(60) Provisional application No. 61/826,303, filed on May 22, 2013, provisional application No. 61/759,784, filed on Feb. 1, 2013.

(51) Int. Cl.
    *A61B 1/045*     (2006.01)
    *A61B 1/05*     (2006.01)
    *A61B 1/12*     (2006.01)
    *A61B 17/34*     (2006.01)
    *A61B 90/00*     (2016.01)
    *A61B 90/30*     (2016.01)

(52) U.S. Cl.
    CPC ........ *A61B 1/0011* (2013.01); *A61B 1/00165* (2013.01); *A61B 1/015* (2013.01); *A61B 1/045* (2013.01); *A61B 1/05* (2013.01); *A61B 1/051* (2013.01); *A61B 1/126* (2013.01); *A61B 2017/3456* (2013.01); *A61B 2090/306* (2016.02); *A61B 2090/3616* (2016.02)

(56) References Cited

U.S. PATENT DOCUMENTS

| | | |
|---|---|---|
| 4,855,838 A | 8/1989 | Jones et al. |
| 5,313,934 A | 5/1994 | Wiita et al. |
| 5,351,678 A | 10/1994 | Clayton et al. |
| 5,368,014 A | 11/1994 | Anapliotis et al. |
| 5,575,756 A | 11/1996 | Karasawa et al. |
| 5,621,830 A | 4/1997 | Lucey et al. |
| 5,643,176 A | 7/1997 | Persidsky et al. |
| 5,785,644 A | 7/1998 | Grabover et al. |
| 5,797,836 A | 8/1998 | Lucey et al. |
| 5,899,851 A | 5/1999 | Koninckx et al. |
| 6,097,423 A | 8/2000 | Mattsson-Boze et al. |
| 6,110,105 A | 8/2000 | Durell et al. |
| 6,152,872 A | 11/2000 | Peck et al. |
| 6,277,064 B1 | 8/2001 | Yoon et al. |
| 6,364,830 B1 | 4/2002 | Durell et al. |
| 6,371,909 B1 | 4/2002 | Hoeg et al. |
| 6,398,725 B1 | 6/2002 | Thompson et al. |
| 6,428,471 B1 | 8/2002 | Durell, Jr. et al. |
| 6,464,631 B1 | 10/2002 | Girke et al. |
| 6,471,637 B1 | 10/2002 | Chatenever et al. |
| 6,511,422 B1 | 1/2003 | Chatenever et al. |
| 6,522,477 B2 | 2/2003 | Anhalt et al. |
| 6,560,375 B1 | 5/2003 | Hathaway et al. |
| 6,638,216 B1 | 10/2003 | Durell et al. |
| 6,887,196 B2 | 5/2005 | Arai et al. |
| 6,916,286 B2 | 7/2005 | Kazakevich et al. |
| 6,929,603 B2 | 8/2005 | Durell et al. |
| 7,037,258 B2 | 5/2006 | Chatenever et al. |
| 7,134,992 B2 | 11/2006 | Schara et al. |
| 7,175,593 B2 | 2/2007 | Durell et al. |
| 7,211,042 B2 | 5/2007 | Chatenever et al. |
| 7,427,263 B2 | 9/2008 | Hoeg et al. |
| 7,517,314 B2 | 4/2009 | Hoeg et al. |
| 7,570,438 B2 | 8/2009 | McKinley et al. |
| 7,585,273 B2 | 9/2009 | Adler et al. |
| 7,713,189 B2 | 5/2010 | Hanke et al. |
| 7,758,497 B2 | 7/2010 | Hem et al. |
| 7,833,152 B2 | 11/2010 | Chatenever et al. |
| 7,901,353 B2 | 3/2011 | Vayser et al. |
| 7,909,756 B2 | 3/2011 | Hoeg et al. |
| 7,956,887 B2 | 6/2011 | Hoeg et al. |
| 8,075,520 B2 | 12/2011 | Reznik et al. |
| 8,167,795 B2 | 5/2012 | Hoeg et al. |
| 8,179,428 B2 | 5/2012 | Minami et al. |
| 8,187,171 B2 | 5/2012 | Irion et al. |
| 8,211,008 B2 | 7/2012 | Henzler et al. |
| 8,216,185 B2 | 7/2012 | Berger et al. |
| 8,226,548 B2 | 7/2012 | Kucklick et al. |
| 8,244,068 B2 | 8/2012 | Thoern et al. |
| 8,372,002 B2 | 2/2013 | Nakano et al. |
| D753,296 S | 4/2016 | Gill et al. |
| D795,424 S | 8/2017 | Sloss |
| 9,907,457 B2 * | 3/2018 | Grant ................ A61B 1/051 |
| D841,160 S | 2/2019 | Cranfield et al. |
| 10,362,927 B2 * | 7/2019 | Grant ................ A61B 1/051 |
| 10,616,491 B2 | 4/2020 | Haggerty et al. |
| 10,863,888 B2 * | 12/2020 | Grant ............. A61B 1/00103 |
| 2002/0077593 A1 | 6/2002 | Perkins et al. |
| 2002/0183592 A1 | 12/2002 | Suzuki et al. |
| 2003/0016883 A1 | 1/2003 | Baron et al. |
| 2003/0032863 A1 | 2/2003 | Kazakevich et al. |
| 2003/0114730 A1 | 6/2003 | Hale et al. |
| 2003/0120130 A1 | 6/2003 | Glukhovsky et al. |
| 2005/0043682 A1 | 2/2005 | Kucklick et al. |
| 2005/0187432 A1 | 8/2005 | Hale et al. |
| 2005/0228230 A1 | 10/2005 | Schara et al. |
| 2006/0020165 A1 | 1/2006 | Adams et al. |
| 2006/0063976 A1 | 3/2006 | Aizenfeld et al. |
| 2006/0129032 A1 | 6/2006 | Durell et al. |
| 2007/0010823 A1 | 1/2007 | Kucklick et al. |
| 2007/0038029 A1 | 2/2007 | Ota et al. |
| 2007/0060915 A1 | 3/2007 | Kucklick et al. |
| 2007/0219412 A1 | 9/2007 | DiGiovanni et al. |
| 2007/0249899 A1 | 10/2007 | Seifert et al. |
| 2007/0270766 A1 | 11/2007 | Kucklick et al. |
| 2007/0293720 A1 | 12/2007 | Bayer et al. |
| 2008/0021272 A1 | 1/2008 | Doguchi et al. |
| 2008/0071144 A1 | 3/2008 | Fein et al. |
| 2008/0214892 A1 | 9/2008 | Irion et al. |
| 2008/0300456 A1 | 12/2008 | Irion et al. |
| 2009/0030283 A1 | 1/2009 | Freystein et al. |
| 2009/0082630 A1 | 3/2009 | Tulley et al. |
| 2009/0112061 A1 | 4/2009 | Kim et al. |
| 2009/0149713 A1 | 6/2009 | Niida et al. |
| 2009/0171147 A1 | 7/2009 | Lee et al. |
| 2009/0299139 A1 | 12/2009 | Yamakawa et al. |
| 2010/0076268 A1 | 3/2010 | Takasugi et al. |
| 2010/0125166 A1 | 5/2010 | Henzler et al. |
| 2010/0141744 A1 | 6/2010 | Amling et al. |
| 2011/0021926 A1 | 1/2011 | Spencer et al. |
| 2011/0026787 A1 | 2/2011 | Hale et al. |
| 2011/0046447 A1 | 2/2011 | Hoeg et al. |
| 2011/0062211 A1 | 3/2011 | Ross et al. |
| 2011/0144576 A1 | 6/2011 | Rothe et al. |
| 2011/0160535 A1 * | 6/2011 | Bayer ................ A61B 1/00154 |
| | | 600/114 |
| 2011/0193948 A1 | 8/2011 | Amling et al. |
| 2012/0029280 A1 | 2/2012 | Kucklick et al. |
| 2012/0029289 A1 | 2/2012 | Kucklick et al. |
| 2012/0041265 A1 | 2/2012 | Kucklick et al. |
| 2012/0053407 A1 | 3/2012 | Levy et al. |
| 2012/0108901 A1 | 5/2012 | Sargeant et al. |
| 2012/0157972 A1 | 6/2012 | Kucklick et al. |
| 2012/0197081 A1 | 8/2012 | Kimura et al. |
| 2012/0229615 A1 | 9/2012 | Kirma et al. |
| 2012/0253121 A1 | 10/2012 | Kitano et al. |
| 2012/0289784 A1 | 11/2012 | Kucklick et al. |
| 2012/0289858 A1 | 11/2012 | Ouyang et al. |
| 2013/0006055 A1 | 1/2013 | Goldfarb et al. |
| 2014/0221749 A1 | 8/2014 | Grant et al. |
| 2017/0078583 A1 | 3/2017 | Haggerty et al. |
| 2017/0238793 A1 | 8/2017 | Govrin et al. |

(56) References Cited

U.S. PATENT DOCUMENTS

2018/0192857 A1 7/2018 Grant et al.
2019/0328217 A1 10/2019 Moreau et al.

FOREIGN PATENT DOCUMENTS

| JP | 2012-245045 A2 | 12/2012 |
|----|----------------|---------|
| WO | 03013349 | 2/2003 |
| WO | 2008033240 | 3/2008 |
| WO | 2010134913 | 11/2010 |
| WO | 2011003013 | 1/2011 |
| WO | 2014031192 | 2/2014 |

OTHER PUBLICATIONS

International Preliminary Report on Patentability dated Aug. 4, 2015, received in International patent application No. PCT/US2014/014243, 12 pgs.
International Search Report & Written Opinion dated Jul. 29, 2014, received in International patent application No. PCT/US2014/014243, 17 pgs.
International Search Report and Written Opinion, dated Jan. 20, 2017, received in International patent application No. PCT/US2016/049743, 15 pgs.
International Search Report and Written Opinion, dated Sep. 18, 2019, received in International patent application No. PCT/US2019/029436, 18 pgs.
Invitation to Pay Additional Fees and, Where Applicable, Protest Fee dated May 9, 2014, received in International patent application No. PCT/US2014/014243, 7 pgs.
Invitation to Pay Additional Fees and, Where Applicable, Protest Fees, dated Nov. 23, 2016, received in International patent application No. PCT /US2016/049743, 8 pgs.
Invitation to Respond to Written Opinion from the Intellectual Property Office of Singapore for Application No. 11201505957U, dated Apr. 26, 2016, 13 pgs.

* cited by examiner

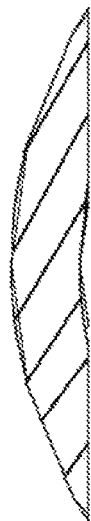
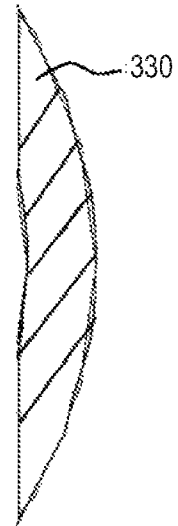
FIG. 18

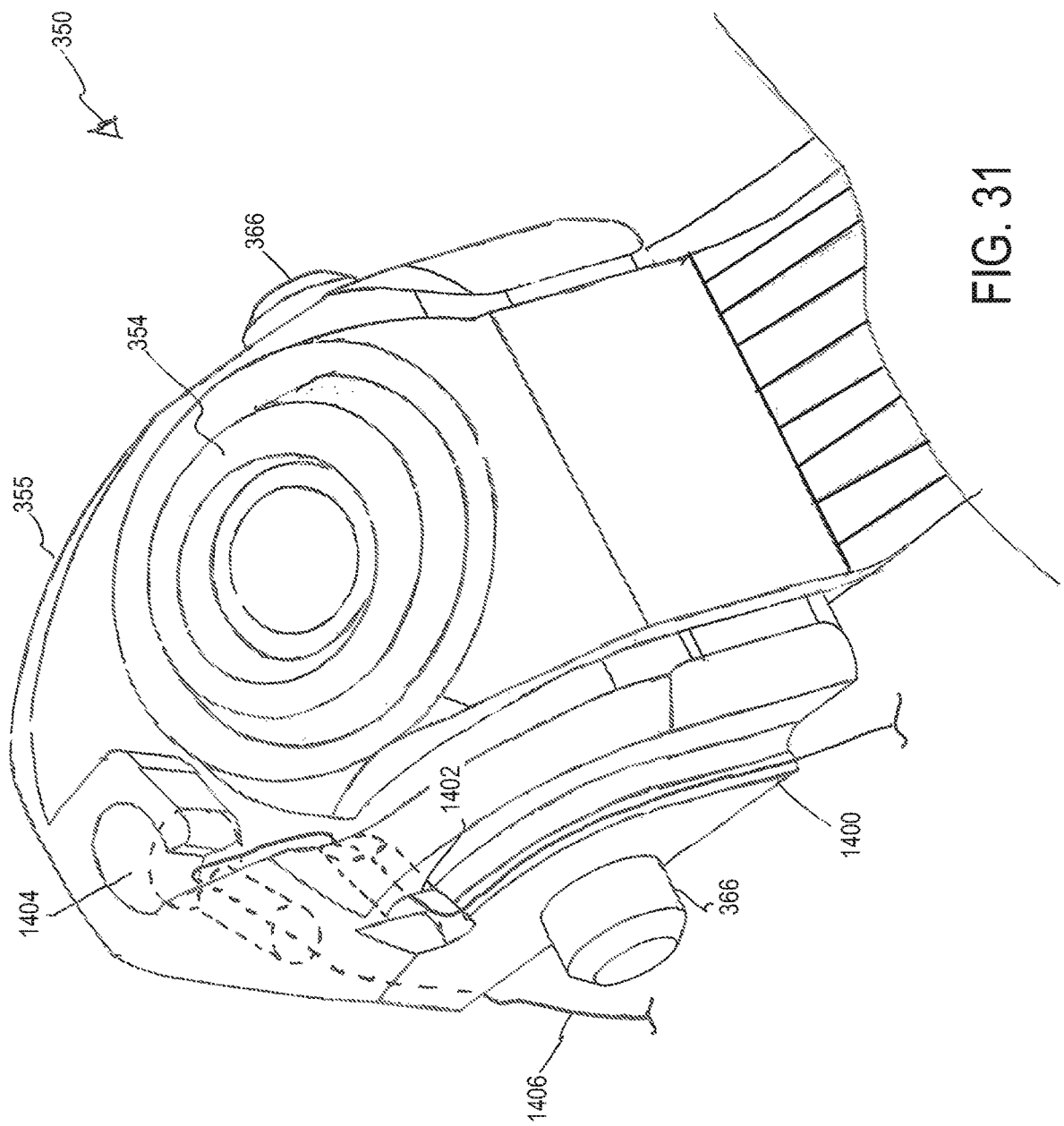

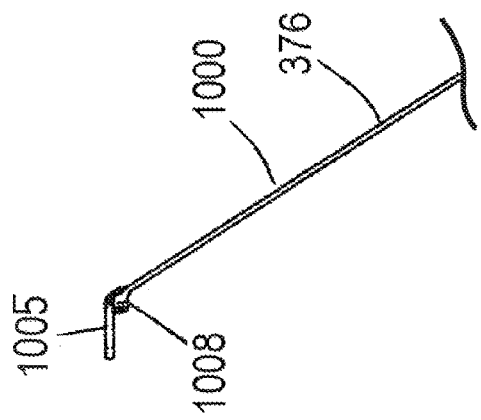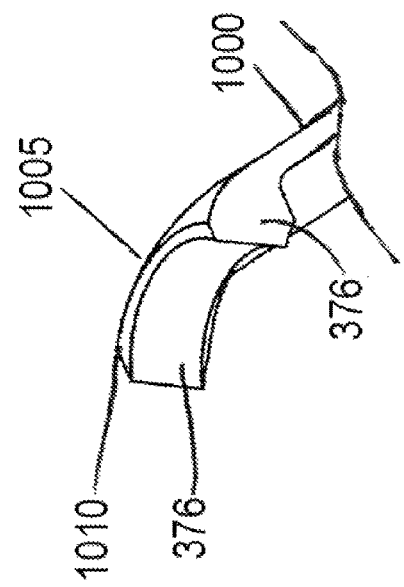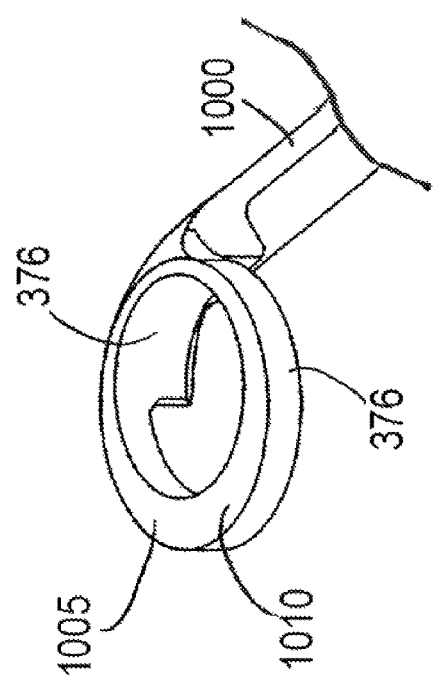

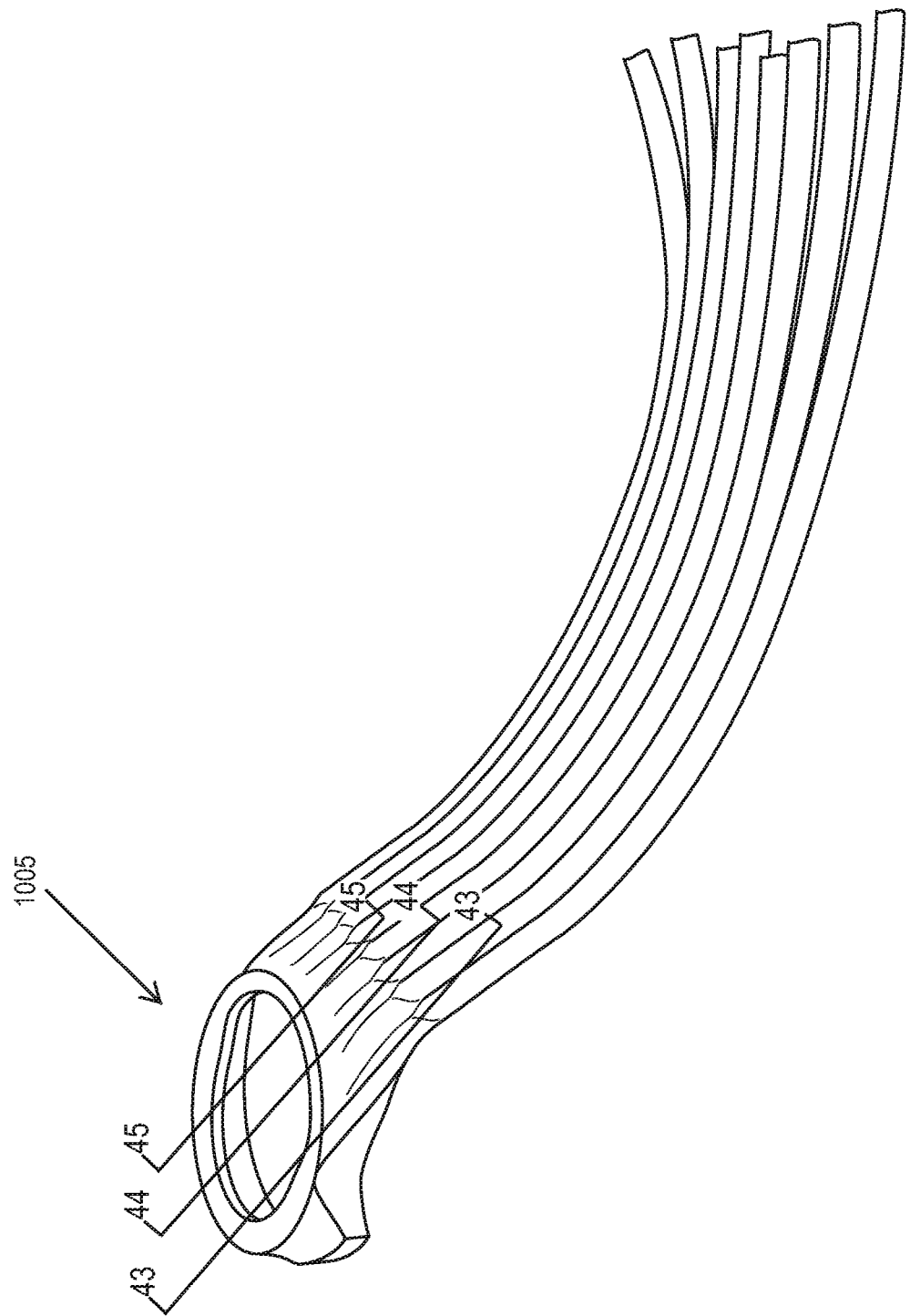

ENDOSCOPE WITH PANNABLE CAMERA

CROSS-REFERENCES TO RELATED APPLICATIONS

This application is a Continuation Application of U.S. patent application Ser. No. 16/460,545, filed on Jul. 2, 2019 and entitled Endoscope with Pannable Camera, which will be U.S. Pat. No. 10,863,888 issuing on Dec. 15, 2020; which is a Continuation Application of U.S. patent application Ser. No. 15/910,495, filed on Mar. 2, 2018 and entitled Endoscope with Pannable Camera, now U.S. Pat. No. 10,362,927 issued on Jul. 30, 2019; which is a Continuation Application of U.S. patent application Ser. No. 14/170,080, filed on Jan. 31, 2014 and entitled Endoscope with Pannable Camera, now U.S. Pat. No. 9,907,457 issued on Mar. 6, 2018; which claims the benefit of U.S. Provisional Patent Application Ser. No. 61/826,303, filed May 22, 2013 and entitled Endoscope with Pannable Camera; and U.S. Provisional Patent Application Ser. No. 61/759,784, filed Feb. 1, 2013 and entitled Pannable Endoscope, each of which is hereby incorporated herein by reference in its entirety.

BACKGROUND

Field of Disclosure

The present disclosure relates to endoscopic instruments for viewing and working in relatively inaccessible spaces; and in some aspects for operating in tight anatomical spaces within a body using an endoscope or arthroscope, or the like.

Background Information

The use of endoscopic instruments in medicine, allowing for remote viewing and operating in difficult-to-access spaces has become well-established. These instruments have also been useful in automotive, aviation, plumbing, electronics, and many other industries. In the field of medicine or veterinary practice, endoscopy or arthroscopy is often used to view or treat an anatomical region when minimal or no incisions are desired, or to avoid disturbing nearby tissues. In orthopedics, for example, the condition of a joint such as a knee or shoulder may be accessed using one or more arthroscopic instruments introduced into the joint through one or more small skin incisions. These instruments may also be used to repair various intra-articular tissues. Standard techniques of open surgery to view and repair these anatomical areas can be comparatively more time consuming, associated with greater risk and trauma to a patient, and can be associated with longer recovery time. Furthermore, anesthesia associated with open surgery may be more complicated, risky and costly. For improved field of view, an endoscope may be equipped with an actively flexible distal segment, controllable by the user at the handle end of the instrument. This may not be an effective option when the tip of the instrument is positioned in a confined space that may not accommodate the range of motion required for flexing the distal segment of an endoscope. In medical applications, one such example would include intra-articular surgery. Generally, using an instrument with a rigid insertion shaft may be preferred if the use of an instrument with an actively flexible distal segment is impractical. A non-flexible shaft may provide improved optics or image reproduction, increased space within the instrument for additional functionality, and greater durability. However, rigid endoscopes or arthroscopes have a limited field of view and may need to be repositioned or rotated frequently to increase the field of view. Some endoscopes or arthroscopes must be physically removed from the patient to have parts swapped out in order to change the field of view. Cannula systems may facilitate this approach, but may also increase the complexity of the procedure and the size of an incision. These limitations may reduce operator efficiency, increase surgery time, and may increase the risk of iatrogenic injury. In medical and other applications, it would be advantageous for an endoscope to have an increased or variable field of view without the use of an actively flexible distal segment. It may also be advantageous to combine functions within a single conduit in order to decrease the overall diameter of the shaft of an endoscope. Additionally, current instruments are prone to degradation in function and optical quality over repeated use, cleaning and/or sterilization. An endoscope design whose manufacturing and assembly cost is low enough to economically justify its non-re-use would also be advantageous. The costs of repeated cleaning or sterilization and re-packaging would be eliminated, and it may also be easier to standardize the quality and reliability of a single-use device.

SUMMARY

An embodiment of the present disclosure comprises a variable view endoscope, useful in industrial as well as medical applications. The endoscope may comprise a proximal end and a distal insertion end opposite the proximal end. The proximal end of the endoscope may further comprise a handle. The endoscope may further include an elongated member comprising an insertion section or shaft, which may extend from the handle to the distal end. The insertion section or shaft may be configured to be rotatable about a longitudinal axis of the insertion section, relative to at least a portion of the handle. Near the distal end, an imaging device (or 'imager') may be pivotably mounted in the insertion section. The imager may be an image sensor. The imager may be disposed within a housing. The housing may comprise at least one lens through which an image is directed to the imager. The imager may have a pre-determined angular field of view, and may be configured to capture an image of the field of view. The imager may be mounted on a pivotable assembly or camera mount. The immediate angular field of view may be rotated between a first angular position and a second angular position of the imager with respect to the long axis of the insertion section, the first and second angular positions defining the bounds of the viewable range of the imager. The immediate field of view may be varied by pivoting the imager on a mount about an axis that is approximately perpendicular or transverse to a longitudinal axis of the insertion section or shaft. The rotational axis of the camera mount may be configured to lie in a plane that roughly bisects the insertion shaft into an upper region and a lower region.

The endoscope may further comprise a pivot control structure; the pivot control structure may be configured to pivot the imager when the pivot control structure is rotated about an axis of rotation approximately perpendicular to the long axis of the insertion shaft. The pivot control structure may further comprise projections. The projections may be configured to optionally operatively engage at least one detent such that the pivot control structure may be rotated in discrete steps, each step providing an immobilizing point for the rotational position of the pivot control structure. One or more of the detents may correspond to a predefined pivotal orientation of the imager. The pivot control structure may be connected to the pivotable camera assembly by an elongate actuator, such as a pull cable or wire.

In an embodiment, the insertion shaft may extend from a handle to the insertion end of the endoscope, the insertion shaft configured to house an elongate pivot actuator that is connected on a proximal end to a control member on the handle, and connected on a distal end to a pivoting assembly. The pivoting assembly may serve as a mount for an image sensor or camera, and may include a lens assembly. The image sensor is configured to capture an image having a pre-determined angular field of view that is rotatable by longitudinal movement of the elongate pivot actuator acting on the pivoting assembly. In an embodiment, a pivoting camera assembly may be housed within a liquid carrying conduit of an endoscope insertion shaft. The camera assembly may be rotatable to an angle of between about 90 degrees and about 120 degrees of the longitudinal axis of the insertion shaft. In this position, the surface of a lens assembly may be washable by passing irrigation liquid through the insertion shaft, the irrigation liquid then passing over the surface of the lens assembly as it exits the distal end of the insertion shaft.

In an embodiment, a terminal segment of the elongate pivot actuator is constrained or re-directed to form an angle with respect to the long axis of the insertion shaft. In one example, the angle formed is within a range of about 30 degrees to about 90 degrees. A re-directing element may be included in a distal portion of the insertion shaft, the re-directing element causing the terminal segment of the pivot actuator to form an angle with respect to the long axis of the insertion shaft. The re-directing element may be located above the axis of the pivoting assembly when the pivot actuator is connected to the pivoting assembly below its axis of rotation, whereas the re-directing element may be located below the axis of the pivoting assembly when the pivot actuator is connected to the pivoting assembly above its axis of rotation. The elongate pivot actuator may comprise a wire or cable, and a first pivot actuator may connect to the pivoting assembly on one side of its axis of rotation, while a second pivot actuator may connect to the pivoting assembly on an opposing side of the pivoting assembly. The terminal segment of a first pivot actuator may be re-directed or constrained to form an angle with respect to the long axis of the insertion shaft, whereas the terminal segment of a second pivot actuator may not be so constrained or re-directed. Alternatively, a first and second pivot actuator may both have terminal segments that are constrained or re-directed to form an angle with respect to the long axis of the insertion shaft. The re-directing element may comprise a wall in a distal portion of the insertion shaft, the wall having a notch or including a post, pulley or eyelet against which the pivot actuator may be re-directed. The re-directing element may be configured to provide an angle of the terminal segment so that the field of view of the image sensor can be rotated over a viewable range of up to 180 degrees, or optionally above 180 degrees.

The insertion section of an endoscope may also comprise a conduit, the conduit being configured to transfer fluid (liquid and/or gas) between a space in which the tip of the insertion section is positioned and a location external to the endoscope. The conduit may also be configured to carry functional components of the endoscope, including (but not limited to) a camera, camera mount, fiberoptic cable, electronic transmission cable, and mechanical pull wires or pushrods. One or more of said components may include insulation or surface features allowing the components to function in a wet environment. The endoscope may be configured to provide a sealing element that allows said functional components to extend from a handle housing to a distal area of the insertion section of the endoscope, the sealing element also inhibiting the infiltration of fluid from the conduit to at least a portion of the handle housing.

A camera assembly comprising a lens and an electronic image sensor may be positioned within a liquid carrying conduit of the insertion shaft of the endoscope, a housing of a handle assembly including a liquid port in fluid communication with the liquid carrying conduit of the insertion shaft. The camera assembly may be mounted on a pivot bearing having an axis of rotation transverse to a longitudinal axis of the insertion shaft. The liquid carrying conduit may include one or more mechanical actuators to move the camera assembly. The liquid carrying conduit may include a communications cable connected to the image sensor, or an optical fiber bundle configured to provide illumination for the image sensor. A barrier may be positioned between the liquid carrying conduit of the insertion shaft and an internal housing of the handle assembly, the barrier configured to inhibit passage of liquid from the liquid carrying conduit to the housing of the handle assembly. The barrier may comprise a pass-through barrier that permits passage of an optical fiber bundle, mechanical actuator cable, or communications cable between the liquid carrying conduit and a housing of the handle assembly. The housing of the handle assembly may comprise a proximal housing section and a distal housing section, the distal housing section interposed between the proximal housing section and the insertion shaft. The distal housing section may comprise a pivot control apparatus to control movement of one or more pivot control cables connected to the camera assembly in the insertion shaft. The proximal housing section may enclose an electronic control board to receive image data from the camera assembly. A first pass-through barrier between the insertion shaft and the distal housing section may permit passage of the one or more pivot control cables, a pivot control cable passage in the first pass-through barrier being configured to permit unrestricted proximal and distal movement of the one or more pivot control cables over a pre-determined distance. A second pass-through barrier between the distal housing section and the proximal housing section may permit passage of a communications cable from the camera assembly to the electronic control board, a communications cable passage in the second pass-through barrier being configured to provide a liquid seal between the distal housing section and the proximal housing section of the handle assembly. The second pass-through barrier between the distal housing section and the proximal housing section may permit passage of an optical fiber bundle configured to provide illumination at a distal end of the insertion shaft, an optical fiber bundle passage in the second pass-through barrier being configured to provide a liquid seal between the distal housing section and the proximal housing section of the handle assembly. The second pass-through barrier between the distal housing section and the proximal housing section may permit passage of a liquid carrying tube configured to pass liquid to or from the distal insertion shaft through the first pass-through barrier, the second pass-through barrier, and an end of the proximal housing section.

In an embodiment, a pivoting camera assembly may be housed in the insertion end of an endoscope shaft, the pivoting camera assembly comprising a lens and an image sensor, and configured to pivot about an axis that is substantially transverse to a longitudinal axis of the shaft. A light emitter may be mounted to the camera assembly, the light emitter being configured to project light into an illumination field substantially coincident with a field of view of the image sensor as the camera assembly pivots about its axis. The light emitter may be a passive light emitter, in that it conducts light that originates from a source external to the endoscope. The light emitter may be made of a light guide material, such as optical fiber material. The light emitter may include a mounting feature that cooperates with a mating feature on the camera assembly to facilitate securing the light emitter on the camera assembly. A mask may be applied to one or more surfaces of the light emitter to inhibit the emission of light from said surfaces. A reflective coating may be applied to one or more surfaces of the light emitter. An emitting surface of the light emitter may be roughened to diffuse light emitted from said surface. The light emitter may have a curved shape to conform to a circumferential shape of the lens. The light emitter may be formed from or fused to a number of optical fibers. Ends of the optical fibers may be disposed in one or more recesses in the camera assembly next to the lens. The light emitter may be formed from a number of individual optical fibers that have been fused together. The light emitter may comprise a transition region that incorporates a number of unfused flexible optical fibers, wherein at least a portion of the transition region is nonflexible. The transition region may be attached to a portion of the camera assembly.

In an embodiment, the camera assembly may comprise a lens assembly spaced apart from an image sensor, the lens assembly and image sensor mounted on a camera housing. The camera housing may be configured to rotate about a pivot bearing having an axis of rotation transverse to a longitudinal axis of an insertion shaft of the endoscope. A light emitter may be mounted on the camera housing and configured to emit light in a direction of a field of view of the image sensor. The light emitter may comprise a terminal portion of a flexible optical fiber bundle. The light emitter may comprise a solid transparent light emitting member molded from or fused to a flexible optical fiber bundle. The camera housing may be configured to rotate about the pivot bearing by the action of a pull cable, the camera housing including a spooling feature providing a surface to guide a terminal portion of the pull cable, and the camera housing including a contact region to secure a distal end of the pull cable. The spooling feature may comprise a curved recess on the camera housing into which the terminal portion of the pull cable can be positioned.

In an embodiment, the camera housing may be configured to rotate by the action of a pull cable about a pivot bearing having an axis of rotation transverse to a longitudinal axis of an insertion shaft of the endoscope. The camera housing may additionally comprise a spooling feature configured to at least partially wind a terminal portion of the pull cable to a connection region on the camera housing configured to secure a distal end of the pull cable. The spooling feature may include an arcuate section and a straight section. An arc of the arcuate section may be defined by a constant radius. The radius may extend from the axis of rotation to a surface of the arcuate section. The spooling feature may be configured to wind the terminal portion of the pull cable up to about 360 degrees around the axis of rotation. The pull cable may be displaced along the longitudinal axis of the insertion section by a control structure in a handle of the endoscope. Displacement of the pull cable along the longitudinal axis of the insertion section in a first direction may be configured to cause displacement of a second pull cable along the longitudinal axis of the insertion section in a second opposite direction and vice versa. The camera housing may include an attachment point for a second pull cable. The camera housing may comprise a second spooling feature configured to at least partially wind a terminal portion of a second pull cable to a connection region on the camera housing configured to secure a distal end of the second pull cable. The second pull cable may be displaced along the longitudinal axis of the insertion section by a control member in a handle of the endoscope. The second spooling feature may be configured to wind the terminal portion of the pull cable up to about 360 degrees around the axis of rotation. The second spooling feature may include an arcuate section and a straight section. An arc of the arcuate section may be defined by a constant radius. The radius may extend from the axis of rotation to a surface of the arcuate section. The first or second spooling feature may comprise a curved recess on the camera housing into which the terminal portion of the second pull cable can be positioned.

In an embodiment, a light emitter may be formed from an optical fiber bundle comprising: a solid transparent light emitting member molded from or fused to a flexible optical fiber bundle. A transition segment of partially fused optical fibers may be formed adjacent the light emitting member at a first end and flexible optical fibers adjacent the optical fiber bundle at a second. The transition segment may comprising an inflexible molded form at the first end that maintains a fixed angular relationship with the light emitting member, wherein the light emitting member has a substantially flat emitting surface configured to emit light transmitted along the optical fiber bundle. The light emitting member may comprise acrylic or polycarbonate material. The light emitting member may be shaped to at least partially encircle a lens assembly, the emitting surface of the member being oriented to emit light in a direction of a field of view of the lens assembly. The light emitting member may be mounted to a rotatable camera assembly, the camera assembly comprising a lens assembly opposite an image sensor, wherein the camera assembly and light emitter are configured to rotate together about a pivot shaft connected to the camera assembly.

In an embodiment, a light emitter may be formed from an optical fiber bundle by placing a section of a distal end of the fiber bundle onto a compression mold form; applying heat to the mold form or a corresponding force or plug member before, during or after placement of the section onto the mold form; moving the force or plug member into a mating relationship with the mold form; applying pressure to the section of fiber bundle; and melting the section to form a shape of the emitter determined by the shape of the mold form and corresponding force or plug member. The mold form may comprise a fiber orienting feature on which a transitional section of cable is placed, and the transitional section may be formed so as to have a fixed angular relation with respect to a face of the light emitter. The fiber orienting feature may be an incline feature. A jacket or heat sink may be applied to a region of the optical fiber bundle proximal to a transitional section. The jacket or heat sink may serve to maintain a band-like cross-sectional shape of the optical fiber bundle proximal to the transitional section during compression and heating of the distal end of the fiber bundle. A band-like cross-sectional shape of a portion of the optical fiber bundle may be maintained proximal to the transitional section during compression and heating of the distal end of the fiber bundle. The band-like cross-sectional shape may comprise placing the portion of the optical fiber bundle in a guide member. Pressure may be from a pneumatic, hydraulic, mechanical, or manual pressure source. The optical fiber bundle may comprise acrylic or polycarbonate material. The distal end of the optical fiber bundle may be wrapped around a mandrel in the mold form. Flashing may be from the light emitter after cooling. A mask or reflective coating may be applied to a surface of the light emitter. Heat may be applied with a resistive heating element. The amount of heat applied may be adjusted based on temperature feedback from a temperature sensor associated with the plug member or mold form. The light emitter may be ejected from the mold form after cooling using an ejector. The emitter may be allowed to cool such that it solidifies following which the force or plug member may be moved out of mating relationship with the mold form. At least a transitional section of the fiber bundle adjacent and proximal to the section under pressure may be actively cooled. This may comprise blowing air across at least the transitional section of the fiber bundle.

In an embodiment, a lens assembly may be positioned relative to an image sensor in the process of assembly a camera for use in an aqueous environment, the lens assembly having an outer optical surface and an opposing optical surface facing the sensor, by: placing the lens assembly on a first surface of a plate having a pre-determined thickness, a second opposing plate surface, and an aperture into which the outer optical surface of the lens element may be inserted; inserting the lens element into the aperture so that the outer optical surface of the lens element does not extend through the full thickness of the plate, leaving a void between the outer surface of the lens assembly and a plane formed by the second surface of the plate; applying a seal between the first surface of the plate and a perimeter of the lens assembly above the first surface of the plate; adding a liquid to the void by capillary action, the liquid completely filling the void;

placing a transparent cover over the second surface of the plate; and adjusting the distance between the sensor and the optical surface of the lens assembly facing the sensor to provide an image in focus on a display screen connected to the sensor, wherein a source of the image is placed at a pre-determined distance from the second surface of the plate. The plate may comprise a glass slide. The aperture may have a diameter of about 1 mm to about 3 mm.

In an embodiment, an endoscope may have a shaft that includes a distal insertion end configured for insertion into an anatomical region of a patient. The shaft may define an interior space, the distal insertion end having an opening fluidly connecting the interior space of the shaft with an anatomical region into which the shaft is inserted. The endoscope may include an electronic image sensor within the interior space of the shaft at or near the insertion end. The image sensor may be configured in relation to the opening to have an unobstructed field of view of the anatomical region into which the shaft is inserted. The opening may be embrasured. A guard feature may be positioned over the opening, partially covering the opening. The guard feature may comprise a cage. A wall of the shaft adjacent the opening may comprise a longitudinal slit opening next to the image sensor. The width of the slit opening may increase as the slit opening extends in a direction proximal to the location of the image sensor. The image sensor may be mounted to a camera assembly. The camera assembly may be configured to pivot about a pivot axis. The opening at the distal end and the slit opening may be configured to provide the image sensor of the camera assembly an unobstructed field of view as the camera assembly pivots from about 0 degrees to about 120 degrees with respect to a longitudinal axis of the endoscope shaft. The camera assembly may comprise a lens assembly opposite the image sensor. And the lens assembly may comprise an optically clear window spaced apart from an outer surface of the lens assembly, sealingly providing a gas or air space between the window and the outer surface of the lens assembly.

BRIEF DESCRIPTION OF THE DRAWINGS

These and other aspects will become more apparent from the following detailed description of the various embodiments of the present disclosure with reference to the drawings wherein:

FIG. 18 depicts a cross-sectional view of example camera assembly mount and inner sheath of FIG. 17 taken at line 18-18 of FIG. 17;

FIG. 31 shows an example camera assembly;

FIG. 37 shows an example of a flexible optical fiber bundle or ribbon;

FIG. 38 shows a side view of the flexible optical fiber ribbon of FIG. 37;

FIG. 39 shows a perspective view of an example of a light projection element;

FIG. 40 shows a perspective view of another example of a light projection element;

FIG. 41 shows a perspective view of another example of a light projection element;

DETAILED DESCRIPTION

The terms 'endoscope' and 'arthroscope' as used herein are meant to be used interchangeably and are to be given their broadest interpretation, each term denoting an instrument having an elongate section for insertion into a space that is otherwise difficult to access, for the purpose of visual inspection, diagnosis and/or treatment or repair. In the field of medicine or veterinary practice, such a space may include a body cavity, joint space, tissue plane or other body structure. The instrument may also be used in a number of non-medical (e.g., industrial) applications, in which the diameter of the insertion portion of an endoscope needs to be minimized, or in which the space within which an endoscope must operate is too confined to permit the use of an actively flexible distal segment.

Figure 1:
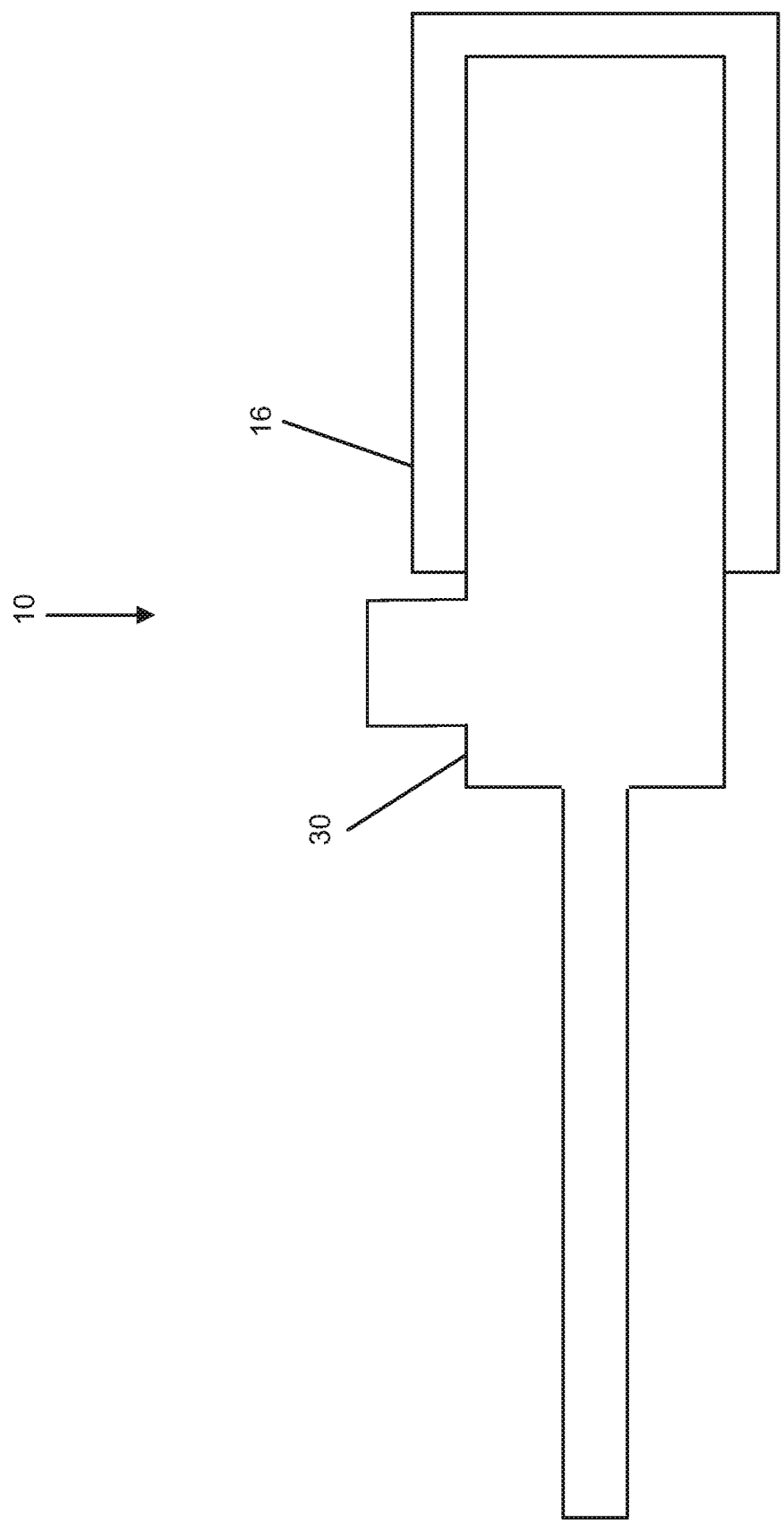
FIG. 1 is a representational illustration of a two-component handle design for an endoscope.

A two-component handle design of an endoscope 10 is shown in FIG. 1. The example endoscope 10 includes a handle proximal section 16 and a handle distal section 30. The handle proximal section 16 may be a housing. As shown, the handle distal section 30 may extend at least partially into the handle proximal section 16. The handle distal section 30 and the handle proximal section 16 may be rotatable relative to each other. In some embodiments, a user may hold the handle proximal section 16 immobile while rotating the handle distal section 30 with a thumb or finger. The endoscope 10 may have a number of features such as, but not limited to, a rotation sensing assembly, fluid conduits, lighting, an imager or camera assembly, pivot control for the imager etc.

Figure 2:
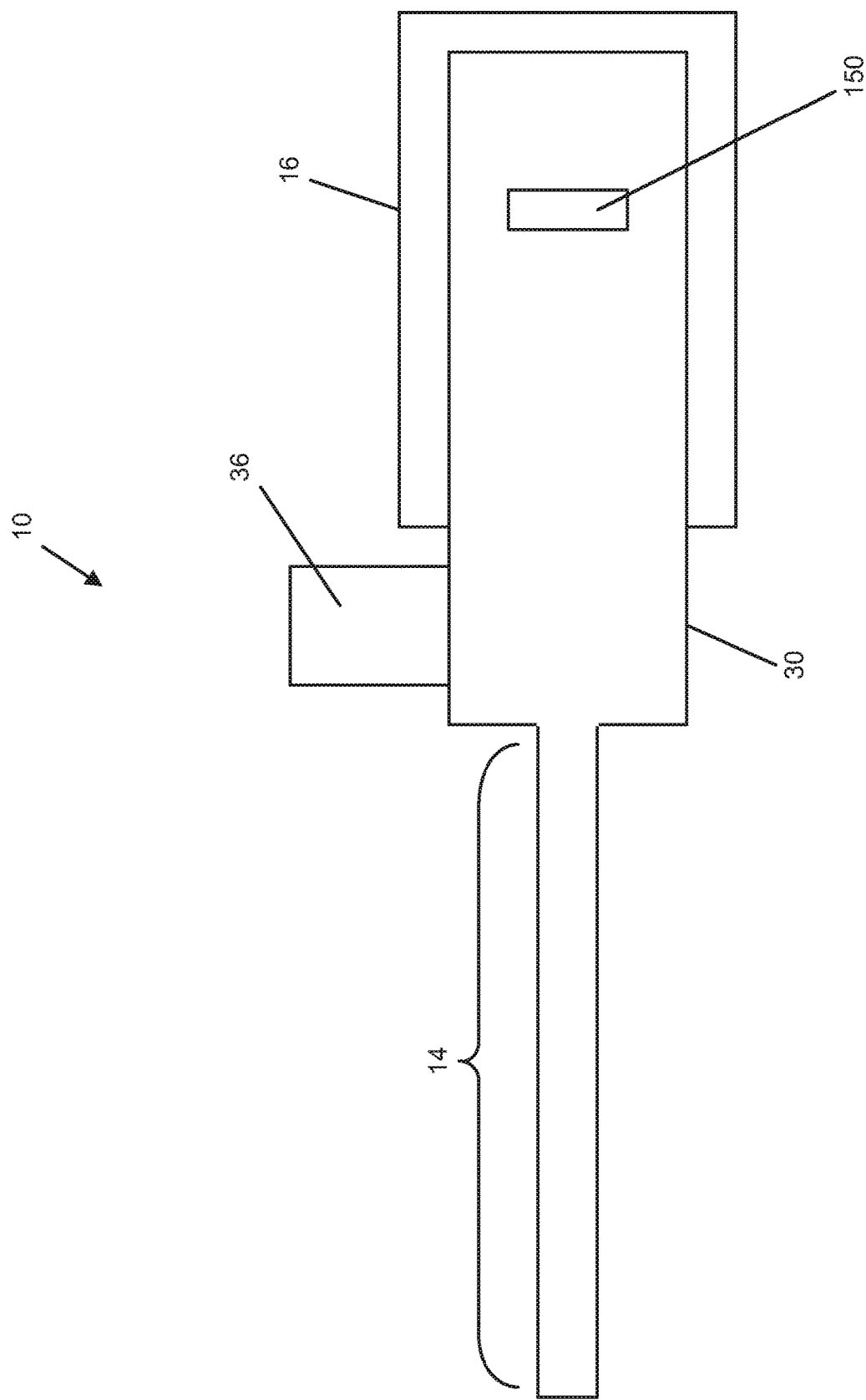
FIG. 2 shows additional features of the illustration of FIG. 1.

Additional features of the endoscope 10 are represented in FIG. 2. The endoscope 10 includes a handle proximal section 16 and a handle distal section 30. In this example, at least a part of an insertion shaft or section 14 is fixed to the handle distal section 30 and moves with the handle distal section 30. The handle distal section 30 includes a handle protuberance or fin 36 which provides a surface for a user to press against to facilitate rotating the handle distal section 30 relative to the handle proximal section 16. In some embodiments, a user's hand may hold the handle proximal section 16 immobile while the handle distal section 30 is rotated using one of the user's fingers or thumb.

In some embodiments, one or both the handle proximal section 16 and the handle distal section 30 may function as a housing or provide a support structure for other components of the endoscope 10. The endoscope 10 shown in FIG. 2 may include a rotation sensing assembly 150. The rotation sensing assembly 150 may track the rotation of handle distal section 30 relative to the handle proximal section 16. In some embodiments, the rotation sensing assembly 150 may include a component which is stationary with respect to the handle proximal section 16 and a component that is stationary with respect to the handle distal section 30. For example, the rotation sensing assembly 150 may include a potentiometer and a keyed shaft. The potentiometer may be mounted, for example to a support member comprising the internal housing of the handle proximal section 16. Alternatively, the handle distal section 30 may also comprise a support member for mounting one or more components of the rotation sensing assembly 150 (see for example the rotation sensor holder in FIG. 7). In either case, a rotational or translational component of the rotation sensing assembly is arranged to move in proportion to the degree of rotation of the handle distal section 30 relative to the handle proximal section 16.

Figure 3:
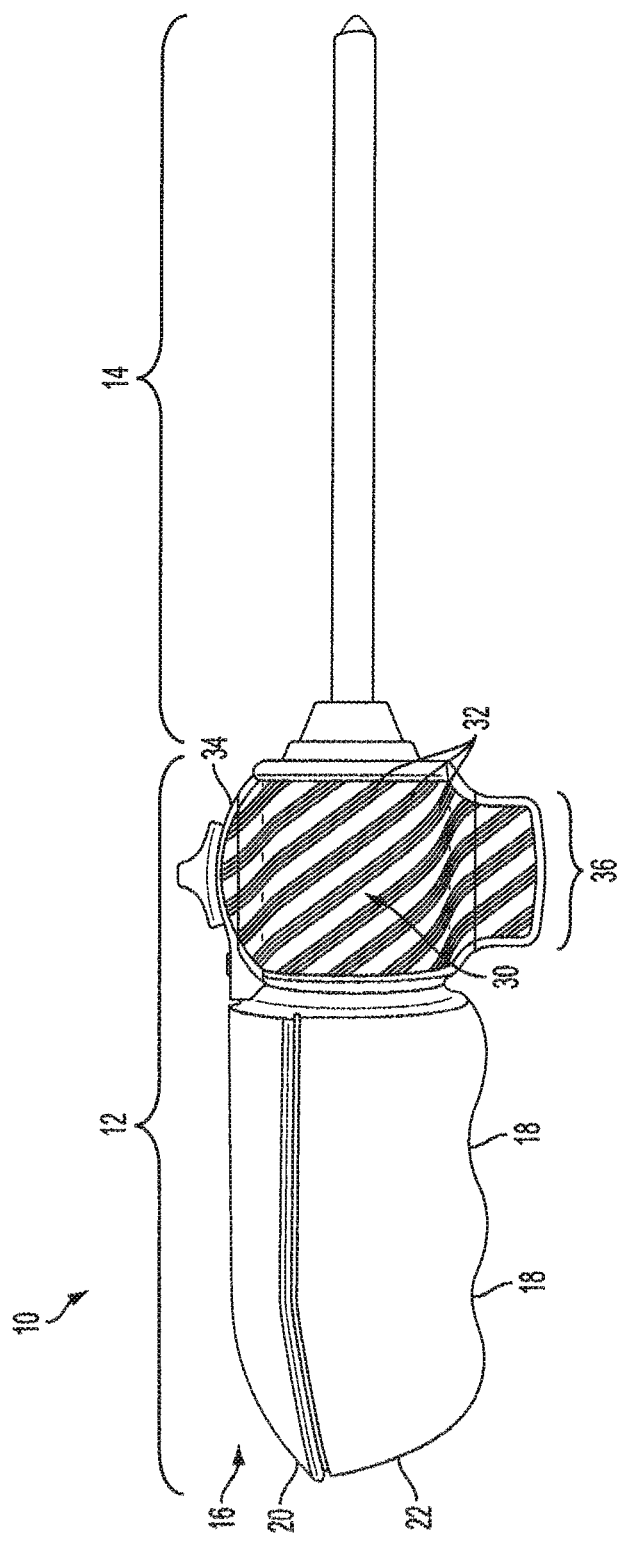
FIG. 3 shows an exemplary side view of an endoscope.

An exemplary embodiment of an endoscope (or, e.g., arthroscope) 10 is shown in FIG. 3. The endoscope 10 may be used in various endoscopic procedures, including arthroscopy, among others. As shown, the endoscope 10 includes a handle 12 and an insertion section or shaft 14, which may comprise an elongate hollow shaft within which one or more actuation members, electrical/communications wires, lighting or light-transmitting cables and/or fluid channels may be located. As shown, in an embodiment the handle 12 may be roughly cylindrical and rounded in shape. The insertion section 14 may also be roughly cylindrical in shape and extend along a longitudinal axis. In an embodiment, the insertion section 14 may be rigid and relatively straight. In other embodiments, the insertion section 14 may be curved or angled along at least a portion of its length. In yet other embodiments, the insertion section 14 may comprise semi-rigid, malleable material permitting it to be bent and held to a desired shape. The diameter of the insertion section 14 is significantly smaller than that of the handle 12. In some embodiments, the diameter of the insertion section 14 may be approximately 5.5 mm or smaller. The insertion section 14 of the endoscope 10 may be roughly the same length as that of the handle 12. In alternative embodiments, the lengths and shapes of the handle 12 and insertion section 14 may differ substantially.

At least a portion of the insertion section 14 may be detachable from the handle 12. In such embodiments, the insertion section 14 or detachable portion of the insertion section 14 may be coupled to the handle 12 by any of a variety of means including, but not limited to friction fit, snap fit, threaded coupling, bayonet mount, etc. In some embodiments, the insertion section 14 may be a disposable component and the handle 12 may be a reusable component. In embodiments in which the insertion section 14 is disposable, the insertion section 14 may be discarded after use. In other embodiments, the insertion section 14 may be sterilized after use via an autoclave, solution soaking, or other suitable sterilization procedure. In a preferred embodiment, both the handle 12 and the insertion section 14 are disposable and may be discarded after use, obviating the need for and cost of sterilization procedures and equipment (aside from a pre-usage sterilization with ethylene oxide, radiation, or the like, during, for example, manufacture, assembly or packaging of the device). Additionally, by making both the handle 12 and insertion section 14 of the endoscope 10 disposable, there is no degradation in function or reliability resulting from repeated use and repeated cleaning. Making the entire endoscope 10 disposable has other benefits, some which will be discussed below.

Preferably, a disposable endoscope 10 may be equipped with a means to prevent its reuse, particularly if sterilization of a used instrument is likely to degrade its function. For example, the endoscope 10 may include a memory chip storing an identification code that can be recognized by an electronic processor in a base unit to which the endoscope 10 must be connected for operability and display of images. The connection may include wired communications between a controller in the base unit and a memory chip in the endoscope 10, or, for example wireless communications using an RFID device mounted in the endoscope 10. (Other types of wireless transmission, such as, e.g. Bluetooth or Wi-Fi, may also be used). In an embodiment, the base unit may be programmed to encode a memory device on the endoscope 10 upon first use, and may be programmed to read and identify a code signifying that the endoscope 10 has been previously used whenever the endoscope 10 is subsequently re-connected to any base unit. Upon identification of a 'used' endoscope 10, the controller may be programmed to prevent electronic and imaging communications between the endoscope 10 and the base unit. The code and its communication may be encrypted to enhance system security. Alternatively, the endoscope 10 may include a disablement feature in its software which renders the endoscope 10 inoperable after usage.

As shown in FIG. 3, the handle 12 of the endoscope 10 may include a number of different features. The handle 12 may include a handle proximal section 16. The handle proximal section 16 may be relatively smooth as shown in FIG. 3. The handle proximal section 16 may comprise one or more hollow sections. The handle proximal section 16 may also be contoured such that it includes a number of ergonomic attributes. In some embodiments, at least a portion of the handle proximal section 16 may not have a smooth surface and may include a knurled, ribbed, roughened, honeycombed, etc. type texture, and/or a rubberized or elastomeric surface layer to facilitate gripping the endoscope 10 during its operation. In the example embodiment, the handle proximal section 16 is formed with a number of finger grooves 18. In some embodiments, the handle proximal section 16 may be made of a material (e.g. rubber or other elastomer) that has a soft feel or is otherwise comfortable to hold. In some embodiments, a pistol grip-like feature (not shown) may be included as part of the handle proximal section 16.

As shown in FIG. 3, the handle proximal section 16 may be divided into two separate parts. The handle proximal section 16 in FIG. 3 includes a handle top section 20 and a handle bottom section 22. The handle top section 20 and handle bottom section 22 of the handle proximal section 16 may be manufactured as two separate parts and coupled together by any suitable means, such as, e.g., adhesive, screws, snap-fit, etc. As shown, the handle top section 20 is smooth and contoured differently from the handle bottom section 22. This may help a user quickly and easily determine orientation of the endoscope 10 by feel. In some embodiments the handle top section 20 and handle bottom section 22 may comprise surface materials that have a different feel (e.g., metallic vs. plastic, metallic vs. elastomeric, smooth vs. textured, etc.).

The handle 12 of the endoscope 10 may also include a handle distal section 30. As shown in FIG. 3, the handle distal section 30 extends from the handle proximal section 16 toward the insertion section 14. The handle distal section 30 may be smaller in diameter than the handle proximal section 16. As shown, the handle distal section 30 may be longer in length than the handle proximal section 16, but in alternate embodiments, the relative dimensions of the handle distal section 30 and handle proximal section 16 may differ.

On at least a portion of the handle distal section 30 there may be a gripping texture as shown in FIG. 3. In the example embodiment shown in FIG. 3, the grip texture is a series of spiraling ribs 32. In other embodiments, other gripping textures, such as non-spiraling ribs, nubs, bumps, grooves, honeycomb patterning or other form of knurling or checkering, etc. may also be used. As shown, the spiraling ribs 32 in the example embodiment encircle most of the outer diameter of the handle distal section 30. In some embodiments including a gripping texture on the handle distal section 30, the gripping texture may not be formed as a continuous part of the handle distal section 30. In such embodiments, the gripping texture may be a 'skin' or sleeve applied onto the handle distal section 30. The gripping texture skin may be coupled to the handle distal section 30 by any suitable means such as, but not limited to, adhesive, snap fit, various fasteners, over-mold, etc. In some embodiments, the gripping texture skin may be made of a material different from the handle distal section 30. The gripping texture skin, for example, may be a softer, elastomeric or rubbery, material which is more comfortable to grip/less slippery than the handle distal section 30 material.

In the example embodiment, the handle distal section 30 includes a handle raised portion 34 projecting from the top of the handle distal section 30. In this example, the handle raised portion 34 does not project sharply up from the rest of the handle distal section 30. Instead, the handle raised portion 34 may be constructed to gently curve up from the rest of the handle distal section 30. In this example, the spiraling ribs 32 do not extend over and onto the top of the handle raised portion 34. Additional features of the handle raised portion 34 will be further described below.

In one aspect, projecting from the bottom of the handle distal section 30 may be a handle fin 36. In this example, the handle fin 36 does not project sharply away from the rest of the handle distal section 30. Instead, the handle fin 36 may be constructed to gently curve away from the rest of the handle distal section 30 toward an inferior or dependent position of the endoscope 10. The spiraling ribs 32 preferably do not extend over and onto the bottom of the handle fin 36. In other embodiments, a handle fin 36 may be configured to project from the top of the handle distal section 30, while the handle raised portion 34 may be configured to project from another aspect of the handle distal section 30. The handle fin 36 may be disposed so as to mimic the location of an entry point for various cables, irrigation, etc. in endoscopes which may already be familiar to a physician. This may be desirable since such an entry point is often used as a surface to press against to facilitate rotation and as an orientation marker. Additional features of the handle fin 36 will be further described below.

Figure 4:
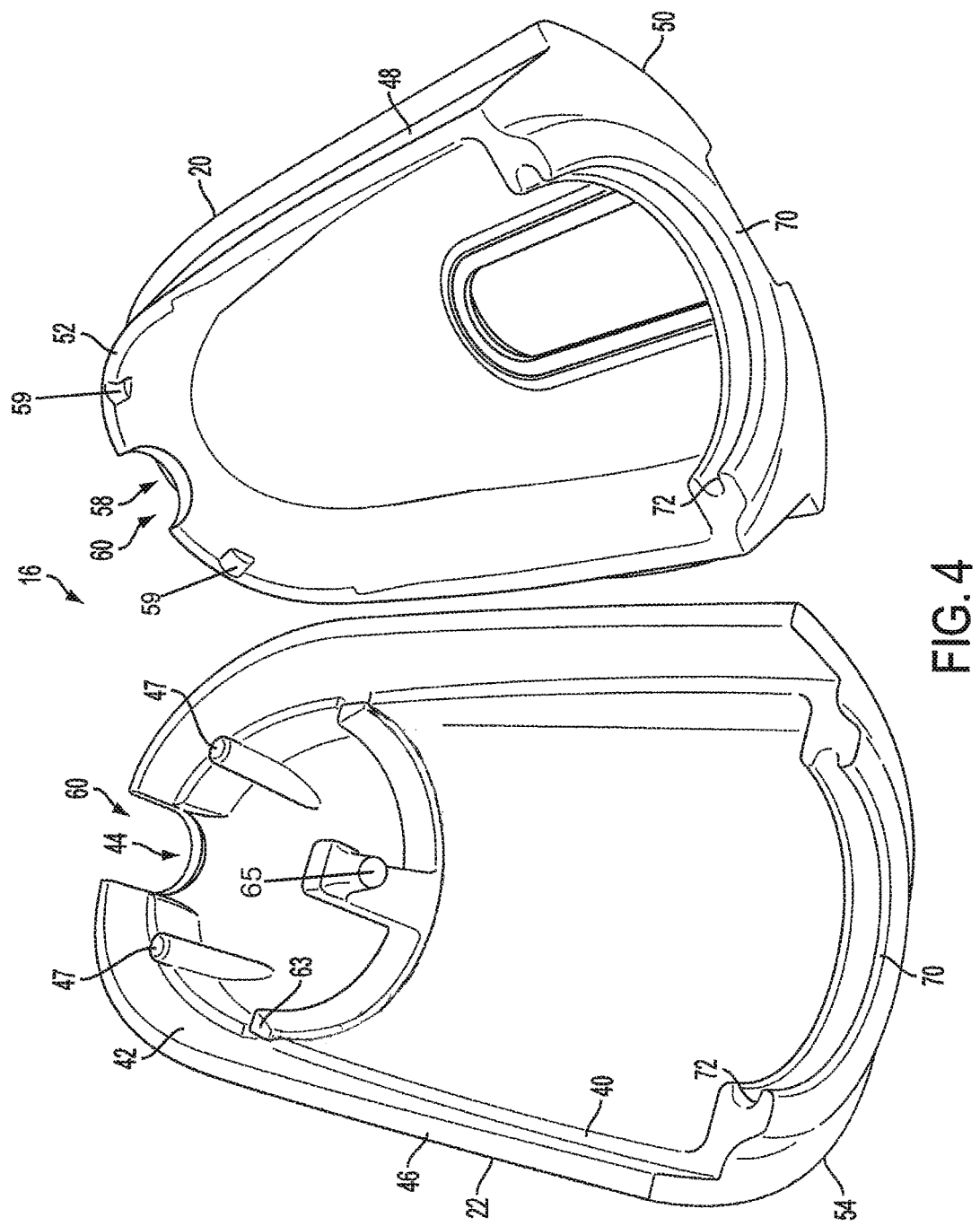
FIG. 4 shows a disassembled view of an example of a handle proximal section of an endoscope.
Figure 5:
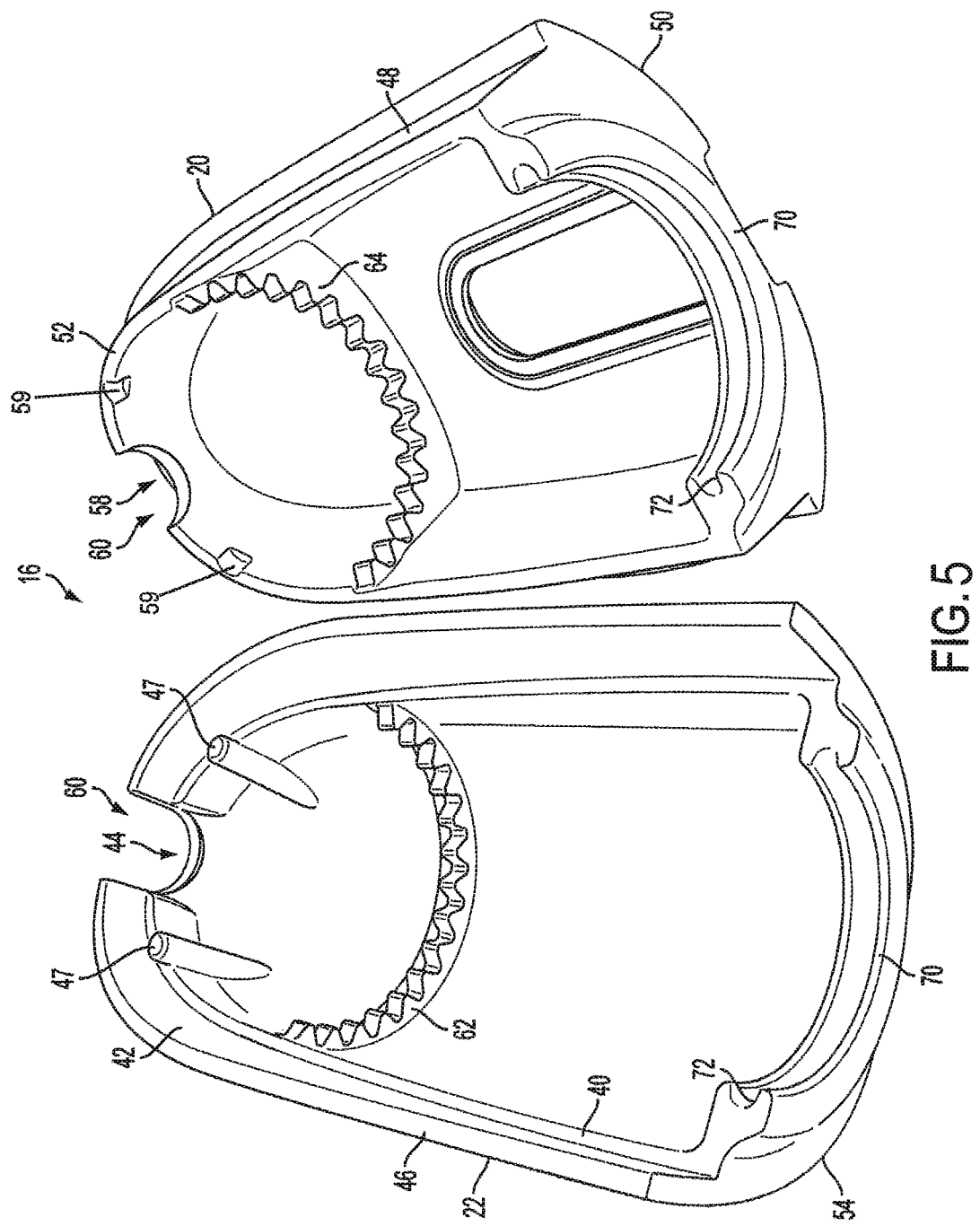
FIG. 5 shows a disassembled view of an alternate example of a handle proximal section of an endoscope.

FIG. 4 and FIG. 5 show example embodiments of the handle top section 20 and handle bottom section 22 of the handle proximal section 16 shown in FIG. 3. The handle top section 20 and handle bottom section 22 are shown in an uncoupled or disassembled view. The handle proximal section 16 may be hollow and form a shell-like structure when assembled. The handle bottom section 22 may include a ledge 40 that wraps around a bottom section inner wall 42 at a distance from the top face 46 of the handle bottom section 22. As shown, there is a curved or U-shaped cutout 44 in the handle bottom section 22 disposed at an angle substantially perpendicular to the top face 46 of the handle bottom section 22. Two peg projections 47 may be included near the rear of the handle bottom section 22. The peg projections 47 may extend slightly above the ledge 40 and be angled approximately perpendicular to the top face of the ledge 40.

As shown in FIGS. 4 and 5, a portion of the handle top section 20 may be dimensioned so that it may be overlapped by the handle bottom section 22 when the handle proximal section 16 is assembled. The overlapped section 48 may be stepped in from the handle top section outer surface 50 as shown in FIGS. 4 and 5. The height of the overlapped section 48 may be selected so that it is approximately equal to or slightly greater than the distance between the top of the ledge 40 of the handle bottom section 22 and the top face 46 of the handle bottom section 22. In such embodiments, when fully assembled, the bottom face 52 (refers to orientation when assembled) of the handle top section 20 abuts the top of the ledge 40 of the handle bottom section 22. Additionally in such embodiments, the handle top section outer surface 50 and handle bottom section outer surface 54 may be flush with each other and form a nearly continuous surface with little gap between the two. In some embodiments, there may be a small gap between the handle top section outer surface 50 and handle bottom section outer surface 54 (small gap shown in FIG. 3).

As shown, the handle top section 20 may include peg cutouts 59 which are shaped and disposed such that they may accept the peg projections 47 in the handle bottom section 22. The handle top section 20 may include a curved cutout 58 at the butt or proximal portion of the handle top section 20. As shown the curved cutout 58 may be recessed into the handle top section 20 at an angle substantially perpendicular to the bottom face 52 (refers to orientation when assembled) of the handle top section 20. When the handle proximal section 16 is assembled, the curved or U-shaped cutout 44 of the handle bottom section 22 and the curved cutout 58 of the handle top section 20 together may form a substantially circular or ovoid handle void or opening 60 which will be further described below. It should be appreciated that the use of the terms "cutout", "cut", etc. herein should not be construed to imply material must be physically removed by a cutting or material removal process. In some embodiments, the curved or U-shaped cutout 44 and the curved cutout 58 may be formed during manufacture without physically removing material.

As shown in FIG. 4 the handle bottom section 22 may include a shaft support member 63. The shaft support member 63 in FIG. 4 has a curved or semi-circular portion which roughly corresponds to the location of the toothed projection 62 in FIG. 5. The shaft support member 63 also includes a post. The post projects perpendicularly from a mid-point of the semi-circular portion, leaving approximately 90° of the semi-circular portion on each side of the post. Projecting perpendicularly from the top of the post of the shaft support member 63 toward the distal end of handle proximal section 16 is a shaft supporting section 65. The shaft supporting section 65 may include a depression in which a portion of a sensor gear shaft 120 (see FIG. 7) may be seated. The post of the shaft support member 63 may be approximately the length of the radius of the semi-circular portion when the handle proximal section 16 is fully assembled. The shaft support member 63, toothed projection 62, and toothed projection 64 will be further described below.

As shown in FIG. 5, the handle bottom section 22 may instead or optionally include a curved toothed projection 62. The curved toothed projection 62 is complemented by a similar toothed projection 64 included on the handle top section 20. The toothed projection 62 and toothed projection 64 may be disposed so that they are in line with one another and form an annulus or internal ring gear when the handle proximal section 16 is fully assembled.

As shown in FIGS. 4 and 5, the face of the handle bottom section 22 opposite the curved or U-shaped cutout 44 and face of the handle distal section 20 opposite the curved cutout 58 may include semi-circular openings or voids 70. A curved or U-shaped track 72 may be recessed into the edges of the semi-circular voids 70 along the entire arc of each semi-circular void 70 as shown in FIGS. 4 and 5.

Figure 6:
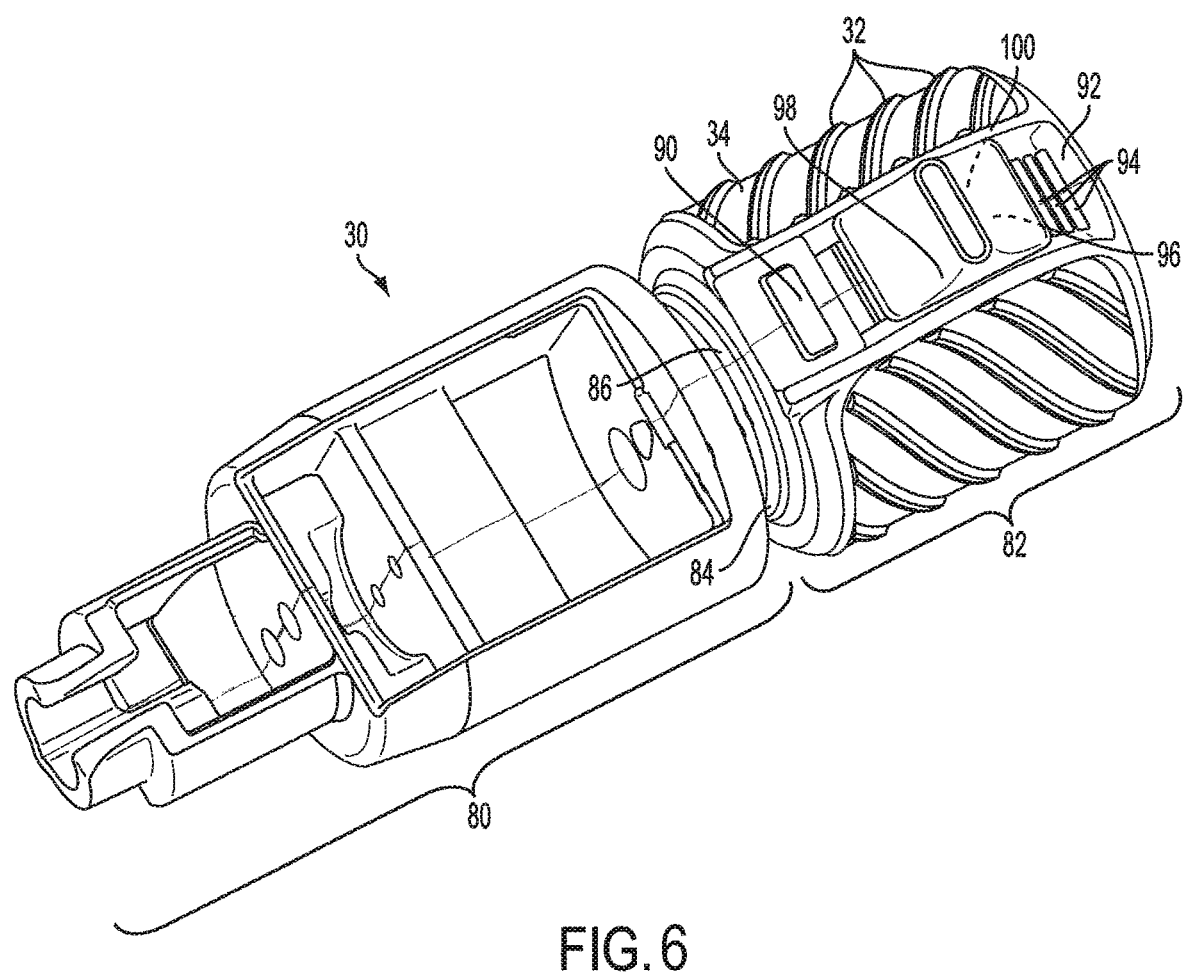
FIG. 6 shows a top perspective view of an example of a handle distal section of an endoscope.

The example handle distal section 30 of FIG. 3 is shown in FIG. 6 isolated from the rest of the handle 12. FIG. 6 shows the handle distal section 30 from a substantially top perspective view. As shown, the spiraling ribs 32 and front handle raised section 34 detailed above are visible on handle distal section 30. As indicated by the seam running down the vertical center plane of the handle distal section 30, the handle distal section 30 may be constructed as two or more separate parts (30a and 30b in the example embodiment) which are coupled together by any suitable means or combination of suitable means, such as, e.g., snap fit, adhesive and/or screws.

The handle distal section 30 in FIG. 6 additionally includes a section not shown in FIG. 3. When the endoscope 10 is assembled, as it is in FIG. 3, part of the handle distal section 30 may be housed inside the handle proximal section 16. For example, a housed handle electronics section 80 projects proximally from the external handle distal section 82 (which is visible in both FIG. 3 and FIG. 6). The housed handle electronics section 80 will be further described below.

Between the housed handle electronics section 80 and the external handle distal section 82 is a small diameter span 84. As shown, the small diameter span 84 may include a rounded groove 86 which is recessed into the outer surface of the small diameter span 84. In some embodiments, when fully assembled, the small diameter span 84 of the handle distal section 30 may be disposed within the semi-circular voids 70 of the handle proximal section 16. The rounded groove 86 in the small diameter span 84 and the curved or U-shaped track 72 in the semi-circular voids 70 may be in line with one another. This may allow the handle distal section 30 and handle proximal section 16 to be rotated relative to one another as the endoscope 10 is used. Optionally, ball bearings (not shown) or other types of bearings may track along the rounded groove 86 in the small diameter span 84 of the handle distal section 30 and the U-shaped track 72 in the semi-circular voids 70 of the handle proximal section 16. In a preferred embodiment, an o-ring (not shown) may be placed in the rounded groove 86 of the small diameter span 84 of the handle distal section 30. The o-ring (not shown) may function as a dynamic seal between the handle proximal section 16 and handle distal section 30. In such embodiments, the handle proximal section 16 and handle distal section 30 may be rotated relative to one another while sealing the interior of the handle proximal section 16 from liquid.

A handle fin 36 or other protuberance may serve as an orientation marker for the user as the handle proximal portion 16 and handle distal section 30 are rotated relative to one another. Orientation may be checked either visually or by feel. In some embodiments, the gripping texture on the handle fin 36 may be different than spiraling ribs 32 on the rest of the handle distal section 30 to facilitate orientation-checking by feel.

As shown in FIG. 6, the handle raised section 34 may include a button 90. In some embodiments, the handle raised section 34 may include more than one button 90, or no button at all. The button 90 may be located elsewhere on the handle distal section 30 or elsewhere on the handle 12. In some embodiments, the handle raised section 34 may include a button 90 and one or more additional buttons 90 may be located elsewhere on the handle 12. The button 90 may be assigned a function. In some embodiments, the button 90 may be assigned multiple functions which may be activated by various user manipulations. In some embodiments one or more of the buttons 90 may be sealed with respect to the external handle section 82 to inhibit liquid infiltration.

The button 90 may be an image capture button. In such embodiments, user depression of the button 90 may cause a photograph to be recorded by the endoscope 10. In some embodiments, a user may double tap the button 90, hold down the button 90, etc. to cause the endoscope 10 to start recording video. To stop recording video, a user may double tap the button 90, hold down the button 90, etc. In some embodiments, a user may only be required to depress the button 90 to stop recording video. In some embodiments, a single depression of the button 90 by a user while the endoscope 10 is recording video may cause a still image to be recorded without the need to pause video recording.

The handle raised section 34 may additionally include a slide button recess 92. As shown in FIG. 6, the slide button recess 92 is arranged to permit fore and aft movement of a slide button or finger contact 98 (see FIG. 13) while constraining lateral movement. The slide button may be part of a pivot control or pivot control structure 100 (see, for example, FIG. 13) in some embodiments. In some embodiments, including the example embodiment shown in FIG. 6, the slide button recess 92 may be slightly curved to conform to the shape of the portion of the handle within which it resides.

As shown in FIG. 6, the slide button recess 92 may include a number of ridges or detents 94 that can engage with a corresponding element on the slide button to provide a series of discrete, positive stops when a user moves the slide button fore and aft. Some embodiments may not include the ridges 94. In some embodiments, the portion of a pivot control structure 100 (see FIG. 11) with which a user may interface may project through a pivot control structure notch 96 (see FIG. 13) located in the slide button recess 92 of the handle raised section 34. In the example embodiment in FIG. 6, such a portion of the pivot control structure 100 includes a finger contact 98. As shown, the finger contact 98 may have sloped contours for ergonomic reasons. The pivot control structure 100 will be further described below.

Figure 7:
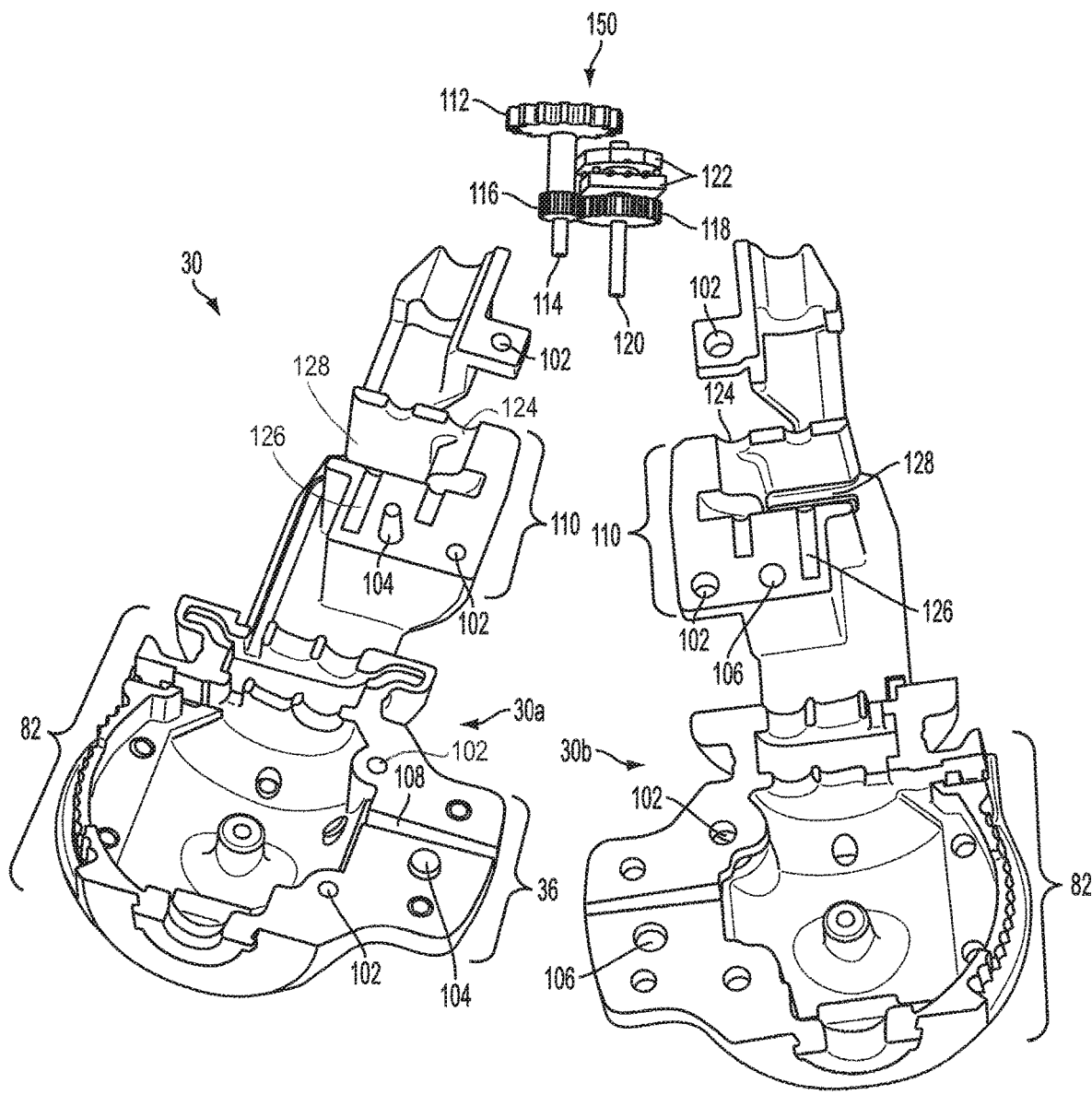
FIG. 7 shows an exploded view of a handle distal section and an example of a rotation sensing assembly of an endoscope.

FIG. 7 shows a more detailed illustration of an exemplary handle distal section 30 without an attached insertion section 14. An example rotation sensing assembly 150 is also shown in FIG. 7. As shown, the handle distal section 30 is manufactured as two separate parts 30*a* and 30*b*. In the example embodiment, the two separate parts 30*a* and 30*b* of the handle distal section 30 include a number of screw holes 102, which may be threaded. Screws (not shown) or other suitable fasteners may be used to couple the two separate parts 30*a* and 30*b* of the handle distal section 30 together. In some embodiments, the two separate parts 30*a* and 30*b* may be coupled together via a snap fit, ultrasonic weld, adhesive, etc.

In some embodiments one of the two separate parts 30*a* and 30*b* of the handle distal section 30 may include peg-like projections 104 which fit into complimentary peg accepting cavities 106 on the other of the two separate parts 30*a* and 30*b*. This may help to align and/or couple the two separate parts 30*a* and 30*b* together. In some embodiments, including the embodiment shown in FIG. 7, the external handle distal section 82 may be substantially hollow. In some embodiments, the hollow of the external handle distal section 82 may not be sealed against fluid. In the example embodiment shown in FIG. 7, a drain channel 108 may be included, for example, in the handle fin 36. The drain channel 108 may allow any fluid which enters the hollow of the external handle distal section 82 to easily drain out. Alternate embodiments may include additional and/or different drain arrangements.

The handle distal section 30 may also include a rotation sensor holder 110 as shown in FIG. 4. The rotation sensor holder 110 may retain the rotation sensing assembly 150 when the endoscope 10 is fully assembled. As shown, the rotation sensing assembly 150 may include a forward gear 112. The forward gear 112 is disposed about a forward gear shaft 114. As shown in FIG. 4, a transfer gear 116 is also placed on the forward gear shaft 114, such that rotation of the forward gear 112 causes the transfer gear 116 to rotate as well. The transfer gear 116 may mesh with a sensor shaft gear 118, disposed on a sensor gear shaft 120. As the forward gear 112 rotates, so will the sensor shaft gear 118 and the sensor gear shaft 120. Use of a gear assembly may allow for placement of an attached potentiometer 122 in a location that is off-center from the central rotational axis of the handle distal section 30, which may advantageously allow for a central placement of other internal structures (e.g., irrigation conduit, optical fiber bundle, electronic flex cable, or other electronic components).

As in the example embodiment in FIG. 7, the sensor gear shaft 120 may include a splined, or keyed (e.g., a D-shaped) portion. The keyed portion may operatively engage with one or more rotational potentiometers 122. In the example embodiment in FIG. 7, there are two rotational potentiometers 122. The potentiometers 122 may be mounted on or otherwise attached to a mounting element, or a part of a printed circuit board in the handle as described in reference to FIG. 85. The potentiometers 122 each include a keyed (e.g. D-shaped) void with which the corresponding keyed portion of the sensor gear shaft 120 mates. As the sensor gear shaft 120 rotates, the electrical resistance of the potentiometer(s) 122 will vary proportionately. Since the resistance will predictably change with the amount of rotation of the sensor gear shaft 120 the measured resistance of the potentiometer(s) 122 may be used to determine the amount of rotation that has taken place between the handle proximal section 16 and the handle distal section 30 (and by extension, the insertion section 14).

In some embodiments, the housing of each potentiometer 122 may be mounted to elements of the housed handle electronics section 80 (or other elements attached to the handle distal section 30), and thus immobilized relative to the handle distal section 30 (and by extension the insertion section 14), while the shaft or rotating hub of the potentiometer 122 is connected to the handle proximal section 16. In other embodiments, the housing of the potentiometer 122 may be immobilized relative to the handle proximal section 16, while its shaft or rotating hub may be connected to elements of the handle distal section 30 or the handle electronics section 80.

The example embodiment in FIG. 7 includes two rotational potentiometers 122 stacked together, and offset rotationally from one another. In an alternate embodiment, the potentiometers 122 may be spaced apart from each other, but share a common rotational axis (e.g., the wipers of both potentiometers 122 are caused to move by a common shaft). This arrangement permits a controller receiving electrical resistance values from both potentiometers 122 to compute the degree of rotation of a sensor shaft (and ultimately of components at the distal end of the endoscope) with a desired accuracy through 360 degrees of rotation, thus helping to eliminate computational "blind spots" in measuring the rotation of the components at the distal shaft (e.g., a camera) of the endoscope. Any blind spot created by the position of a wiper of one potentiometer 122 at the end of its range of motion may be compensated by a wiper of a second potentiometer 122 whose position is not at the end of its range of motion. In alternative embodiments, more than two rotationally offset potentiometers 122 may be used. The rotational offset between the potentiometers 122 may be 180 degrees for computational simplicity, but other angular offsets may be used to achieve the same result, as long as the rotational offset allows any blind spot created by one potentiometer 122 to be overlapped by a functional range of another potentiometer 122. In alternative embodiments, the gearing ratios between the forward, transfer, and sensor shaft gears 112, 116, 118 may vary, depending on the degree of precision desired in measuring rotation, the sensitivity of the potentiometers 122, and other factors. In alternative embodiments, the rotation sensing assembly 150 may use belts rather than one or more of the gear assemblies. For example, the transfer gear 116 and sensor shaft gear 118 may be replaced by a belt. Other rotation to rotation arrangements known in the art may also be used. In some embodiments, the forward gear shaft 114 may include a keying feature (e.g., a D-shaped portion) which operatively engages the potentiometers 122 directly. Rotation sensors other than potentiometers 122 may also be used. Alternative embodiments may include rotation sensors such as, a rotary encoder, a rotary variable differential transformer, or other encoding devices. In embodiments using a rotary encoder, the encoder may be a gray encoder, magnetic encoder, optical encoder, etc.

In an embodiment, the sensor gear shaft 120 may not extend to the shaft bearing section of a shaft support member 63. Rather, the rotation sensing assembly 150 may be supported by the rotation sensor holder 110. Among other benefits, this arrangement allows for an unlimited degree of rotation of the handle distal section 30 relative to the handle proximal section 16. Additionally, as would be appreciated by one of skill in the art, it allows for components a of rotation sensing assembly 150 to be located in an off-center position. This may provide benefits during assembly. For example, it may simplify routing of an irrigation line 434 (see FIG. 85), power cable 432 (see FIG. 85), etc.

In other embodiments, the shaft support member 63 and potentiometers 122 may be directly connected by a shaft. A shaft splined or keyed on a distal end may extend from the shaft bearing section of the shaft support member 63 and extend through a corresponding splined or keyed (e.g., D-shaped) void in the potentiometers 122. Since the shaft support member 63 may be fixed relative to the handle proximal section 16, rotation of the distal handle section 30 relative to the handle proximal section 16 will vary the resistance measured by the potentiometers 122. As mentioned above, since the resistance will predictably change with rotation of one handle section relative to the other, the resistance measurement may be used to determine the amount of rotation achieved by the handle distal section (and ultimately, the distal end of the endoscope or camera assembly 350 shown, for example, in FIG. 19).

In other embodiments, the rotation sensing assembly 150 may include a range finder which may be disposed on the housed handle electronics section 80 (see FIG. 6). The interior walls of the handle proximal section 16 (see FIG. 4) may include a variable-thickness or variable-height raised surface that wraps around most or all of the 360° of the interior wall of the handle proximal section 16, and varies in thickness or height in a pre-determined manner along its circumferential path. As the handle proximal section 16 and handle distal section 30 rotate relative to one another, the range finder may provide a controller with a signal that varies according to the distance read by the range finder to the varying surface (either its varying thickness or height). The signal may be correlated to the thickness/height or distance measured by the range finder relative to a pre-determined base position in which the surface has a specified thickness or height and is correlated to a specified angular rotation of the handle distal section 30 relative to the handle proximal section 16. This distance may be compared to a previous distance to thereby determine the amount of rotation that has occurred. The range finder may be any type of range finder (e.g. a mechanical position sensor, a sonic range finder, laser or other optical range finder, etc.).

In yet another alternative embodiment, an optical mouse like sensor arrangement may be used. The sensor may be mounted on one of the housed handle electronics section 80 or handle proximal section 16 and may be configured to track movement of the other of the housed handle electronics section 80 or handle proximal section 16. In such embodiments, the amount and direction of movement sensed by the sensor may be used to determine the amount and direction of rotational displacement that has occurred. In some embodiments, the surface tracked by the sensor may have a reference grid, number of unique indicators, pattern, markings, or other differentiating features, which allow sensor determination of rotational orientation upon start up. Other varieties of rotation sensing assemblies 150 known to those skilled in the art may also be used in various embodiments.

As shown in FIG. 7, the rotation sensor holder 110 of the handle distal section 30 may be shaped such that when the two separate parts 30a and 30b of the handle distal section 30 are coupled together, the rotation sensing assembly 150 may be captured between the two separate parts 30a and 30b. Each side of the rotation sensor holder 110 may include a forward gear shaft trough 124 and a sensor gear shaft trough 126. When assembled the forward gear shaft trough 124 and the sensor gear shaft trough 126 may act as bearing surfaces respectively for the forward gear shaft 114 and the sensor gear shaft 120. Each side of the rotation sensor holder 110 may also include a holder void 128. The holder void 128 may be sized and shaped such that the transfer gear 116, sensor shaft gear 118, and potentiometers 122 may fit within the rotation sensor holder 110 when the handle distal section 30 is fully assembled.

Figure 8:
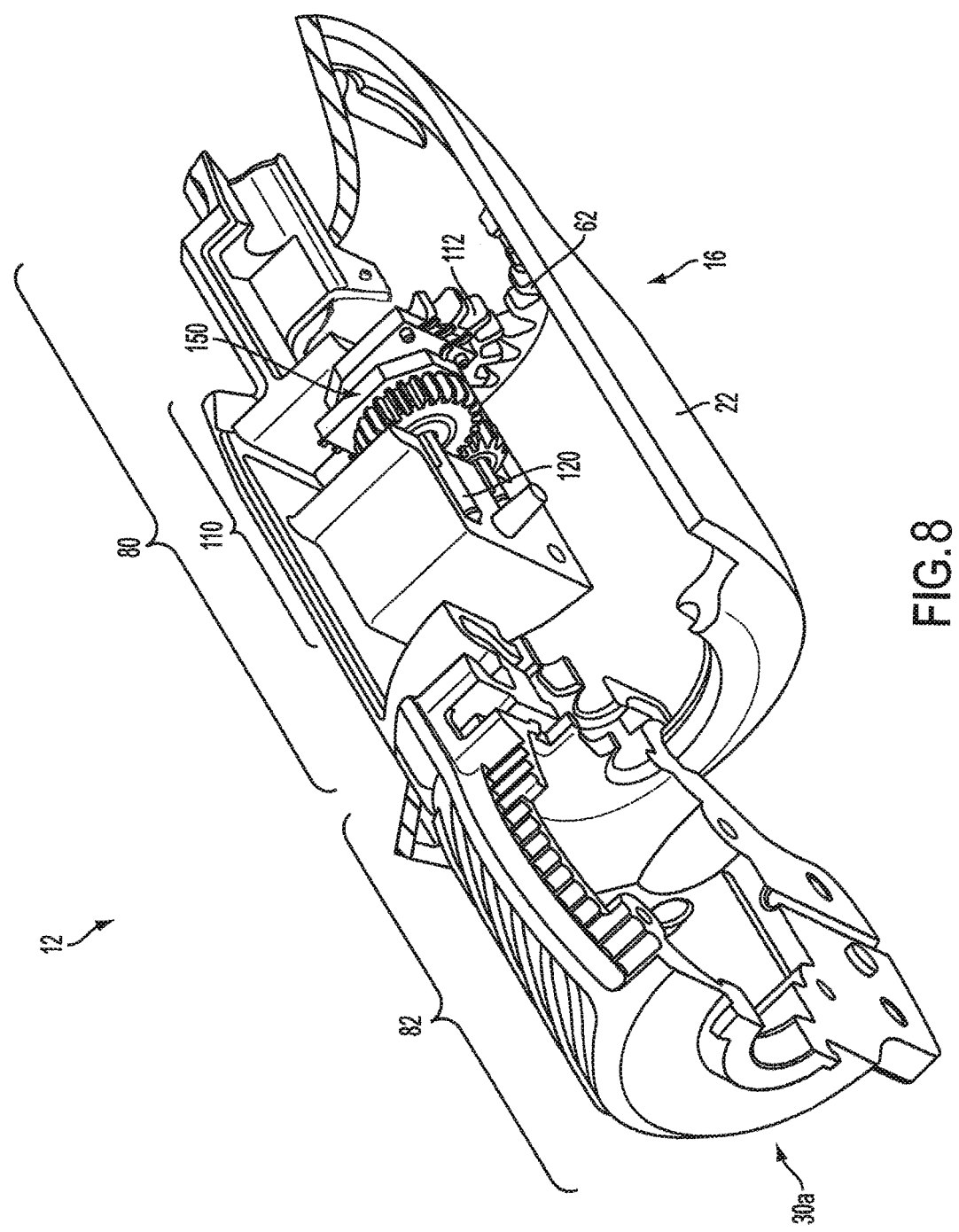
FIG. 8 shows a partially assembled view of an exemplary endoscope.

FIG. 8 shows a partially assembled view of the handle 12 of the endoscope 10. Only the handle bottom section 22 of the handle proximal section 16 is shown in FIG. 8. As shown, a part of the handle bottom section 22 of the handle proximal section 16 has been cut away. Additionally, in the embodiment shown in FIG. 8, the handle distal section 30 is assembled from two separate parts 30a and 30b (see FIG. 7). One of the halves (30b) of the handle distal section 30 has been removed in FIG. 8 for clarity. The housed handle electronics section 80 may be located inside the handle proximal section 16. The external handle distal section 82 extends beyond the handle proximal section 16 and is exposed to the environment.

As described above, the rotation sensing assembly 150 is disposed within the rotation sensor holder 110. As shown, the forward gear 112 of the rotation sensing assembly 150 may mesh with the annulus gear formed by the toothed projection 62 and toothed projection 64 (best shown in FIG. 5). In such embodiments, when the handle 12 is fully assembled, any rotation of the handle distal section 30 in relation to handle proximal section 16 causes the forward gear 112 to rotate since it meshes with the annulus gear formed by the toothed projection 62 and the toothed projection 64. This rotation may then be translated through the rest of the rotation sensing assembly 150 allowing the rotation to be measured by the rotation sensing assembly 150. In a preferred embodiment, the overall gear ratio may be approximately 1:1.

Alternatively, rather than gear elements, the handle proximal section 16, similar to that shown in FIG. 4, may comprise a keyed shaft or partially keyed shaft, affixed to the shaft support section 65 of the shaft support member 63. The keyed portion of the shaft may be arranged to mate with the hub of one or more potentiometers 122, which are held in rotation sensor holder 110. Thus as the handle distal section 30 is rotated relative to the handle proximal section 16, the wiper of the one or more potentiometers 122 is able to convert the relative positions of the handle distal section 30 and proximal section 16 into an electrical resistance value usable to determine rotational orientation.

Figure 9:
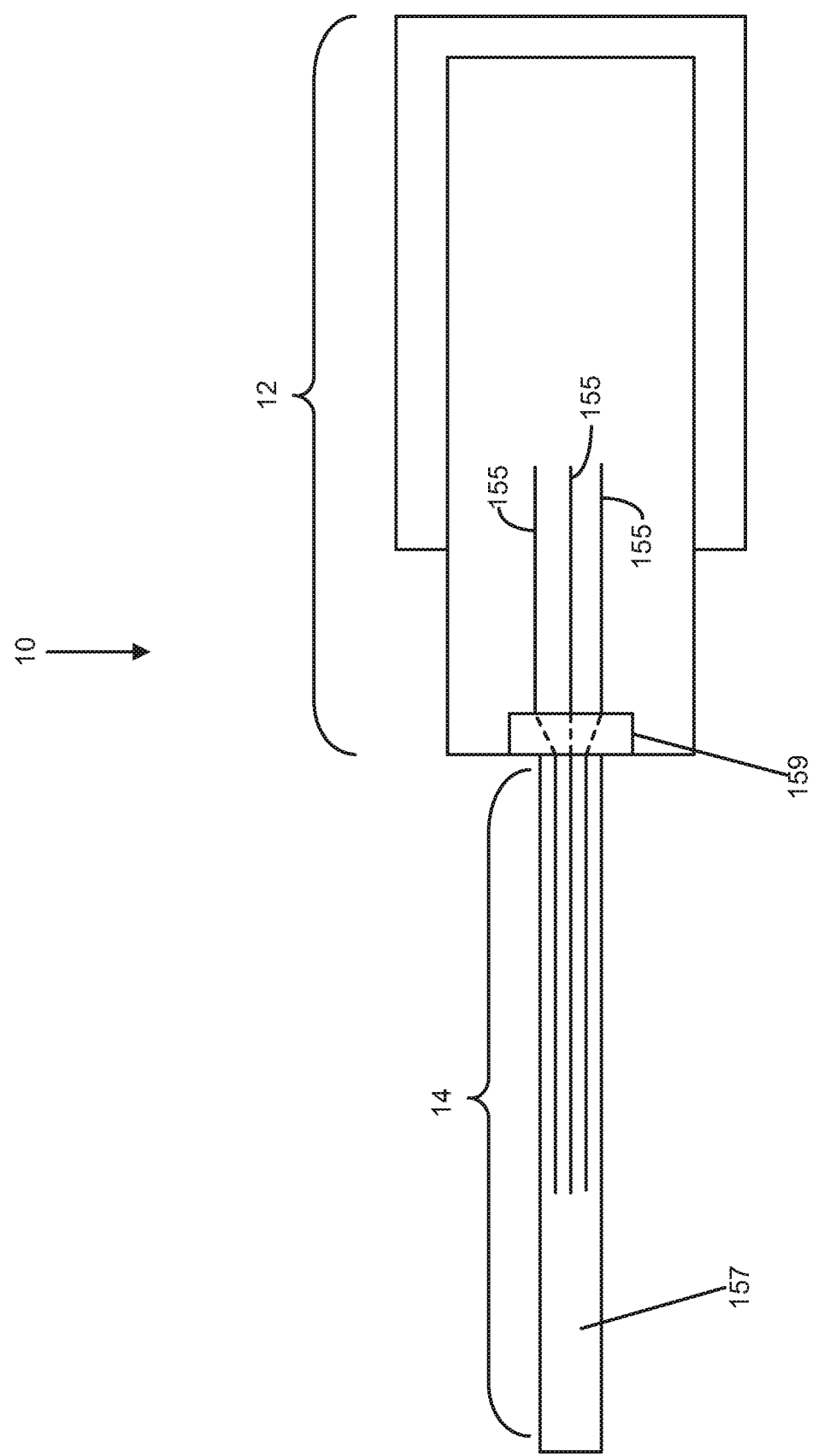
FIG. 9 is a representational illustration of a pass-through barrier allowing utility components to pass from the handle to a conduit of an endoscope.

Referring now to FIG. 9, in an embodiment, the insertion section 14 of an endoscope 10 includes a conduit 157 through which operations or functions may be performed. In industrial or medical applications, this conduit 157 may be used to pass instruments to manipulate objects at the end of the insertion section 14 (instruments such as graspers, forceps, clamps, wire baskets, dilators, knives, scissors, magnetic pickups, etc.). Fluid (gas or liquid) may also be passed to/from an external source from/to the space within which the insertion section 14 is placed. In medical applications, such a conduit 157 may be used to insufflate a body cavity with a gas, evacuate gas from a body cavity, irrigate a space with liquid, or aspirate liquid and/or suspended particulates from a space. The conduit 157 optionally may carry utility components such as light transmission, information transmission, power transmission, and mechanical control components, saving space within the insertion section 14 and helping to reduce the overall diameter of the insertion section 14. A light transmission component may include, for example, a fiberoptic bundle, ribbon, light pipe, light projection element, and/or the like. An information transmission component may include, for example, an electrical cable bundle or ribbon connecting an imager or image sensor at the end of the insertion section 14 to an image processing unit situated in the handle 12 or external to the endoscope 10. Such a cable may also provide power to the image sensor. Mechanical control components may include, for example, pushrods, pull wires, etc. to control the movement of an element near the end of the insertion section 14. This may include, for example, an actively flexible distal segment of the insertion section 14 that can be actively flexed by the use of the mechanical control component(s) extending from the handle 12. It may also include, for example, a rotatable camera or camera mount at the end of insertion section 14 that can be actively moved by the use of the mechanical control component (s) extending from the handle 12.

In a specific embodiment, a fluid carrying conduit 157 within the insertion shaft or section 14 is configured to enclose utility components of the endoscope 10, such as, for example, fiberoptic bundles, communication cables and mechanical actuators. In a further embodiment, the conduit 157 may be in fluid communication with a camera assembly 350 (see, for example, FIG. 19) at the distal end of insertion shaft 14. The camera assembly 350 may include a camera sensor or imager having connections to a communications cable. In this case, the camera sensor and communications cable connections, and the internal components of any associated lens assembly may be sealed against exposure to liquids present within the conduit 157. Allowing a camera assembly 350, lens assembly, communications cable, mechanical actuators (e.g. pull-wires) and fiberoptic cables or bundles to be exposed to a 'wet' conduit may be feasible if at least a portion of the endoscope 10 is configured to be a single use device, i.e., disposable after use in a medical procedure. Any technical challenges in adequately sterilizing intra-conduit components are thus obviated.

Some components of the endoscope 10, particularly electronic components located within the handle section 12, preferably should be kept dry. A barrier element 159 between the conduit 157 of the insertion section 14 and the interior of the handle 12 may allow passage of components from the handle 12 to the insertion section 14 conduit 157 (represented in FIG. 9 by line segments 155 and referred to as pass-through components), while also inhibiting infiltration of fluid from the conduit 157 into the interior space of the handle 12. The barrier 159 may comprise passageways (holes, slits, etc.) through which pass-through components 155, such as the utility components described supra, may pass from the handle 12 to the conduit 157 of the insertion section 14. The passageways may be formed to provide a relatively tight fit around the outside surface of the pass-through components 155. In some embodiments, elastomeric gaskets, O-rings, or other similar elements may further aid in inhibiting fluid infiltration from the conduit 157 of the insertion section 14 to the interior spaces of the handle 12. The barrier 159 may comprise a wall separating a junction region between the handle 12 and a proximal end of the insertion section 14. The junction region may be near an area where the conduit 157 connects to a conduit port providing an external fluid connection for the conduit 157. The barrier 159 may alternatively comprise a block through which a routing channel connects a utility hole communicating with the conduit 157 on a first side of the block with one or more features (e.g. a conduit port) on a second side of the block opposite the first side of the block, or on a third side of the block (which in some embodiments, may be roughly perpendicular to the first side of the block). Passageways for cables, ribbons, wires, pushrods or other components from the handle 12 may be formed on the second side of the block, opposite the first side of the block and may be aligned with the utility hole of the block. The conduit 157 may be formed from a sheath (such as inner sheath 312 of FIG. 15) connected or attached to the handle 12 of the instrument. In some embodiments, the pass-through barrier 159 between the handle 12 and a sheath of the insertion section 14 may comprise a sheath mount, which serves to support the sheath of the insertion section 14 near its origin proximally at the handle 12, and to attach or connect it to the handle 12. In some embodiments, the insertion section 14 may comprise a cannula within which the sheath may be positioned. The cannula may be mounted to the handle 12 via a disconnect feature, allowing the cannula to remain in situ while the endoscope 10—including handle 12 and sheath—can be withdrawn from a site.

Figure 10:
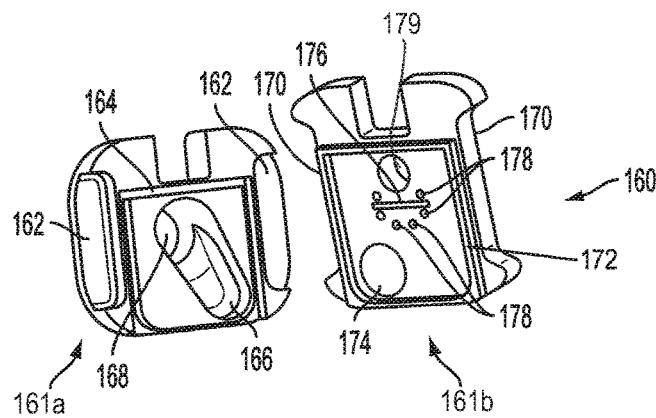
FIG. 10 shows an exploded view of an example of an inner sheath mount serving as a pass-through barrier.

A barrier 159 described in relation to FIG. 9 is shown in FIG. 10 and is referred to as an inner sheath mount 160. As shown, the inner sheath mount 160 includes a distal section 161a and a proximal section 161b, separated in FIG. 10 from one another to reveal the interior of the inner sheath mount 160. As shown the distal section 161a may include notches 162 on each side of the distal section 161a. As shown in the example embodiment in FIG. 10, a portion of an interior face 164 (when assembled) of the distal section 161a may be recessed. An irrigation or suction routing channel 166 may also be recessed into the distal section 161a of the inner sheath mount 160. As shown, the irrigation routing channel 166 is located within the recessed face 164. The irrigation routing channel 166 may be in communication on a first end with a utility hole 168. In the example embodiment, the utility hole 168 may be located substantially near the center of the distal section 161a, within the recessed face 164 (although in other embodiments, the utility hole 168 need not be centered).

The proximal section 161b of the inner sheath mount 160 may also include notches 170 in its right and left sides similar to the notches 162 recessed into distal section 161a. The notches 170 may extend all the way through the proximal section 161b. The notches 162 and 170 of the inner sheath mount 160 may be sized to accept a projection of the handle distal section 30, which may help to hold the inner sheath mount 160 in place when the endoscope 10 is fully assembled.

The proximal section 161b may also include a raised portion 172 of an interior face (when assembled). As shown, the raised portion 172 is of similar outer dimensions as the recessed face 164 in the distal section 161a. When assembled, the raised portion 172 may be pressed into the recessed face 164 to couple the distal section 161a and proximal section 161b together. In some embodiments, glue or another suitable adhesive between the recessed face 164 and raised portion 172 may be used to bind the proximal section 161b to the distal section 161a. This may also serve to create a hydraulic seal between the two components.

The proximal section 161b may include a number of other features. As shown, the proximal section 161b includes an irrigation or suction passage 174. The irrigation or suction passage 174 may be situated to align with a second end of the irrigation routing channel 166 when the proximal section 161b is mated to the distal section 161a. When the endoscope 10 is in use, irrigation or suctioned fluid may flow between the utility hole 168 and irrigation passage 174 via the irrigation routing channel 166.

As shown in the example embodiment in FIG. 10, the proximal section 161b of the inner sheath mount 160 may include a sheath mount slit 176. As shown, the sheath mount slit 176 may be oriented horizontally (orientation refers to that shown in FIG. 10) and located in the proximal section 161b of the inner sheath mount 160, roughly aligned with the utility hole 168. The sheath mount slit 176 may be oriented differently in alternate embodiments. In the example embodiment in FIG. 10, the sheath mount slit 176 extends through the entire proximal section 161b at an angle substantially perpendicular to the plane of the interior face (when assembled) of the proximal section 161b.

The proximal section 161b of the inner sheath mount 160 may also include a number of orifices 178. In the example embodiment in FIG. 10, the orifices 178 are small diameter holes which extend through the entire proximal section 161b, and can be used to allow passage of pull or push cables or wires from within the handle to the distal end of the endoscope 10. The proximal section 161b may also include a fiber optics passageway 179. In the example embodiment, the orifices 178 and fiber optics passageway 179 are angled perpendicular to the interior face (when assembled) of the proximal section 161b. In alternate embodiments, the orifices 178 and fiber optics passageway 179 may be angled differently or may have a different diameter. As shown, the orifices 178 are arranged around the sheath mount slit 176. When the inner sheath mount 160 is fully assembled, the sheath mount slit 176 and orifices 178 are aligned with the utility hole 168 of the distal section 161a.

In alternative embodiments, the shape, location, dimensions, etc. of some features of a pass-through barrier or inner sheath mount 160 may differ. A pass-through barrier or inner sheath mount 160 may include additional features or may omit certain features. In some embodiments, there may be a larger or smaller number of orifices 178. In some embodiments, the orifices 178 may not be arranged in the spatial arrangement shown in FIG. 10. There may be more than one irrigation passage 174. In some embodiments, the inner sheath mount 160 may be associated with or include a gasket to further inhibit fluid infiltration into sensitive areas within the handle of the endoscope.

The handle electronics section 80 is configured to enclosed mechanical and electronic components that are preferably protected against fluid infiltration. The handle distal external section 82 (the pivot control housing), configured to house the pivot control structures and actuation cables for controlling movement of a camera assembly in the distal end of the endoscope shaft or insertion shaft, may be exposed to liquid with relatively minimal effect on the operation of the endoscope. Therefore, it is more important to maintain a liquid seal between the handle electronics section 80 and the handle distal external section 82. A pass-through barrier such as sealing member 210, shown in FIGS. 12 and 13 may be constructed to provide a tight seal (e.g. elastomeric seal) around an electronic flex cable, an optical fiber bundle, or other structures that must pass from the distal end of the endoscope to its proximal end before exiting. On the other hand, a pass-through barrier such as inner sheath mount 160, shown in FIGS. 10 and 13, may allow for a lesser seal, particularly as it may apply to any pull wires or cables that pass from the pivot control structure to the distal end of the endoscope shaft. Any fluid infiltration into the handle distal section 82 may be allowed to exit the housing through one or more drain holes or passages built into a dependent part of the housing, such as for example, passage 108 shown in FIG. 7.

In an alternate embodiment, a pass-through barrier between the handle distal section or pivot control housing 82 and the shaft of the endoscope may comprise a fully sealed structure that yet permits movement of the pull cables or actuation cables that extend from the pivot control housing to the distal end of the endoscope shaft. For example, the pass-through barrier may comprise a flexible (or floppy) diaphragm, a pleated elastomeric diaphragm, accordion-structured rubber boot, bellows structure, or otherwise displaceable diaphragm that is attached at its periphery to the housing, that forms a fluid-tight seal around any structures passing through it near its central region, and whose central region may freely move back and forth distally and proximally to permit free movement of any pivot control cables passing therethrough. With a more complete seal at this portion of the endoscope, the need for a secondary seal between the pivot control housing and the handle electronics section 80 may be reduced or eliminated.

Figure 11:
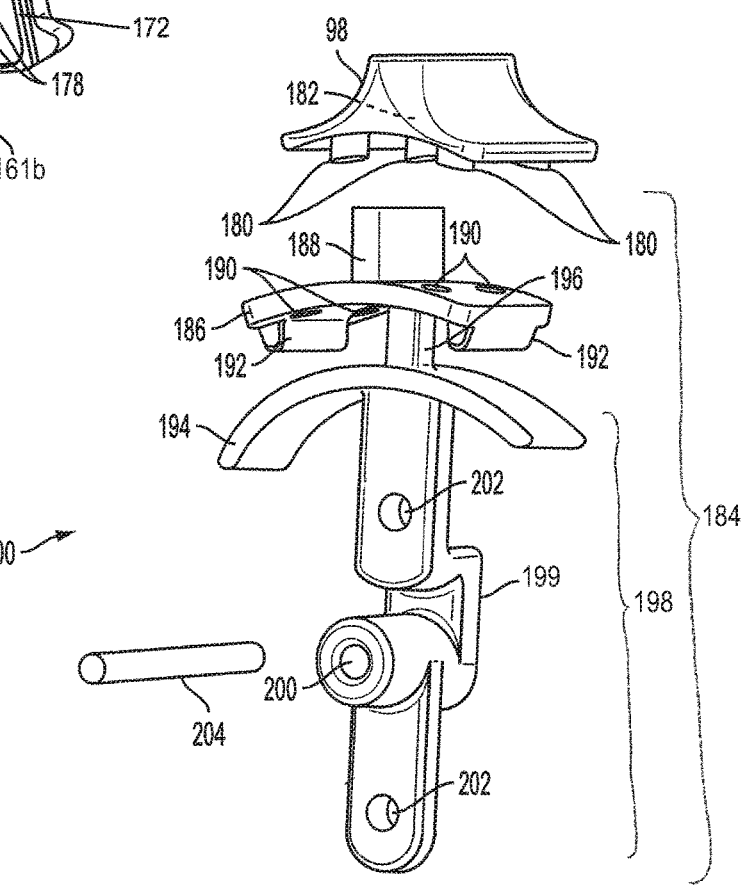
FIG. 11 shows an exploded view of an example of a pivot control structure.

FIG. 11 shows an example exploded view of an embodiment of a pivot control structure 100. The pivot control structure 100 may control pivoting of a structure. The structure may for example be a camera assembly 350 (see FIG. 19) at a distal end of the insertion section 14 (see FIG. 3). In alternate embodiments, the pivot control structure 100 may be used to instead or additionally control the flexing of a flexible section of the insertion section 14. Some embodiments of the pivot control structure 100 may include gearing, a motor, multi-bar linkage, dials, etc. that differ from the embodiment disclosed below.

The example pivot control structure 100 in FIG. 11 is shown in an exploded view. The finger contact 98 detailed above is shown separated from the pivot control structure 100. As shown, the bottom face of the finger contact 98 optionally may include a number of peg projections 180. In the example embodiment shown in FIG. 11, there are four peg projections 180 which are generally cylindrical in shape (number and shape of peg projections may differ). The finger contact 98 additionally includes a finger contact slot 182 situated in the under-surface of the finger contact 98.

Below the finger contact 98, an example embodiment of a pivoting portion 184 of the pivot control structure 100 is shown. The top of the pivoting member 184 of the pivot control structure 100 may include a slider 186. Projecting from the center of the slider 186 is a finger contact post 188 arranged to mate with finger contact slot 182. Optionally, finger contact peg holes 190 flank the finger contact post 188 on each side of the finger contact post 188. When the finger contact 98 is attached to the pivot control structure 100 the finger contact slot 182 may be slid onto the finger contact post 188 on the slider 186. Additionally, when assembled, the peg projections 180 of the finger contact 98, if present, may be seated in the finger contact peg holes 190 of the slider 186.

A pivot control structure 100 may interact with one or more feature of the endoscope allowing it to be locked or held in a desired orientation. As shown, the bottom face of the slider 186 of the pivoting member 184 optionally may include one or more catch bars or detent elements 192. In other embodiments, multiple catch bars 192 may be disposed along the bottom of the slider 186, arranged to engage with opposing raised features or ridges 94 on the handle 12.

The catch bars or detent elements 192 may interact with the raised features or ridges 94 of the slide button recess 92 of the handle raised portion 32 described above (best shown in FIG. 6). As the pivot control structure 100 is displaced by the user, the spaces between ridges 94 may act as detents in which the catch bars 192 of the slider 186 may be "parked". This helps to prevent drifting or movement of the pivot control structure 100 once a user moves it to a desired position and releases it. It may also help to ensure that the pivot control structure 100 is not accidentally displaced during use of the instrument.

As shown, the pivoting member 184 of the pivot control structure 100 includes a curved inner shield 194. The inner shield 194 is tiered below the slider 186, and under the handle housing when assembled. A post 196 may span the distance between the top face of the inner shield 194 and the bottom face of the slider 186. In some embodiments, the catch bars 192 may be located on the top of the inner shield 194. In such embodiments, the ridges 94 described above may be located on the interior wall of the housing of the handle distal section 30 such that the ridges 94 may form detents for the catch bars 192 on the inner shield 194. As described above, this allows the pivot control structure 100 to be "parked" in a desired position.

Extending from the bottom face of the inner shield 194 may be a pivot arm 198. In the example embodiment, the pivot arm 198 includes two mechanical cable attachment points or holes 202. One hole 202 is situated on one side of a pivoting shaft 204, while the second hole 202 is situated on the other side of pivoting shaft 204. In the illustrated embodiment, forward movement of slider 186 causes a mechanical cable connected to the lower hole 202 to be retracted proximally, while aft movement of slider 186 causes a mechanical cable connected to the upper hole 202 to be retracted proximally. In order to accommodate a relatively unimpeded passage of a fiberoptic or electrical cable from the proximal end of the handle to the distal end of the handle, the pivot arm 198 may be, for example, notched over its pivot shaft 204, so that a passing cable may rest freely on the pivot shaft 204 (or a concentric sleeve or hub surrounding the shaft 204). Such an arrangement would allow passage with minimal displacement laterally or vertically.

Figure 13:
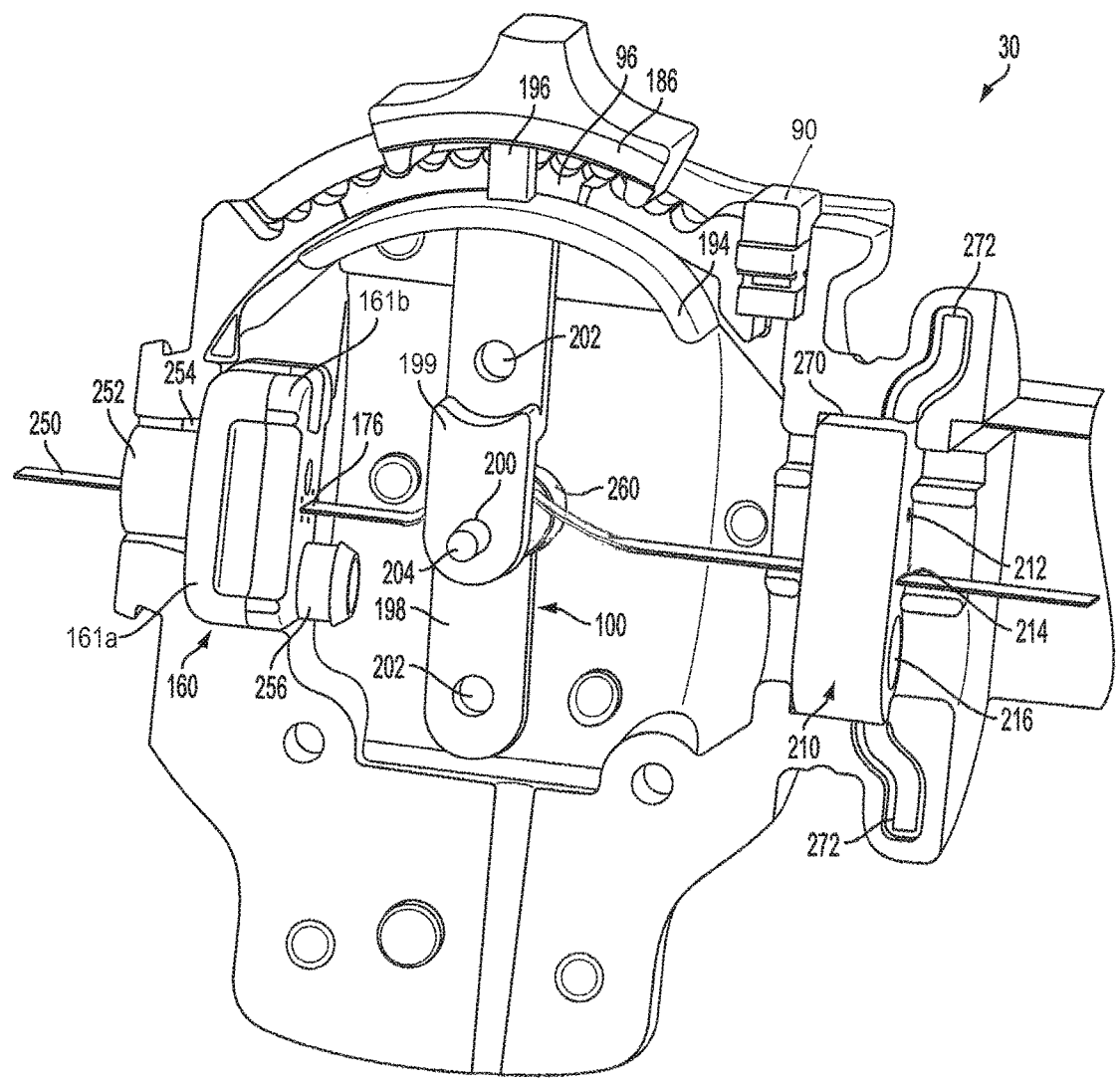
FIG. 13 shows a partially assembled view of an exemplary endoscope with an example of an inner sheath mount, pivot control structure, and sealing member in their assembled locations.

Referring now to both FIGS. 11 and 13, the pivot arm 198 is constructed to have a laterally displaced section 199 encompassing pivoting region 200 and pivot shaft 204. Thus a hub or sleeve encompassing pivot shaft 204 (when assembled) is shown to serve as a bearing surface upon which a passing cable 250 may rest. A lower portion of pivot arm 198 extends downward from a location beneath the hub or sleeve of pivot shaft 204. In some embodiments, the lower portion of pivot arm 198 optionally may be vertically aligned with the upper portion of pivot arm 198, so that mechanical cables connected to points or holes 202 are also aligned vertically. In other embodiments, one or more cables (e.g., cable 250) may travel around (or through) a hub of pivot shaft 204 in a variety of other ways, so that its path is minimally obstructed by the pivot arm 198 of the pivot control structure 100.

Optionally, but in a preferred embodiment, a secondary pass-through seal provides an additional barrier between fluid that may infiltrate into the housing of the handle distal section 30 and the housing of handle proximal section 16, in which electronics section 80 may be housed. The seal may include orifices, holes or slits through which components such as though not limited to, fiberoptic bundle, electronic cable and/or fluid conduit tubing may pass. The holes or slits may be sized to provide a snug fit over these components as they pass through the seal. In an embodiment, the secondary pass-through seal is formed from a rubber or other elastomeric material to enhance its fluid sealing characteristics.

Figure 12:
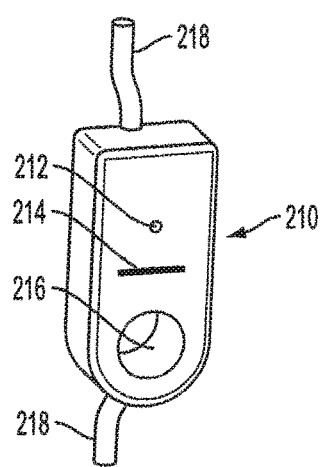
FIG. 12 shows a perspective view of an example of a sealing member.

FIG. 12 shows an example embodiment of a secondary seal, i.e. sealing member 210. The sealing member 210 may be roughly rectangular in shape as shown in FIG. 12. As shown in FIG. 12, one end of sealing member 210 may be of a first (e.g. a rectangular) shape, while a second end of sealing member 210 may be of a second shape (e.g. have rounded edges or be rounded). This may provide an advantage during assembly to ensure that the sealing member 210 is mounted in the proper orientation. The sealing member 210 may include a number of orifices. In the example embodiment, the sealing member 210 includes a fiberoptic bundle (e.g., an illumination fiber) orifice 212, a flex cable (i.e., electronic cable) orifice 214, and a fluid tubing (e.g., an irrigation line) orifice 216. In the example embodiment shown in FIG. 12 the illumination fiber orifice 212, flex cable orifice 214, and irrigation line orifice 216 extend through the entire sealing member 210. The illumination fiber orifice 212 has a relatively small diameter to match the diameter of a fiber bundle or light pipe. The flex cable orifice 214 is a slit, matching the size and shape of an electronic flex cable. The irrigation line orifice 216 is cylindrical and has a diameter larger than that of the illumination fiber orifice 212. The illumination fiber orifice 212, flex cable orifice 214, and irrigation line orifice 216 extend through the sealing member 210 at an angle that is substantially perpendicular to the front face (relative to FIG. 12) of the sealing member 210. In alternative embodiments, the orifices in the sealing member 210 may differ in number, size or shape. In some embodiments, the sealing member 210 may include an additional hole for wiring to the button 90, for example.

As shown in the example embodiment in FIG. 12, the sealing member 210 may also include a number of gasketing arms 218. In the example embodiment in FIG. 12, the gasketing arms 218 project away from the top and bottom faces of the sealing member 210 near the back edge of the sealing member 210. As shown, there may be two gasketing arms 218. In some embodiments, the gasketing arms 218 may be straight. In the example embodiment, the gasketing arms 218 include two straight sections connected by an arcuate section which bends the gasketing arms 218 away from the sealing member 210.

FIG. 13 shows an example embodiment of one half (30*a*) of the handle distal section 30. As shown, the inner sheath mount 160, pivot control structure 100 and the sealing member 210 are assembled and placed within the shown half (30*a*) of the handle distal section 30. A flex cable 250 (e.g., flexible electronic communications/power cable) is also shown. In the example embodiment shown in FIG. 13, the distal section 161*a* of the inner sheath mount 160 includes a sheath mounting hub 252. The sheath mounting hub 252 extends distally along the same axis as the utility hole 168 (see FIG. 10). In the example embodiment, the sheath mounting hub 252 may be hollow and substantially cylindrical. The inner diameter of the sheath mounting hub 252 optionally may be approximately equal to or somewhat larger than the diameter of the utility hole 168. In the example embodiment, a sheath mount mounting tab 254 projects superiorly from the outer surface of the sheath mounting hub 252. The sheath mount mounting tab 254 is located next to the face of the insertion side piece 160a from which the sheath mounting hub 252 projects. The mounting tab 254 may serve to properly orient a sheath (e.g. inner sheath 312 shown in FIG. 15) as it is mounted onto the sheath mounting hub 252, and optionally may also serve as a locking member to secure a sheath to the sheath mounting hub 252 and sheath mount 160.

In other embodiments, the sheath mount tab 254 may be disposed on the inside surface of the sheath mount hub 252. This may be desirable because it obviates the need to nest the inner sheath mount hub 252 inside of a sheath removing a restriction in the diameter of the conduit of the sheath. Consequentially, a higher flow rate through such a conduit may be achieved. Alternatively, a sheath mount nub 254 may not be included in some embodiments. The sheath may instead be oriented and secured to a sheath mount hub 252 in any suitable fixture (not shown).

As shown the flex cable 250 extends through the inner sheath mount 160. The flex cable 250 passes through the sheath mounting hub 252 into the distal section 161a of the inner sheath mount 160. The flex cable 250 is also routed through the sheath mount slit 176 of the proximal section 161b.

The proximal section 161b of the inner sheath mount 160 includes a fluid conduit attachment site or port 256. The fluid conduit attachment site 256 may be a hollow, roughly cylindrical projection which extends toward the right of the page (in relation to FIG. 13) from the proximal section 161b of the inner sheath mount 160. Tubing of an irrigation line 434 (see FIG. 85) may be slid over the outer surface of the fluid conduit port 256, which optionally may be barbed to aid in retaining an installed section of tubing. As shown, the right edge of the fluid conduit port 256 may be chamfered in a manner to also facilitate ease of installation of a tubing segment to the port 256. Additionally, as shown in FIG. 13, the proximal end of the fluid conduit port 256 tapers to a slightly larger diameter than the rest of the port 256 surface. This may act as a barb and help ensure that once attached, the tubing of an irrigation line 434 (see FIG. 85) is not easily dislodged. In an alternative embodiment, the conduit port 256 may extend and be fitted into an irrigation line orifice 216 of a sealing member 210. The barbed portion/attachment site for an irrigation line 434 may then be placed on the sealing member 210.

The pivot control structure 100 may be pivotally coupled into the handle distal section 30 as shown in FIG. 13. As shown, the pivot shaft 204 extends through the pivot shaft hole 200 in the pivot arm 198 of the pivot control structure 100. The end of the pivot shaft 204 (or of a surrounding hub) inserted into the far wall of the handle distal section 30 may be seated in a pivot bearing 260 projecting from the inner wall of the handle distal section 30. When fully assembled, the opposite end of the pivot shaft 204 may similarly be seated in a pivot bearing 260 projecting from the inner wall of the other half (30b) of the handle distal section 30.

As shown in FIG. 13, the slider 186 and inner shield 194 of the pivot control structure 100 may be offset from each other by the post 196 a distance slightly larger than the thickness of the walls of the handle distal section 30. The post 196 may extend through the pivot control structure notch 96 described above. The curvature of the slider 186 and inner shield 194 may be selected such that the slider 186 and inner shield 194 may freely move fore and aft with input from a user without interfering with the walls of the handle distal section 30 housing. The length of the pivot control structure notch 96 may determine the amount of pivotal displacement a user may create with input to the pivot control structure 100.

In some embodiments, the walls of pivot control structure notch 96 may exert a frictional force against the post 196. In such embodiments, this frictional force may allow the pivot control structure 100 to be "parked" in a position. In such embodiments, the walls of the pivot control structure notch 96 may be made of a high friction material such as rubber or other elastomeric material. In such embodiments, the pivot control structure 100 may not need to include the catch bars 192 or the ridges 94 described above.

The endoscope 10 may also include mechanical pivot actuators in the form of pull cables or wires, belts, or pushrods. An actuator may be any elongate member, solid, braided, or otherwise extending from the handle of the endoscope 10 to a movable element at the distal end of the insertion section. The elongate member may be flexible or substantially rigid. The elongate member may be round (as in the example of a cable), ovoid, relatively flat, or may have any other shape or cross section. In some embodiments, the actuator may be a belt.

In an endoscope having a pannable camera or camera mount at or near the distal end of the insertion section, the pannable camera or camera mount may be rotated using pull wires or pushrods. In a pull wire embodiment, panning cables may be attached or connected to, or looped through the cable attachment holes 202. In some embodiments, two panning cables may be attached to each cable attachment hole 202. In a preferred embodiment both ends of a single panning cable are attached to each cable attachment hole 202 creating a loop. Alternatively, a single cable may be looped through the cable attachment hole 202 at about its midpoint, the ends of the cable then being connected distally to the rotatable camera or camera mount. The panning cables may extend from the cable attachment holes 202 in the pivot arm 198 and be routed through one or more orifices 178 in the proximal section 160b of the inner sheath mount 160. The panning cables may then extend through the utility hole 168 and through the conduit formed by the inner sheath, optionally alongside the length of an electronic flex cable 250 and/or fiberoptic bundle. By pivoting the pivot control structure 100, the panning cable or cables connected to one of the cable attachment holes 202 will be pulled, while the cable(s) connected to the other attachment hole 202 will slacken. By attaching the panning cable or cables associated with one cable attachment hole 202 to one side of a pivot point and attaching the panning cable or cables associated with the other cable attachment hole 202 to the opposite side of the pivot point, the pivot control structure 100 may be used to selectively rotate a pivoting object distally in the insertion section of the endoscope. In other embodiments, a similar cabling mechanism may be used to actively flex a flexible distal segment of the insertion section.

In some embodiments, the pivot arm 198 of the pivot control structure 100 may be pivoted via gearing. In such embodiments, the finger contact 98, finger contact post 188 (see FIG. 11), slider 186, vertical post 196, and inner shield 194 may not be necessary. At least a portion of a user input gear contained in the handle distal section 30 may project out of the handle raised section 34. The user input gear may be rotated about a pivot axis disposed within the handle distal section 30. This rotation may be user-initiated via, for example, a user's finger or thumb. The user input gear may mesh with a pivot shaft gear disposed about the pivot shaft 204 for the pivot arm 198 of the pivot control structure 100. In such embodiments, as the user input gear is rotated, the pivot shaft gear and pivot arm 198 are also caused to rotate, acting on the pivot actuators (e.g. panning, actuating or pull cables) as described above. In some embodiments, there may be an intermediary gear or any number of intermediary gears between the user input gear and the pivot shaft gear to provide any desired gear reduction to meet precision-of-movement and ergonomic requirements.

In other embodiments, the pivot arm 198 may be caused to rotate via an electric motor (e.g., brushless motor, stepper motor, etc.). Rotation via the motor may be controlled by one or more user input means such as a button 90. In embodiments including at least one button 90, the button 90 or buttons 90 may control the speed and direction of movement of the pivot arm 198.

In some embodiments, the pivot shaft 204 may project to the outside of the handle distal section 30. In such embodiments, the pivot shaft 204 (or an overlying hub or sleeve) may be directly rotated by the user. In some embodiments, the portion of the pivot shaft 204 projecting out of the handle distal section 30 may include a knob, dial, crank, etc. so that a user may easily rotate the pivot shaft 204 by grasping and rotating the knob, dial, crank, etc.

As shown in FIG. 13, the sealing member 210 is positioned in a gasket recess 270. The gasket recess 270 may include gasketing arm recesses 272. Various components may pass through the sealing member 210 as mentioned above. As shown, a flex cable 250, connected to a printed circuit board 430a (see, for example, FIG. 85) in the electronics section 80 housed in the handle proximal section 16 may pass through the flex cable orifice 214 of the sealing member 210 and extend beyond the sealing member 210 through the housing of the handle distal section 30 and sheath mount 160, ultimately to travel distally in the insertion section of the endoscope. The irrigation line 434 (see FIG. 85) and fiberoptic bundle (e.g., illumination fibers 364, see FIG. 85) may pass through their respective irrigation line orifice 216 and fiberoptic bundle orifice 212 and extend through the housing of the handle distal section 30 similar to the flex cable 250.

Only one half of the gasket recess 270 is shown in FIG. 13. The other half of the gasket recess 270 may be located on the other, not shown half (30b, see FIG. 7, for example) of the handle distal section 30. When fully assembled, the sealing member 210 is captured between the two halves of the gasket recesses 270. When fully assembled the sealing member 210 may ensure that fluid which may be present in the handle distal section 30 may be inhibited from infiltrating into the handle proximal section 16, which contains electronics components comprising electronics section 80. The sealing member 210 may be made of suitably compliant (e.g., elastomeric) material or other suitable gasketing material and may be pressed into the gasket recesses 270 to ensure a tight seal. In some embodiments, the sealing member 210 may be held in place using an adhesive.

Figure 14:
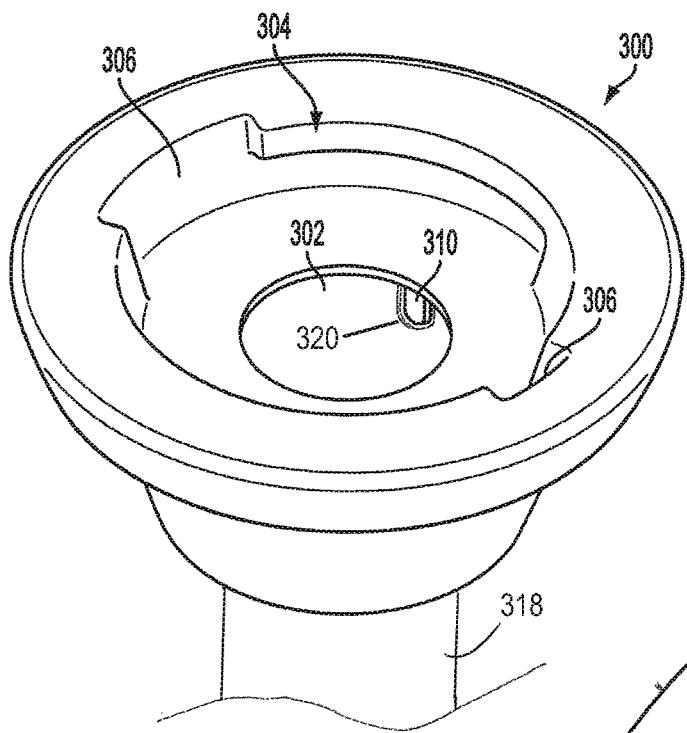
FIG. 14 shows a perspective view of an outer sheath mount.

FIG. 14 shows an example embodiment of an outer sheath or cannula mount 300. An outer sheath or cannula 318 may be employed to provide additional protection to components in the distal end of the insertion section, or to allow a user to withdraw the insertion section of the endoscope while leaving the cannula 318 in situ, to allow later re-insertion of an insertion section of the endoscope. As shown, the cannula mount 300 may have a frustoconical shape, with the larger diameter section proximally forming a connector (e.g. bayonet mount) for the mounting of a cannula 318 over an inner sheath 312 (see, for example, FIG. 15). A cannula mount hole 302 may extend through the cannula mount 300 to merge with a cannula channel. The cannula or outer sheath mount hole 302 may be configured to accept and retain a cannula 318. The cannula 318 may be configured to act as a sleeve over an inner sheath 312 of the insertion section.

As shown, the female bayonet mount portion 304 includes two slots 306. The slots 306 optionally may have different dimensions to ensure proper orientation of the cannula 318 with respect to a mating (male) connector on a distal portion of the handle distal section 30. In some embodiments, the slots 306 of the female bayonet mount portion 304 may include a serif into which the male bayonet mount portion 308 may be spring loaded using, for example, a Belleville washer. In such embodiments, a spring-loaded connection may help ensure the two pieces (cannula 318 and handle distal section 30) are more securely locked together.

In some embodiments, an alignment feature may be included on the cannula mount 300 in order to properly orient the cannula 318 with the cannula mount 300 during assembly, and ultimately with the inner sheath 312 (see, for example, FIG. 15) when installed over the inner sheath 312 of the insertion section. In the example embodiment in FIG. 10, an outer sheath mount tab 310 may project from the inner wall of the outer sheath mount hole 302. The outer sheath mount tab 310 may extend from a distal face of the female bayonet mount portion 304, which may then be used to align the bayonet mount 300 with a cannula 318 having a mating slot during assembly. Alternatively, the need for such a feature may be removed by coupling the outer sheath or cannula 318 and cannula mount 300 in a suitable fixture.

Figure 15:
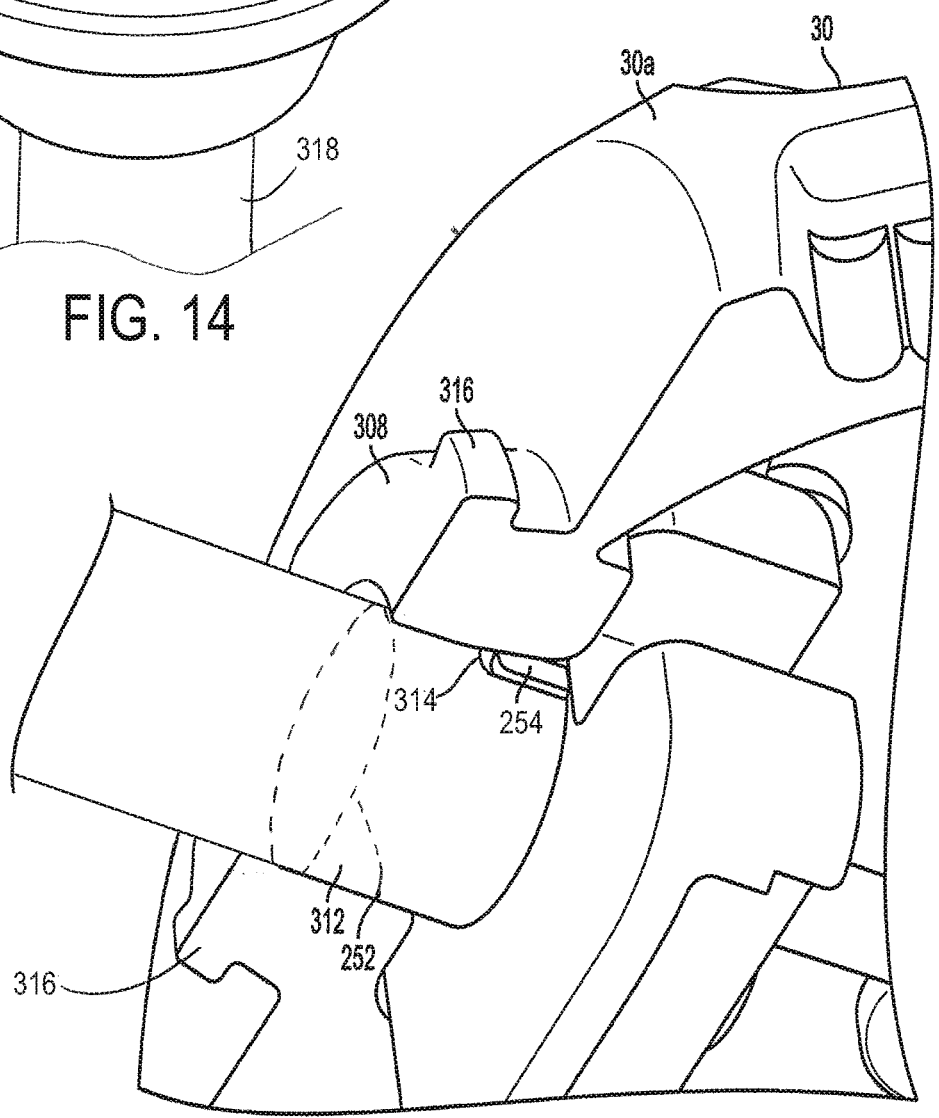
FIG. 15 shows a close up partial view of an endoscope in which an inner sheath mount, inner sheath, and outer sheath are in their assembled locations.

FIG. 15 shows a partial cutaway view of an example embodiment of the distal face of the handle distal section 30. An inner sheath 312 is mounted on the sheath mounting hub 252 of the inner sheath mount 160. The inner sheath 312 includes a sheath mount notch 314. The inner sheath mount notch 314 may be dimensioned to accept the sheath mounting tab 254 on the sheath mounting hub 252. In such embodiments, the sheath mounting tab 254 and inner sheath mount notch 314 may ensure that the inner sheath 312 is correctly oriented on the endoscope 10.

The inner sheath 312 (and/or the outer sheath or cannula 318, see FIG. 14) may be formed from steel, any of a number of hardened plastics or other rigid, durable material. Alternatively, the inner sheath 312 or a portion thereof may be flexible, allowing the insertion section of the endoscope to bend as needed for insertion into a non-line-of-site target area. In these embodiments, a user may forgo the use of an outer sheath or cannula 318, or the cannula 318 itself may also be constructed of a similarly flexible material.

The male bayonet mount portion 308 is also visible in the example embodiment shown in FIG. 15. The male bayonet mount portion 308 may include two prongs 316. The prongs 316 may be sized to fit in the legs of the L-shape slots 306 of the female bayonet mount portion 304 referring now also to FIG. 14. The outer sheath 318 and cannula mount 300 may be coupled to the handle distal section 30 by aligning the prongs 316 with the slots 306, pressing the bayonet mount over prongs 316, and then turning the bayonet mount to lock it into position. As shown, optionally the two prongs 316 are dimensioned differently such that the outer sheath mount 300 may only have one possible orientation when coupled onto the handle distal section 30.

Still referring now to both FIGS. 14-15, an outer sheath or cannula 318 may be slid over the inner sheath 312, forming a sleeve. The inner diameter of the outer sheath 318 may be only slightly larger than the outer diameter of the inner sheath 312 to ensure a snug fit. The outer sheath 318 may include an outer sheath notch 320. The outer sheath notch 320 may be dimensioned to accept the outer sheath mount tab 310 when the endoscope 10 is fully assembled. In some embodiments, the outer sheath 318 may be friction fit, glued or otherwise fused or attached to the wall surrounding the outer sheath mount hole 302. The outer sheath mount tab 310 may help to ensure correct orientation of the outer sheath 318 when the endoscope 10 is fully assembled.

When the insertion section 14 (see FIG. 3) of the endoscope 10 is inserted into a target region, the outer sheath 318 and outer sheath mount 300 may be uncoupled from the rest of the endoscope 10 as mentioned above. This may allow the outer sheath 318 to be used as a cannula, remaining in situ to permit the endoscope 10 to be re-introduced into the target region. If desired, the outer sheath or cannula 318 may be used as a conduit through which other instruments may be introduced into the target region. The outer sheath 318 may also function as a conduit through which fluid may be introduced or withdrawn from the target region.

Figure 16:
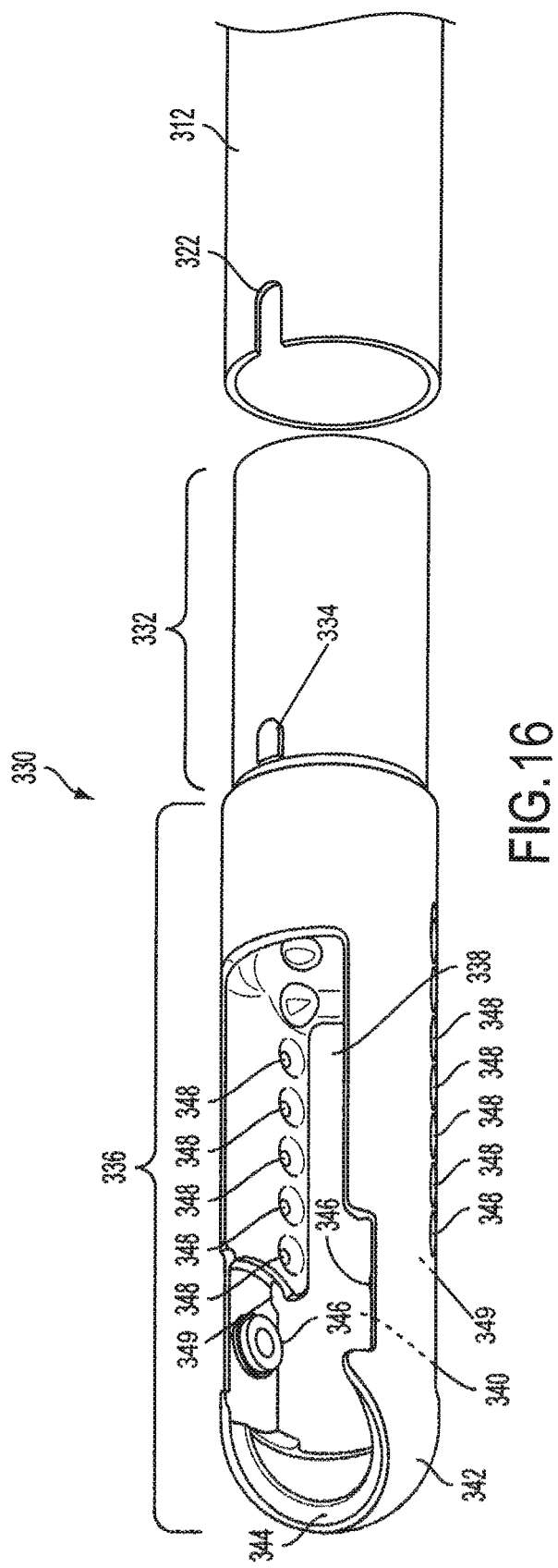
FIG. 16 shows an example of a camera assembly mount separated from an inner sheath.

A camera assembly housing 330 or distal working section is shown in FIG. 16, separated from a distal end of an inner sheath 312. In this embodiment, the distal working section of an insertion section of an endoscope may be constructed separately from the inner sheath 312, and subsequently mated to a distal end of the inner sheath 312 during assembly. In other embodiments the inner sheath 312 may be constructed as a single piece, incorporating a distal working section. In embodiments where the distal working section is constructed separately, the distal working section may be made from a material different from that of the inner sheath 312. Additionally, it may be constructed from a number of assembled parts.

In the example embodiment in FIG. 16, the distal edge of the inner sheath 312 includes an inner sheath distal notch 322. The camera assembly housing 330 may include a nested segment 332, shaped and having an outer diameter suitable for insertion into the distal end of inner sheath 312 during assembly of the endoscope 10. The nested segment 332 may include a nested segment tab 334 or other alignment feature. The nested segment tab 334 may be dimensioned so that it may be mated to the inner sheath distal notch 322 when the endoscope 10 is assembled. The nested segment tab 334 and inner sheath distal notch 322 may help ensure that the camera assembly housing 330 is properly oriented and aligned when the endoscope 10 is assembled.

The camera assembly housing 330 may additionally include a working segment 336. As shown, the working segment 336 in FIG. 16 may include a top void 338 with or without a bottom void 340. The top void 338 and bottom void 340 may extend along most of the working segment 336 of the camera assembly mount 330. A rounded tip 342 may be included at the distal end of the working segment 336 of the camera assembly mount 330. As shown, the rounded tip 342 may optionally include an embrasured opening 344. The edges of the embrasured opening 344 may be beveled, chamfered or rounded. In the example embodiment, the embrasured opening 344 is continuous with the top void 338. In some embodiments, the top void 338 and bottom void 340 may be similarly embrasured.

A rounded tip 342, such as the rounded tip 342 shown in FIG. 16 may provide a number of benefits. A rounded tip 342 may facilitate the insertion of the insertion section 14 into a target region of a patient. In some cases, this may eliminate the need for a trocar. In arthroscopic applications, the contours of the rounded tip 342 allow the endoscope 10 to be maneuvered into tight spaces within a joint. A rounded tip 342 additionally may allow a surgeon to exert pressure atraumatically on tissues within a target region. The rounded tip 342 may also serve as a guard feature for a camera assembly 350.

As shown in FIG. 16, the interior walls of the working segment 336 of the camera assembly housing 330 include two camera mount pivot bearings 346. In the example embodiment shown in FIG. 16, the camera pivot bearings 346 project substantially perpendicularly from the inner side walls of the camera assembly mount 330. The camera assembly housing 330 may be made of steel, any number of hardened plastics, or any other suitably strong, rigid material.

In the example embodiment shown in FIG. 16, the interior walls of the working segment 336 of the camera assembly housing 330 include a number of cable guide holes 348. In a preferred embodiment, there may only be two cable guide holes 348. One cable guide hole 348 may be located on one side wall while another cable guide hole 348 may be located on an opposing side wall. Preferably, the cable guide holes 348 may be disposed below the camera mount pivot bearings 346, so that the distal end of a control cable may form an angle with respect to a camera, camera mount, or camera assembly 350 (see, for example, FIG. 23) to which it is connected. The camera assembly housing 330 may also include one or a number of constraining features. In the example embodiment shown in FIG. 16, there are two restraining notches 349. One restraining notch 349 is located on one side wall and the other restraining notch 349 is located on an opposing side wall. As shown in FIG. 16, the restraining notches 349 are roughly in line with the cable guide holes 348. The cable guide holes 348 and restraining notches 349 will be described further below.

Figure 17:
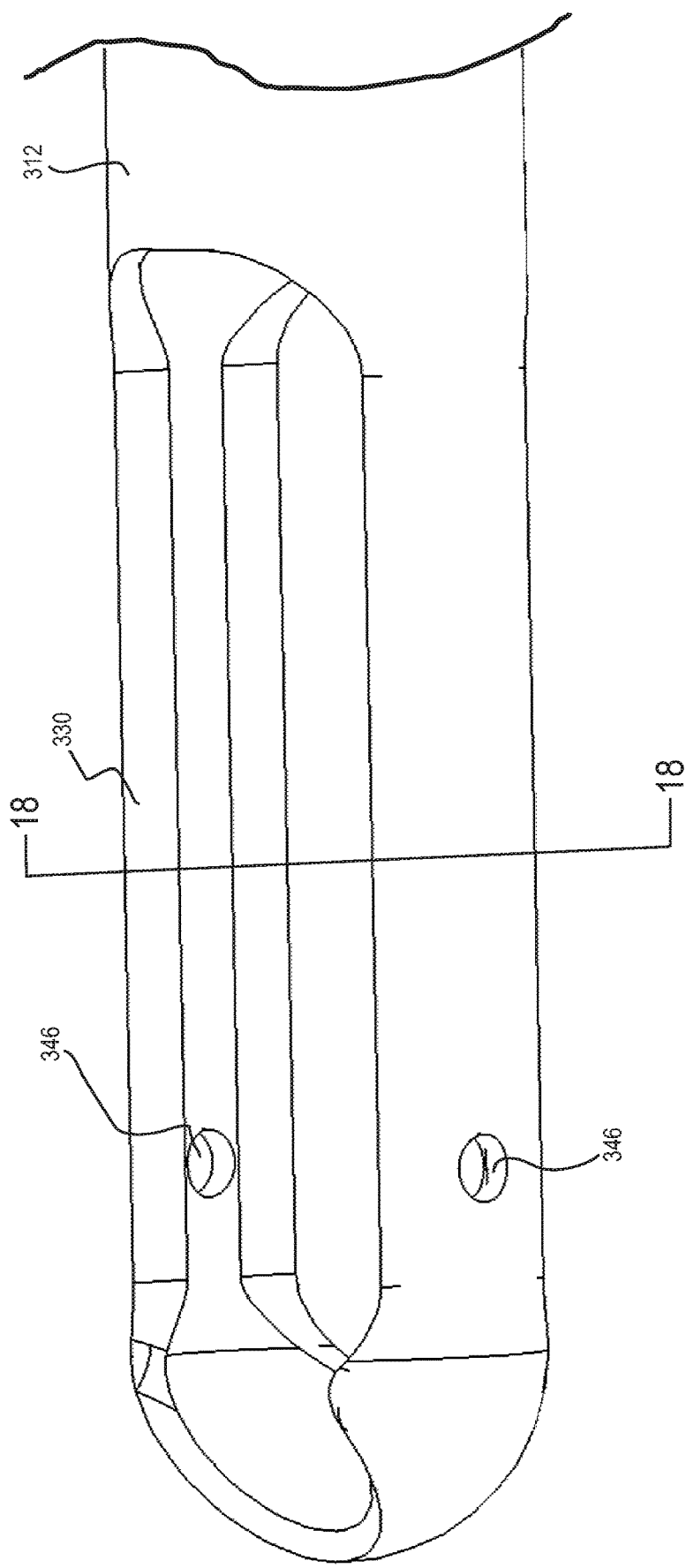
FIG. 17 shows an alternate example of a camera assembly mount as part of an inner sheath.

FIG. 17 depicts an embodiment of a distal working section or camera assembly housing 330 and inner sheath 312 which are constructed as a single part. Referring also to FIG. 18C, a cross section taken at line 18-18 of the camera assembly housing 330 is shown. In embodiments where the distal working section or camera assembly housing 330 and the inner sheath 312 are constructed as a single part, they may be made from steel. In such instances the tip shape of the inner sheath 312 and camera assembly housing 330 may be created via a rolling process. Various voids, openings, and other features, for example those described above, may then be post machined into the part. In the example embodiment in FIG. 17, the camera assembly housing 330 includes only the camera mount pivot bearings 346.

It may be advantageous to create the inner sheath 312 and the camera assembly housing 330 as a single part. Among the advantages, the part may be stronger. Another advantage is that the need for a nested portion is removed. Consequently, a "choke point" in cross-sectional area at the junction of the inner sheath 312 and camera assembly housing 330 is removed. This may provide a number of benefits. Removing such a choke point allows more room for various components, such as utility components within the inner sheath 312 and camera assembly housing 330. Moreover, removal of such a choke point allows for increased flow of irrigation fluid within the inner sheath 312 and camera assembly housing 330. Alternatively or additionally, the overall diameter of the inner sheath 312 and camera assembly housing 330 may be decreased. The inner sheath 312 and camera assembly housing 330 may also be thickened. This helps to strengthen the part. Since thickening will strengthen the part, it may also allow an outer sheath or cannula 318 to be made thinner. A thinner outer sheath or cannula 318 in turn may allow for a larger diameter inner sheath 312 and camera assembly housing 330. That is, without increasing the overall diameter of an insertion section 14 (comprised of an outer sheath 318, inner sheath 312 and camera assembly housing 330), the cross-sectional area of a conduit within the insertion section 14 may be made larger. Thickening furthermore enables the camera mount pivot bearings 346 to have a larger bearing surface allowing pressure exerted against the bearing to be spread over a larger area.

Figure 19:
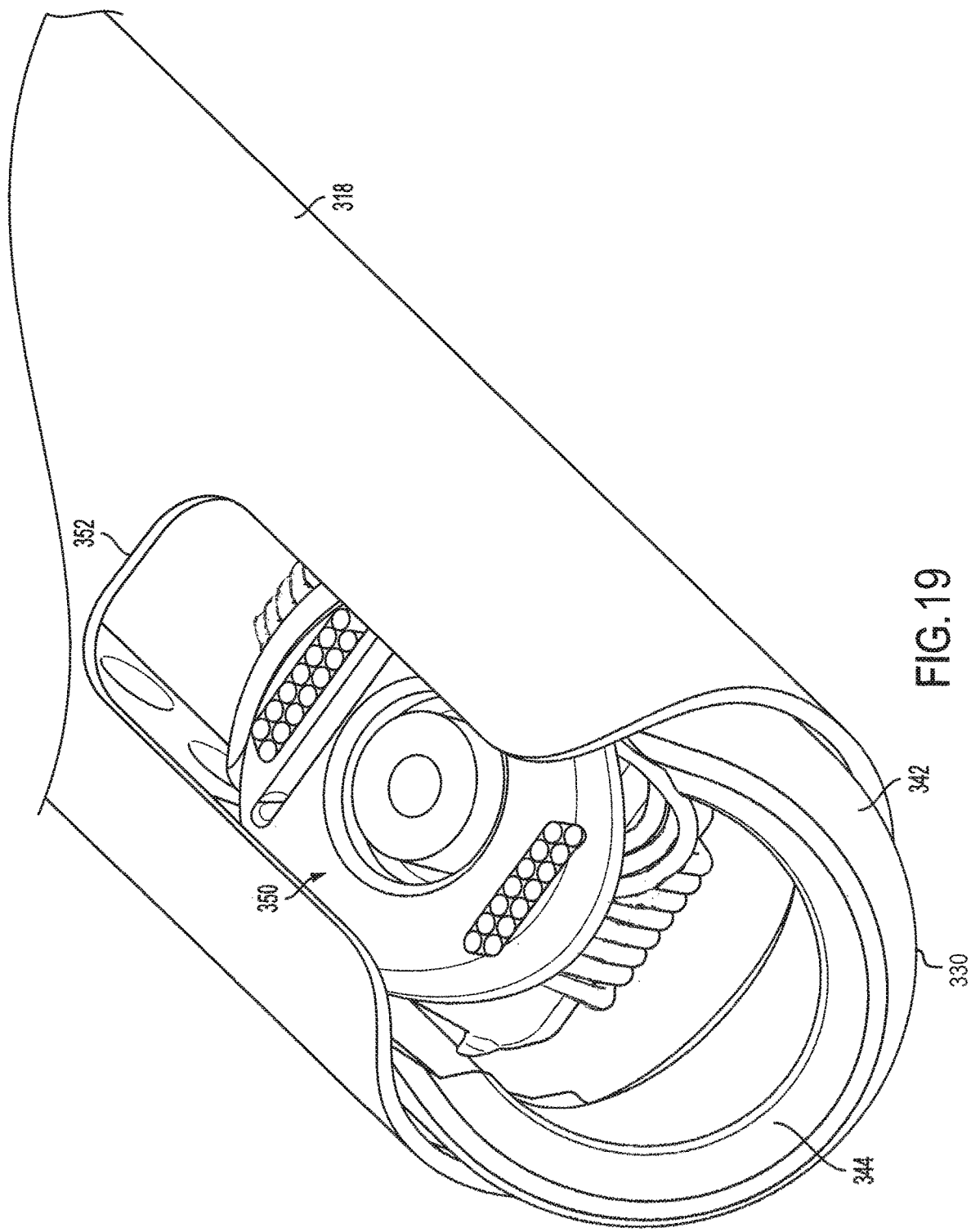
FIG. 19 shows an example of a camera assembly, part of an outer sheath, and part of a camera assembly mount.

FIG. 19 shows an assembled view of the tip of the insertion section 14 (best shown in FIG. 3). The camera assembly housing 330, camera assembly 350, and outer sheath or cannula 318 are visible in FIG. 19. As shown, the rounded tip 342 of the camera assembly housing 330 projects past the distal end of the outer sheath or cannula 318. A viewing notch 352 is recessed into the top of the outer sheath 318. The camera assembly 350 may be pannable throughout the viewable range as defined by the opening created by the combination of the embrasured opening 344 and the viewing notch 352. In some embodiments the pannable range may be approximately 180°. When panning, the camera assembly 350 may pivot on the camera pivot bearings 346 (see, for example, FIG. 16). Panning actuation will be described further below.

In some embodiments, the outer sheath 318 may be rotated to an insertion position (not shown) when the insertion section 14 (see FIG. 3) of the endoscope 10 is being inserted into the target region. In the insertion position, the viewing notch 352 may not be aligned with the embrasured opening 344 and top void 338. This may help protect the camera assembly 350 during insertion, and in medical applications may reduce the risk of damage to tissue upon insertion of the insertion section 14. After insertion, the outer sheath 318 may be rotated back to a position in which the viewing notch 352 is aligned with the embrasured opening 344 and top void 338 so that the full viewable range is again available.

In some embodiments, a cap or window material may cover or be placed in the openings defining the viewing notch 352 and embrasured opening 344 to protect the camera assembly 350. In some embodiments, the distal edge of the outer sheath 318 and the viewing notch 352 may be embrasured, rounded, beveled, etc. to help prevent damage that might result from having sharp edges.

In the example embodiment, a cap or window is not used. Such an arrangement provides a number of benefits. For example, by not using a cap or window at the tip of the insertion section 14, the cost of the endoscope may be reduced because no expensive scratch and wear resistant materials such as sapphire, specialized glass, etc. are used. Not having a cap or window may also eliminate any undesirable reflections from the surface of the cap or window, which could otherwise affect the clarity of any image captured by a camera. Moreover, by not using a cap or window, irrigation of the target area may be conducted through the conduit of the inner sheath 312 (see FIG. 15) of the endoscope 10. This enables the total diameter of the insertion section 14 to be kept small while retaining irrigation capabilities. Furthermore, irrigation flow within the inner sheath 312 may help to clear/clean any debris or material away from the camera assembly 350 and any associated lens or lenses. In one example, a user may be able to effectively irrigate the camera assembly 350 by panning the camera assembly 350 during irrigation so that the irrigation flow washes over a lens assembly 354 (see, for example, FIG. 122) of the camera assembly 350 and carries away the debris or unwanted material. As an added benefit, the irrigation flow may also help to cool an image sensor 380 (see, for example, FIG. 61) associated with the camera assembly 350.

As shown, the embrasured opening 344 and viewing notch 352 may be dimensioned in order to protect the camera assembly 350 without the need for a cap or window. In the example embodiment in FIG. 19, the embrasured opening 344 and viewing notch 352 partially envelop the camera assembly 350, which is recessed from the outer surfaces formed by the embrasured opening 344 and viewing notch 352. Thus the embrasured opening 344 and viewing notch 352 define the edges of a guard for the camera assembly 350. The partial envelopment helps to protect movable components of the camera assembly 350 and any associated components (e.g. control, electric, information cables, etc.) from contact with external objects either during insertion of the insertion section into the target region, or during use of the instrument once in the target region. The embrasured opening 344 and viewing notch 352 provide the camera assembly 350 an unrestricted view while exposing only a small part of the camera assembly 350 to possible damage from objects external to the insertion section (such as, e.g., a medical instrument such as a shaver). This helps to ensure that the camera assembly 350 is not damaged during insertion or during a procedure.

As the camera assembly 350 rotates, the distance between the camera assembly 350 and the outer sheath 318 will change. As a consequence, the amount of the outer sheath 318 which falls into the field view of the camera assembly 350 will also change. The greater the distance from the camera assembly 350 to the inner sheath 318, the greater the amount of the outer sheath 318 which will be in the field of view of the camera assembly 350. Thus, an optimized amount of protection while still affording the camera assembly 350 and unrestricted view may be achieved by varying the width of a viewing notch 352.

Figure 20:
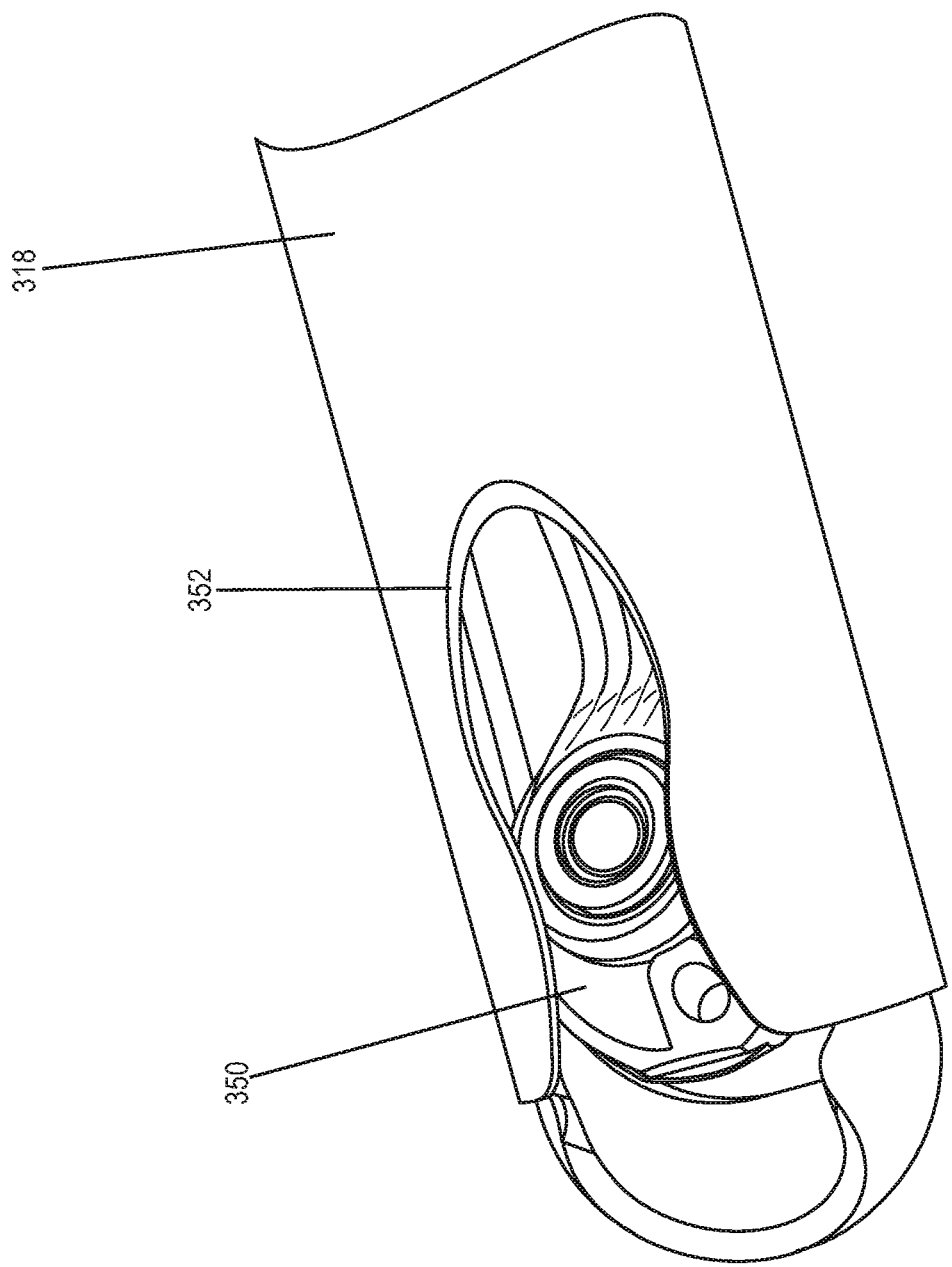
FIG. 20 shows an alternate example of a camera assembly, part of an outer sheath, and part of a camera assembly mount.

FIG. 20 depicts an alternate assembled view of the tip of an insertion section 14 (best shown in FIG. 3) in which the viewing notch 352 has a varying width. The width of the viewing notch 352 varies such that the viewing notch 352 is just outside of the field of view of the camera assembly 350 in any angular orientation of the camera assembly 350. This allows for a greater degree of envelopment of a camera assembly 350 by an outer sheath 318.

Figure 21:
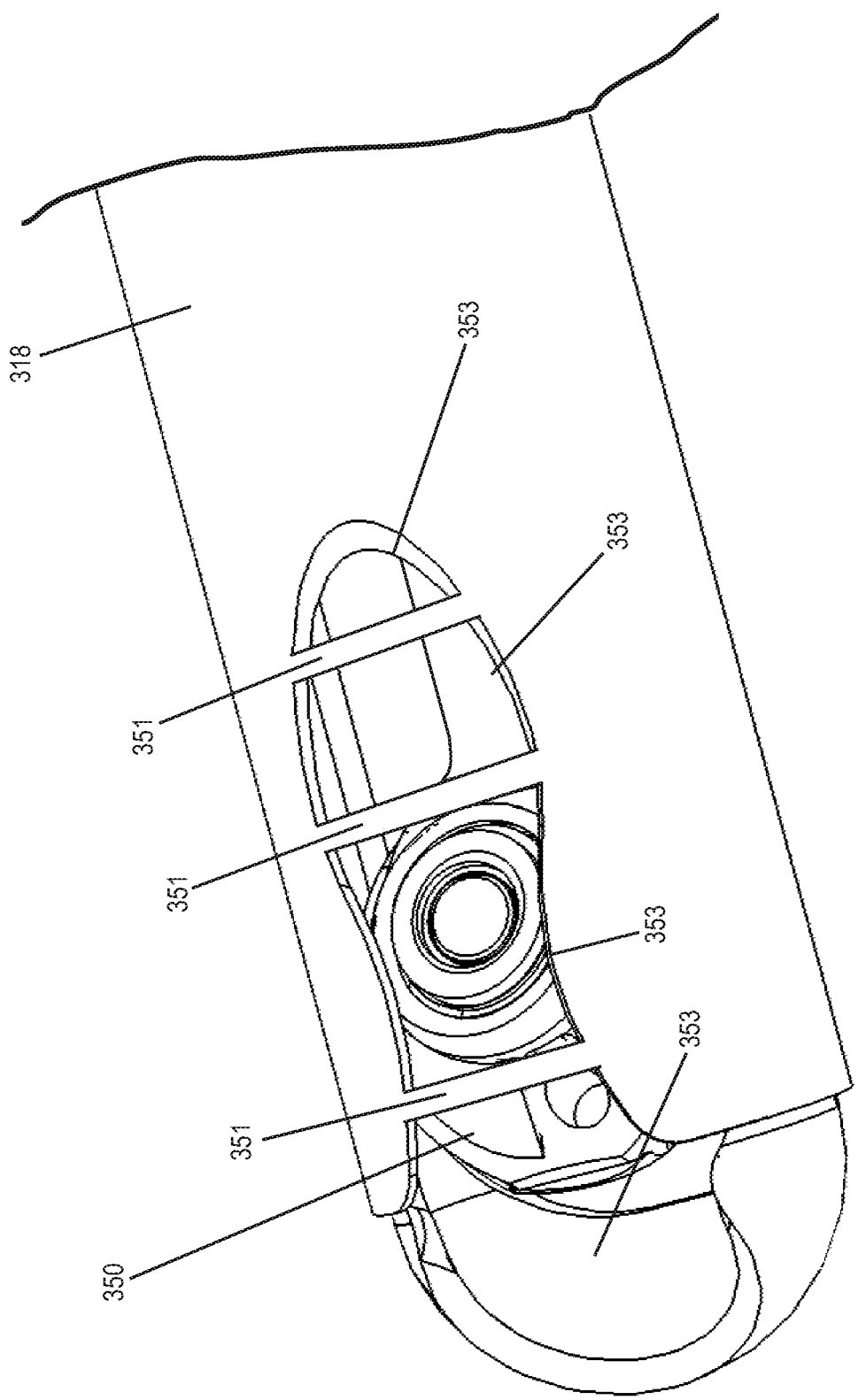
FIG. 21 shows an alternate example of a camera assembly, part of an outer sheath, and part of a camera assembly mount.

FIG. 21 depicts another alternate embodiment of a tip of an insertion section 14 (best shown in FIG. 3) in which a number of openings 353 separated by bars 351 are included in place of a viewing notch 352 like that shown in FIG. 20. Such an arrangement may provide additional protection to a camera assembly 350. To minimize the amount that the bars 351 obscure the field of view of the camera assembly 350, the bars 351 may be made of a transparent material. In other embodiments the bars 351 may be made of an opaque material, for example, the same material as the outer sheath 318.

Alternatively a cover member (not shown) which partially covers a viewing notch 352 (see FIG. 20) or one or more openings 353 (see FIG. 21) may be mounted to the distal tip of an insertion section 14 (see, for example, FIG. 1) Such a cover member may for example be a cage which allows a substantially clear field of view for the camera assembly 350 while providing additional protection for the camera assembly 350. In some embodiments, the cover member may include an optically clear partial covering.

Figure 22:
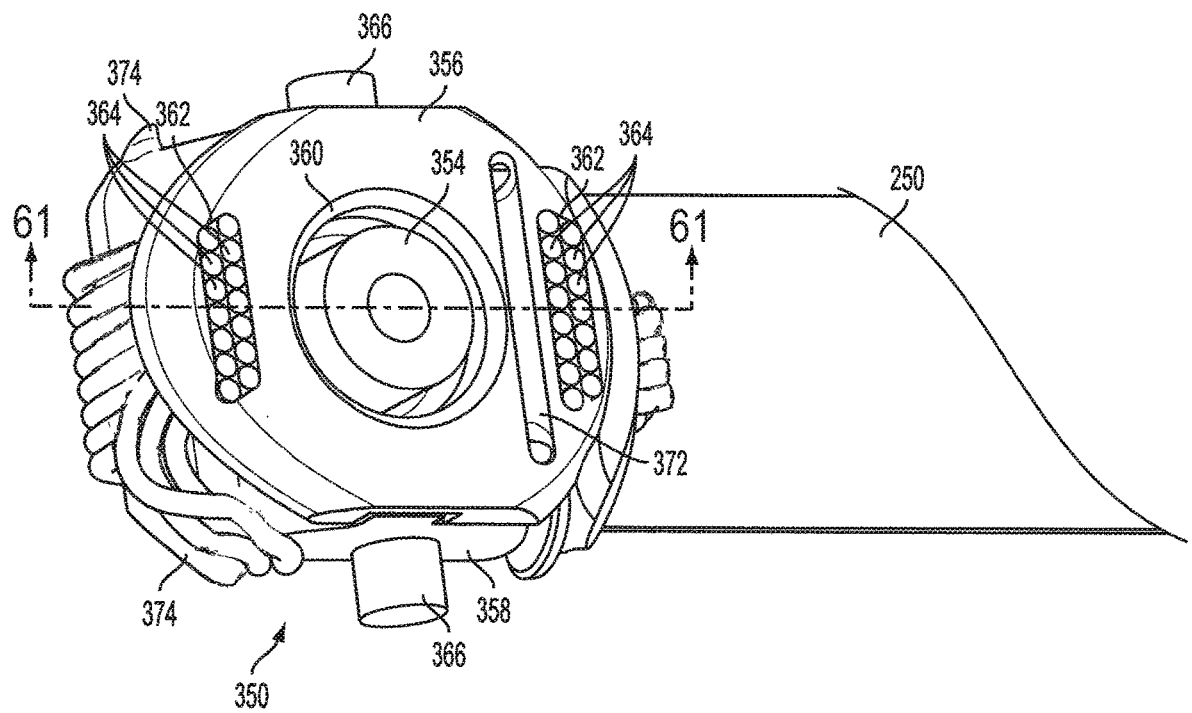
FIG. 22 shows a perspective view of a camera assembly.

The camera assembly 350 is shown in isolation in FIG. 22. As shown, a flex cable 250 is coupled into the camera assembly 350 and may provide power and data communication paths to and from the camera assembly 350. The camera assembly 350 may be any suitable structure configured to support the camera of the endoscope 10. In embodiments where the camera assembly 350 may be panned, the camera assembly 350 may include pivot actuator attachment features.

As shown, the camera assembly 350 may include a lens assembly 354. As shown, the lens assembly 354 may be held in place between a camera housing top 356 and a camera housing bottom 358. When assembled, the camera housing top 356 and camera housing bottom 358 may be coupled together by any suitable means, such as, but not limited to glue, adhesive, ultrasonic welds, press fit of cooperating features, etc. In the example embodiment in FIG. 22, the lens assembly 354 projects through a lens opening 360 in the camera housing top 356 such that it may have a clear view of the target anatomical area. In some embodiments, at least a portion of the lens assembly 354 may be proud of the camera housing top 356.

The camera housing top 356 may include a number of other voids. In the exemplary embodiment shown in FIG. 22, the camera housing top 356 includes two elongate light projection voids 362 disposed on the right and left (relative to FIG. 22) flanks of the lens opening 360, the voids 362 being designed to accommodate terminal elements of optical fibers (or optionally other light sources such as LED's) to project light onto a target area coinciding with the direction at which a camera lens or lens assembly 354 may be aimed. In the example shown, the right elongate void 362 is trapezoidal in shape while the left elongate void 362 is rhomboid in shape. In alternative embodiments, the shape of the voids 362 may differ, for example, both may be ovoid. In alternative embodiments, there may be additional voids 362. For example, in some embodiments, there may be three voids 362 arranged in a triangular configuration around the lens opening 360. In some embodiments there may be four voids 362 arranged in a rectangular, square, circular, or ovoid configuration around the lens opening 360.

One or more illumination sources for the endoscope 10 may be included at least partially within the endoscope 10. The illumination source or sources may illuminate the field of view of the camera of the camera assembly 350 regardless of its panned position. In some embodiments, the illumination source may be in the camera assembly 350. In the example embodiment in FIG. 22, the illumination source is a number of optical fibers (e.g. fiberoptic fibers) 364 which may transmit light from a lighting element (not shown) external to the endoscope 10. The optical fibers 364 may be routed and coupled into the voids 362 in the camera housing top 356. In the example embodiment, 28 optical fibers 364 are routed into the voids 362 of the camera housing top 356. The number of optical fibers 364 may differ in alternate embodiments. The light emitting ends of the optical fibers 364 may be roughly flush with the top face of the camera housing top 356. In some embodiments, other illumination sources, for example LEDs, may be used. The optical fibers 364 or other illumination source may be configured to supply any desired color or intensity of light at a predetermined light projection angle.

As shown in the example embodiment in FIG. 22, the camera assembly 350 may include pivot pins 366. The pivot pins 366 may be pivotally coupled into the pivot pin bearings 346 in the camera assembly housing 330 (see FIG. 16). The pivot pins 366 may project substantially perpendicularly from the long axis of the insertion section. The pivot pins 366 may allow the camera assembly 350 and optical fibers 364 (or other illumination source) to pivot in tandem with one another.

The camera assembly 350 may also include a pivot actuator attachment feature as mentioned above. In the example embodiment in FIG. 22, the camera assembly 350 includes a top cable attachment feature or anchor point 372 and a bottom cable attachment feature or anchor point 374. The top cable attachment feature 372 and bottom cable attachment feature 374 will be further discussed below.

As mentioned above, the endoscope 10 may also include a pivot actuator or actuators. A pivot actuator may be an elongate member used to pull on or push the camera assembly 350 via a pivot attachment feature. In the illustrated examples, the pivot actuators are mostly pull cables or wires, but these examples should not be construed as strictly limiting pivot actuators to a cable-like structure. The elongate member may be flexible or substantially rigid. The elongate member may be round (as in the example of a cable), flat, or may have any other shape or cross section. In some embodiments, the pivot actuator may be a belt routed around a cooperating attachment feature frictional engaged or otherwise meshed with features on the inner circumference of the belt. In a preferred embodiment, the pivot actuator may be used to only supply a pulling force. Such an arrangement allows for a smaller diameter insertion section 14 (see FIG. 3) because the pivot actuator does not have to be sufficiently thick or cross-sectionally strengthened, or confined within a supporting track to prevent substantial lateral displacement within the insertion section 14 in response to a pushing force against the pivot actuator. A pull-wire or pull-cable arrangement also allows a greater range of materials to be used in constructing the pivot actuator because the material only needs to have tensile strength, rather than compressive stiffness.

Figure 23:
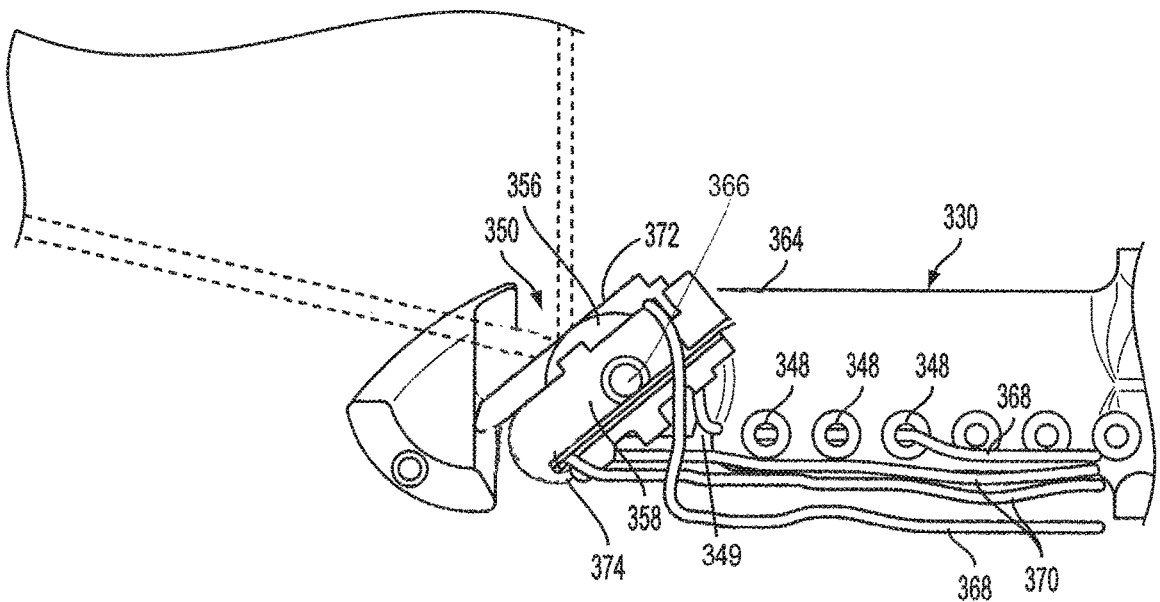
FIG. 23 shows a side view of a camera assembly and a camera assembly mount with a wall of the camera assembly mount removed for clarity.

As shown in FIG. 23, panning cables may be attached to the camera assembly 350 above and below the pivot pins 366. In the example embodiment, the panning cables are shown as relatively slack for ease of illustration. In operation one or more panning cables on one side of the pivot pins 366 would be under tension, while one or more panning cables on the other side of the pivot pins 366 would be slack. As detailed above and referring now also to FIG. 13, the panning cables may be attached proximally to the cable attachment holes 202 of the pivot control structure 100 (see FIG. 13). In some embodiments, two panning cables may be attached to each cable attachment hole 202. The panning cables may extend from the cable attachment holes 202 in the pivot arm 198 and be routed through one or more orifices 178 in the proximal section 161b of the inner sheath mount 160 (see FIG. 10). The panning cables may then extend through the utility hole 168 alongside the flex cable 250. Since the cable attachment holes 202 are located on opposite sides of the pivot point of the pivot arm 198, pivoting the pivot control structure 100 may cause the panning cables attached to one of the cable attachment holes 202 to slacken and panning cables attached to the other to become taut. By attaching the panning cables associated with one cable attachment hole 202 to the camera assembly 350 on one side of the pivot pins 366 and attaching the panning cables associated with the other cable attachment hole 202 to the opposite side of the pivot pins 366, the pivot control structure 100 may be used to selectively rotate the camera assembly 350. In some embodiments, pushing the pivot control structure 100 forward may pan the camera assembly 350 forward while pulling the pivot control structure 100 aft may pan the camera assembly 350 backward. In some embodiments, when assembled, all of the panning cables may be under tension.

In a preferred embodiment, only a single panning cable may be attached to each cable attachment hole 202 on the pivot control structure 100 pivot arm 198 (see FIG. 13). In such embodiments, there may be a top panning cable 368 and a bottom panning cable 370. The top panning cable 368 and bottom panning cable 370 may extend as described above to the camera assembly 350. The top panning cable 368 may wrap around a top cable attachment feature 372 on the camera assembly 350 and return back to the same cable attachment hole 202 on the pivot arm 198 from which it originates. The bottom panning cable 370 may wrap around a bottom cable attachment feature 374 on the camera assembly 350 and return back to the same cable attachment hole 202 from which it originates. Alternatively, the panning cable may be looped through attachment hole 202, with both ends of the cable terminating on the cable attachment feature distally.

In the example embodiment, the top cable attachment feature 372 (best shown in FIG. 22) includes two holes in the camera housing top 356. The top cable attachment feature 372 additionally includes a recess that connects the two holes. The top panning cable 368 may enter one of the holes, follow the recess, and exit the other of the two holes to return to the cable attachment hole 202 (see FIG. 13) in the handle. The bottom cable attachment feature 374 (best shown in FIG. 22) includes two attachment points or hooks which project off opposite sides of the camera housing bottom 358. The bottom cable attachment feature 374 is on the opposite side of the pivot pins 366 than the top cable attachment feature 372. The bottom panning cable 370 may be wrapped around one attachment point or hook of the bottom cable attachment feature 374, strung over to the second attachment point or hook of the bottom cable attachment feature 374 and from there return to its cable attachment hole 202 on the pivot arm 198 of the handle. In alternate embodiments, the top cable attachment feature 372 and/or bottom cable attachment feature 374 may comprise, for example, eyelets, prongs, pegs, etc.

The top panning cable 368 and bottom panning cable 370 may be made from any suitable cable or wire-like material, either metallic or synthetic polymer, either braided or monofilament. The top panning cable 368 and bottom panning cable 370 may, for example, be metal or plastic strips or bands that are laterally flexible. In a preferred embodiment, the top panning cable 368 and bottom panning cable 370 are made from a material which is resistant to stretching under tension. Wrapping a single panning cable from each cable attachment hole 202 on the pivot arm 198 (see FIG. 13) around a pivot actuator attachment feature on the camera assembly 350 may be desirable because it ensures that the side of the panning cable running to the camera assembly 350 is under the same tension as the side of the panning cable returning from the camera assembly 350; any stretching of some portion of the cable over time or use will have an equal effect on both halves of the cable.

In a preferred embodiment, the top panning cable 368 may be run through one of the cable guide holes 348 on each interior wall of the camera assembly mount 330. As shown in FIG. 23, the top panning cable 368 is threaded through one of the cable guide holes 348 and continues extending toward the camera assembly 350 along the exterior of the camera assembly housing 330. In some embodiments, there may be a depression or trough recessed into the exterior of the camera assembly housing 330 along the path taken by the top panning cable 368. In such embodiments, the depression or trough may serve as a guide. The depression or trough may also help to ensure that the top panning cable 368 is roughly flush to exterior surface of the camera assembly housing 330. This may help to ensure that the outer sheath 318 (see FIG. 19) does not impinge on the top panning cable 368 to impair its movement during the use of a fully assembled endoscope 10.

As shown in FIG. 23, the top panning cable 368 is strung through the constraining notch 349 as it re-enters the interior of the camera assembly housing 330. The top panning cable 368 then runs to the top cable attachment feature 372 as describe above. On return to the cable attachment hole 202 (see FIG. 13), the top panning cable 368 runs from the top cable attachment feature 372 to the constraining notch 349 on the opposite wall (see FIG. 16) of the camera assembly housing 330. The top panning cable 368 then runs along the exterior surface of the front wall of the camera assembly housing 330 and optionally along a depression or trough in the wall. The top panning cable 368 then re-enters the interior volume of the camera assembly housing 330 and travels back to the cable attachment hole 202 in the handle as described previously.

A terminal segment of a pivot actuator (such as a wire or cable) proximal to its connection to a pivoting assembly at the distal end of the insertion section may be constrained at a fulcrum or support point to re-direct the actuator so as to form an angle with respect to the long axis of the insertion section or shaft. For example, by running the top panning cable 368 through the cable guide holes 348 and the constraining or re-directing notches 349, and then angling it up to the top cable attachment feature 372 on the other side of pivot pin 366, an increased pivotal range for the pivoting camera assembly 350 may be achieved. Thus an image sensor having a pre-determined or fixed angular field of view may be rotated to allow for a rotatable field of view, so that the viewable area can be increased to a range of up to 180 degrees. In other embodiments, an image sensor may be rotated so as to achieve a viewable area that exceeds 180 degrees. As shown in FIG. 23, having the cable routed as described places the cable at a more acute angle of incidence to its attachment point 372, and thus permits a greater degree of back-rotation of the camera assembly 350.

Figure 24:
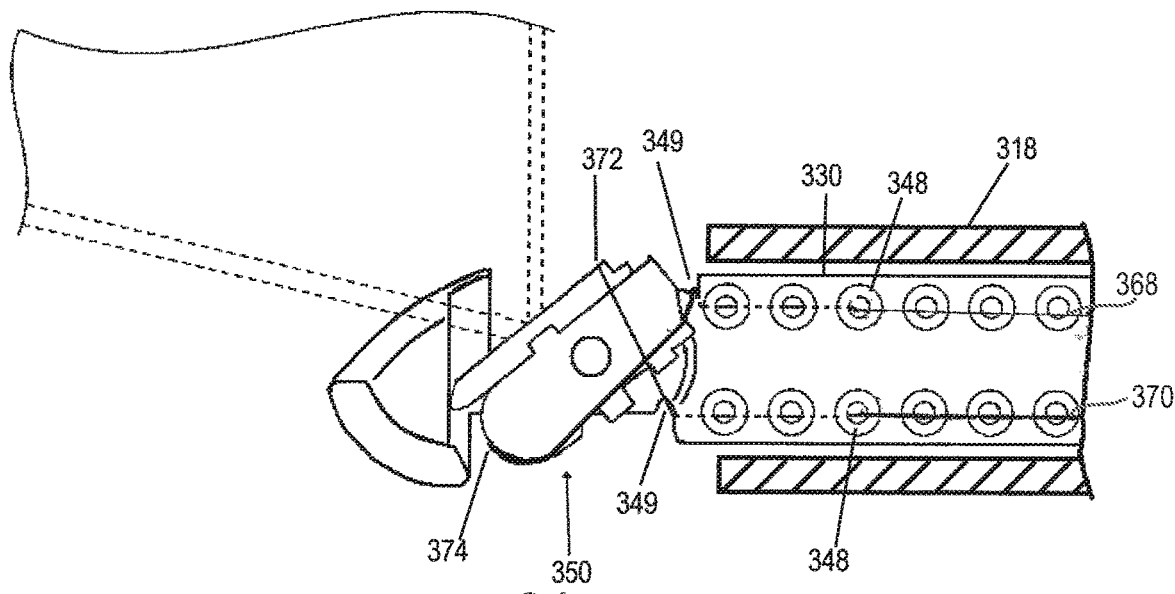
FIG. 24 shows a side view of an alternate exemplary camera assembly and camera assembly mount with a wall of the camera assembly mount removed for clarity.

In some embodiments, and referring now also to FIG. 24, the camera assembly 350 may be capable of rotating a full 180 degrees or more, because of the presence of two sets of cable guide holes 348: a lower set of guide holes 348 to control the camera housing top section, and an upper set of guide holes 348 to control the camera housing bottom section. The degree to which the camera assembly 350 can be rotated is a function of the angle that the terminal portion of the panning cable makes with respect to the proximal portion of the panning cable or the longitudinal axis of insertion section (or endoscope shaft) 14 (see FIG. 1). The greater the angle the terminal portion of the panning cable makes as it re-enters the exterior of the camera assembly housing 330 in relation to the longitudinal axis of the insertion section 14, the greater the range of motion it can induce in the camera assembly 350. In a preferred embodiment, the re-entry surface or re-directing guide of the camera assembly housing 330 is positioned to provide for an angle of the terminal portion of the panning cable to be within a range of about 30-90 degrees with respect to the long axis of insertion section 14. In other embodiments, the rotational range of motion of the camera assembly 350 may be improved while limiting the frictional resistance of the panning cable by positioning the cable re-entry surface or guide to achieve an angle of the terminal portion of the panning cable to be within a range of about 45-80 degrees. Such an embodiment, as described above, only requires a pulling force on either of a pair of complementary cables 368, 370 one angled up at a distal or terminal location in insertion section 14 to attach to the top cable attachment feature 372, and one angled down at a distal or terminal location in insertion section 14 to a corresponding bottom cable attachment feature 374. With this arrangement, neither actuating cable is required to move laterally or transversely within most of the length of insertion section 14, which allows the internal space within insertion section 14 to be narrower, helping to minimize its overall diameter.

In some embodiments, a constraining or re-directing notch 349 may not be used. Some embodiments may use a different type of constraint or re-directing element incorporated into a wall at the distal end of the insertion section. In some embodiments, a pulley or an eyelet may be used as a constraint. A pin, peg, post, etc. may also be used as a constraint or re-directing element. In some embodiments, a curved finger or prong may be formed in the side walls of the camera assembly housing 330. The curved finger may extend into the interior volume of the camera assembly housing 330 such that there is a space between the interior wall of the camera assembly housing 330 and the curved finger. The top panning cable 368 may be run through this space so that it is constrained by the curved finger. In most embodiments, it may be desirable that the point of contact between the constraint and the cable has a smoothness or radius of curvature sufficient to minimize the potential for frictional damage to the panning cable during operation of the endoscope. In some cases, the constraint may be coated with a material having a low coefficient of friction such as Teflon.

In some embodiments, the bottom panning cable 370 instead of the top panning cable 368 may be constrained similarly to the preceding description to enable a greater pivotal range of the camera assembly 350 in one direction of rotation over another. As shown in FIG. 24, in some embodiments, both the bottom panning cable 370 and top panning cable 368 may be constrained or redirected, allowing for even greater pivotal ranges.

In FIG. 24, the outer sheath 318, camera assembly housing 330, and camera assembly 350 are shown. There are two sets of cable guide holes 348. One set is above the longitudinal axis of the camera assembly housing 330 and the other is below the longitudinal axis of the camera assembly housing 330. There are also two constraining notches 349. One of the constraining notches 349 is located above the longitudinal axis of the camera assembly housing 330 and the other is located below the longitudinal axis of the camera assembly housing 330.

An improved mechanical advantage of the panning cables may be obtained by positioning the re-directing element (e.g. notch) on one side of (e.g., below) the pivoting axis of the camera assembly 350, while attaching the terminal end of the panning cable to a point on the camera assembly located on the opposing side of (e.g. above) the pivoting axis of the camera assembly 350.

As shown, the top panning cable 368 is run through one of the cable guide holes 348 below the longitudinal axis, and re-enters the camera assembly housing 330 at the constraining notch 349 below the longitudinal axis. The top panning cable 368 then redirects up to the top cable attachment feature 372 on the camera assembly 350. In FIG. 24, the bottom panning cable 370 is run through a cable guide hole 348 above the longitudinal axis of the camera assembly housing 330. The bottom panning cable 370 then re-enters the camera assembly housing 330 through the constraining notch 349 above the longitudinal axis of the camera assembly housing 330. The bottom panning cable 370 then redirects down to the bottom cable attachment feature 374. The top panning cable 368 and bottom panning cable 370 may wrap around a portion of the camera assembly 350 depending on where the camera assembly 350 has been pivoted to. In FIG. 24 the bottom panning cable 370 is shown wrapping around a portion of the camera assembly 350.

Figure 25:
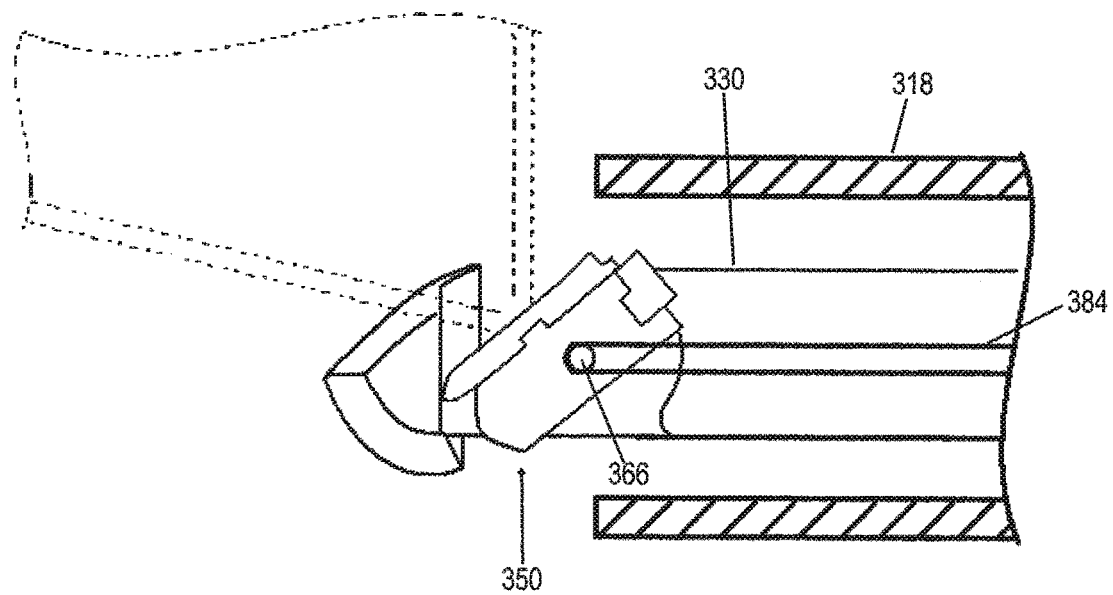
FIG. 25 shows a side view of an alternate exemplary camera assembly and camera assembly mount with a wall of the camera assembly mount removed for clarity.

Some embodiments may make use of a belt 384 as a pivot actuator. An embodiment which includes a belt 384 as a pivot actuator is shown in FIG. 25. As shown, the belt 384 wraps around one of the pivot pins 366 of the camera assembly 350. In some embodiments, the pivot pins 366 may be elongated such that a portion of at least one of the pivot pins 366 extends from the pivot bearings 346. In such embodiments, the belt 384 may be wrapped around this portion of the pivot pins 366 as shown in FIG. 25. In some embodiments, the shape of the camera assembly 350 may differ such that the belt 384 may wrap around the camera assembly 350. For example, the camera assembly 350 may be a substantially cylindrical shape. The substantially cylindrical shape of the camera assembly 350 may be coaxial with the pivot pins 366. In such embodiments, the belt 384 may be wrapped around the circumference of camera assembly 350.

In some embodiments, the surface over which a belt 384 is wrapped may be recessed (e.g., V-shaped) in relation to the surfaces which flank it. This may help to keep the belt 384 in place during operation. In other embodiments, any other type of guide may be used. For example, the surface over which a belt 384 is wrapped may be flanked by two walls which keep the belt 384 in place during operation.

A belt 384 may be made of a high friction material so that the belt 384 does not slip over the surface which it wraps around as the belt 384 is driven. In some embodiments, the belt 384 may have a coarse surface, or may be toothed to aid in its ability to grip or positively engage a camera assembly pivot pin 366 (which may be geared). Use of a belt 384 may allow for a wide range of pivoting of the camera assembly 350 without the need for a pull-cable pivot actuator to be redirected laterally within the insertion section 14 to achieve an equivalent range of motion of the camera assembly 350. This allows the insertion section 14 to be made with a smaller diameter.

In embodiments using a belt 384, the belt 384 may be configured to be driven by displacement of the pivot control structure 100 (see FIG. 13). In some embodiments, the opposite end of the belt 384 from that which wraps around the camera assembly 350 or pivot pins 366 may wrap around the pivot shaft 204 of the pivot control structure 100. In such embodiments, rotation of the pivot shaft 204 may drive the belt 384. The portion of the pivot shaft 204 which the belt 384 wraps around may have a relatively large diameter. This may be desirable so that only a small pivotal displacement of the pivot shaft 204 is needed to drive the belt 384 a relatively large amount. In embodiments where the belt 384 includes teeth, the teeth of the belt 384 may interdigitate with a gear located on the pivot shaft 204 of the pivot control structure 100. In such embodiments, rotation of the pivot shaft 204 and gear on the pivot shaft 204 may drive the belt 384. As the belt 384 is driven, the movement of the belt 384 will exert a driving force on the camera assembly 350 causing the camera assembly 350 to pivot.

In yet another arrangement using one or more panning cables, a similar pivotal range may be achieved without requiring any routing of a panning cable through various features included in a camera assembly mount 330. This may be desirable because it may allow the diameter of an insertion section 14 (see FIG. 1) to be made smaller. Additionally, a camera assembly mount 330 for such an embodiment would not require any fenestrations (e.g. the cable guide holes 348 of FIG. 16) or re-directing elements/constraints (e.g. the constraining notch 349 of FIG. 16) thus simplifying manufacture of a camera assembly mount. Such an embodiment may for example use the camera assembly mount 330 and inner sheath 312 shown in the example embodiment in FIG. 17.

In such an embodiment, a camera assembly 350 may include one or more spooling features or surfaces 1400. The spooling feature is configured to at least partially wind the terminal portion of a panning cable around the housing of the camera assembly. A connection or attachment point for the terminal end of the panning cable may be situated on the camera assembly housing distal to the spooling feature. The spooling feature preferably has a curved, somewhat recessed surface, which may partially or completely wrap around a portion of the camera assembly housing. Thus, in various embodiments, a panning cable may wind around the housing only partially, or in one or more complete loops around the housing. A longer spooling feature provides for a more extensive range of rotation of the camera assembly. During actuation, an associated panning cable may be wound or unwound from the spooling feature 1400. Spooling feature 1400 may increase the pivotal range of a camera assembly 350. Spooling feature 1400 may allow a more consistent torque to be applied to a camera assembly 350 during rotation. Spooling feature 1400 may be constructed to create a moment arm of desired or varying length. Additionally, positioning the spooling feature 1400 radially apart from the axis of rotation of the camera assembly may help a panning cable to generate rotational torque more efficiently.

The progression of FIGS. 26-30 conceptually illustrate a camera assembly 350 including a spooling feature 1400 in a number of rotational positions. As shown, the spooling feature 1400 may include an arcuate portion and a straight portion. The arcuate portion is shaped such it has a radius of curvature which extends from the pivot axis of the camera assembly 350. The straight portion of the spooling feature 1400 is angled such that is serves as a torque increasing feature. Additionally, the straight portion of the spooling feature 1400 allows the camera housing 355 to be made with more material (which would otherwise need to be removed to continue the arcuate section) and thus increases the structural integrity of the camera housing 355. This may be particularly important in embodiments where the camera assembly 350 is designed to fit in a very small space and thus must be made with a very small form factor.

Figure 26:
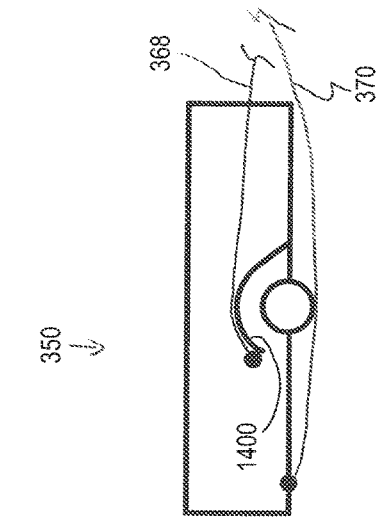
FIGS. 26-30 depict some of the possible rotational positions of an alternate camera assembly.

As shown in FIG. 26 the top panning cable 368 may be wound around the spooling feature 1400. A pulling force exerted by the top panning cable 368 would create a torque about the pivot axis of the camera assembly 350 causing the camera assembly 350 to rotate in a clockwise direction. Additionally, the straight portion of the spooling feature 1400 creates a longer moment arm thus increasing the torque generated for a given amount of pulling force.

Figure 27:
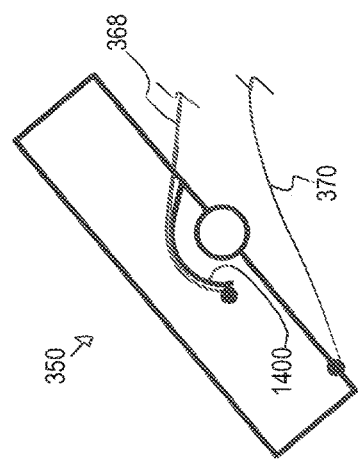
Figure 28:
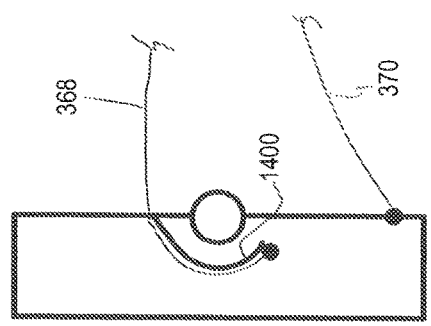

As the camera assembly 350 rotates to the position shown in FIG. 27, the top panning cable 368 begins to unwind from the spooling feature 1400. As force continues to be applied and the camera assembly continues to rotate, the top panning cable 368 will continue to unwind from the spooling feature as shown in FIG. 28. When sufficiently unwound, the point at which the top panning cable 368 leaves the spooling feature 1400 will be located on the arcuate section of the spooling feature 1400 (as shown in both FIG. 27 and FIG. 28). In an embodiment, all points on the arcuate section of the spooling feature 1400 may be located an equal distance from the pivot axis.

Figure 30:
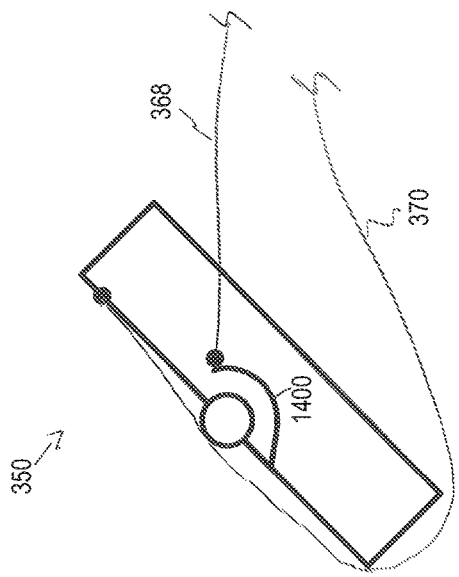
Figure 29:
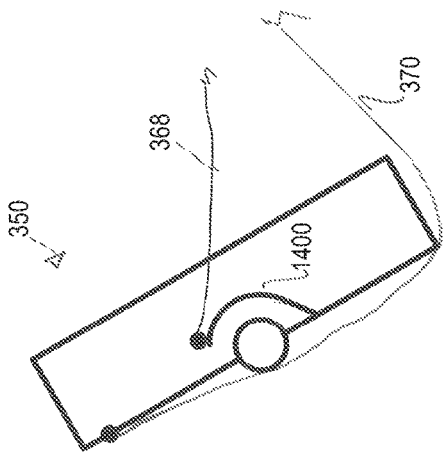

In an exemplary embodiment, as a pulling force continues to be exerted by the top panning cable 368, the camera assembly 350 will continue to rotate until the top panning cable 368 no longer contacts the surface of the spooling feature 1400 as shown in FIG. 29. The camera assembly 350 may then continue to rotate until the pulling force of the top panning cable 368 approaches coincidence with the axis of rotation of the camera assembly. This position is depicted in FIG. 30. As would be understood by one skilled in the art, a panning cable may be wound around a spooling feature 1400 one or more times to increase the amount of rotation which may be created using the panning cable. The degree to which a panning cable winds around a contact surface on the camera assembly allows for a range of rotation of the camera assembly that exceeds 90 degrees. The degree of rotation of the camera assembly would then be limited only by the amount of slack and the flexibility of the attached electronic flex cable and/or the optical fiber bundle.

In an embodiment, the panning cable and spooling surface are arranged to permit the camera assembly to rotate to a position between about 90 degrees to about 120 degrees of the long axis of the distal endoscope shaft, orienting the lens surface of the camera assembly at least partially in the direction of the proximal end of the endoscope shaft. In this position, any debris or other contamination of the lens surface may be washed away by irrigation fluid traveling distally in the endoscope shaft.

To rotate the camera assembly 350 from its position in FIG. 30 to the position shown in FIG. 30, a pulling force may be exerted via the bottom panning cable 370. In some embodiments, the bottom panning cable 370 may also be associated with a spooling feature. For example, the corners or edges of the camera assembly 350 around which the bottom panning cable 370 may wrap may be rounded.

Figure 32:
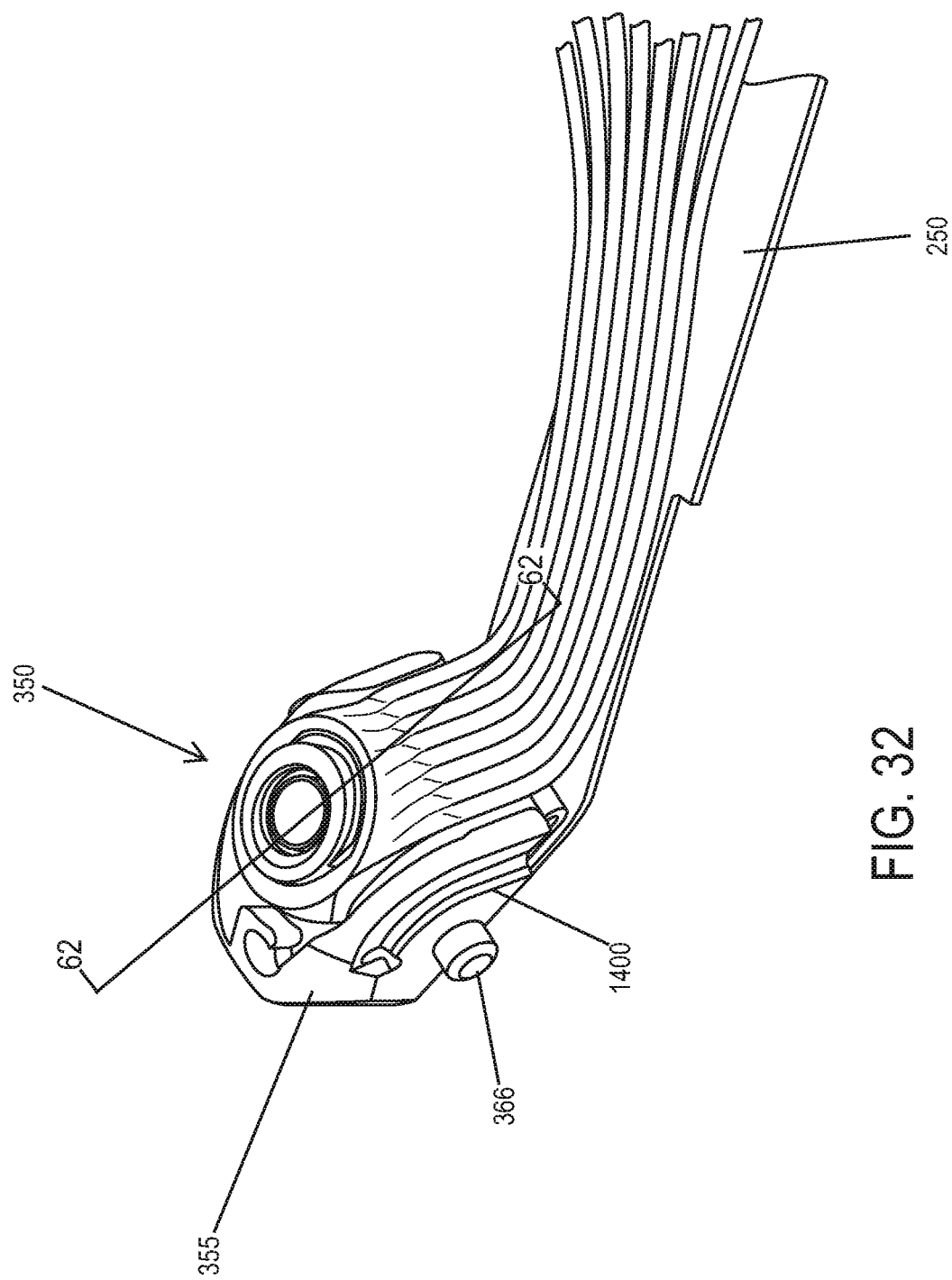
FIG. 32 shows an example camera assembly with attached optical fiber bundle and electronic flex cable.

FIG. 31-32 depicts a top perspective view of a specific example embodiment of a camera assembly 350 which includes a spooling feature 1400. The camera assembly 350 includes a lens assembly 354. The lens assembly 354 is disposed inside of a camera housing 355. The spooling feature 1400 may be recessed into a side of the camera housing 355 as shown. The spooling feature 1400 in the example embodiment includes an arcuate portion and a straight portion. The arcuate portion of the spooling feature 1400 is shaped such it has a radius of curvature which extends from the center of the pivot pins 366 or pivot axis.

As best shown in FIG. 31, the wall into which the spooling feature 1400 is recessed may include a first void 1402. The camera housing 355 may also include a second void 1404. The second void 1404 may pass through the top face of the camera housing 355 to the bottom face of the camera housing 355.

As shown, only a single panning cable 1406 may be used. The panning cable 1406 may extend through both the first void 1402 and the second void 1404 in the camera housing 355. One end of the panning cable 1406 may be attached to a cable attachment hole 202 on the pivot arm 198 (see FIG. 13). The other end of the panning cable 1406 may be attached to the other cable attachment hole 202 on the pivot arm 198. In some embodiments, the panning cable 1406 may be fixedly attached to the camera housing 355 at one or more points. For example, an adhesive of glue may be placed into one of the voids 1402 or 1404. This may ensure that the panning cable 1406 does not slip or move over the surface of the camera housing 355 during actuation. Additionally, in some embodiments, the panning cable 1406 may be knotted in one or more location. For example, the panning cable 1406 may be fed through one of the voids 1402 or 1404, knotted, and then fed through the other of the voids 1402 or 1404. Preferably, the width of the knot may be sufficiently wide so as to not fit through either of the voids 1402 or 1404. Such a knot may again help to keep the panning cable 1406 from slipping or moving over the surface of the camera housing 355 during actuation.

As would be appreciated by one skilled in the art, the embodiment shown in FIG. 31-32 may easily be modified to use two panning cables. One panning cable may terminate and be fixedly attached to the camera housing 355 in or at the location of the first void 1402. A second panning cable may terminate and be fixedly attached to the camera housing 355 in or at the location of the second void 1404.

In other embodiments, the pivot actuator may be the rack of a rack and pinion arrangement. In such embodiments, the pivot pins 366 of the camera assembly 350 may include a toothed portion. The toothed portion of the pivot pins 366 may be the pinion gear that interdigitates with the rack of the pivot actuator. As the rack displaces longitudinally within the insertion section 14, this motion is translated into rotation of the camera assembly 350 via the toothed, pinion portion of the pivot pins 366. While such an embodiment does not solely rely on a pulling force to rotate the camera assembly 350, the pivot actuator still does not require lateral displacement of the actuator within the insertion section 14. A push-pull rack-type actuator may nevertheless require features (e.g., rigidity, thickness) or may otherwise be constrained within a track to prevent lateral or side-to-side flexion during the application of a compressive force on the rack.

Referring now back to FIG. 13, the pivot control structure 100 may be capable of being "parked" in detents defined by ridges 94 in the slide button recess 92 of the handle raised portion 34. In some embodiments, the ridges 94 may be spaced such that the detents formed by the ridges 94 may correspond with specific angular orientations of the camera assembly 350. In some embodiments, the detents formed by the ridges 94 may be spaced such that their location corresponds to specific angular increments (e.g. 30°) of the camera assembly 350.

As mentioned above (see FIG. 6), the handle distal section 30 may be rotatable relative to the handle proximal section 16. Such rotation would also cause the longitudinal axis of the insertion section 14 to rotate as well. In turn, the camera assembly 350 may rotate with the insertion section 14. This may allow a user to get a near-global view of the anatomical area in question with minimal to no angular repositioning of the endoscope 10. A user may need only to pan the camera assembly 350 and rotate the handle distal section 30 relative to the handle proximal section 16 to obtain a desired field of view within an anatomical area.

Repeated contortion and bending of optical fibers such as the optical fibers 364 may lead to fracturing or failure of one or more fibers. In the instance of the optical fibers 364, this leads to light and illumination loss which increases as more optical fibers 364 become compromised. Such bending may occur if the optical fibers 364 terminate and are attached or fused to a portion of a pivoting camera assembly 350 as described above. If the endoscope 10 is designed to be disposable, then any decrement in the integrity or performance of the optical fibers 364 may be within acceptable limits relative to the intended lifespan of the instrument. Consequently, in some embodiments the optical fibers 364 may be attached or fused to a pivotal camera assembly 350 with minimal concern for optical fiber 364 breakage and resultant light loss. A terminal illuminator, light projection element or light emitter associated with the optical fibers 364 may, in some embodiments, be advantageously mounted to the camera assembly 350 in order to project light at whatever target or field of view a lens assembly 354 of the camera assembly 350 has been rotated or panned to. Such an arrangement helps to ensure that the field of view (shown with dashed lines in FIG. 23-25) for the lens assembly 354 is always illuminated by the optical fibers 364 regardless of where the in the camera assembly's 350 pannable range the camera assembly 350 has been rotated to.

In some embodiments, the illumination system may include a light guide or light pipe 375. In some embodiments, the optical fibers 364 may comprise a light guide or light pipe 375 (see, for example, FIG. 33) along at least a part of the path of the illumination system. The terms "light guide" and "light pipe" are herein used interchangeably. When an optical fiber is relatively straight, light loss is relatively small because the angle of incidence of the light within the fiber is shallow enough to facilitate near total reflection within the optical fiber. Bending the optical fiber, however, may alter the angle of incidence to the point where some transmission of light out of the fiber is possible. Bends of a light pipe or guide may, however, be controlled. For this reason, use of a light guide 375 where feasible may help to minimize light loss in an illumination system comprising opitcal fibers 364 or may replace the optical fibers altogether. A light guide 375 may also provide a number of other benefits. For example, a light guide 375 may aid in assembly and shorten assembly time for a device. The light guide 375 may be of the types described herein or may be any suitable type light guide known to those skilled in the art.

Figure 33:
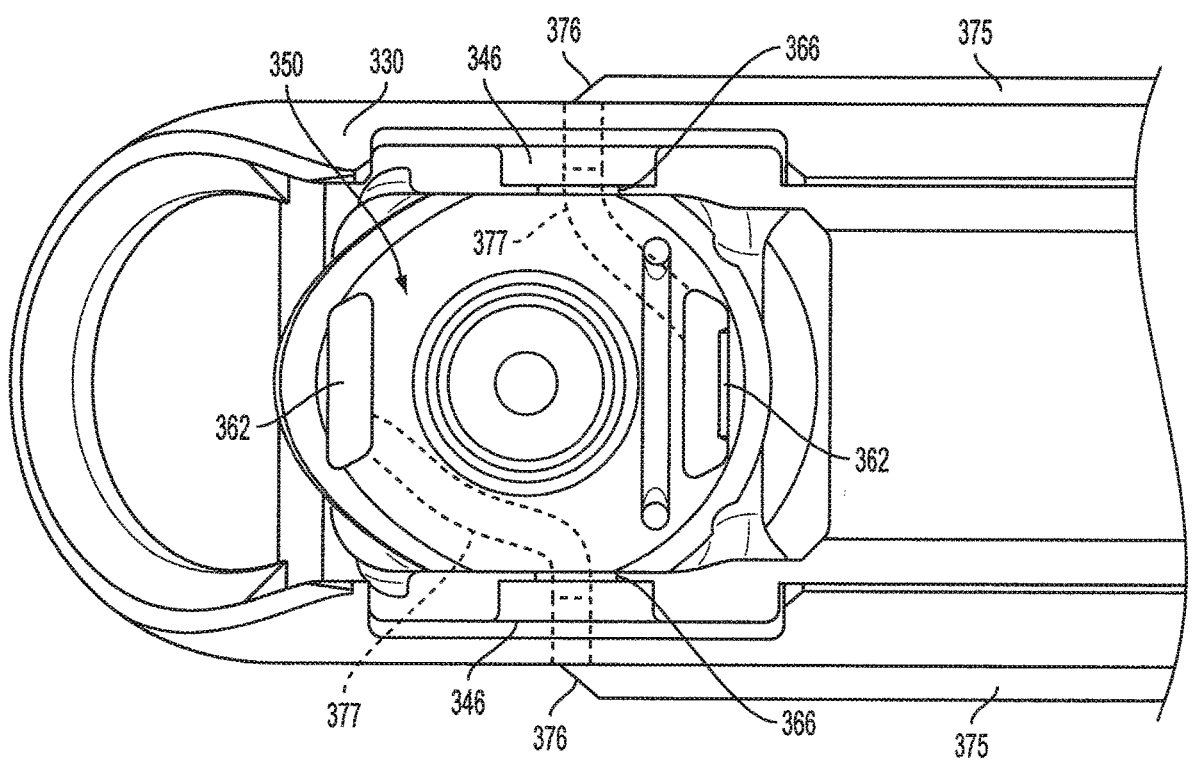
FIG. 33 shows a top view of an exemplary camera assembly and camera assembly mount.

FIG. 33 shows an example embodiment of an endoscope 10 utilizing light pipes 375. Two larger diameter light pipes 375 may extend along one or more sections of the wall of the inner sheath 312 (see FIG. 16) to the camera assembly housing 330 and then bend or curve into one of the camera assembly pivot bearings 346. The bent section of each light pipe 375 may be coated with a highly reflective material 376 in order to minimize loss of light out of the light pipe 375 as it changes direction. Any suitable highly reflective material 376 known to one skilled in the art may be used. In such embodiments, the camera assembly 350 may also have built-in camera assembly light pipes 377 that are formed in a junction with the light pipes 375 at the pivot bearings 346. The light carried by the light pipes 375 may be transferred to the camera assembly light pipes 377 at the junction. The camera assembly light pipes 377 may extend from each of the pivot pins 366 into the camera assembly 350. The camera assembly light pipes 377 terminate in the light projection voids 362 so that the field of view of the camera assembly 350 will be illuminated regardless of the rotational position of the camera and lens assemblies. In such an embodiment, any bends taken by the camera assembly light pipes 377 may be coated with a highly reflective material 376 as described above. In some embodiments, the highly reflective material 376 may be included on other portions of the light pipes 375 and camera assembly light pipes 377 in addition to the bends of the light pipes 375 and camera assembly light pipes 377.

Creating a light pipe junction coinciding with the pivoting region of the camera assembly 350 may be desirable because it avoids the bending or twisting of optical fibers 364 as the camera assembly 350 is rotated, removing the risk of damage to the optical fibers 364. Such a design can be adapted for use in either a reusable or disposable endoscope 10. This arrangement may also reduce the manufacturing or assembly costs of the endoscope 10.

In another example embodiment (not shown) which uses light pipes 375, a larger diameter light pipe 375 may extend substantially along the path of the flex cable 250. The end of the light pipe 375 nearest the inner sheath mount 160 may form a junction with the optical fibers 364 or be arranged to draw in light from another illumination source. The end of the light pipe 375 nearest the camera assembly 350 may also form a junction with illumination fibers 364 which extend to the camera assembly 350.

Figure 34:
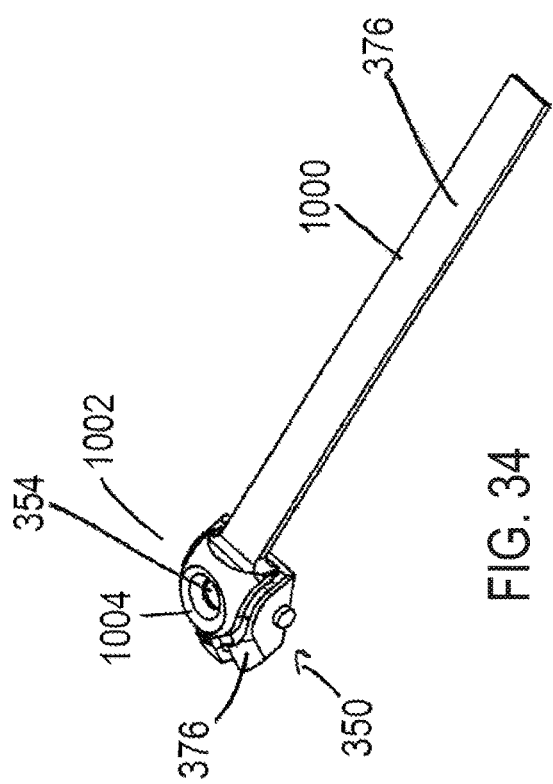
FIG. 34 shows a perspective view of a camera assembly and flexible optical fiber bundle or ribbon.

In some embodiments, the optical fibers 364 to the camera assembly 350 may be arranged to form a flexible ribbon 1000, creating a linear array of fibers that can be terminated into a light projection element with minimal bending or bending in only one dimension (see, e.g., FIG. 34). Alternatively, the flexible ribbon 1000 need not be a linear array of fibers and instead may, in some embodiments, be a single, ribbon-like, flexible piece of light guide material. In some embodiments there may be two flexible ribbons 1000 each extending to one of the light projection voids 362 in the camera assembly 350. In some embodiments, the flexible ribbons 1000 may be coated with a reflective material 376 to maximize the amount of light at the camera assembly 350. In some embodiments, a flexible ribbon 1000 may form a junction with a light pipe.

In some embodiments, a camera housing top 356 may comprise a light piping material to serve as a light projection element or illuminator. In this case, light may be emitted from most of the camera housing top 356 and into the viewing field of the camera assembly 350. In some embodiments, some areas of the camera housing top 356 may be blacked out or masked so that light is only emitted from a desired region or regions of the camera housing top 356. In some embodiments, some regions of the camera housing top 356 may be coated with a highly reflective material 376 to prevent the unwanted emission of light from those areas.

FIG. 34 shows an embodiment in which the optical fibers 364 are incorporated into a flexible ribbon 1000, which optionally may be coated in a highly reflective material 376. As shown, the flexible ribbon 1000 extends to the camera assembly 350. The flexible ribbon 1000 may be over-molded to, potted into, fused with or otherwise coupled to the camera assembly 350.

Figure 35:
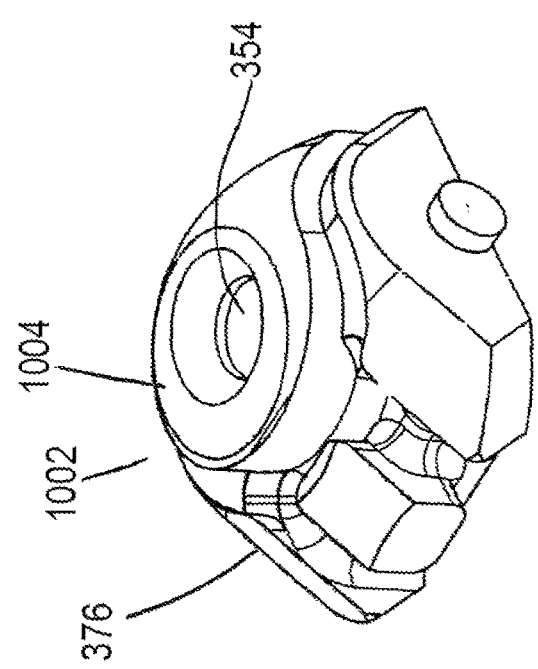
FIG. 35 shows a perspective view of a camera assembly having a monolithic camera housing and light emitting feature.

In the example embodiment in FIG. 34 the camera assembly 350 comprises a monolithic camera housing 1002. An example monolithic camera housing 1002 without an attached flexible ribbon 1000 is shown in greater detail in FIG. 35. In the example embodiment, the monolithic camera housing 1002 is made from a light piping or transmitting material and functions as a light projection element. The monolithic camera housing 1002 in the example embodiment may be nearly entirely coated with a highly reflective material 376 to maximize light output from the non-coated or non-masked regions of the monolithic camera housing 1002. A light projection or illumination surface 1004 having a shape suitable for placement adjacent a lens and image sensor assembly on the monolithic camera housing 1002 may be constructed by masking the area during application of a highly reflective material 376 (or alternatively a simple dark mask). In the example embodiment, the light projection surface 1004 has the shape of a ring. In other embodiments, the light projection surface 1004 may be crescent-shaped, semi-circular, or may have any other desired shape. Light may be emitted from the light projection surface 1004 of the monolithic camera housing 1002 to illuminate the field of view of the lens assembly 354. As in the above-described embodiments, the field of illumination preferably pivots with the camera assembly 350, ensuring that the field of view of the lens assembly 354 is always illuminated.

Figure 36:
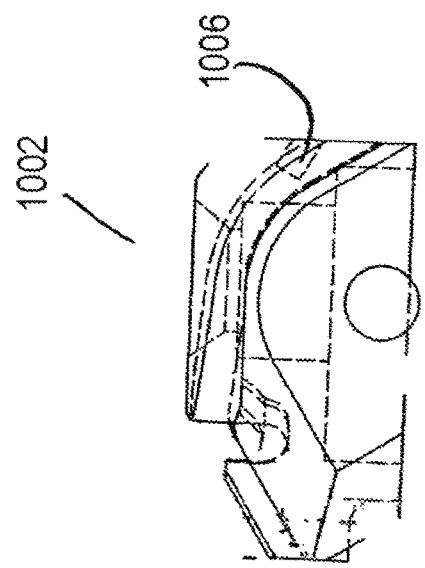
FIG. 36 shows a side view of the camera assembly of FIG. 35.

FIG. 36 shows another example embodiment of a monolithic camera housing 1002. As shown in outline form, the monolithic camera housing 1002 includes a coupling recess 1006. The coupling recess 1006 may allow a flexible ribbon 1000 to be suitably coupled into the monolithic camera housing 1002. In some embodiments, the coupling recess 1006 may allow a flexible ribbon 1000 to be coupled, for example, via snap fit into the monolithic camera assembly 1002. In some embodiments, the coupling recess 1006 may accommodate optical fibers 364 not formed in a flexible ribbon 1000. Similar to FIG. 35, in FIG. 36, the monolithic camera housing 1002 may function as a light projecting element. The monolithic camera housing 1002 may also be similarly coated and/or masked as the monolithic camera housing 1002 described in relation to FIG. 35.

FIG. 37 and FIG. 38 show an embodiment in which a light projection element 1005 is incorporated in an end of a flexible ribbon 1000. The light projection element 1005 may be formed from a light piping material, which in some embodiments may be a fusion of a group of fibers into a shape suitable for projecting light from a fiberoptic bundle or flexible ribbon 1000 in a desired manner. In some embodiments, the light projection element 1005 and flexible ribbon 1000 may be two separate parts fused together (e.g., by heating or by chemical means). In other embodiments the light projection element 1005 and flexible fiberoptic ribbon 1000 may be a single molded part. In some embodiments the light projection element 1005 may be created as described in relation to FIGS. 47-60.

Still Referring to FIGS. 37 and 38, the flexible ribbon 1000 may be coated with a highly reflective material 376. The bottom and side walls of the light projection element 1005 may also be coated with a highly reflective material 376. This may ensure that light is only emitted from the non-coated top of the light projection element 1005 and into the field of view of the lens assembly 354. As show in FIG. 38, the light projection element 1005 or the flexible ribbon 1000 may include a coupling feature 1008. The coupling feature 1008 may allow the light projection element 1005 and flexible ribbon 1000 to be coupled onto or into a camera assembly 350. The coupling feature 1008 may be an integral part of the light projection element 1005.

FIG. 39 and FIG. 40 depict two example embodiments of a flexible ribbon 1000 which include light projection elements 1005, which may be formed from a light piping material. The light projection element 1005 in FIG. 39 has a generally ring-like shape while the light projection element 1005 in FIG. 40 is generally crescent shaped, although other shapes may be selected as desired. In the example embodiments in FIGS. 39 and 40 only the top surfaces of the light projection elements 1005 are left uncoated with a highly reflective material 376.

A light projection element 1005 may comprise one or a number of textures 1010 that help to direct the light emitted from the light projection elements 1005. In some embodiments, the texture 1010 or textures 1010 may be included to encourage light to be emitted in a diffuse manner. The texture 1010 or textures 1010 may be created, for example, during molding of the light projection element 1005, or alternatively, the light piping material forming the light projection element 1005 may include a fill material that encourages light to be emitted from the light projection element 1005 in a diffuse manner.

Figure 42:
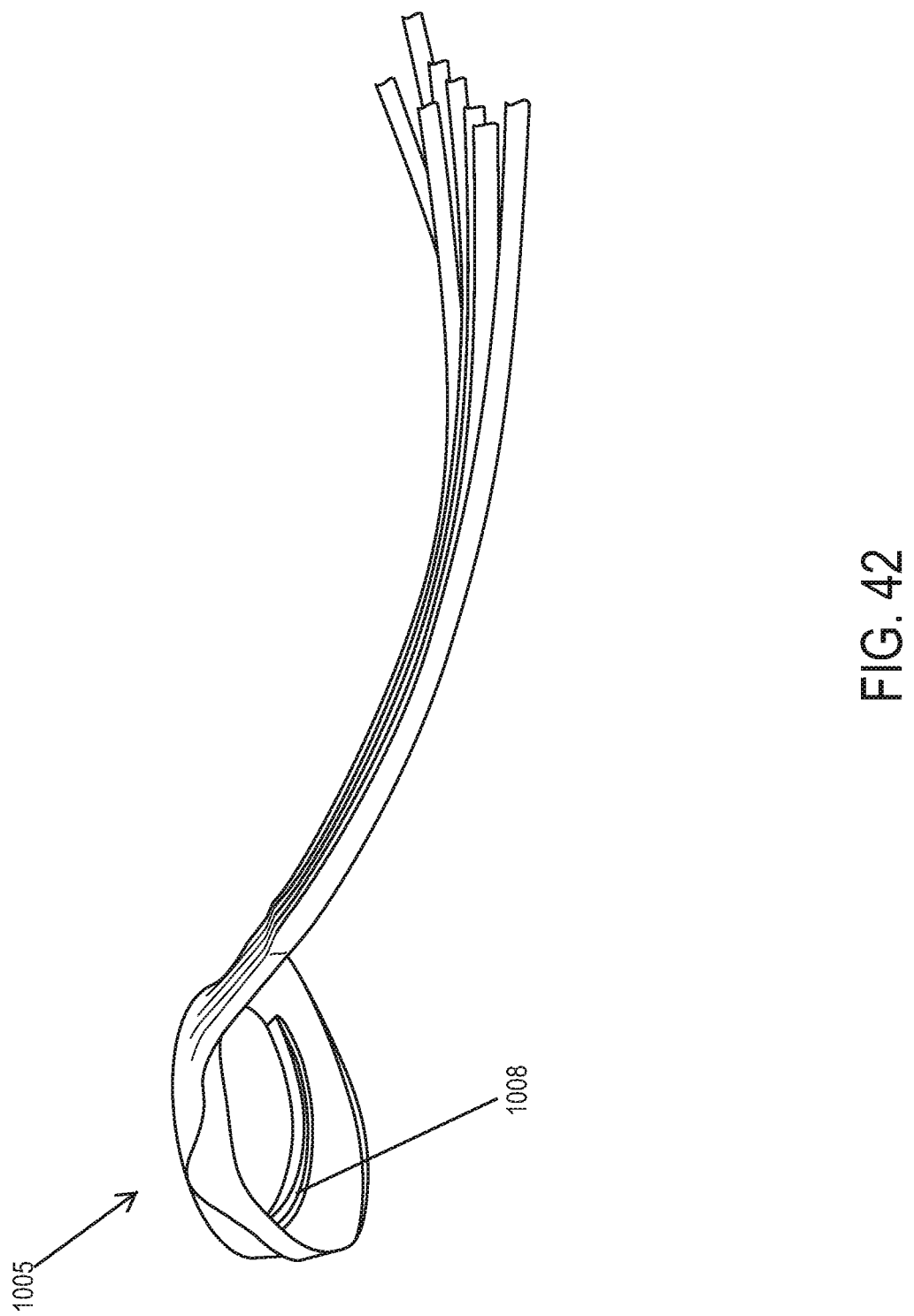
FIG. 42 shows a bottom perspective view of the light projection element shown in FIG. 41.

FIGS. 41 and 42 respectively depict top and bottom perspective views of another example embodiment of a light projection element 1005. As shown, the light projection element 1005 is ring-like in shape. The light projection element 1005 also includes a coupling feature 1008 as shown in bottom perspective view in FIG. 42. The coupling feature 1008 in FIG. 42 is an integral part of the light projection element 1005. In the example embodiment, the coupling feature 1008 is a ledge or shelf. The ledge coupling feature 1008 may help to locate and/or align the light projection element 1005 on another component such as a camera assembly 350. Additionally, in some embodiments, adhesive or glue may be placed along the ledge coupling feature 1008 to fix the light projection element 1005 to another component such as a camera assembly 350. The light projection element 1005 is shown attached to an example camera assembly 350 in FIG. 46.

The light projection element 1005 shown in FIGS. 41-42 does not include a highly reflective coating or material 376 (see, for example. FIG. 37). The need for such a highly reflective coating or material 376 may be minimized by dimensioning the light projection element 1005 to increase or maximize the total internal reflection of light entering and within the light projection element 1005 where the emission of light is not desired. This may be done by ensuring any bend or bends have a large radius in areas of the light projection element 1005 where the emission of light is undesired. Additionally, this may be done by dimensioning a light projection element 1005 such that thickness variations throughout the light projection element 1005 do not introduce changes in the angle of incidence of light within the light projection element 1005 which would make the angle of incidence less than the critical angle. It may be desirable that the thickness of the light projection element 1005 does not decrease to less than the thickness of the optical fibers or flexible ribbon to which the light projection element is attached 1005. It may also be desirable that the surface of the light projection element 1005 be smooth in areas where the emission of light is not desired.

Figure 43:
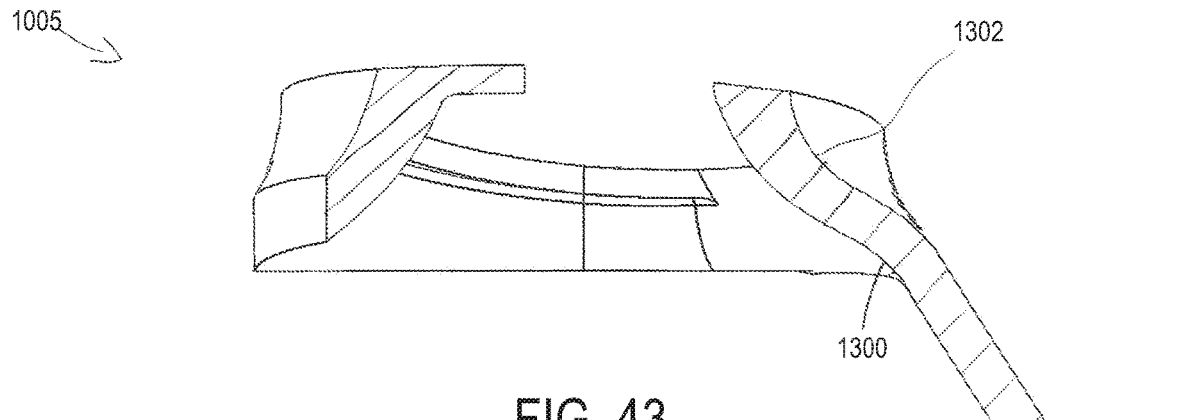
FIG. 43 shows a cross sectional view of the light projection element shown in FIGS. 41 & 42 taken at line 43-43 of FIG. 41.
Figure 44:
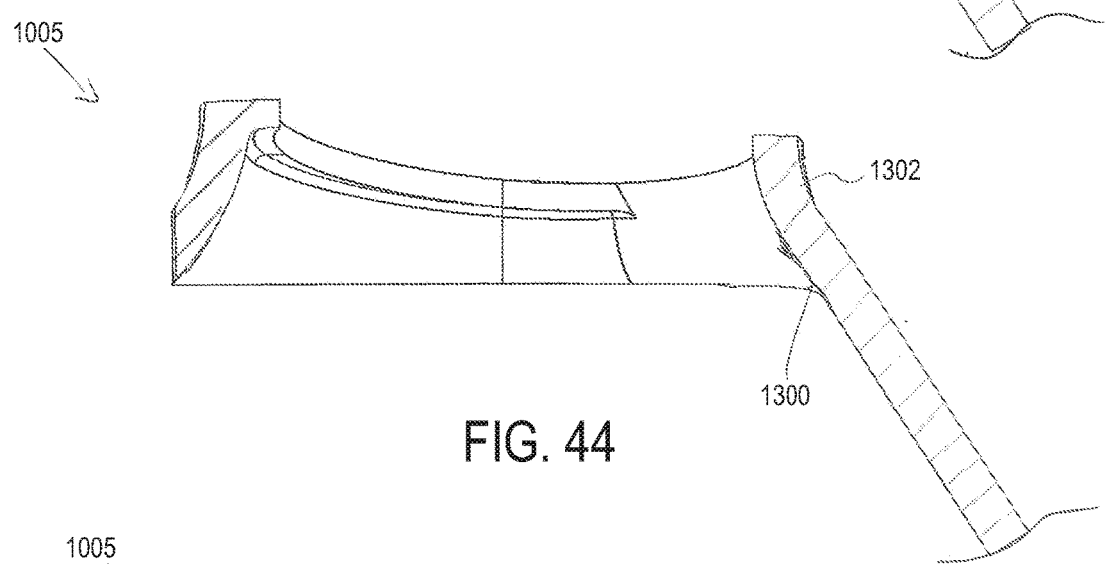
FIG. 44 shows a cross sectional view of the light projection element shown in FIGS. 41 & 42 taken at line 44-44 of FIG. 41.
Figure 45:
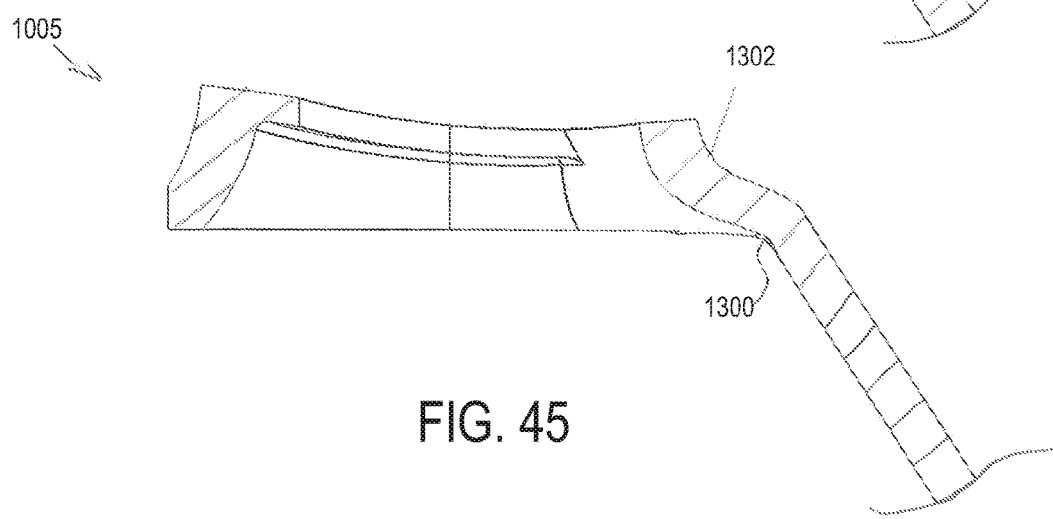
FIG. 45 shows a cross sectional view of the light projection element shown in FIGS. 41 & 42 taken at line 45-45 of FIG. 41.

FIGS. 43, 44, and 45 depict a number of cross sections of the light projection element 1005 depicted in FIGS. 41-42. The cross sections are respectively taken at lines 43-43, 44-44, and 45-45 of FIG. 41. As shown, light entering the light projection element 1005 must traverse a first bend 1300 and second bend 1302 before being emitted out of the top surface of the light projection element 1005. As shown in FIGS. 43-45, the light projection element 1005 may be shaped such that the radii of these bends vary depending on the plane of the light projection element 1005. The radius of each of these bends 1300 and 1302 may be chosen so as to be as gradual as possible in the available space in a given plane. Also as shown, the thickness of the light projection element 1005 is kept generally constant. This ensures that changes in angle incidence due to thickness variation are minimized.

Figure 46:
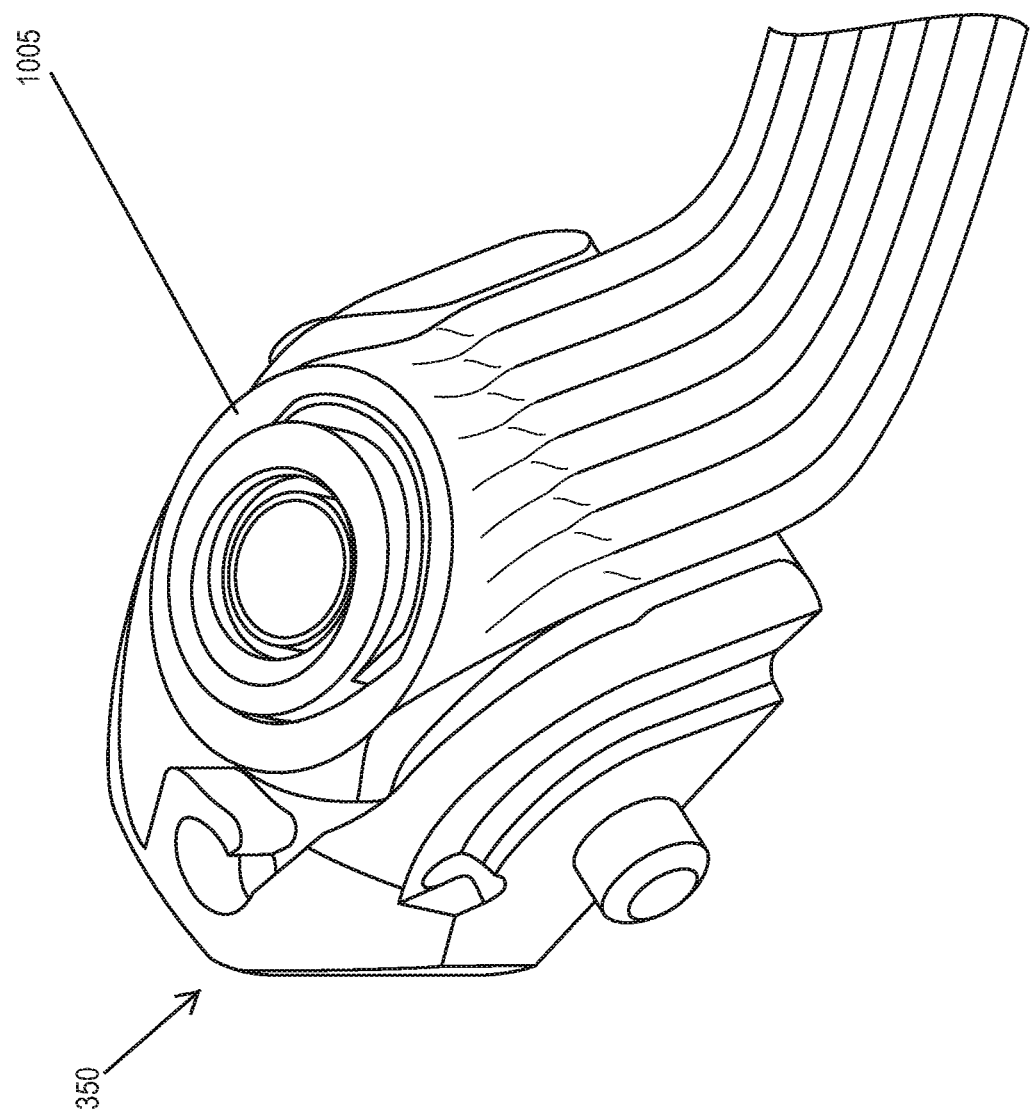
FIG. 46 shows a top perspective view of a camera assembly on which the light projection element of FIG. 41 is mounted.

The light projection element 1005 shown and described in relation to FIGS. 41-45 is attached to an example camera assembly 350 in FIG. 46. As shown the light projection element 1005 is arranged such that it projects light into a primary illumination field (the surrounding area around this primary illumination field also may be illuminated due to diffusion and reflection of the emitted light) which is substantially coincident with the field of view of the lens assembly 354.

FIGS. 47-60 detail a process and a number of example apparatuses for creating a light projection element of a desired size and shape connected to one or more optical fiber(s). Such a process may be useful in any number of applications. As indicated above, the process may be used to create a light projecting element for an endoscopic instrument or other medical apparatus. A light projecting element created via such a process may also be used in any of a variety of imaging applications. Such a process may also be useful to create light projecting elements in other articles or for other applications.

The process described in relation to FIGS. 47-60 may be advantageous for a number of reasons. Among these reasons, the process allows a light projecting element of a desired size and shape to be constructed for little more than the material cost. It also allows for there to be no mechanical break between an optical fiber or fibers and the light projection element. This may help to avoid light loss which may otherwise be introduced at a junction. It obviates the need for time consuming routing of individual optical fibers. The process allows for easily repeatable creation of a light projection element optimized for maximum light output. Furthermore, among other advantages, the process allows a number of individual fibers to be brought to or routed to a location and then formed into the shape of the desired light projection element. Thus the final light projection element may be dimensioned such that it is larger than any restrictions in the routing pathway.

Figure 47:
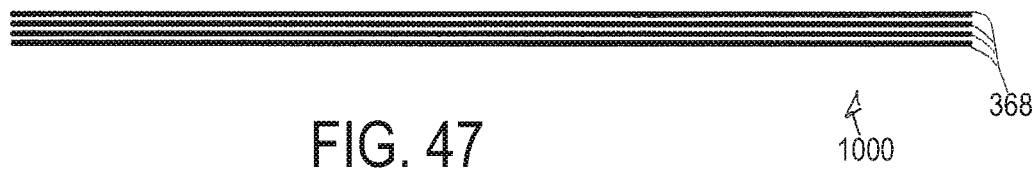
FIG. 47 shows a top view of number of illumination fibers which are included in a flexible ribbon.
Figure 48:
FIG. 48 shows a top view of a number of illuminations fibers of a flexible ribbon in which one end of the ribbon has been looped over itself.

FIGS. 47-50 depict an example process of making an exemplary light projection element or emitter 2005 molded from, fused with or attached to a flexible plastic optical fiber bundle or ribbon 1000. Particularly if molded from a flexible plastic optical fiber bundle, the light emitter comprises a solid transparent plastic light emitting member of the flexible optical fiber bundle, shaped in a pre-determined manner according to the molding forms selected to produce it. The emitter in this case may be considered a passive light emitter, in that it conducts and emits light sourced from a proximal end of the optical fiber bundle. Examples of plastic optical fiber material may include acrylic or polycarbonate, among other materials. A flexible optical fiber ribbon 1000 is shown in FIG. 47. The individual optical fibers 364 comprising the flexible ribbon 1000 are shown in FIG. 47. One end of the flexible ribbon 1000 may be looped around until the ends of the optical fibers 364 lay back on themselves as shown in FIG. 48. The looped end of the flexible ribbon 1000 may then be formed and fused using, for example, compression molding, into the desired functional shape as a light projection element or light emitter 2005. Preferably, the looping of optical fibers 364 at the end of the flexible optical fiber ribbon 1000 allows the light projection element 2005 to be formed without creating any internal voids in the formed element. Alternatively, the ends of the various optical fibers 364 may be melted into a slug of sufficient material prior to the final molding process to form the desired light projection element 2005. Some light projection elements 2005 may not require this melting or looping so long as enough material is present to form the light projection element 2005. The light projection element 2005 may be formed by any suitable means or combination of means such as a coining process, compression molding, stamp/die cut process, RF heating process, etc.

In some embodiments, a top form 1052a, (see FIG. 51) may include a mandrel or the like to facilitate looping of the optical fibers 364. Additionally, in some specific embodiments, optical fibers 364 may, for example, be wrapped around a mandrel on a camera assembly 350 (see, for example, FIG. 22) and then formed and fused into the light projection element 2005. In such embodiments, a portion of the end product, in this case a camera assembly 350 (see, for example, FIG. 22), may thus act as one of the forms 1052a,b of FIG. 51. In other applications, one or more of the forms 1052a,b may be another part of an assembly of an end product. In the example embodiment depicted in FIGS. 47-50, the forms 1020 may comprise a force or plug member and mating mold form or cavity.

Figure 49:
FIG. 49 shows a side view of a looped end of a flexible ribbon being formed into a light projection element.
Figure 50:
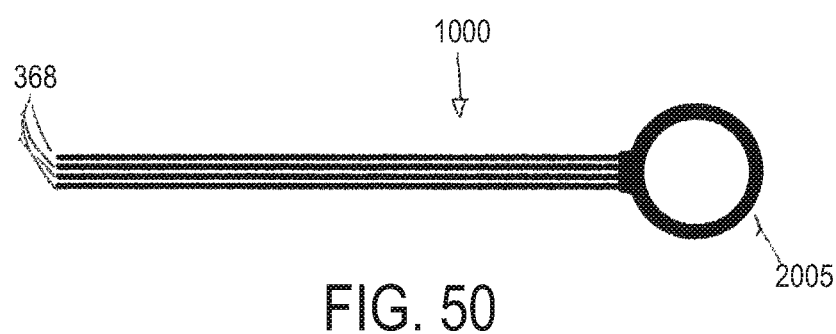
FIG. 50 shows a top view of a flexible ribbon with a fully formed light projection element.

FIG. 49 illustrates a side view of a flexible optical fiber ribbon 1000 and the loop of optical fibers 364 being formed into a light projection element or emitter 2005. As shown in the example in FIG. 49, the light projection element 2005 is formed through a coining/stamping process in which pressure is applied between two forms 1020. FIG. 50 shows a completed flexible ribbon 1000 in which the loop of optical fibers 364 has been formed and fused into a light projection element or emitter 2005. There is no mechanical break between the flexible ribbon 1000 and the light projection element 2005. This gives the assembly a robustness and integrity, while also allowing for the efficient transmission of light. As shown, the light projection element 2005 is shaped as a ring, although any other desired shape that places the light emitter next to the lens elements of the camera assembly may be formed in this manner. In some embodiments, selective portions of the flexible optical fiber ribbon 1000 and/or light projection element 2005 may then be coated or masked with a highly reflective material 376 (as described, for example, in relation to FIGS. 33-40). In some embodiments, a texture 1010 or textures 1010 may be added to the light projection element 2005 after it has been formed. As mentioned above, the light projection element 2005 may be formed such that it includes a coupling feature 1008 (see, for example, FIG. 38). Additionally, in some embodiments, a fill material may be placed into one or both forms 1020 before forming the light projection element 2005.

Figure 51:
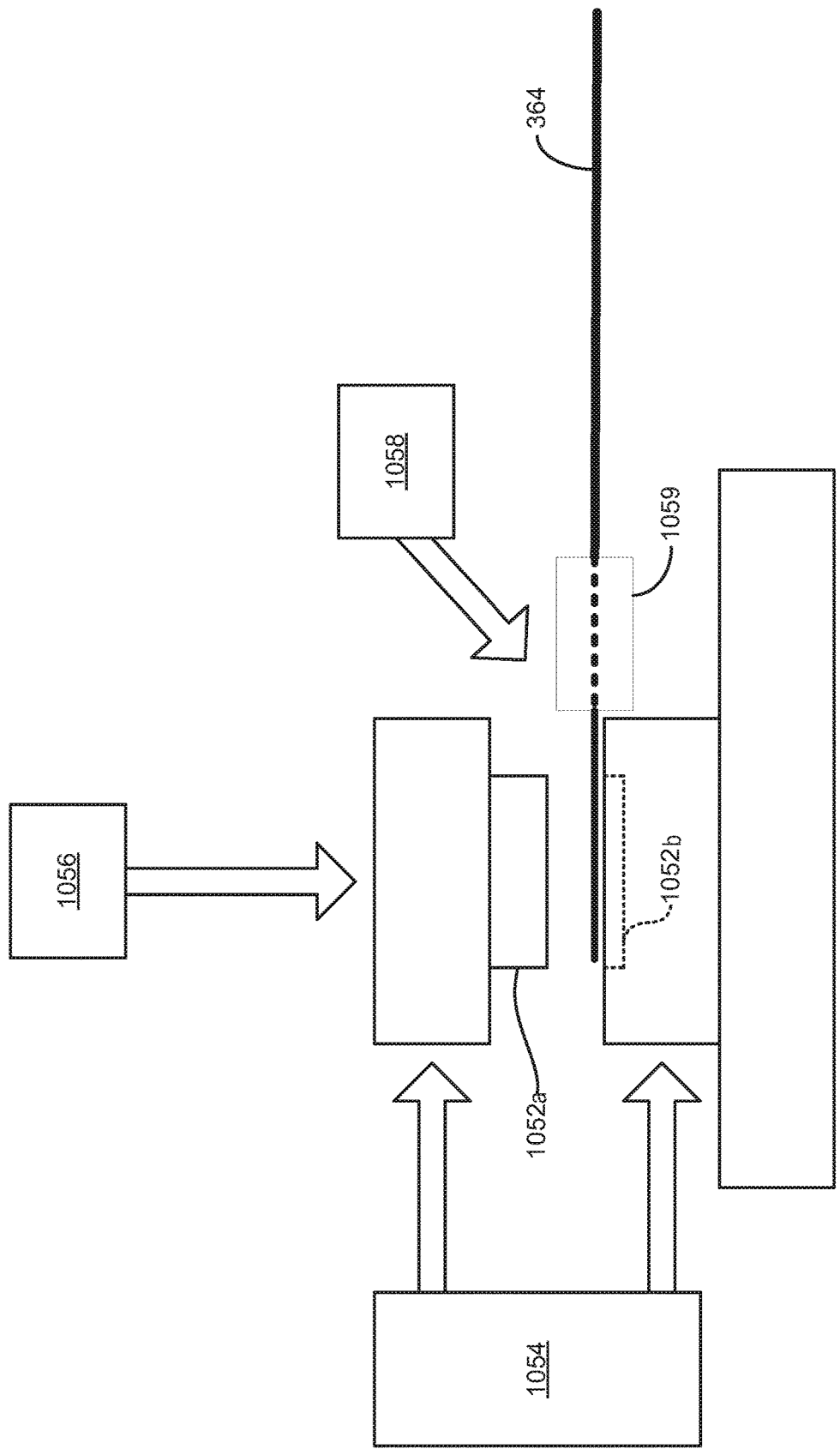
FIG. 51 shows a representational illustration of an apparatus which may be used to form a light projection element.

FIG. 51 depicts an example block diagram of an apparatus 1050 which may be used to create a light projection element or light emitter. In the example in FIG. 51, a light projection element may be created by fusing one or a number of optical fibers 364. In FIG. 51, the fibers 364 are fused together into the desired light projection element with a combination of heat and pressure, as in, for example, compression molding. Alternatively, the fibers 364 may be fused by a chemical process (e.g. using a solvent). As shown, the apparatus 1050 includes forms 1052a, b. The apparatus 1050 also may include a heat source 1054 in thermal communication with the forms 1052a, b. Heat may be applied to the forms before, during and/or after the placement of the fiber bundle on the mold form. A pressure source 1056 may be included in the apparatus 1050 and may be arranged to exert pressure on one or both forms 1052a, b and/or cause the forms 1052a, b to be brought together. Additionally, a cooling source 1058 may be included in the apparatus 1050.

The cooling source 1058 is configured to cool at least a transitional section of the fiber bundle adjacent to the section on the mold form. The transitional section will consequently have a distal region comprising partially merged and solidified fibers, and a more proximal region in which the individual flexible fibers are preserved. The transitional section thus has the ability optionally to maintain a fixed angular relation to the formed light emitter after cooling. Optionally, a jacket or heat sink 1059 may be placed on the optical fiber(s) 364 proximal to the transition section while a light projection element or emitter is being formed.

In operation, the heat source 1054 may be used to heat the forms 1052a and/or 1052b. The forms 1052a, b may be heated to a predefined temperature. The temperature selected may depend on the optical fiber 364 material being used. The temperature used may be selected such that it is not so high as to burn the optical fiber 364 material, or in some cases any coating on the material, but sufficient to cause complete melting of the optical fiber material 364. Additionally, the temperature selected may be sufficient to melt the optical fiber material within the forms 1052a, b while leaving the material near but not in the forms 1052a, b substantially unaltered or undistorted. In an embodiment, the temperature range chosen straddles the temperature point at which the material melts. Such a temperature selection may be advantageous because it reduces the amount of time that the material remains in the apparatus 1050 to cool. In some embodiments, the temperature used may be dependent on the amount of heat energy which a cooling source 1058 and/or heat sink 1059 is capable of removing. In a specific embodiment in which the optical fiber 364 material being used is acrylic, an appropriate temperature range may be between about 270 degrees to 280 degrees Fahrenheit.

The optical fiber or fibers 364 may be placed on one of the forms 1052b. The forms 1052a, b may then be brought together and pressure may be exerted on the forms 1052a, b. The heat and pressure may cause the optical fiber or fibers 364 to melt and fuse into the desired light projection element as dictated by the shape and internal features of forms 1052a, b. In some embodiments, a fill material may also be placed in the forms 1052a, b such that the desired light projection element is laced or impregnated with the fill material during melting and fusing.

In embodiments where the fibers 364 are fused by a chemical process, a solvent may for example be introduced to the mold form 1052b before or after the illumination fiber or fibers 364 has been placed onto the mold form 1052b. The forms 1052a, b may be brought together and pressure may be exerted on the forms 1052a, b. The action of the solvent may then cause the fiber or fibers 364 to dissolve and fuse into a shape as dictated by the forms 1052a, b. The fiber or fibers 364 may then be allowed to set before the forms 1052a, b are separated. In embodiments using a solvent, a cooling source 1058 and heat sink 1059 may not be necessary.

In some embodiments, a cooling source 1058 may be used to remove heat energy from portions of the optical fiber or fibers 364 where melting/fusing is not desired (e.g. near the heated forms 1052a, b or at the transition area between the light projecting element and the unaltered fiber or fibers). A heat sink 1059 (e.g. a metallic sleeve placed around the fiber bundle or ribbon) may also or additionally be employed to the same end.

The forms 1052a, b may then be allowed to cool. Once the forms 1052a, b have sufficiently cooled, they may be separated and the optical fibers 364 and fused light projection element or emitter may be removed. In some embodiments, a cooling source 1058 may be used to speed cooling of the forms 1052a, b. Cooling the forms 1052a, b allows the melted optical fibers 364 to solidify and fuse into the shape of light projection element. Preferably, the forms 1052a, b are cooled until the optical fiber 364 material is no longer hot enough to flow. In some embodiments, the apparatus 1050 may include an ejector (not shown) which may eject the light projection element once the forms 1052a, b are separated. After ejection, any flashing on the light projection element may then be removed.

The forms 1052a, b may be constructed of metal or other suitable heat-stable material. The shape of the desired light projection element may be cut, milled, recessed, etc. into the forms 1052a, b. As described above in relation to FIGS. 39 and 40, the light projection element may include surface texturing over the illumination surfaces 1010 and/or features such as coupling features 1008. Such texturing and features may be included as part of the shape which is cut, milled, recessed, etc. into the forms 1052a, b.

In some embodiments, the heat source 1054 may be electric. In some embodiments, the forms 1052a, b may include resistive heating elements therein. In some embodiments, the heat source 1054 may be one or more heat rods in thermal communication with the forms 1052a, b. Any other suitable heating element may also be used. Additionally, a thermocouple (not shown) or temperature sensor may be used to provide temperature feedback to ensure that the forms 1052a, b are maintained at the desired temperature. The heat output of the heat source 1054 may be adjusted based upon readings from the temperature sensor.

The pressure source 1056 may be any suitable pressure source. In various embodiments, the pressure source 1056 may be a manual pressure source, mechanical or electromechanical pressure source, pneumatic pressure source, hydraulic pressure source, etc.

The cooling source 1058 may be any suitable cooling source. In various embodiments, the cooling source 1058 may be a fan, compressor or the like connected to a conduit to direct cooling air to flow around a desired portion of the optical fiber or fibers 364. In some embodiments, the cooling source 1058 may be a liquid cooling source, for example, a water jacket surrounding the optical fiber or fibers 364.

The heat sink 1059 may be made of any suitable material and may take any suitable shape or form. Preferably, the heat sink 1059 is made of a material with a higher melting temperature than the optical fiber material or operating temperature of the apparatus 1050. In some embodiments, a jacket or heat sink 1059 may also serve additional purposes. For example, the heat sink 1059 may also function as a guide member which serves to constrain the optical fiber(s) 364 in a desired orientation (e.g. a flat ribbon) while the light projection element is being formed. In some embodiments where a heat sink 1059 may not be necessary, a guide member may still be included. Such a guide member may not require the heat dissipating properties of a heat sink 1059.

Figure 52:
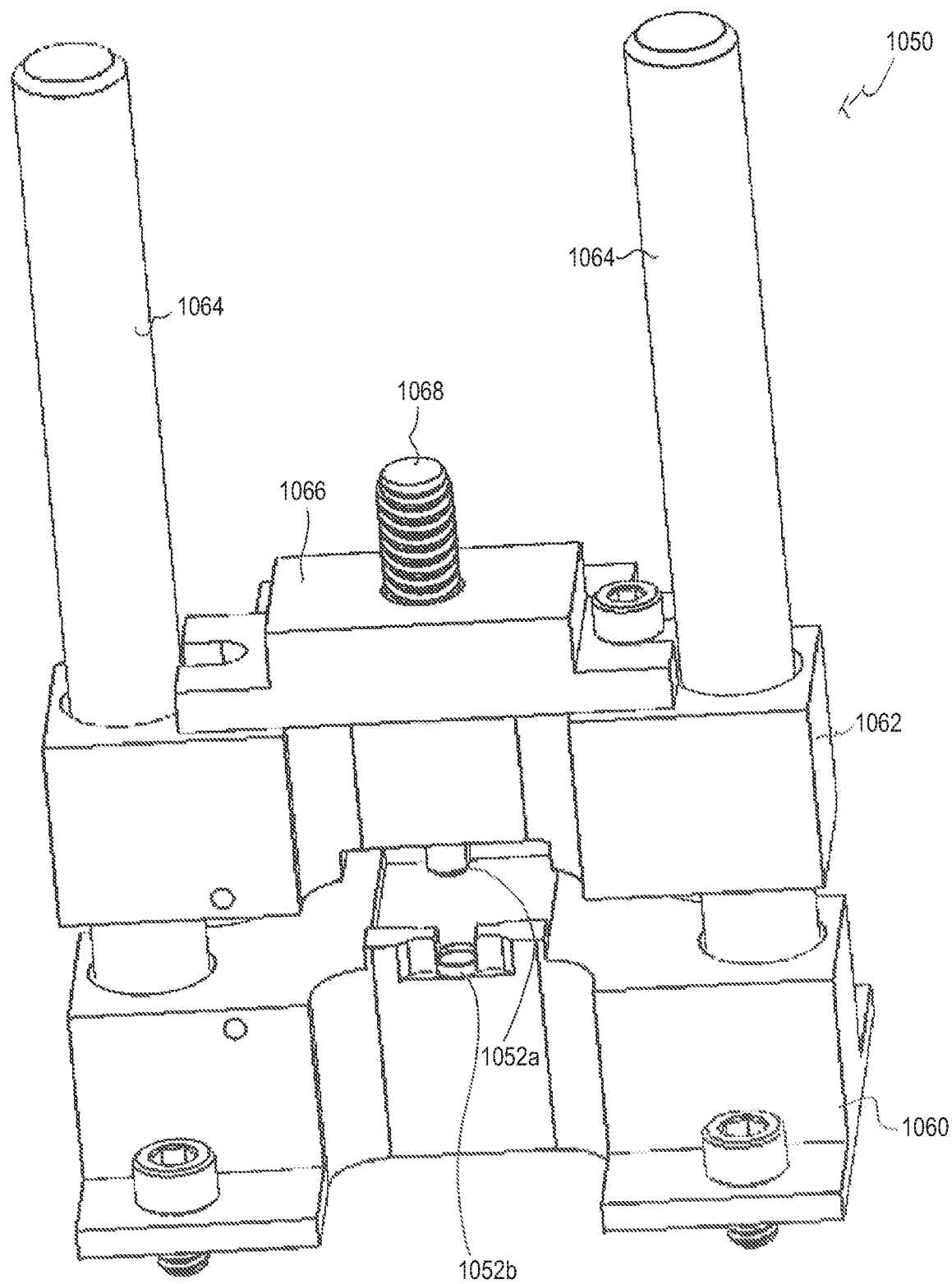
FIG. 52 shows an example embodiment of an apparatus which may be used to form a light projection element.
Figure 53:
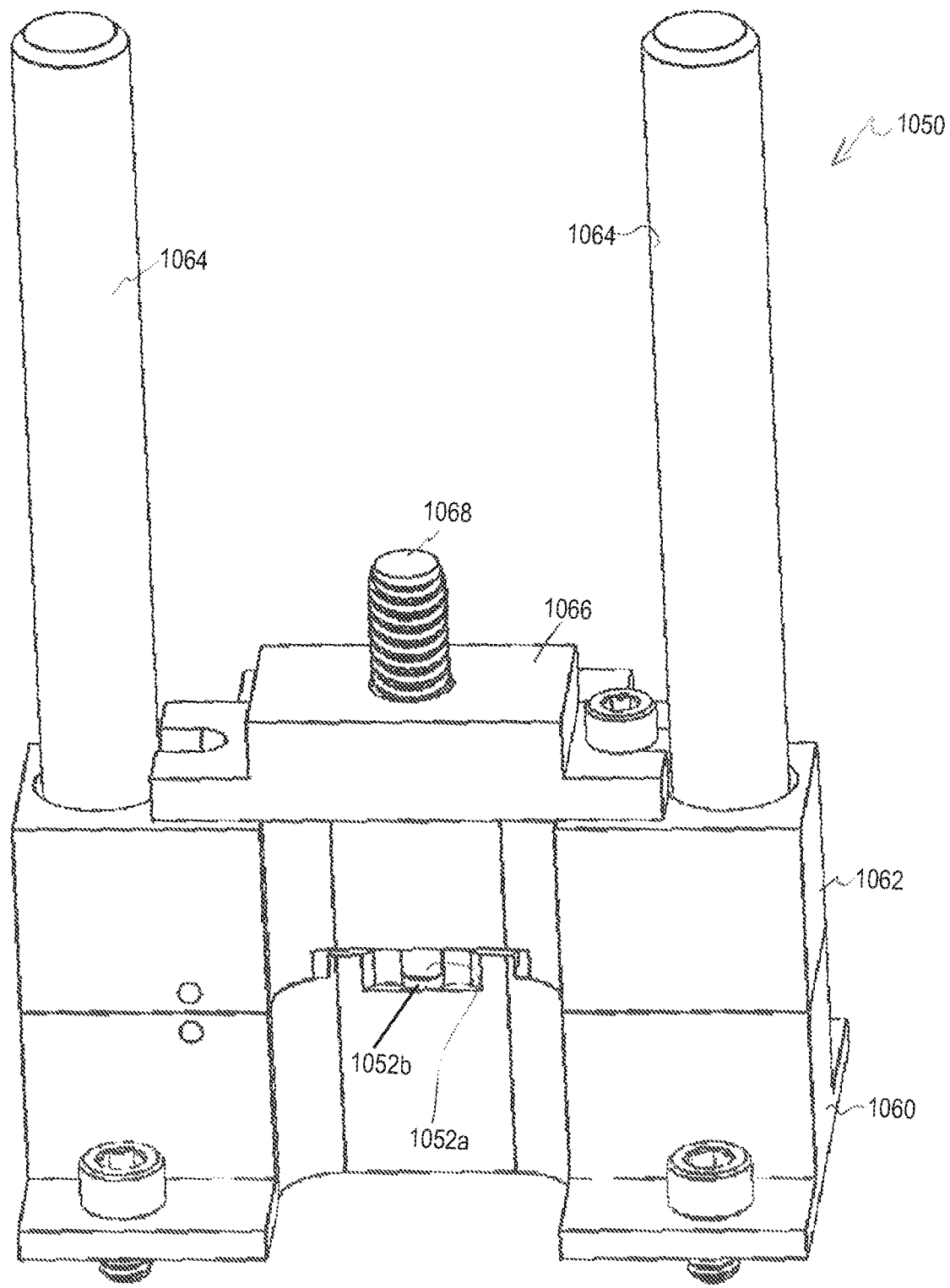
FIG. 53 shows an example embodiment of an apparatus which may be used to form a light projection element.
Figure 54:
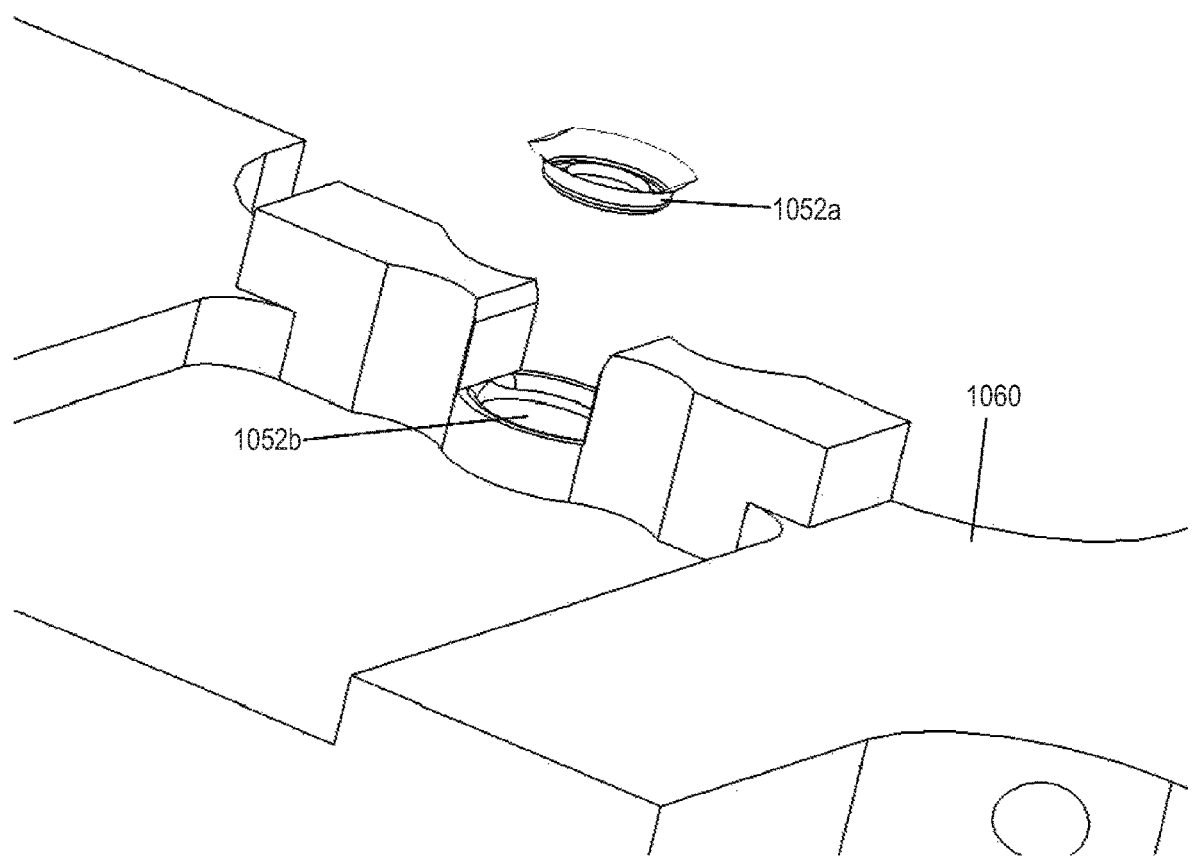
FIG. 54 show an embodiment of two opposing forms which may be used to make a light projection element.

Referring now to FIGS. 52 and 53 a specific example of an apparatus 1050 which may be used to create a light projection element is depicted. As shown, the apparatus 1050 is similar to that shown in FIG. 51. The apparatus 1050 includes a stationary element 1060 and a moving or force element 1062. The apparatus 1050 additionally may include guides 1064 which precisely constrain the movement of the moving element 1062. In the example embodiment shown in FIG. 52, the guides 1064 are rails. A form 1052a or 1052b is included on both the stationary element 1060 (e.g. a mold cavity) and the moving element 1062 (e.g. a force or plug member). The forms 1052a, b are disposed on opposing surfaces of the stationary element 1060 and the moving element 1062. When the moving element 1062 is brought together with the stationary element 1060 (see FIG. 53) in the presence of an appropriate amount of heat and pressure, the forms 1052a, b cooperate to melt the optical fiber material and form a light projection element from one or more optical fibers placed in the apparatus 1050. A close up perspective view of the form (or mold cavity) 1052b of the stationary element 1060 and the form (or force/plug member) 1052a of the moving element 1062 is depicted in FIG. 54.

Once the stationary element 1060 and the moving element 1062 are brought together, pressure from a pressure source 1056 (see FIG. 51) may be exerted on the optical fiber(s) via the forms 1052a, b to aid in formation of the light projection element or light emitter. As mentioned above, the forms 1052a, b (and in some embodiments, stationary element 1060 and moving element 1062 to which they are attached) may be heated as mentioned above. The heat may also aid in the formation of the light projection element.

The apparatus 1050 shown in FIG. 52 additionally includes a coupling element 1066. The coupling element 1066 allows the moving element 1062 to be attached to a pressure source 1056 (see FIG. 51). To facilitate such coupling, the coupling element in FIG. 52 includes a threaded shaft 1068. In some embodiments, the threaded shaft 1068 may be threaded into a ram element (not shown) of a pressure source 1056.

Figure 55:
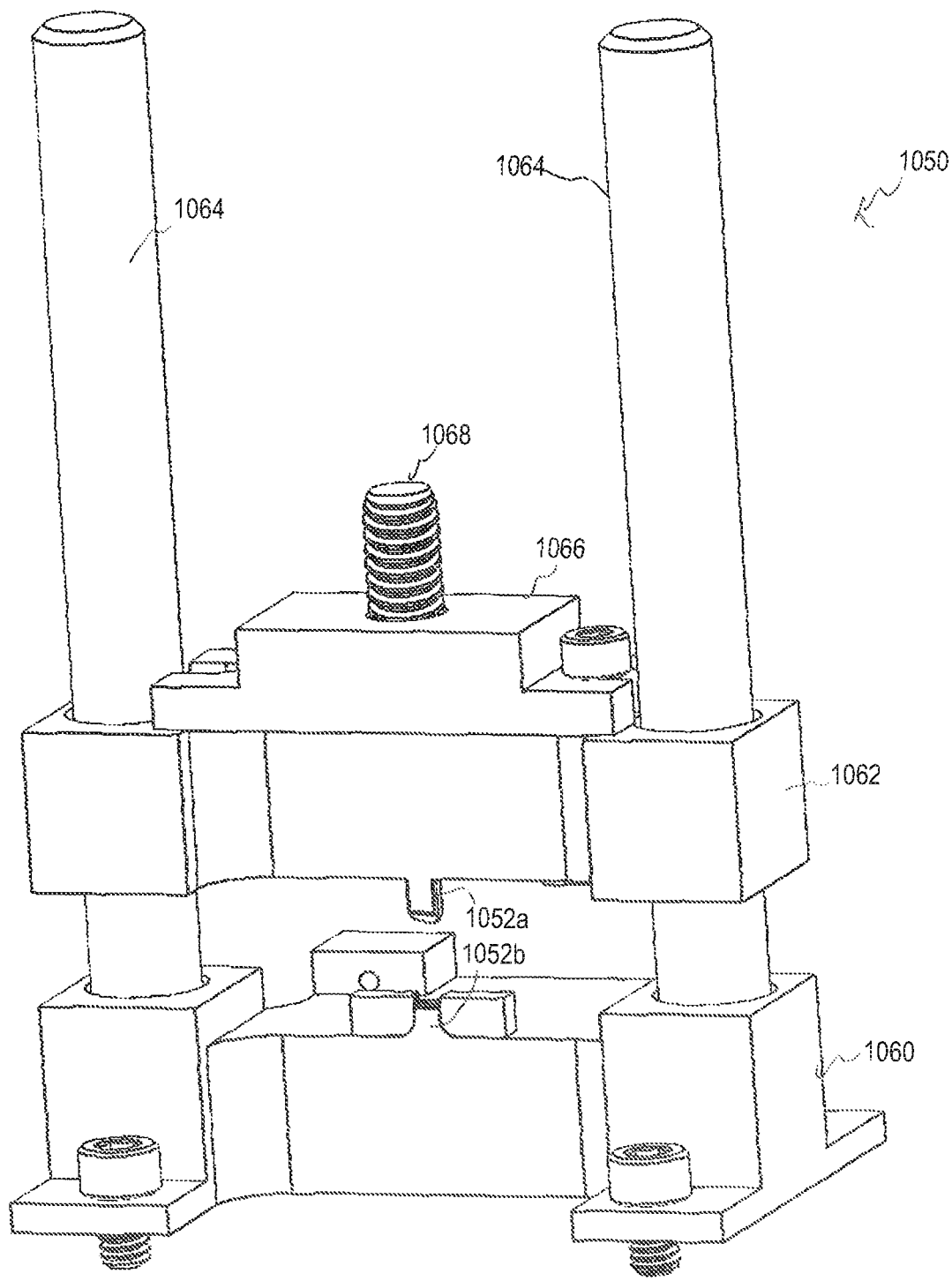
FIG. 55 shows an embodiment of an apparatus which may be used to make a light projection element.
Figure 56:
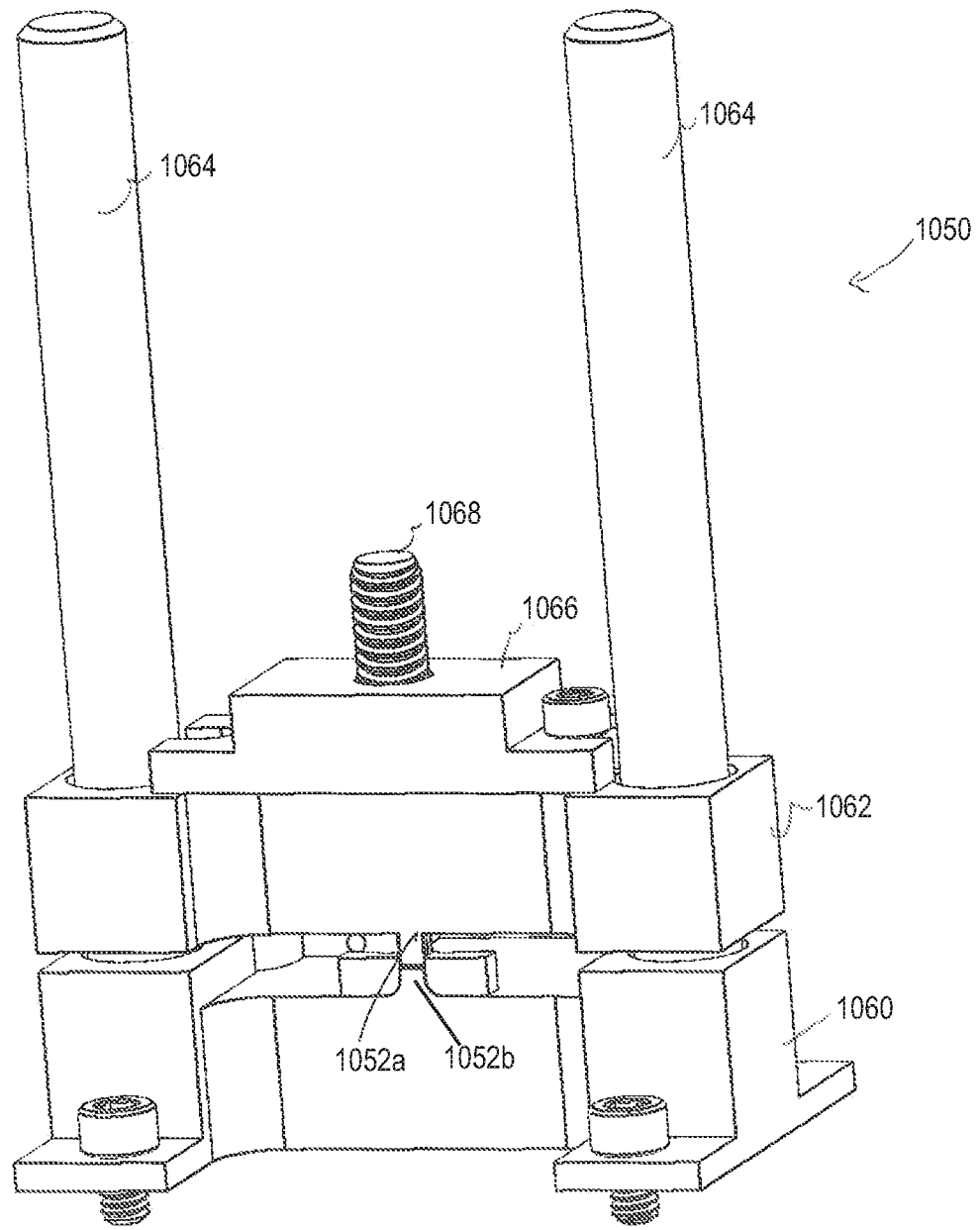
FIG. 56 shows an embodiment of an apparatus which may be used to make a light projection element.
Figure 57:
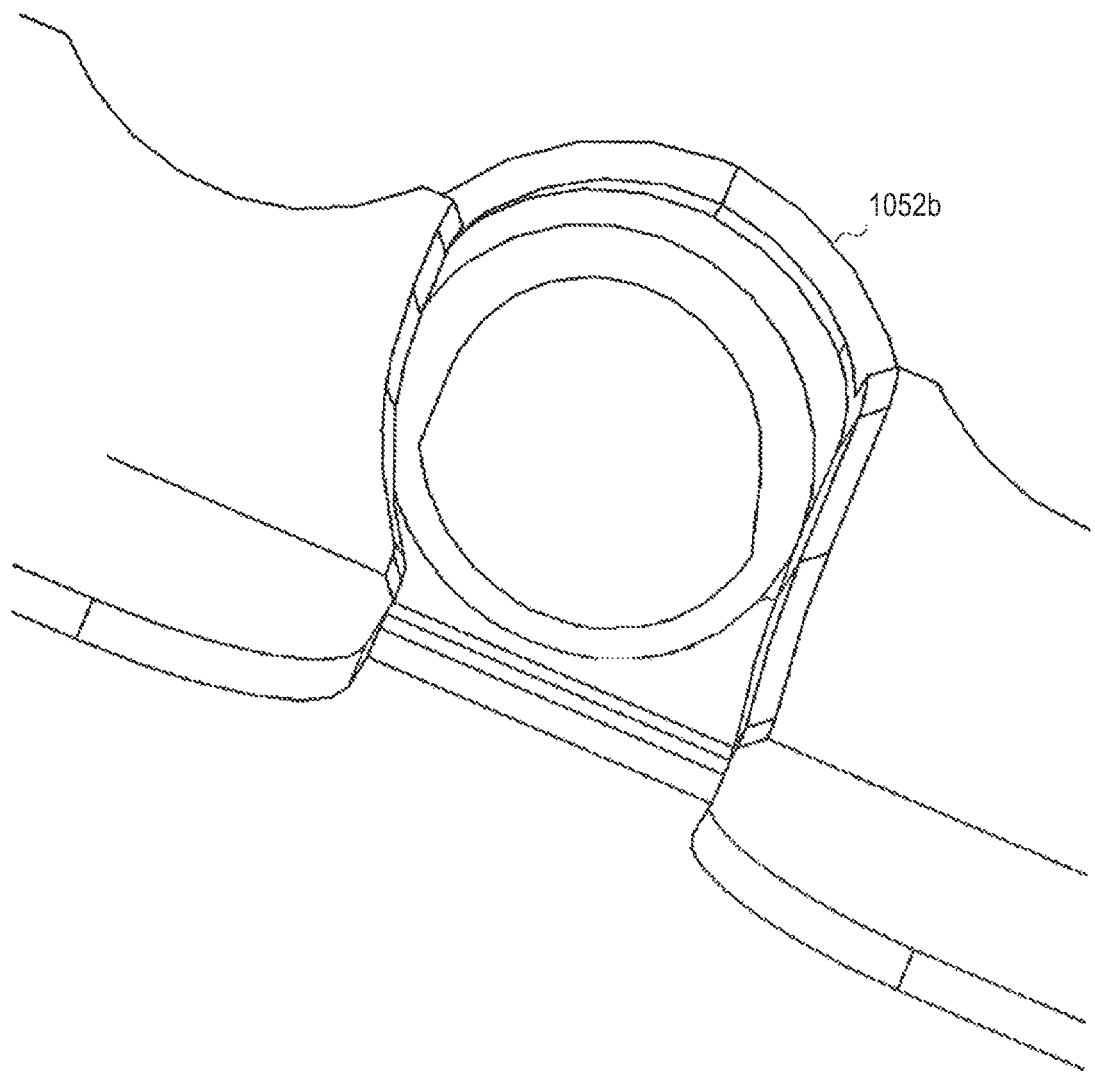
FIG. 57 shows an embodiment of a form which may be used to make a light projection element.
Figure 58:
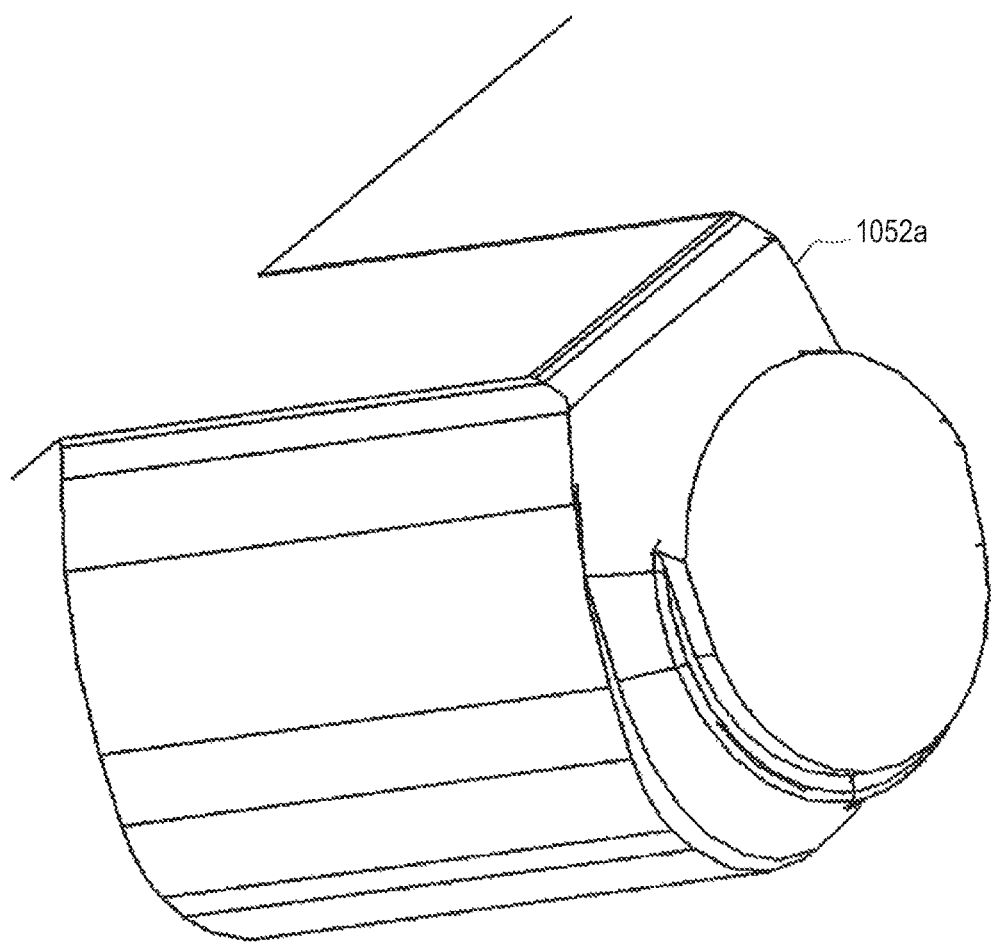
FIG. 58 shows an embodiment of a form which may be used to make a light projection element.

FIG. 55 and FIG. 56 depict another example embodiment of an apparatus 1050 which may be used to create a light projection element. As shown, the apparatus 1050 is similar to that shown in FIGS. 52-53. The apparatus 1050 includes a stationary element 1060 and a moveable element 1062. As in FIGS. 52 and 53 guides 1064, and a coupling element 1066 including a threaded shaft 1068 are also included. Also as in FIGS. 52 and 53, a form 1052a or 1052b is included on both the stationary element 1060 and the moving element 1062. The forms 1052a, b are disposed on opposing surfaces of the stationary element 1060 and the moving element 1062. When the moving element 1062 is brought together with the stationary element 1060 (see FIG. 56), the forms 1052a, b cooperate to form a light projection element from one or more optical fibers placed in the apparatus 1050. The forms 1052a, b included on the stationary element 1060 and the moving element 1062 in FIGS. 55-56 differ from those shown in FIGS. 52-53. A close up perspective view of the form 1052b of the stationary element 1060 and the form 1052a of the moving element 1062 in FIGS. 17 55-56 are respectively depicted in FIG. 57 and FIG. 58.

Figure 59:
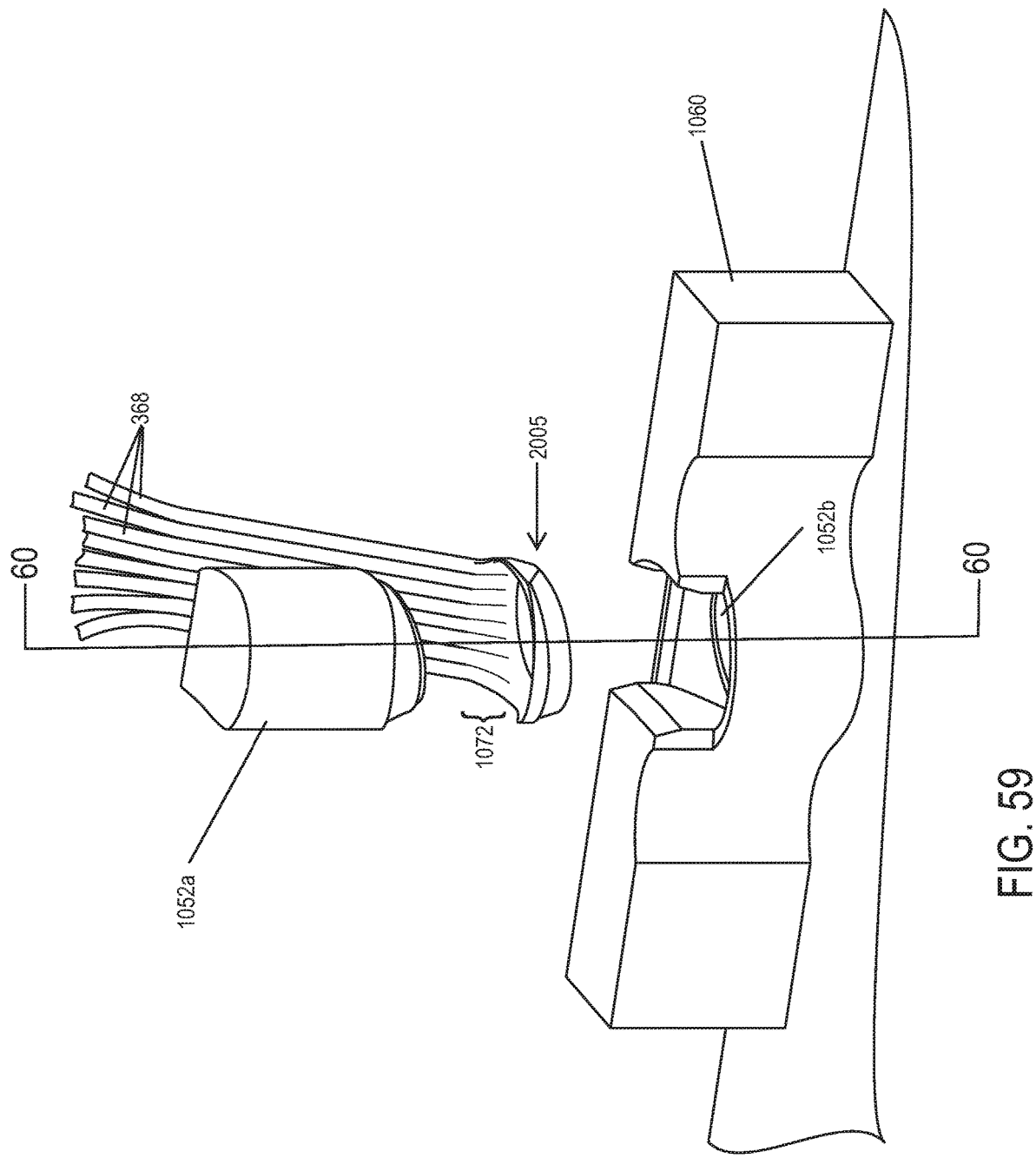
FIG. 59 shows an embodiment of an example apparatus which may be used to make a light projection element and a light projection element which may be made therefrom.

A close up perspective view of the form 1052b of the stationary element 1060 and the form 1052a of the moving element 1062 of FIGS. 55-56 are shown in FIG. 59. Also shown in FIG. 59 is an example light projection element 2005 which would result from use of the shown forms 1052a, b. The example light projection element 2005 in FIG. 59 is similar to that shown and described in relation to FIGS. 41-46.

As shown, a transition span or region 1072 is shown in FIG. 59 (and also FIGS. 41-46). The transition span 1072 is located between the light projection element 2005 and the individual optical fibers 364. A transition span 1072 may be created as a result of high heat in the area surrounding the light projection element 2005 dissipating as the element 2005 transitions to the more proximal optical fiber bundle. It may be desirable to produce as small a transition span 1072 as possible since the transition span 1072 may be brittle and relatively less pliant. As mentioned above, this may be accomplished through use of a heat sink 1059 (see, for example, FIG. 51) and/or a cooling source 1058 (see, for example, FIG. 51). In applications where the light projection element or emitter 2005 is to be placed on a pivoting or rotating assembly (e.g. the camera assembly 350 shown in FIG. 32) it may be desirable that such a span be fixedly attached to the assembly. This may ensure that the transition span 1072 is not subjected to excessive stress or bending. Instead, the stress and bending would then be applied to the more pliant, individual optical fibers 364 further away from the light projection element 2005 which are left substantially unaltered during the formation of the light projection element 2005.

Figure 60:
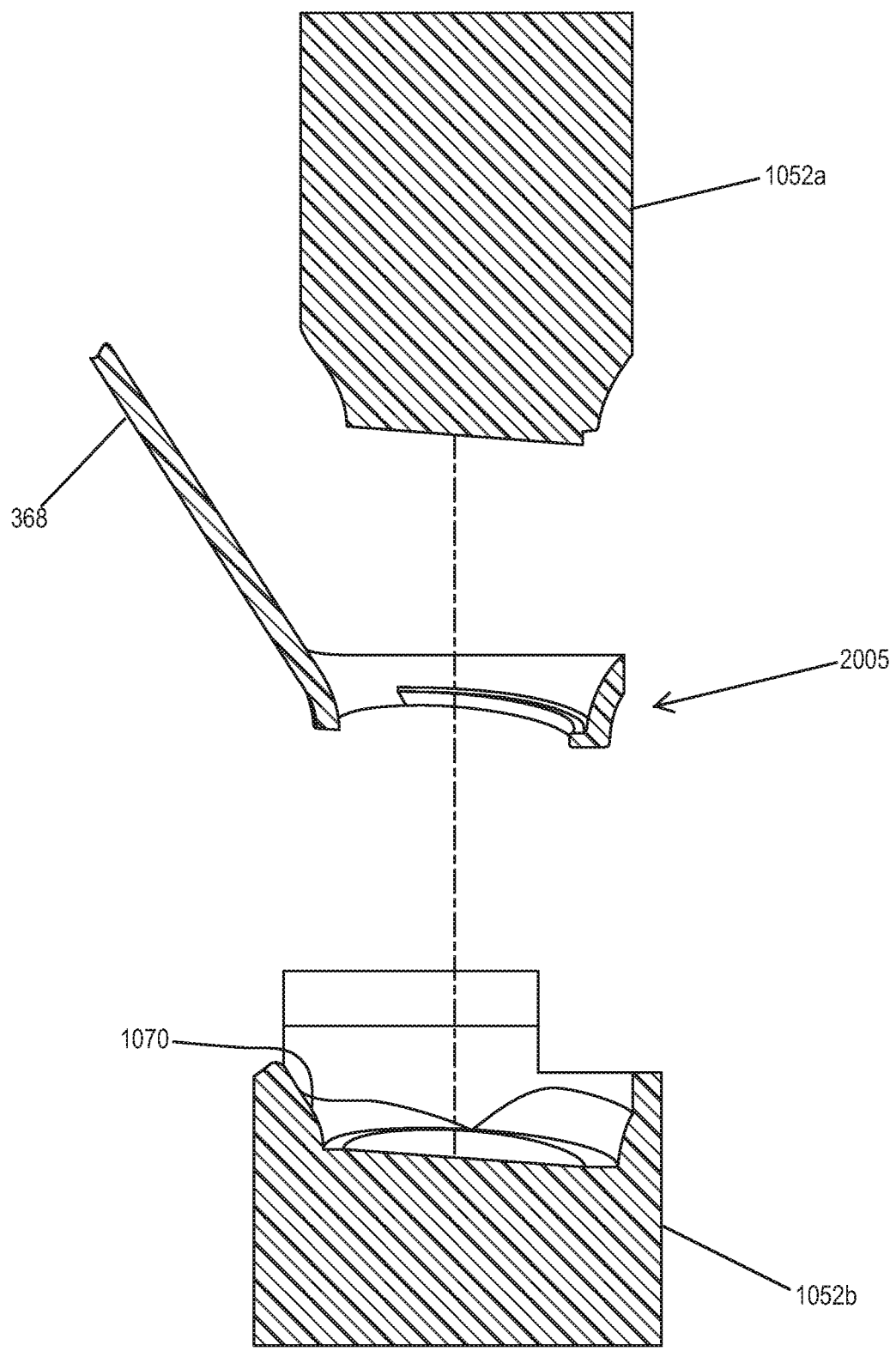
FIG. 60 shows a cross-sectional view of the apparatus in FIG. 59 taken at line 60-60 of FIG. 59.

Referring now also to FIG. 60, a cross-section of the apparatus 1050 and light projection element 2005 taken at line 60-60 of FIG. 59 is shown. One or more of the forms 1052a, b may include a fiber orienting feature. As shown, the mold form 1052b of the stationary element 1060 includes a fiber orienting incline feature 1070. Such an incline feature 1070 may be advantageous for a number of reasons. For example, an incline feature 1070 may help to ensure the optical fibers 364 transition into the light projection element or emitter 2005 in a desired arrangement, angle, orientation, etc. with respect to an illumination face of the formed light emitter. In the example embodiment, the incline feature 1070 serves to keep the optical fibers 364 in a substantially flat ribbon like arrangement. Additionally, the incline feature 1070 serves to constrain the optical fibers 364 such that they transition to the light projection element 2005 at a desired angle. At least part of the resulting transition section of the fiber bundle has been exposed to sufficient heat and/or pressure to solidify into a non-flexible material upon cooling.

Figure 61:
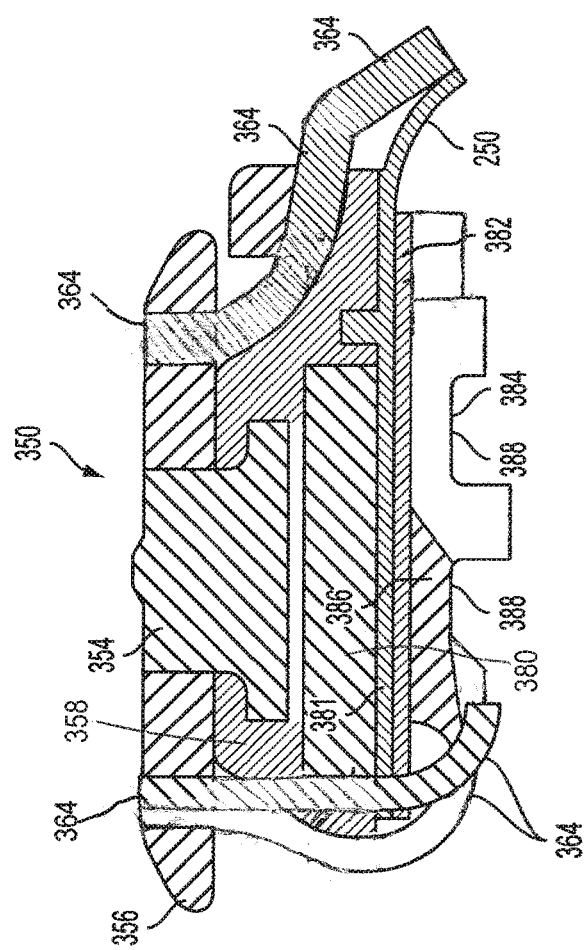
FIG. 61 shows a cross sectional view of an example camera assembly taken at line 61-61 of FIG. 22.

FIG. 61 shows a cross sectional view of an exemplary camera assembly including a lens assembly 354 taken at the cross-sectional plane represented by line 61-61 of FIG. 22. The lens assembly 354 is shown housed between the camera housing top 356 and camera housing bottom 358 as in FIG. 22. As shown, the lens assembly 354 is positioned to project an image onto the plane of an image sensor 380. The type of image sensor 380 may include, for example, a CCD image sensor, CMOS image sensor, etc. Preferably, the image sensor 380 may be housed in a sealed section of the camera assembly 350 to guard against fluid exposure. In a disposable endoscope, a less costly process may be used to seal the image sensor against fluid exposure (e.g., using a clear epoxy compound), because the assembly would not then be designed to withstand the rigors of sterilization and reuse.

As shown in FIG. 61 the image sensor 380 may be electrically coupled to a flex board 381 of the flex cable 250. In some embodiments, a conformal coating material may be used to give added protection against moisture, and optionally may be constructed to support the joints of a ball grid array mounting for the image sensor 380. The flex cable 250 may provide power to the image sensor 380, as well as the means of conveyance of data and/or commands from/to the image sensor 380. In some embodiments, a stiffener 382 may be included in the camera assembly 350. In the example embodiment shown in FIG. 61, a stiffener 382 is positioned to strengthen the structure on which the image sensor 380 is supported, which may help to protect the physical integrity of the image sensor 380. The stiffener 382 may comprise, for example, a thin aluminum backing (which in an exemplary embodiment may be about 0.002 inch thick).

The camera assembly 350 may also include one or a number of fiber guides 384. In the example shown in FIG. 61, a fiber guide 384 is coupled to the bottom face of the camera housing bottom 358. The example fiber guide 384 includes a guide trough 386. The back wall of the guide trough 386 of the fiber guide 384 may be seen projecting toward the bottom of the page in FIG. 61. The fiber guide 384 may also be or include a number of directing notches or channels 388 which in the example fiber guide 384 shown in FIG. 61 are recessed into the back wall of the guide trough 386. In some embodiments, including the exemplary embodiment in FIG. 61, directing notches or channels 388 may be formed in one or both of the camera housing top 356 and camera housing bottom 358. The fiber guide 384 may help to route the illumination fibers 364 during assembly of the endoscope 10. The fiber guide 384 may also act to keep the illumination fibers 364 in place during operation of the endoscope 10. The location, shape, number, size, etc. of the fiber guides 384 may vary depending on the specific configuration of the endoscope 10. In some embodiments, glue, epoxy or another suitable adhesive or agent may be used in addition to the fiber guides 384 to help keep the illumination fibers 364 in the desired location. In some cases, for example, in which light guides or light projection element (as shown, e.g., in FIG. 33-40 or as shown in FIG. 62) are used, fiber guides 384 may not be used in an assembly.

Figure 62:
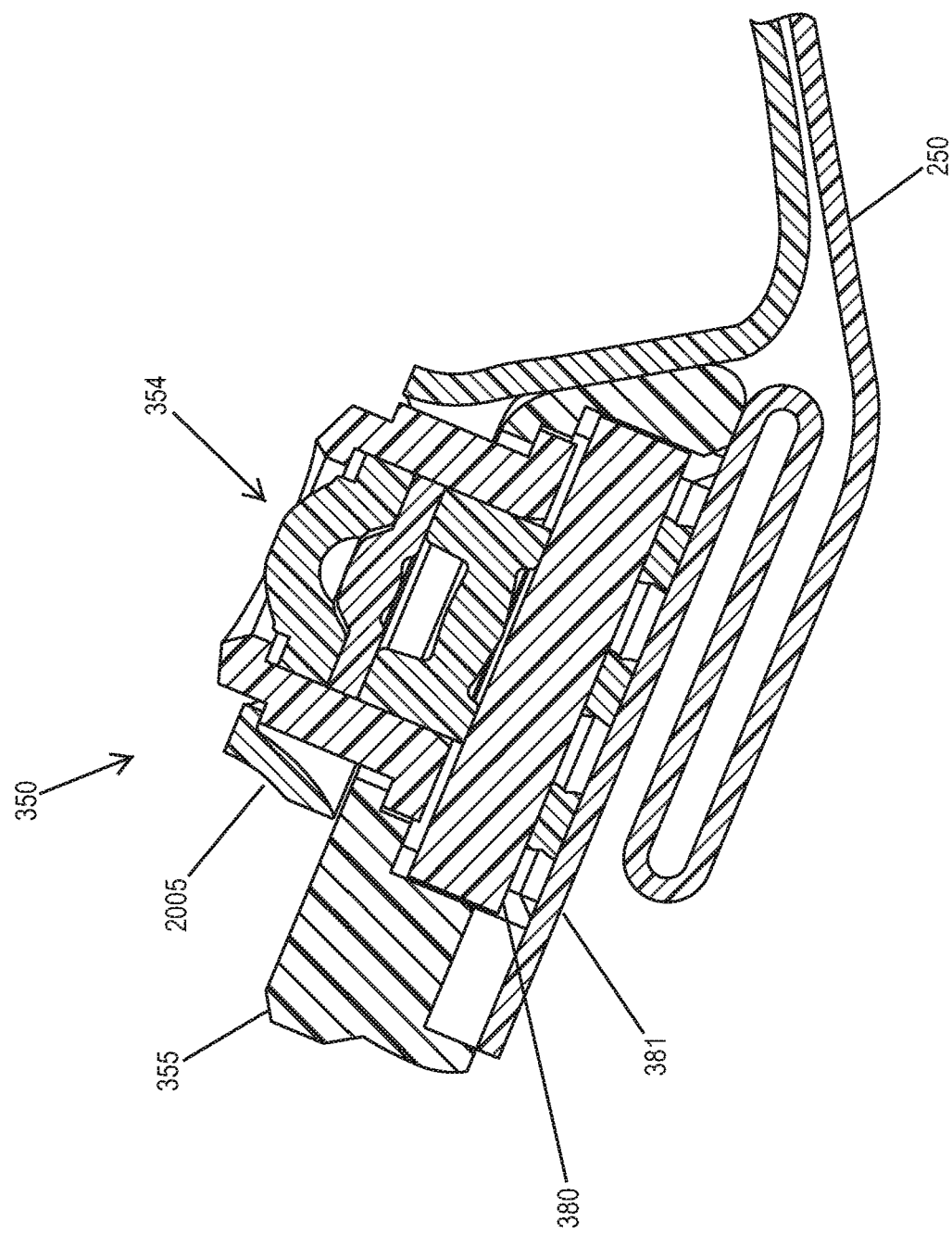
FIG. 62 shows a cross sectional view of an example camera assembly taken at line 62-62 of FIG. 32.

FIG. 62 depicts a cross section of the camera assembly 350 depicted in FIG. 32 taken at line 62-62 of FIG. 32. As shown, a lens assembly 354 is shown in place in the camera housing 355. An image sensor 380 is also shown in place within the camera housing 355. The lens assembly is positioned to project an image to the image sensor 380. As above, the image sensor 380 may be any type of image sensor (e.g. CCD, CMOS, etc.) and may be sealed against fluid exposure. Also as above, the image sensor 380 is coupled onto a flex board 381 attached to a flex cable 250. The camera assembly 350 shown in FIG. 62 does not include a fiber guide 384 (see FIG. 61). Instead a light projection element or light emitter 2005 is in place on the camera assembly 350 in FIG. 62.

As shown, the flex cable 250 is doubled back upon itself in the example embodiment. This may be accomplished by bending the flex cable 250 and then maintaining the bend by applying glue or another fixative to the affected areas of the flex cable 250. Double-looping the flex cable 250 below the camera assembly 350 may be advantageous in embodiments in which the camera assembly 350 is enclosed in a confined space. For example, confining the camera assembly 350 to the space within an inner sheath 312 as shown in FIG. 20 may limit the amount of flex cable 250 available for bending. The flex cable 250 may then have to bend over an undesirably small radius in certain rotation positions of the camera assembly 350. Such a small bend radius can be detrimental to a flex cable 250 especially if it occurs repeatedly. This problem becomes more of an issue as the diameter of the inner sheath 312 decreases. By arranging the flex cable 250 to double back upon itself, however, a greater length of flex cable 250 is available for repeated bending upon rotation of the camera assembly 350 and a larger minimum bend radius may be obtained. Thus, this may allow the inner sheath 312 to then be made with a smaller diameter without concern for the integrity of the flex cable 250 due to the repeated bending and unbending over a small radius.

Figure 63:
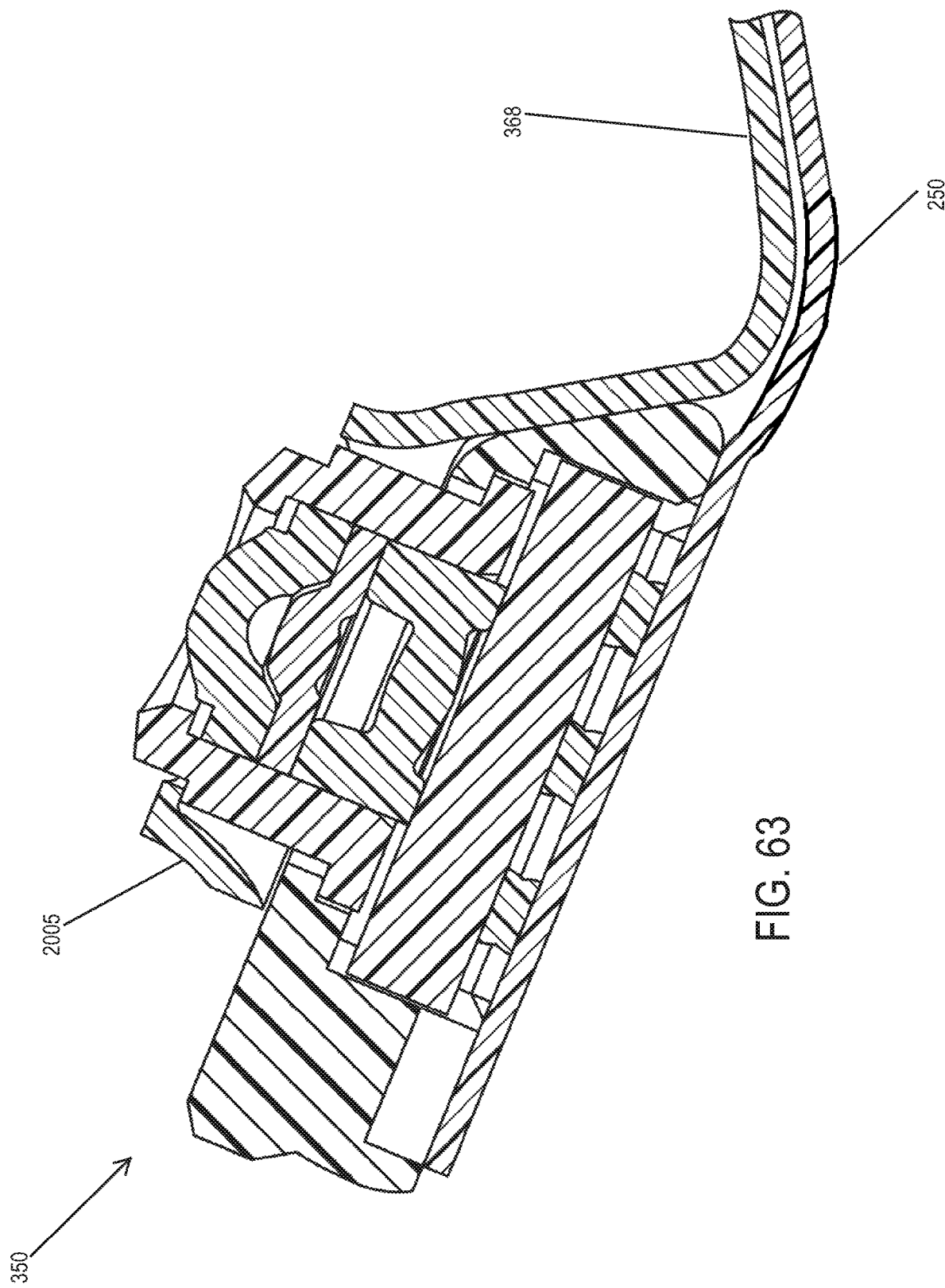
FIG. 63 shows a cross-section view of an example camera assembly taken at line 62-62 of FIG. 32.

Both the flex cable 250 and the optical fibers 364 leading the light projection element 2005 exhibit some resistance to bending. Additionally, both can exert a restoring spring force when bent. This resistance to bending may increase the camera assembly's 350 resistance to rotation. As shown in FIG. 63, the flex cable 250 and the optical fibers 364 may be angled toward one another. Such an arrangement may leverage the stiffness of the flex cable 250 against the optical fibers 364 or vice versa to assist in rotating camera assembly 350. To best illustrate this concept, the flex cable 250 is not doubled back upon itself in FIG. 63.

Figure 64:
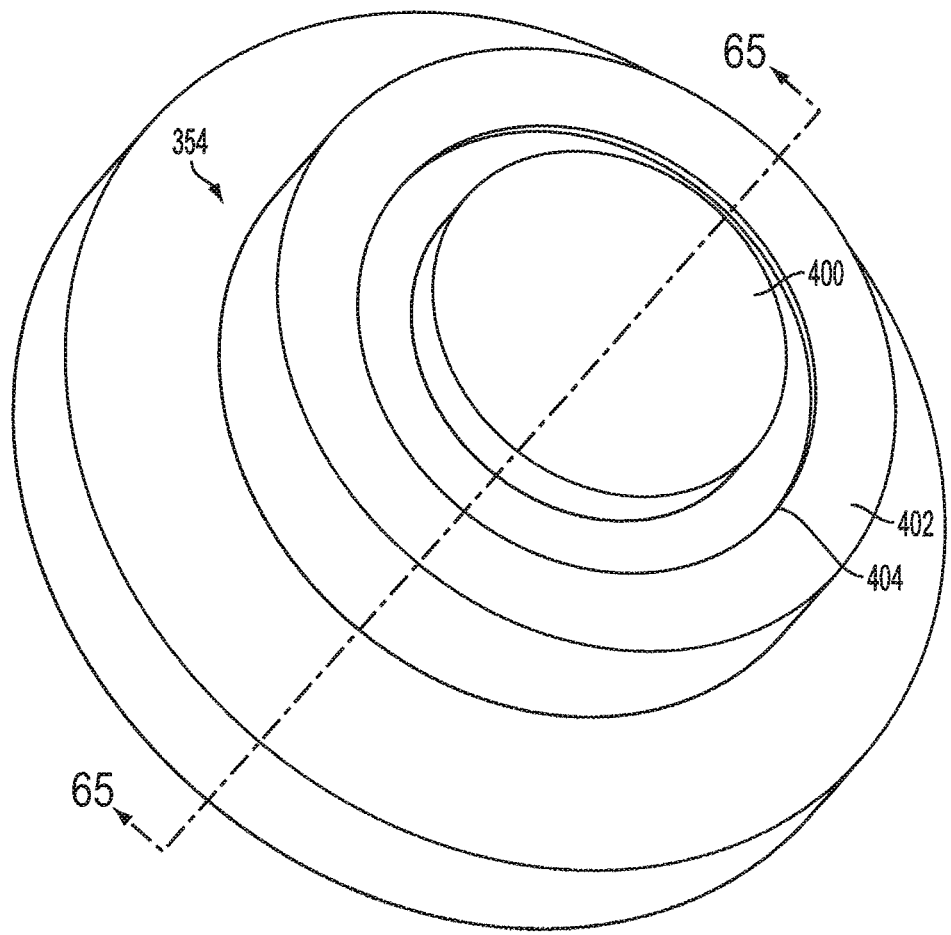
FIG. 64 shows a perspective view of an example lens assembly.

FIG. 64 depicts an example embodiment of a lens assembly 354. The lens assembly 354 is shown in isolation in FIG. 64. It may be installed in/on a camera assembly 350 (see FIG. 61) during assembly of the endoscope 10. As shown, the lens assembly 354 includes an objective lens 400. The objective lens 400 may be seated in a lens housing 402. The lens housing 402 may be made of a rigid material such as aluminum, steel or a hardened polymer or plastic compound. In an embodiment, the lens housing 402 may be cylindrical, or may have an ovoid or otherwise shaped cross-section to accommodate the shape of the lens or lenses being used. In the example embodiment shown in FIG. 64 the lens housing 402 may have a flange section at its base to facilitate its installation in a camera housing or camera assembly 350. The lens housing 402 is configured to enclose the lens or lenses of a lens assembly 354. In the example embodiment, a lens enclosure 404 extends through the entire lens housing 402. The objective lens 400 of the lens assembly 354 is disposed mostly within the lens enclosure 404. In some embodiments, glue, epoxy or another suitable adhesive may be used to couple and seal the objective lens 400 into the lens housing 402. In some embodiments, the adhesive may be added where the objective lens 400 contacts the lens enclosure 404.

Figure 65:
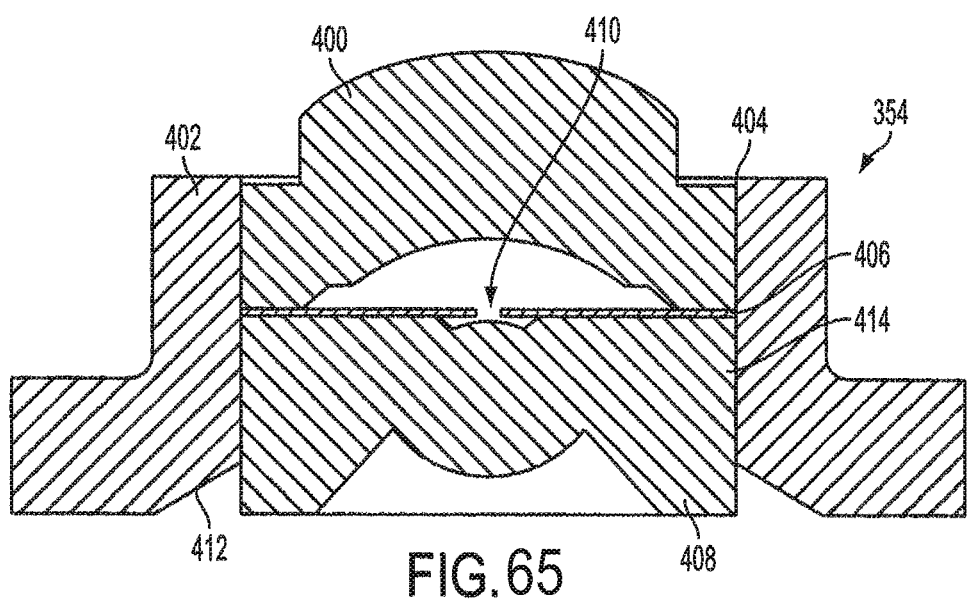
FIG. 65 shows a cross sectional view of an example lens assembly taken at line 65-65 of FIG. 64.

FIG. 65 shows a cross sectional view of a lens assembly 354 in a plane defined by line 65-65 shown in FIG. 64. As in FIG. 64, the objective lens 400 is disposed within the lens enclosure 404 of the lens housing 402 in FIG. 65. A disc 406 is also shown in FIG. 65. The disc 406, which may be constructed from a thin metal or plastic, is located within the lens enclosure 404 between the objective lens 400 and a second lens 408 of the lens assembly 354. As shown in FIG. 65, the disc 406 includes a central aperture 410. The aperture 410 size may vary depending on the optical arrangement of the lenses in relation to the camera sensing element. In some embodiments, glue, epoxy or another suitable adhesive may be used to couple and seal the second lens 408 into the lens housing 402

In some embodiments, a focusing element may be included in the lens assembly 354. In the example embodiment depicted in FIG. 65, the lens assembly 354 does not include a focusing element. The lens assembly 354 may be arranged to project an image of objects at a distance between approximately 9 mm and 50 mm in focus onto the plane of the image sensor 380 (see FIG. 61). In the example embodiment shown in FIG. 65, the immediate field of view (the field of view visible at any one time) of the lens assembly 354 is approximately 75°, although alternate embodiments may provide larger or smaller immediate fields of view.

In alternative embodiments, the lens assembly 354 may include a focusing element (not shown) capable of moving the objective lens 400, second lens 408, or both the objective lens 400 and second lens 408 in order to bring various anatomical objects into focus without the need to reposition the endoscope 10.

Any of a variety of suitable focusing elements may be used. For example, in some embodiments, Nitinol wires may be used to adjust the focus of the lens assembly 354. The Nitinol wires may be selectively heated and cooled to move a lens in a lens assembly 354 to bring an object into focus. In some embodiments, one Nitinol wire or set of Nitinol wires may be used to pull the lenses apart and another Nitinol wire or set of Nitinol wires may be used to bring the lenses closer together.

In some embodiments, an electro-active polymer (such as, e.g., an ionic electro-active polymer) may be used as an actuator to bring a desired object into focus. An ionic electro-active polymer may be advantageous in medical applications because it only requires a small voltage for actuation.

In some embodiments, the lens assembly 354 may be constructed to be bi-stable, so that a focusing element may be capable of focusing on either a close depth of field or a more distant depth of field. A user may operate the focusing element in a binary manner to select which depth of field is desired or appropriate. A button such as button 90 described above, may be used to adjust the focus of the endoscope 10.

Figure 66:
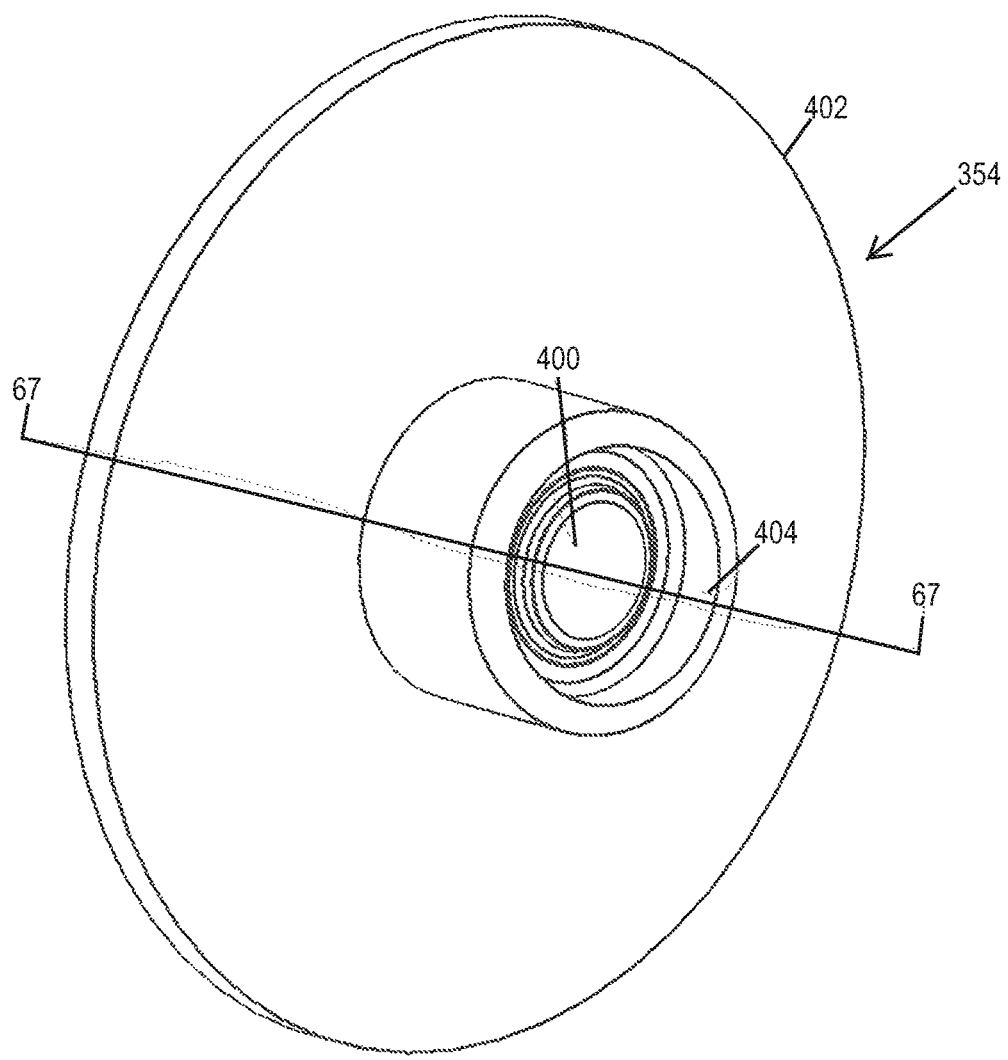
FIG. 66 shows a perspective view of an example lens assembly.

FIG. 66 depicts an example embodiment of a lens assembly 354. The lens assembly 354 is shown in isolation in FIG. 66. It may be installed on a camera assembly 350 (see FIG. 61) during assembly of the endoscope 10. As shown, the lens assembly 354 includes an objective lens 400. The objective lens 400 may be seated in a lens housing 402. The lens housing 402 may be made of a rigid material such as aluminum, steel or a hardened polymer or plastic compound. In an embodiment, the lens housing 402 may be cylindrical, or may have an ovoid or otherwise shaped cross-section to accommodate the shape of the lens or lenses being used. In the example embodiment shown in FIG. 66 the lens housing 402 may have a flange section at its base to facilitate its installation in a camera housing or camera assembly 350. The lens housing 402 may include a lens enclosure 404 configured to enclose the lenses of a lens assembly 354. The objective lens 400 of the lens assembly 354 is disposed such that it is not proud of the top of the lens housing 402. This may help to shelter the objective lens 400 from contact with medical instruments (e.g. a shaver) during use of the endoscope 10. In some embodiments, glue, epoxy or another suitable adhesive may be used to couple and seal the objective lens 400 into the lens housing 402. In some embodiments, the lenses, including the objective lens 400, may be compression fit into the lens housing 402.

Figure 67:
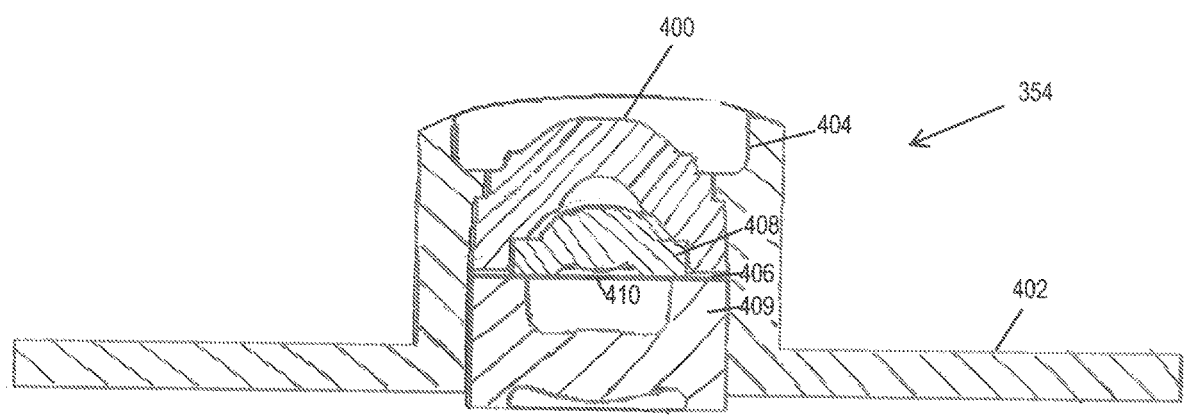
FIG. 67 shows a cross sectional view of an example lens assembly taken at line 67-67 of FIG. 66.

FIG. 67 shows a cross sectional view of a lens assembly 354 in a plane defined by line 67-67 shown in FIG. 66. As in FIG. 66, the objective lens 400 is disposed within the lens enclosure 404 of the lens housing 402 in FIG. 23. A disc 406 is also shown in FIG. 67. The disc 406, which may be constructed from a thin metal or plastic, is located within the lens enclosure 404 between the objective lens 400 and second lens 408 and a third lens 409 of the lens assembly 354. As shown in FIG. 67, the disc 406 includes a central aperture 410. The aperture 410 size may vary depending on the optical arrangement of the lenses in relation to the camera sensing element.

The lens assembly 354 is arranged to project an image of objects at a distance between approximately 4 mm and 50 mm in focus onto the plane of the image sensor 380 (see FIG. 61). In the example embodiment shown in FIG. 67, the immediate field of view (the field of view visible at any one time) of the lens assembly 354 is approximately 75°, although alternate embodiments may provide larger or smaller immediate fields of view.

Figure 68:
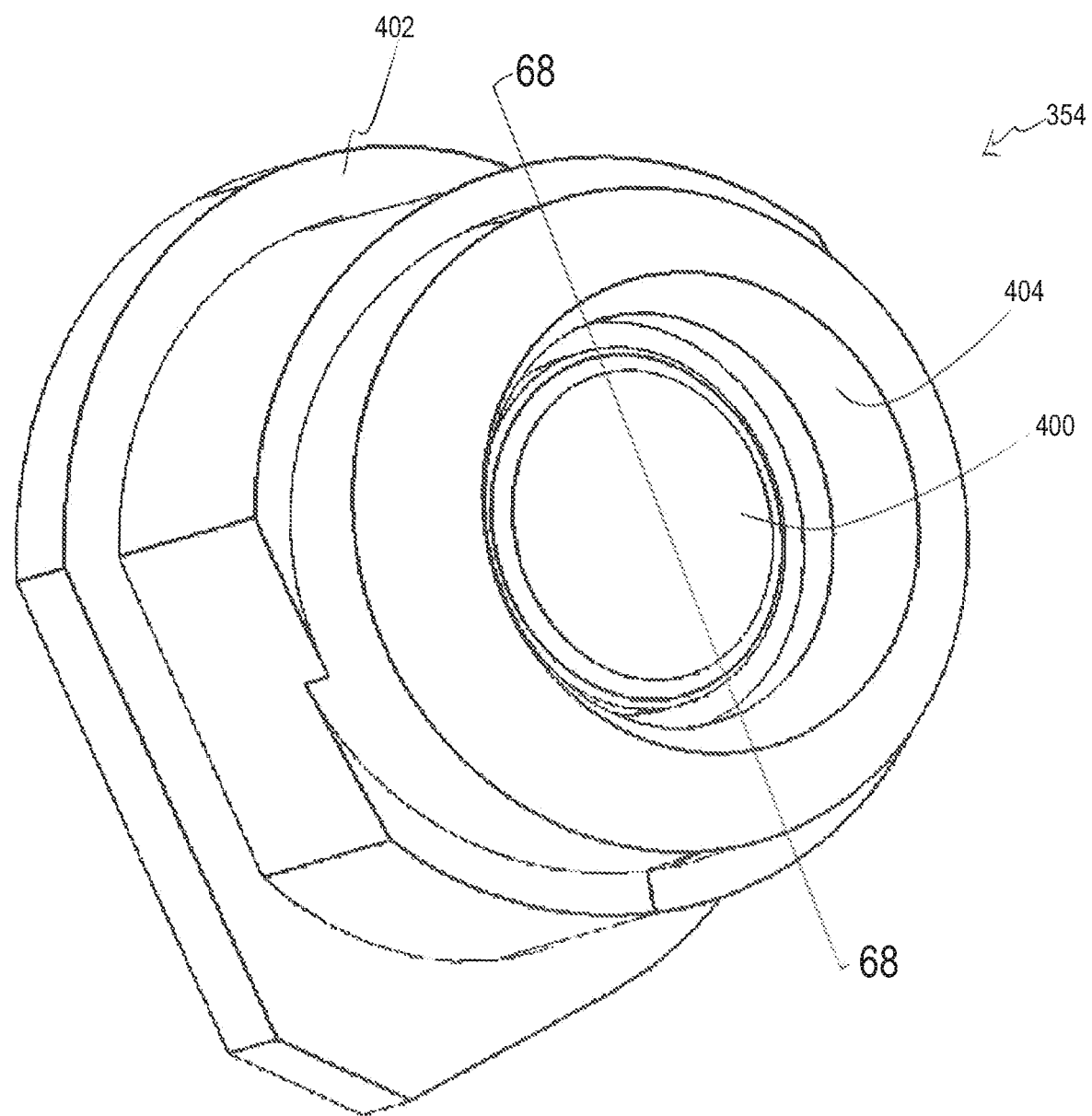
FIG. 68 shows a perspective view of an example lens assembly.

FIG. 68 depicts another example embodiment of a lens assembly 354. The lens assembly 354 is shown in isolation in FIG. 68. It may be installed on a camera assembly 350 (see, for example, FIG. 61) during assembly of the endoscope 10. As shown, the lens assembly 354 includes an objective lens 400. The objective lens 400 may be seated in a lens housing 402. The lens housing 402 may be made of a rigid material such as aluminum, steel or a hardened polymer or plastic compound. In an embodiment, the lens housing 402 may be cylindrical, or may have an ovoid or otherwise shaped cross-section to accommodate the shape of the lens or lenses being used. In the example embodiment shown in FIG. 268 the lens housing 402 may have a flange section at its base to facilitate its installation in a camera housing or camera assembly 350. Other portions of the lens housing 402 may also be shaped to facilitate its installation into a camera housing or camera assembly 350. The lens housing 402 may include a lens enclosure 404 configured to enclose the lenses of a lens assembly 354. The objective lens 400 of the lens assembly 354 is disposed such that it is not proud of the top of the lens housing 402. This may help to shelter the objective lens 400 from contact with medical instruments (e.g. a shaver) during use of the endoscope 10. In some embodiments, glue, epoxy or another suitable adhesive may be used to couple and seal the objective lens 400 into the lens housing 402.

Figure 69:
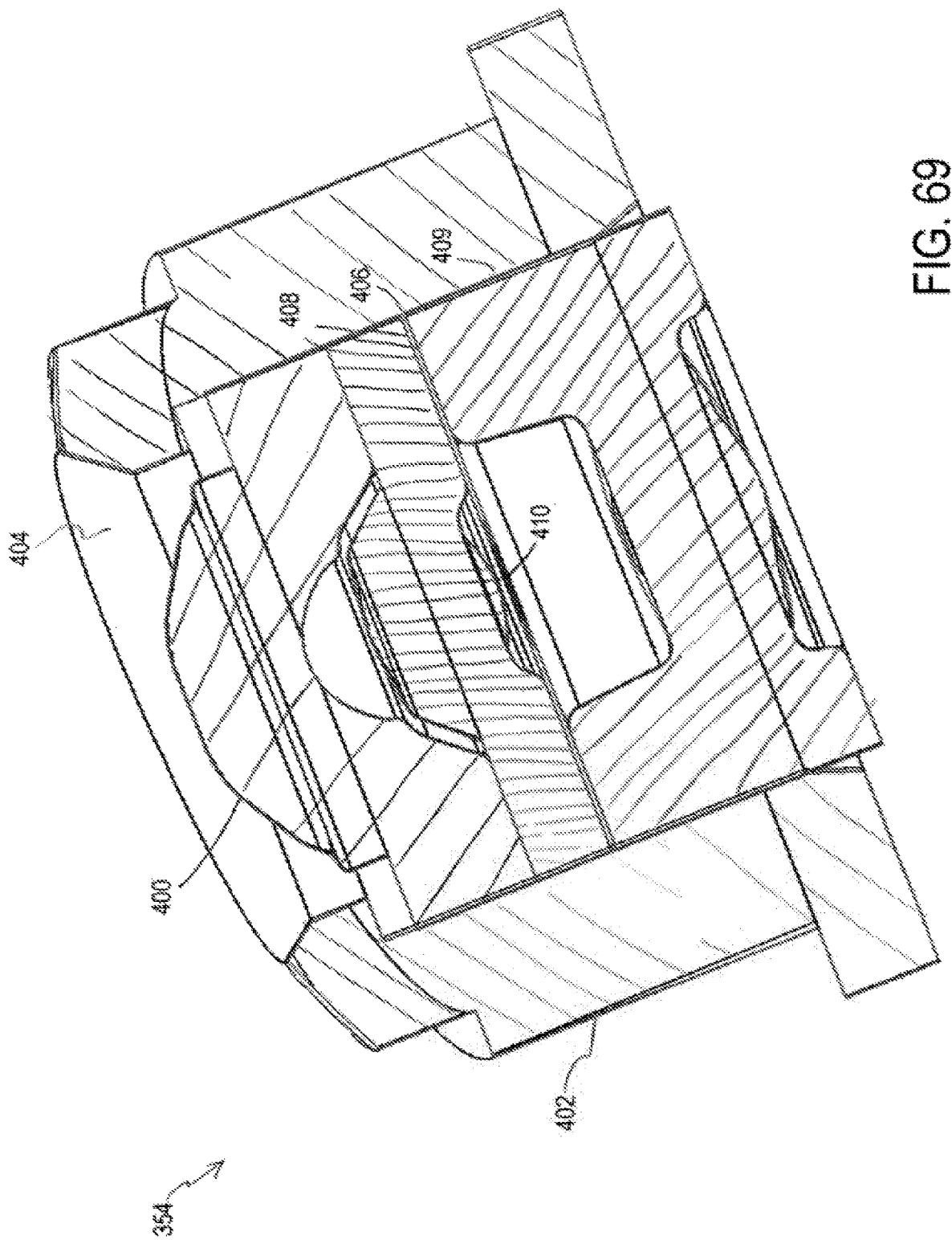
FIG. 69 shows a cross sectional view of an example lens assembly taken at line 69-69 of FIG. 68.

FIG. 69 shows a cross sectional view of a lens assembly 354 in a plane defined by line 69-69 shown in FIG. 68. As in FIG. 68, the objective lens 400 is disposed within the lens enclosure 404 of the lens housing 402 in FIG. 69. A disc 406 is also shown in FIG. 69. The disc 406, which may be constructed from a thin metal or plastic, is located within the lens enclosure 404 between the objective lens 400 and second lens 408 and a third lens 409 of the lens assembly 354. As shown in FIG. 69, the disc 406 includes a central aperture 410. The aperture 410 size may vary depending on the optical arrangement of the lenses in relation to the camera sensing element.

As shown in FIG. 69, the outer diameter of each lens 400, 408, and 409 in a lens assembly 354 may be made to have substantially equal diameters. Having equal outer diameters on the lenses 400, 408, and 409 will cause the lenses 400, 408, and 409 to self center as the lenses 400, 408, and 409 are placed in the lens enclosure 404. This may help in assembly of and cut down on assembly time for a lens assembly 354. Such a self centering design may be particularly desirable in lens assemblies 354 in which precise lens alignment is needed.

Figure 70:
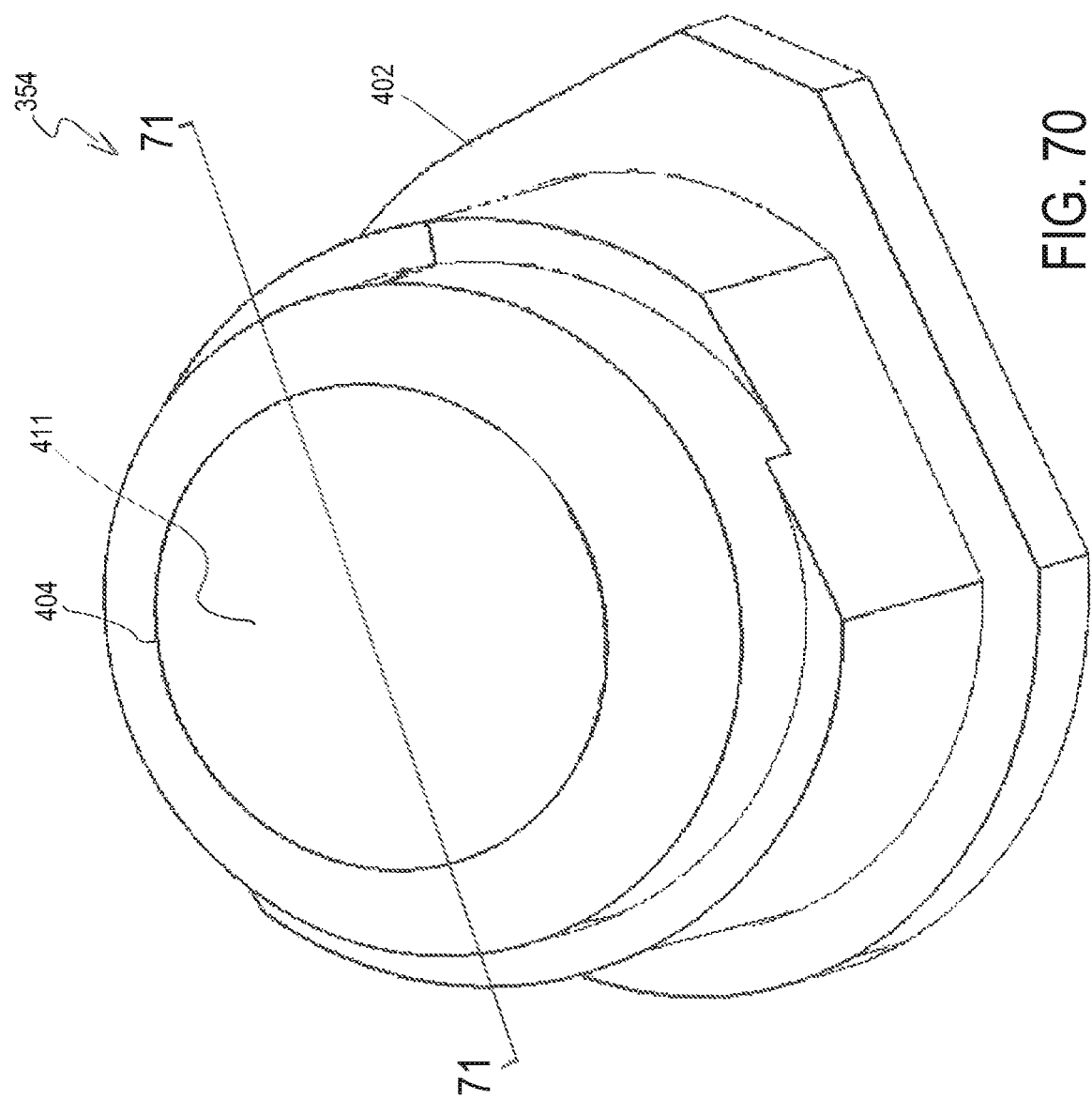
FIG. 70 shows a perspective view of an example lens assembly.

FIG. 70 depicts another example of embodiment of a lens assembly 354. The lens assembly 354 is shown in isolation in FIG. 70. It may be installed on a camera assembly 350 (see, for example, FIG. 61) during assembly of the endoscope 10. As shown, the lens assembly 354 includes a window 411. The window 411 may be seated in a lens housing 402. The lens housing 402 may be made of a rigid material such as aluminum, steel or a hardened polymer or plastic compound. In an embodiment, the lens housing 402 may be cylindrical, or may have an ovoid or otherwise shaped cross-section to accommodate the shape of the lens or lenses being used. In the example embodiment shown in FIG. 70 the lens housing 402 may have a flange section at its base to facilitate its installation in a camera housing or camera assembly 350. Other portions of the lens housing 402 may also be shaped to facilitate its installation into a camera housing or camera assembly 350. The lens housing 402 may include a lens enclosure 404 configured to enclose the lenses of a lens assembly 354. The window 411 of the lens assembly 354 is disposed such that it substantially flush with the top of the lens housing 402. In some embodiments, glue, epoxy or another suitable adhesive may be used to couple and seal the window 411 into the lens housing 402. Preferably, the window 411 may be coupled to the lens housing 402 such that a fluid seal is created between internal components in a lens housing 402 and the outside environment.

Figure 71:
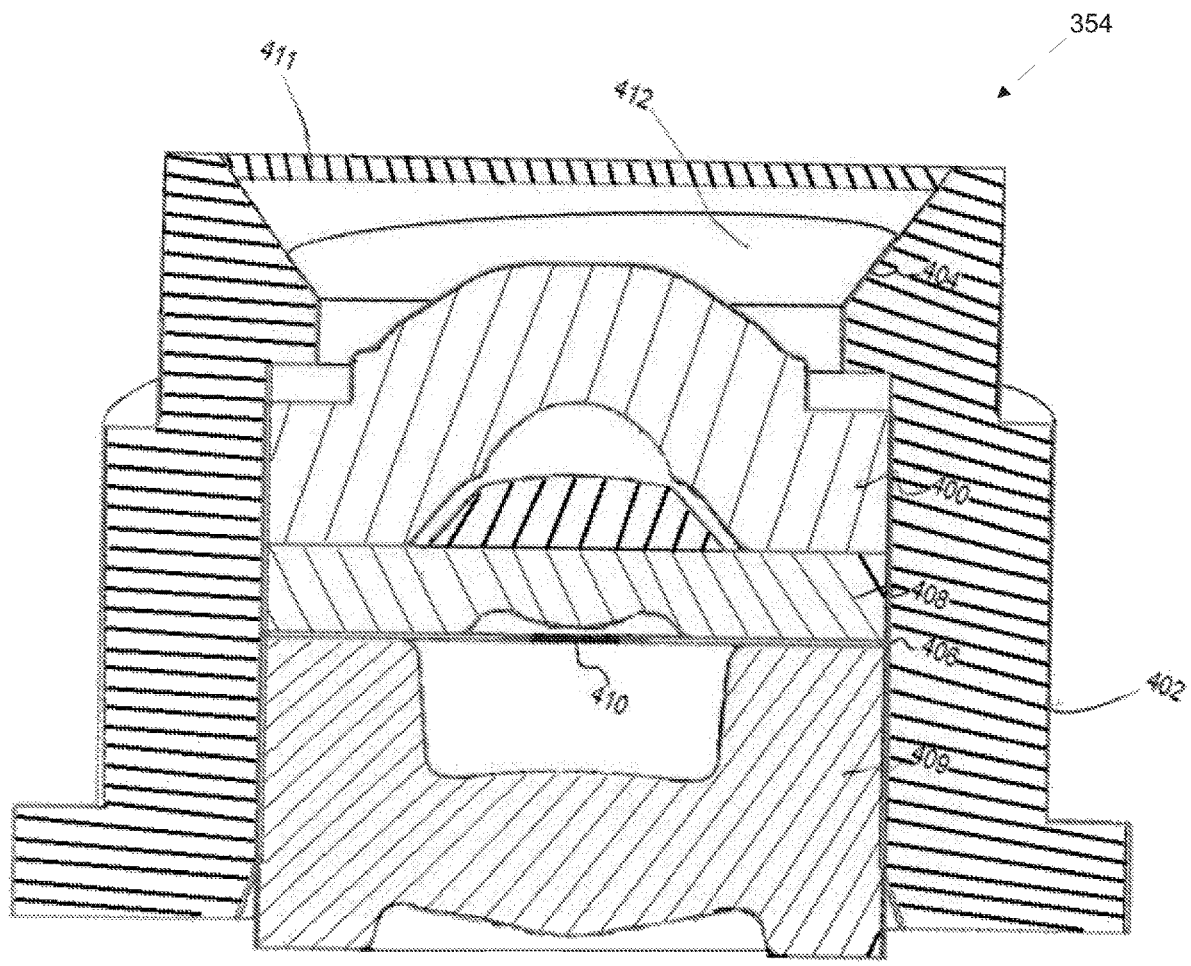
FIG. 71 shows a cross sectional view of an example lens assembly taken at line 71-71 of FIG. 70.

FIG. 71 shows a cross sectional view of a lens assembly 354 in a plane defined by line 71-71 shown in FIG. 70. As in FIG. 70, the window 411 is flush with the top of the lens housing 402. The lens assembly 354 includes an objective lens 400. The objective lens 400 is disposed within the lens enclosure 404 of the lens housing 402 in FIG. 71. A disc 406 is also shown in FIG. 71. The disc 406, which may be constructed from a thin metal or plastic, is located within the lens enclosure 404 between the objective lens 400 and second lens 408 and a third lens 409 of the lens assembly 354. As shown in FIG. 71, the disc 406 includes a central aperture 410. The aperture 410 size may vary depending on the optical arrangement of the lenses in relation to the camera sensing element. Similar to the lens assembly 354 shown in FIG. 69, the lenses 400, 408, and 409 of the lens assembly 354 in FIG. 71 are of equal outer diameters. As described above, this may aid in assembly and alignment of the lenses 400, 408, and 409.

The lens assembly 354 shown in FIG. 71 additionally includes a sealed space 412. The sealed space 412 exists between the internal face of the window 411 and the surface of the objective lens 400. This sealed space 412 may be filled with a medium in which the lenses 400, 408, and 409 of the lens assembly 354 are designed to operate in (e.g. air). The window 411 may thus, form a "goggle" which allows the lens assembly 354 to operate in any medium. For, example, if the lenses 400, 408, and 409 are designed to be used in air, the sealed space 412 may be filled with air. The lens assembly 354 may then be placed into another medium, for example, a liquid (e.g. water) and remain in proper focus. Preferably the window 411 is shaped such that it does not distort the image transmitted through the lenses 400, 408, and 409 of the lens assembly 354.

FIG. 72-84 depict an example process and apparatus for determining the proper spatial arrangement of a lens or lens assembly and an image sensor (or other desired destination or imaging surface, e.g. a film plate or holder for a piece of film) associated with the lens or lens assembly. Such a spatial arrangement is key to ensuring that the image received by the image sensor is in focus. The apparatus and process may allow the determination of the focal length of a lens or lens assembly and may allow determination of the image plane of a lens or lens assembly. For illustrative example, focal length for a single lens may be determined as follows:

$$1/f_{lens} = (n_{lens} - n_{incident}) * (1/R_1 - 1/R_2)$$

Where: n=index of refraction

R1 and R2=respectively the radii of the curvature of the entrance and exit of the lens.

As indicated by the formula, such a process and apparatus may be necessary in scenarios where the shape of the lens or lenses are not precisely known. Also as indicated, since the lens or lens assembly must be in contact with the medium it is intended to be used in, such determinations may become complicated in applications where the lens or lens assembly is designed for use in a liquid environment. Specifically, the process and apparatus depicted in FIGS. 72-84 may be advantageously used for lenses or lens assemblies which are designed for use in a liquid environment or liquid working medium.

The process may involve fixing the lens or lens assembly within a fixture included as part of the apparatus. The process may then involve introducing an amount of the liquid medium into the fixture such that the liquid medium abuts the lens or lens assembly. The liquid medium may then be enclosed such that it is retained against the lens or lens assembly and no air bubbles are present. The process takes advantage of the small size of the lens assembly being focused to use capillary action to introduce the liquid medium, effectively eliminating the trapping of air between the liquid medium and the surface of the lens. For example, liquid introduction by capillary action may be used for lens assemblies having diameters of about 1 mm to about 3 mm in diameter. Additionally, the liquid medium may be enclosed and retained by a transparent plate that creates no lensing effect on the image transmitted through the lens or lens assembly. The imaging surface may then be adjusted until it is substantially on the image plane of the lens or lens assembly in the fixture.

Figure 72:
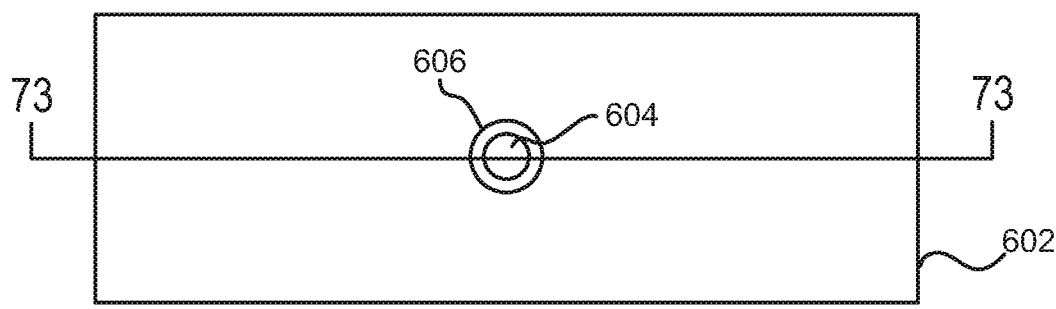
FIG. 72 shows a top down view of part of an example fixture which may be placed into a larger apparatus used for determining the proper spatial arrangement of an optical element and image sensor.

FIG. 72 depicts a top down view of part of an example fixture which may be placed into a larger apparatus used for determining the proper spatial arrangement. A plate or block 602 is shown in FIG. 72. The plate 602 may be made of any suitable material, such as glass (e.g., glass microscope slide). Preferably, the plate 602 is of a material which will not degrade, dissolve, or become otherwise compromised when it comes into contact with the liquid which the lens or lens assembly is designed to work in. The plate 602 may be made of a dark material or may include at least one darkened region.

The plate 602 has a defined thickness and includes an aperture or a void 604. The aperture 604 extends through the entirety of the plate 602. The aperture 604 is sized and shaped to accept a lens or lens assembly. As shown, a gasket 606 may also be include. The gasket 606 may surround the void 604. The gasket 606 may, for example, be an o-ring. Other embodiments may use any other suitable gasket 606.

Figure 73:
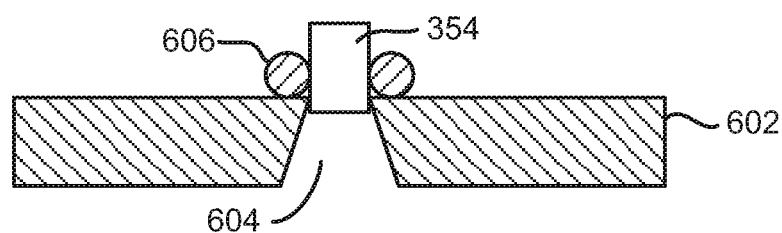
FIGS. 73-75 conceptually depict a process for enclosing an optical element in its intended working medium.
Figure 74:
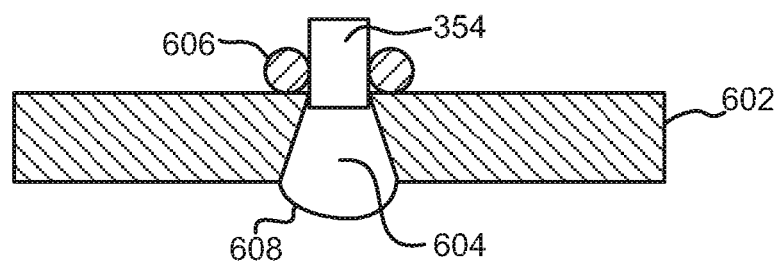
Figure 75:
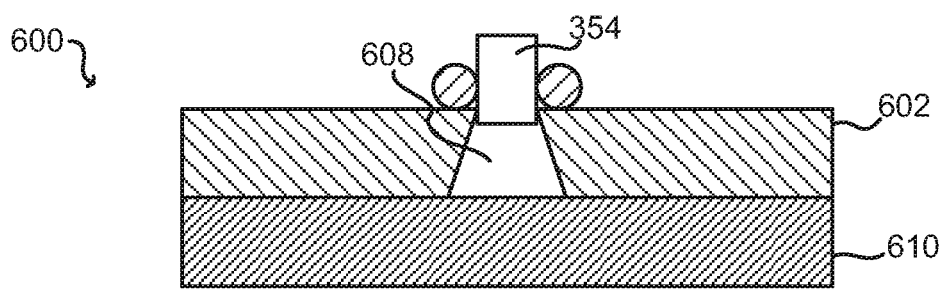

The progression of block diagrams in FIGS. 73-75 conceptually depict an example process which may be used to assemble a completed fixture 600 (shown in FIG. 75). The process depicted in FIGS. 73-75 encloses a lens or the objective lens of a lens assembly 354 in a wet environment or liquid working medium. For illustrative purposes, FIGS. 73-75 depict a number of cross-sectional views taken at line 73-73 of FIG. 72.

As shown in FIG. 73, the lens or lens assembly 354 may be introduced into the aperture or void such that its outer surface or an outer lens element is situated within the interior volume of the void 604. In this example, an inner surface of the lens is defined to be that surface of the lens assembly or element that faces the sensor, and an outer surface or an outer lens element is defined to be that surface of the lens assembly or element that faces the plate or its aperture/void. Optionally, the void 604 is chamfered or countersunk such that it widens as it extends toward the bottom face of the plate 602. Once the lens or lens assembly 354 has been introduced, the gasket 606 may create a fluid impermeable seal between the lens or lens assembly 354 and the top of plate 602. The gasket 606 may also serve to hold the lens or lens assembly 354 in place.

A volume of liquid or working medium 608 may then be inserted into that portion of the void 604 not occupied by the lens. The volume of liquid 608 inserted is preferably greater than the air volume in the void 604. The liquid 608 introduced may be of the type in which the lens or lens assembly 354 is designed to function, such as, e.g. water or saline solution. The aperture or void 604 is sufficiently small that liquid can move to fill the void via capillary action of the liquid along the surfaces of the outer lens and contiguous surfaces of the plate defining the void. Using this method, the migration of the liquid into the void completely displaces any air, thus forming a completely air-free environment in the interface between the liquid and the surface of the lens within the void. Thus any distortions created by air against the surface of the lens during the alignment of the lens with the sensor can be eliminated. The liquid 608 shown in FIG. 74 has sufficient surface tension that a droplet may hang from the void 604 against the force of gravity. For liquids with differing surface tensions, the plate 602 may be flipped over such that gravity is not an issue when the liquid 608 is placed in the void 604. As shown, the liquid 608 wets or contacts the lens or objective lens of a camera assembly 354. Also as shown, it is ideally desirable that the liquid 608 includes no air bubbles.

Referring now to FIG. 75, once liquid 608 has been introduced, a second plate 610 such as a plastic or glass cover slip may be placed against a surface of the first plate 602. This may be similar to wet mounting a microscope slide. As shown, the second plate 610 encloses the liquid 608 in the void 604. The second plate 610 may be held against the first plate 602 by surface tension of the liquid 608. In other embodiments, the second plate 610 may be actively held in place. Such embodiments may be desirable in instances where the lens or lens assembly 354 is designed for use in a liquid with a lesser degree of surface tension.

The second plate 610 preferably is made from a material which is optically clear at the desired wavelengths (e.g. transparent for visual optical purposes). Additionally, it may be desirable that the second plate 610 be made from a material which will not degrade, dissolve, or become otherwise compromised when it comes into contact with the liquid which the lens or lens assembly 354 is designed to work in. The second plate 610 may also be planar as shown in FIG. 75. This may be desirable to ensure that no lensing effect is created by the second plate 610.

Figure 76:
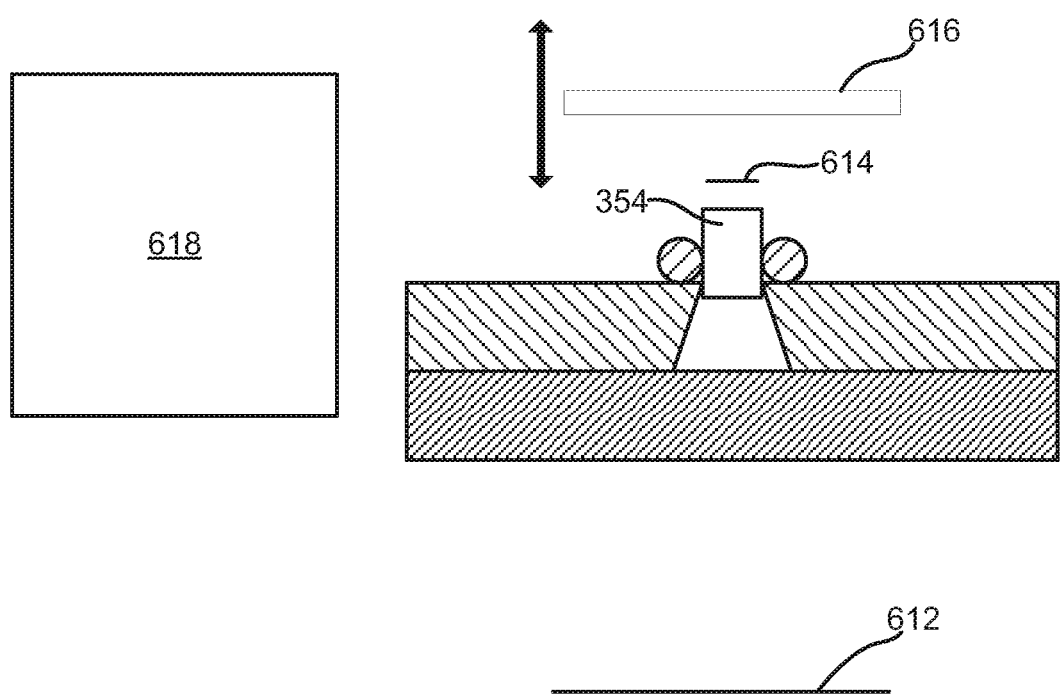
FIG. 76 conceptually depicts a process for aligning a sensor in the image plane of an optical element.

Once the working medium has been enclosed such that it is retained against the lens or lens assembly 354, the fixture 600 may be completed. Determinations of the focal length or image plane may then be made as described and shown in relation to FIG. 76. A reference object 612 may be placed in the field of view of the lens or lens assembly 354 at a desired distance from the lens assembly 354. The desired distance may be the intended distance from the subject to the lens or lens assembly 354 during usage of the lens assembly 354. The reference object 612 may be any suitable reference. Various embodiments may, for example, use a reference grid, cross hairs, checkerboard, dot arrangement, image, etc. In FIG. 76, the reference object 612 is conceptually illustrated as a solid line. Light from the reference object 612 may be transmitted through the lens or lens assembly 354. An image 614 of the reference object 612 will be in focus at the image plane of the lens or lens assembly 354.

An image sensor 616 is also shown in FIG. 76. An image sensor 616 may be adjusted until its imaging surface is approximately in line with the image plane or acceptably within the depth of focus of the lens or lens assembly 354. While moving the image sensor 616, a user may monitor the image captured by the image sensor 616 on a display 618 until the image is in acceptable or crisp focus. In alternate embodiments, an image sensor 616 may remain stationary while the fixture 600 and reference object 612 are moved relative to the image sensor 616.

In some embodiments, the focusing process may not be a manual process. In such embodiments, adjustment of an image sensor 616 may be executed by a computer which, for example, moves the image sensor 616 to the image plane using an auto-focusing algorithm. In one such example, a passive auto focus system using contrast detection may be used. In such an embodiment, the image sensor 616 may be adjusted until a point of maximum intensity difference between adjacent pixels is found.

Once the imaging surface of the image sensor 616 is approximately aligned with the image plane of the lens or lens assembly 354, the image sensor 616 and lens or lens assembly 354 may be secured in fixed spatial relation to one another. This may be done by any suitable method.

Figure 78:
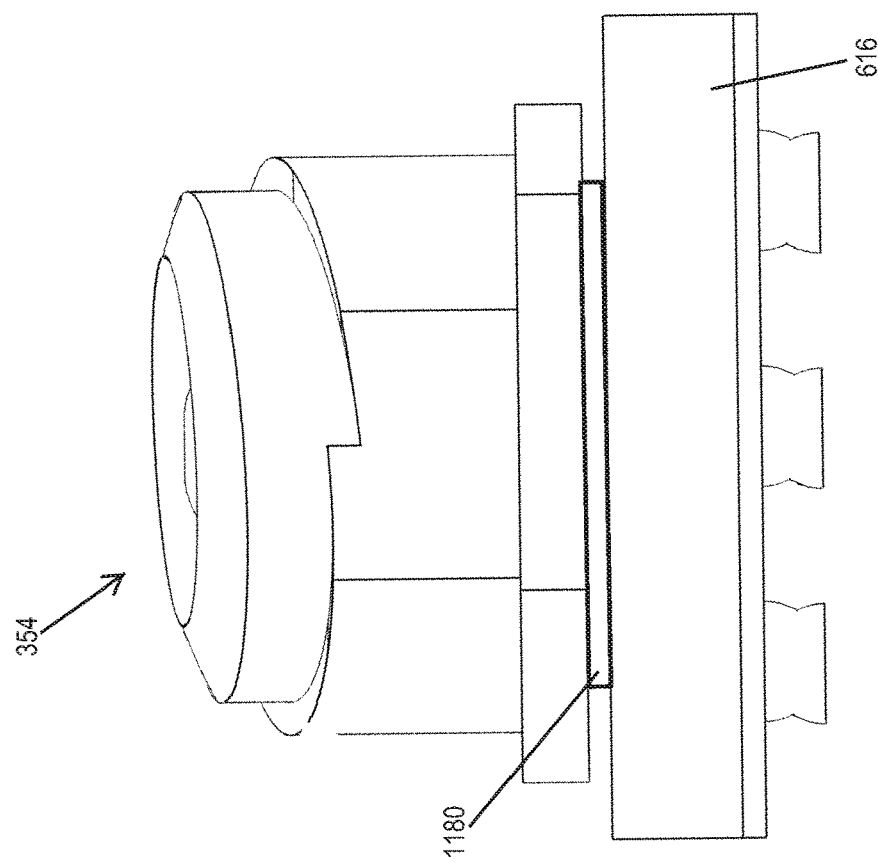
FIG. 78 depicts an example image sensor which has been affixed to an example lens assembly after alignment.
Figure 77:
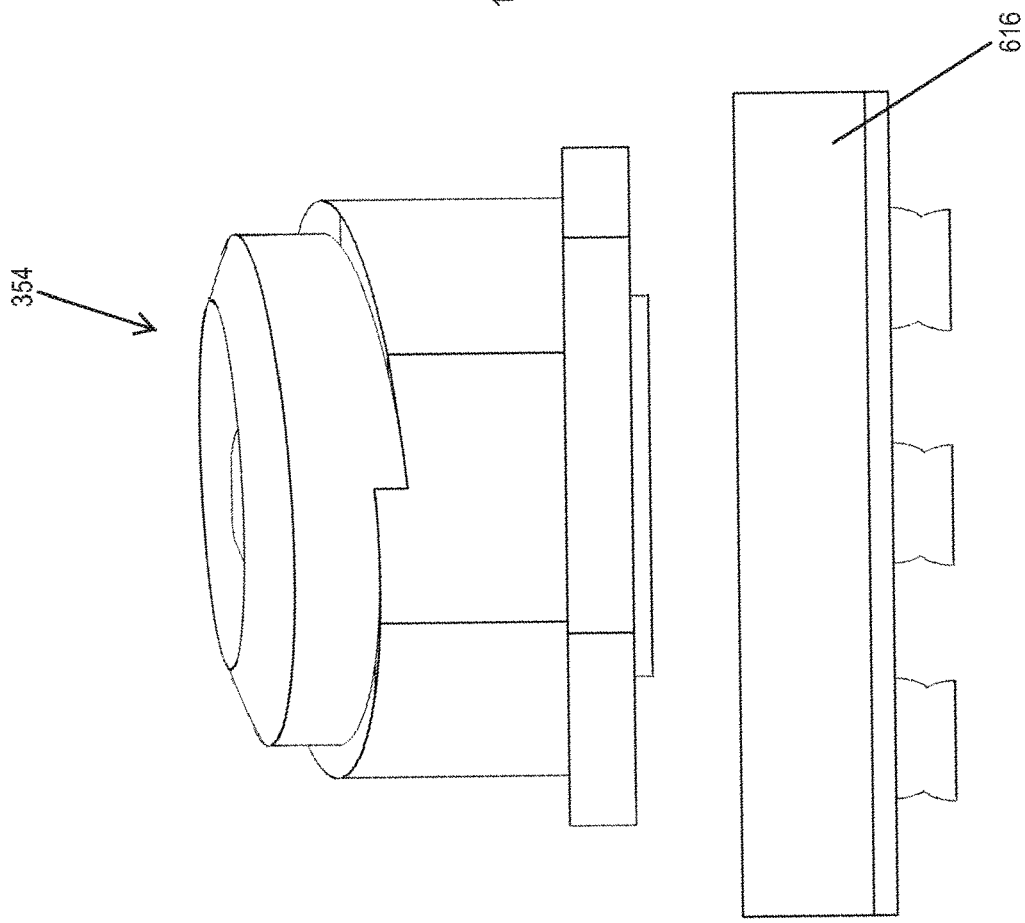
FIG. 77 depicts an example image sensor and lens assembly which are separated from one another such that the image plane of the lens assembly is not aligned with the image sensor.

In a specific embodiment, shown in FIGS. 77 and 78 the image sensor 616 may be secured in fixed spatial relation to a lens assembly 354 by glue, adhesive or another suitable agent. As shown in FIG. 77, the lens assembly 354 and the image sensor 616 are shown separated from one another. As described above, the distance between the lens assembly 354 and the image sensor 616 may be varied until the desired focus is achieved. Once the appropriate distance is determined, the two may then be secured together as depicted in FIG. 78. As shown, there is a small space between the lens assembly 354 and the image sensor 616. A bead of glue 1180 has been applied between the flange of the lens assembly and the image sensor 616. This bead of glue 1180 the serve to secure the image sensor 616 to the lens assembly 354 at the appropriate distance from the lens assembly 354.

Figure 79:
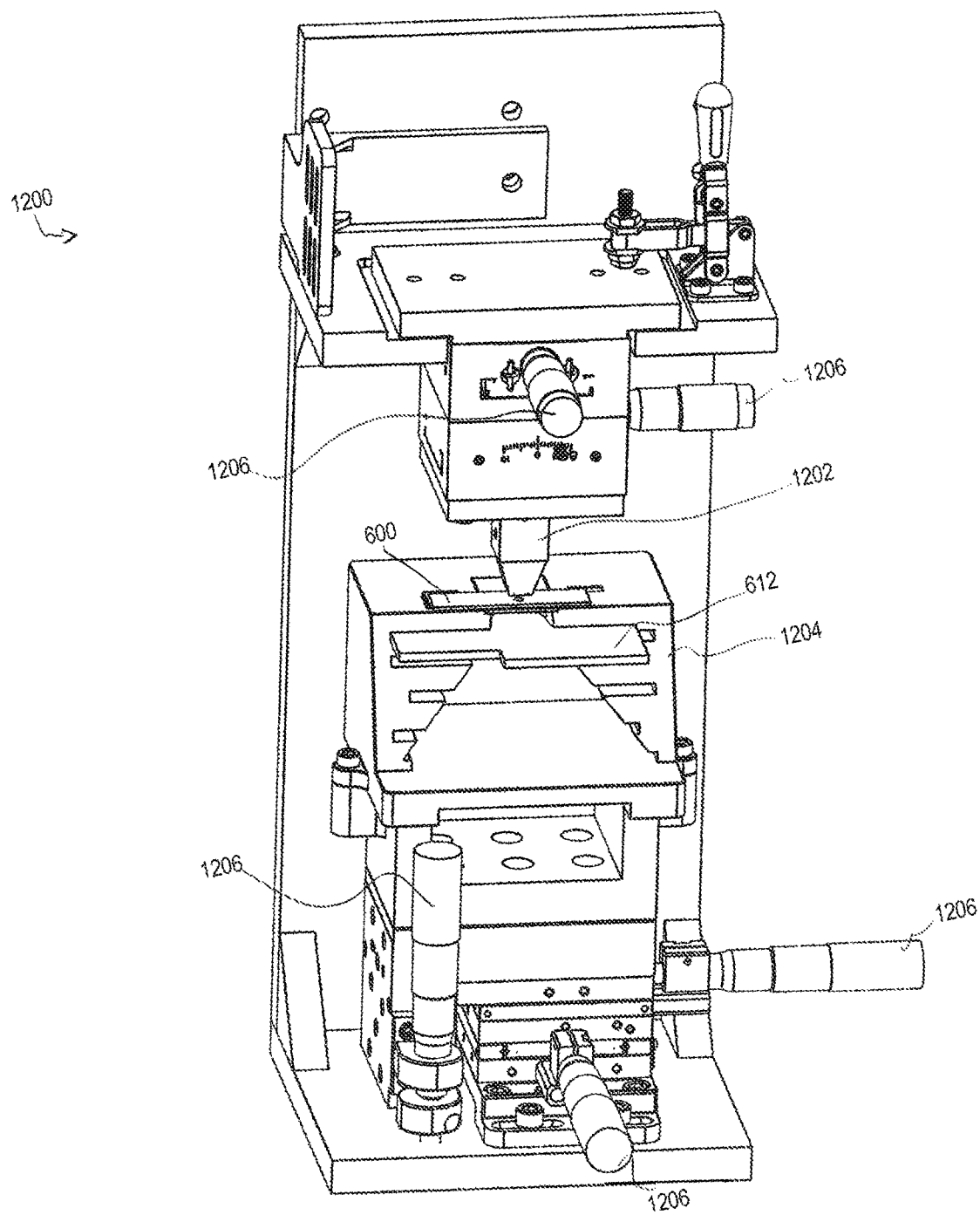
FIG. 79 depicts a perspective view of an example apparatus which may be used to determine the proper spatial arrangement of an optical element and image sensor.

FIG. 79 depicts a specific example apparatus 1200 for determining the proper spatial arrangement of a lens or lens assembly and an image sensor (or other desired destination or imaging surface, e.g. a film plate or holder for a piece of film) associated with the lens or lens assembly. As shown, the apparatus 1200 includes an image sensor mount 1202. An image sensor (not shown in FIG. 79) may be mounted to the image sensor mount 1202. The apparatus 1200 also includes a fixture holder 1204. The fixture holder 1204 may hold a fixture 600. The fixture 600 may be assembled following a process such as that shown and described in relation to FIGS. 72-75. The fixture holder 1204 may also be configured to hold a reference object 612. A close up view of the fixture holder 1204 is shown and described in FIG. 80.

The apparatus 1200 also includes spatial adjusters 1206 configured to adjust the spatial locations of the image sensor mount 1202 and the fixture holder 1204 relative to one another. In the example embodiment shown in FIG. 79, the spatial adjusters 1206 are micrometer adjusters. In other embodiments, other varieties of spatial adjusters 1206 may be used. In some embodiments, spatial adjusters 1206 may only be included for one of the image sensor mount 1202 or the fixture holder 1204. A user may adjust the spatial orientation of the image sensor holder 1202 and fixture holder 1204 relative to one another using the spatial adjusters 1206. As described in relation to FIG. 76, this may be done until the imaging surface of the image sensor is approximately in line with the image plane of the lens or lens assembly.

Figure 80:
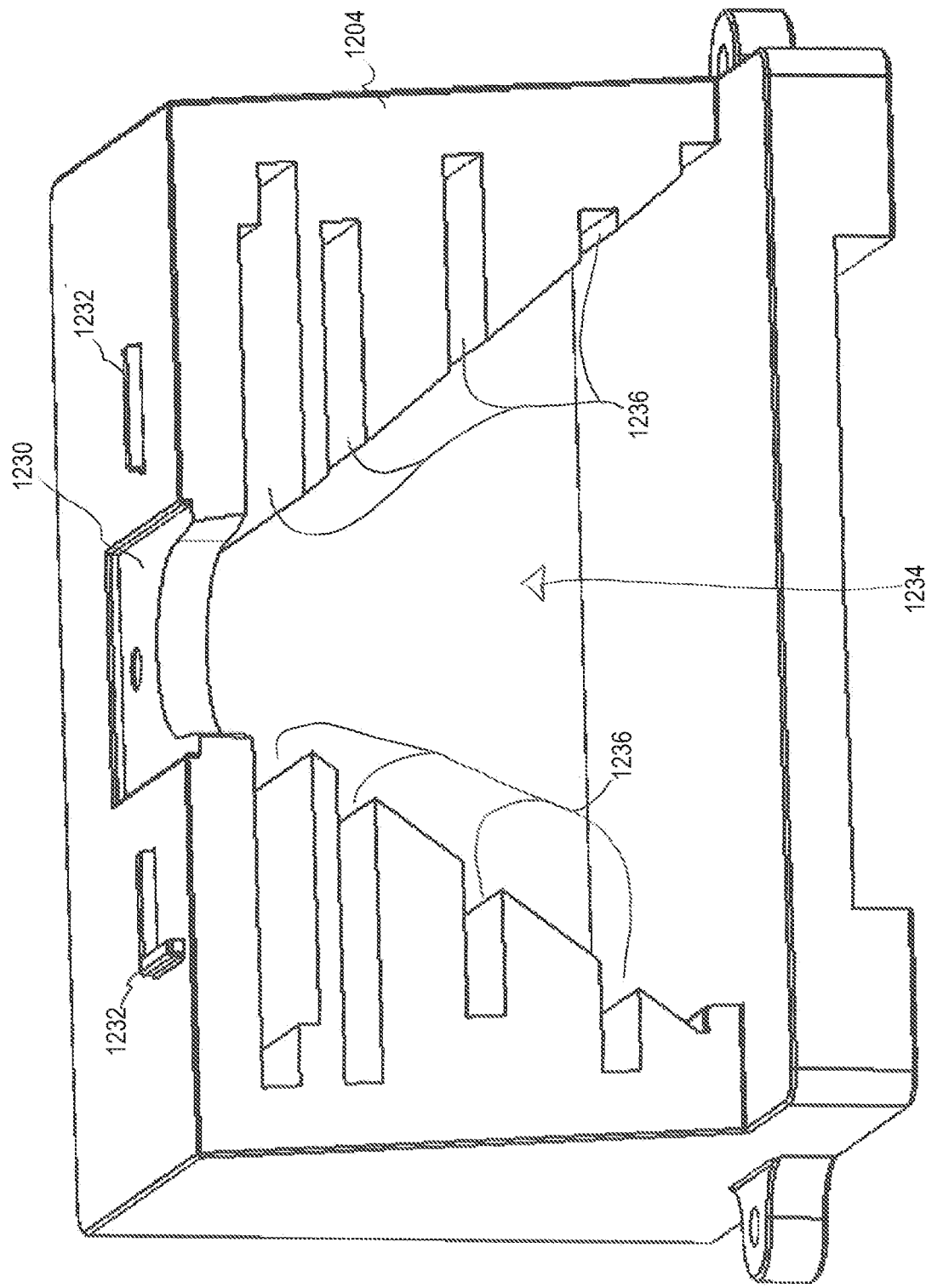
FIG. 80 depicts a perspective view of part of the apparatus depicted in FIG. 79.

FIG. 80 depicts a close up view of the fixture holder 1204 shown in FIG. 79. As shown, the fixture holder 1204 includes a recess 1230 in its top face. This recess 1230 may help retain and properly orient a fixture on the fixture holder 1204. Also shown are two alignment features 1232. The alignment features 1232 may help to properly orient a fixture on the fixture holder 1204.

In the example embodiment in FIG. 80, the fixture holder 1204 includes a void 1234. The void 1234 may be sized and shaped to allow a clear field of view for a lens or lens assembly included in an assembled fixture placed on the fixture holder 1204. A number of slots 1236 are also included in the fixture holder 1204. A reference object may be inserted into any of the desired slots 1236. The slots 1236 are disposed such that a reference object may be placed at predetermined distances from a fixture in place on the fixture holder 1204.

Figure 81:
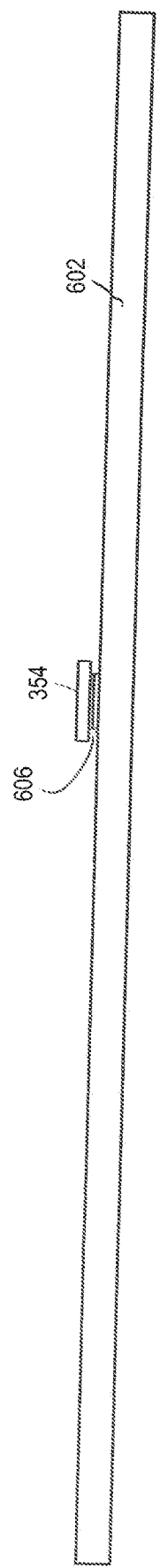
FIGS. 81-84 depict an example process which may be used to assemble a completed fixture and place the fixture into a larger apparatus.
Figure 82:
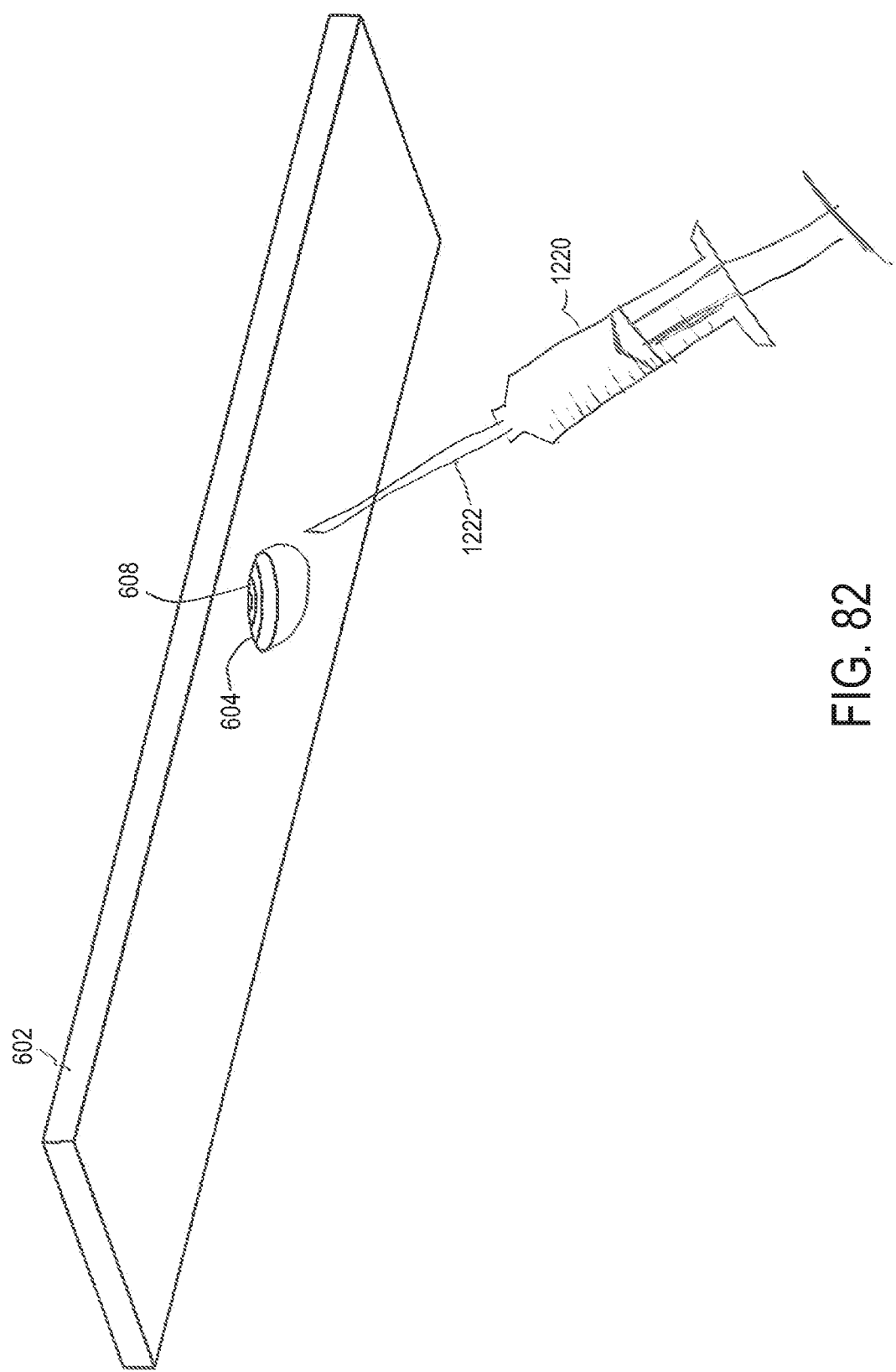

The progression of FIGS. 81-82 depict an example process which may be used to assemble a completed fixture 600 (shown in FIG. 82) and place the fixture 600 into a larger apparatus such as the apparatus 1050 shown in FIG. 79. FIG. 81 depicts a front view of a plate 602. A lens assembly 354 is also shown in FIG. 81. As shown, the lens assembly 354 includes a flange which sits on top of the gasket 606. The flange may be helpful in creating a fluid seal with the gasket 606. The flange may cooperate with the gasket 606, such that the gasket 606 acts as a stop which helps to position the lens assembly 354 such that it protrudes a desired depth into the plate 602.

FIG. 82 depicts a bottom perspective view of the plate 602. As shown, a small portion of the lens assembly 354 is also visible protruding into the void 604 in the plate 602. An amount of liquid or working medium 608 is also shown being placed into the void 604. In the example in FIG. 82, the liquid 608 is introduced via a syringe 1220 and hypodermic needle 1222. The liquid 608 may be inserted into the void 604 using any other suitable means such as a dropper, pipette, etc.

It may be desirable that the liquid be introduced such that it first contacts a side wall of the void 604. The volume of liquid may then be increased such that the liquid wicks around the lens assembly 354 before filling the center of the void 604 and eventually forming a droplet as shown in FIG. 82. This wicking may help to minimize the trapping of air bubbles within the void 604. It may also help to ensure that the lens assembly 354 is not damaged, for example by the hypodermic needle 1222 during the introduction of the liquid.

Figure 83:
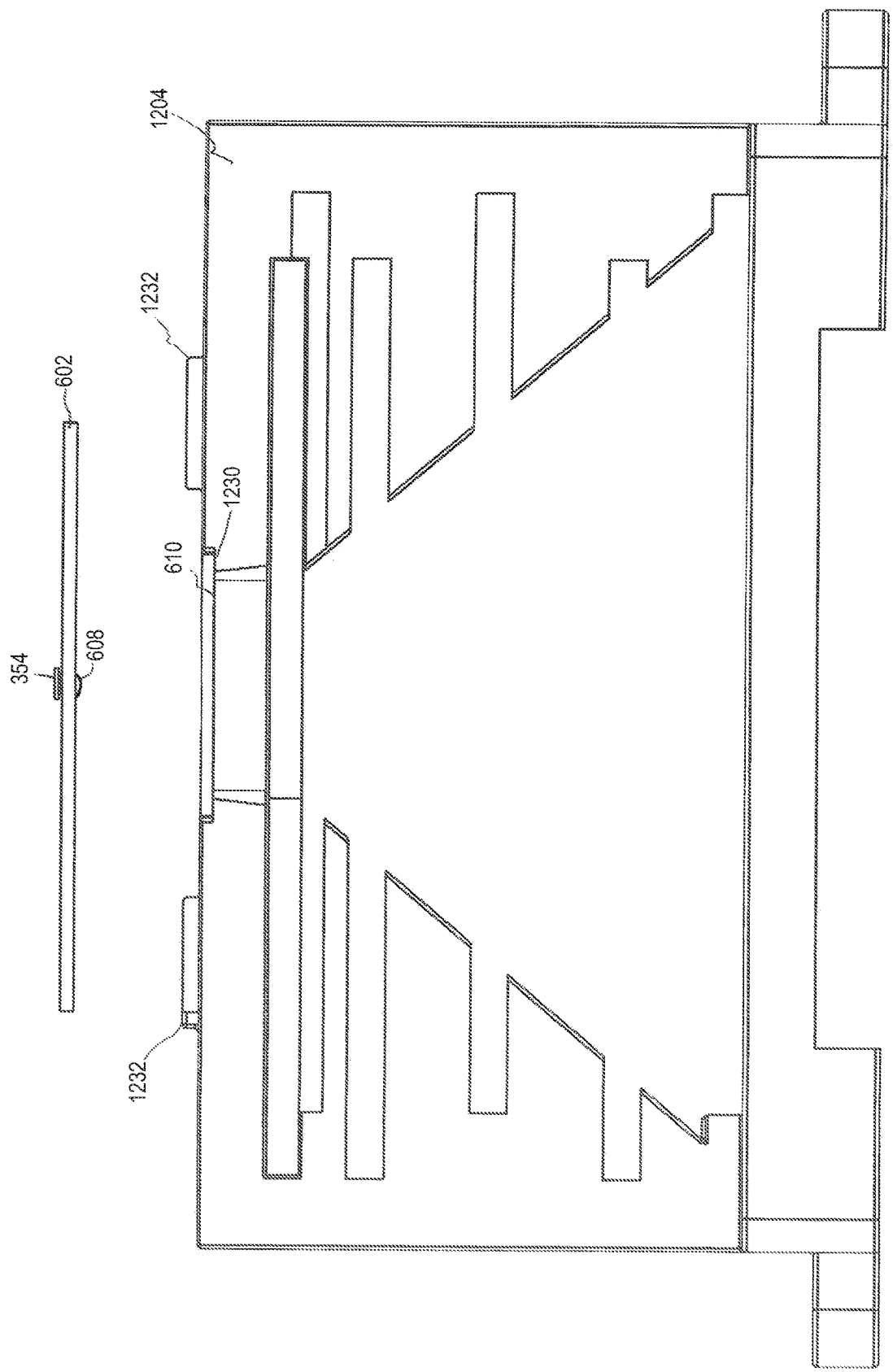
Figure 84:
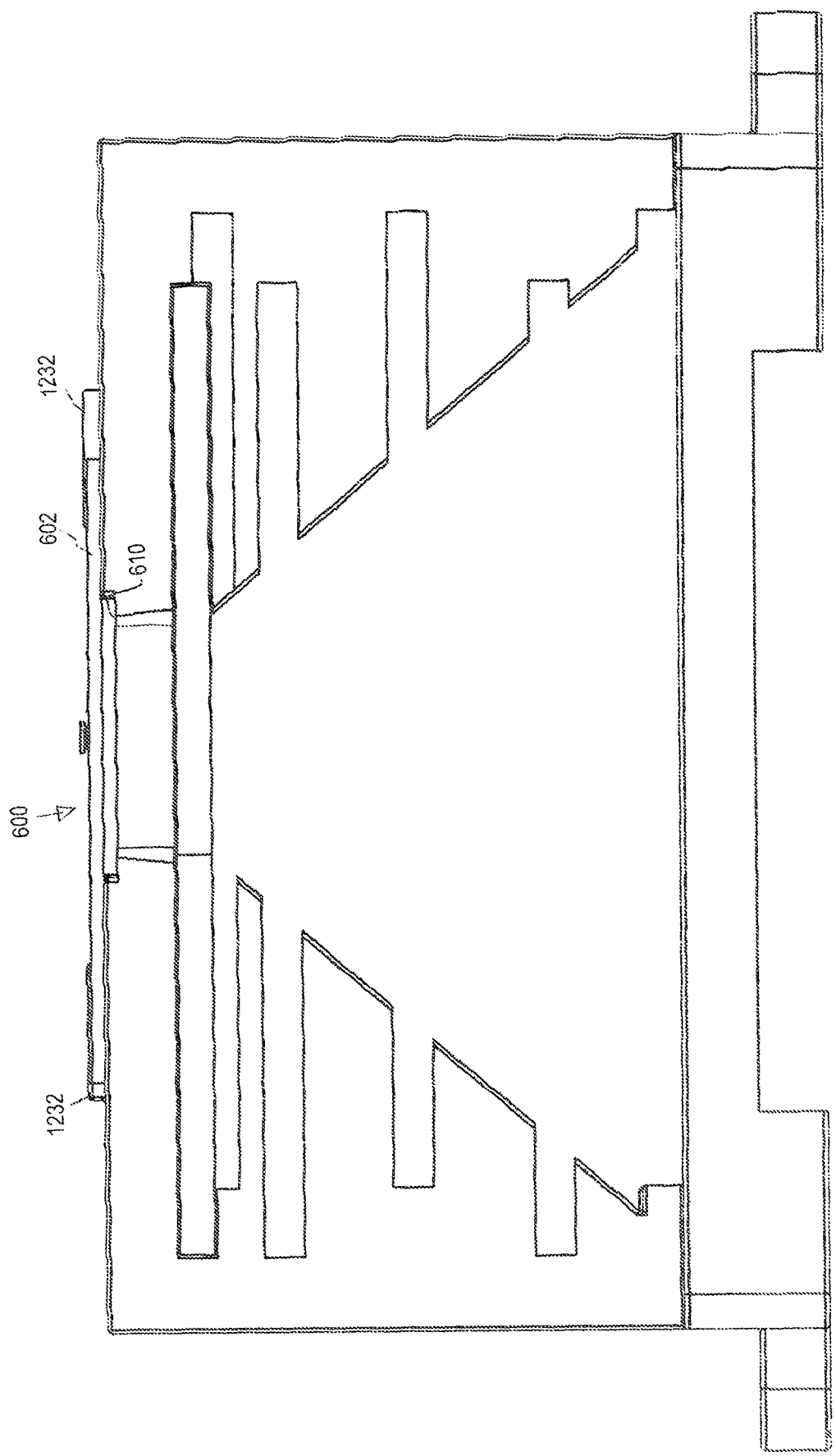

Once liquid 608 has been introduced, a second plate 610 may be brought into contact with a surface of the first plate 602 similar to wet mounting a microscope slide. The second plate 610 encloses the liquid 608 in the void 604. FIG. 83 depicts a front view of the plate 602, as it is being placed onto a fixture holder 1204. The fixture holder 1204 depicted is the same as the example fixture holder shown in FIGS. 79-80. A second plate 610 is in place on the fixture holder 1204. As shown, the recess 1230 is sized to accept and locate the second plate 610. Referring now also to FIG. 84, the first plate 602 may be brought into contact with the second plate 610 to complete assembly of the fixture 600. The alignment features 1232 may serve to properly locate the first plate 602 on the fixture holder 1204.

Figure 85:
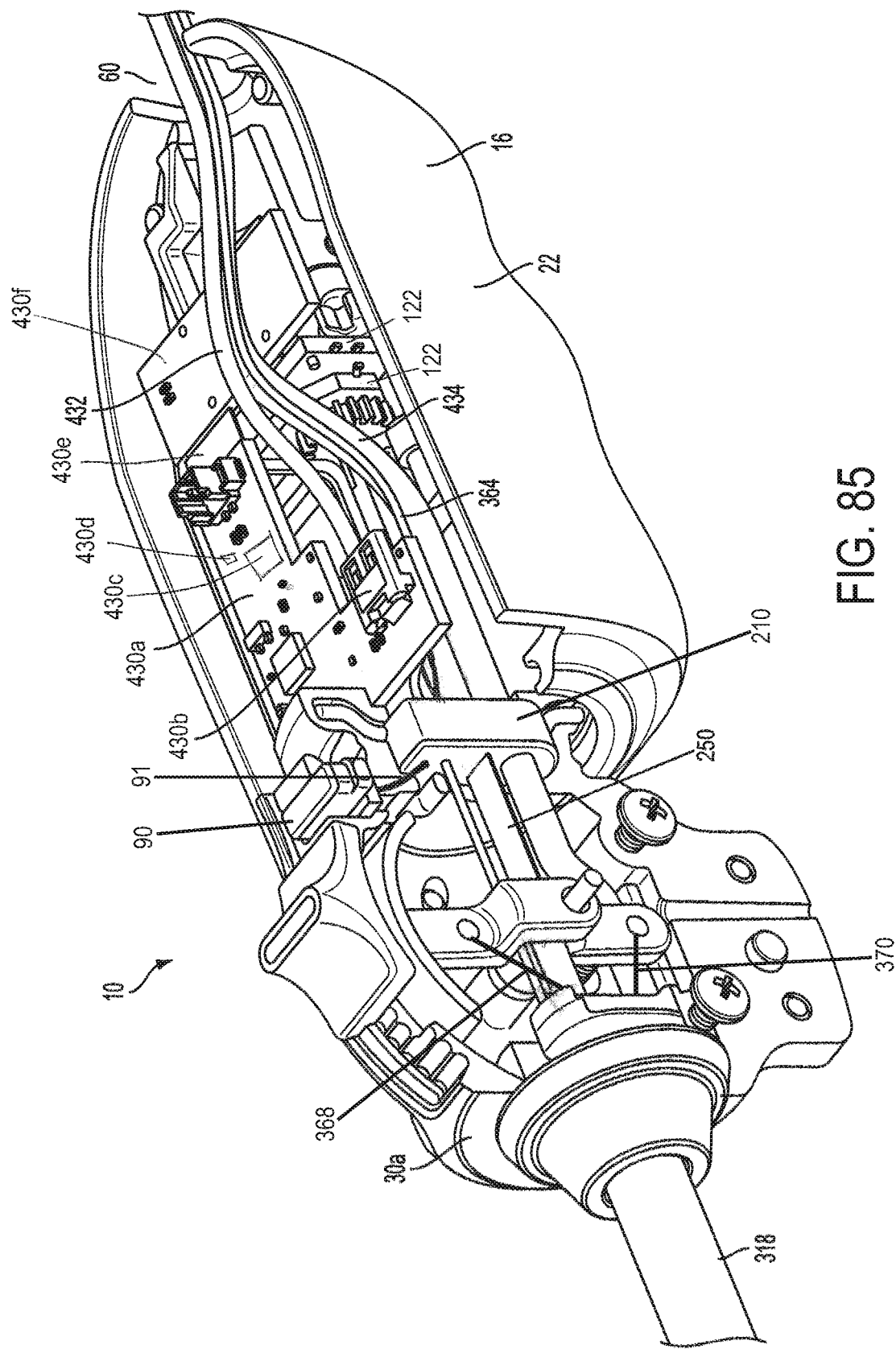
FIG. 85 shows a partially assembled view of an endoscope with a handle printed circuit board, power/HDMI cable, illumination fibers, and irrigation line in their assembled locations.

FIG. 85 shows another example embodiment of the endoscope 10. Only an inner sheath 312 is shown in FIG. 85. Additionally, the bottom section 22 of the handle proximal section 16, and half (30*a*) of the handle distal section 30 are visible. As shown, the endoscope 10 includes a handle-enclosed printed circuit board 430*a* (also referred to herein as handle PCB 430*a*). A power/HDMI cable 432, optical fibers 364, and irrigation line 434 are also shown. FIG. 85 shows example routing pathways for the power/HDMI cable 432, optical fibers 364, and irrigation line 434. As shown, the power/HDMI cable 432, optical fibers 364, and irrigation line 434 enter the endoscope 10 through an opening 60 at the rear or butt of the handle proximal section 16. This entry point may be more advantageous than a handle side-entry point because it reduces the potential of various cords and cables to get tangled as the insertion section is rotated relative to the handle proximal section 16.

In some embodiments, the power/HDMI cable 432, optical fibers 364, and irrigation line 434 may enter the endoscope 10 at an angle with respect to the rear handle opening 60. Such an arrangement would afford an ergonomic benefit to the user by allowing the user to grasp a greater portion of the rear portion of the handle proximal section 16.

As shown, the power/HDMI cable 432, optical fibers 364, and irrigation line 434 extend over a portion of the handle PCB 430*a* after entering the handle proximal section 16. The power/HDMI cable 432 plugs into a power/HDMI connector 430*b* on the handle PCB 430*a*. The power/HDMI cable 432 may provide power to the endoscope 10. Image data may pass to the handle PCB 430*a* via the flex cable 250. The power/HDMI cable 432 may transmit visual data collected by the endoscope 10 to an external graphical user interface display (not shown). The optical fibers 364 and irrigation line 434 extend under the handle PCB 430*a* and follow the pathways previously described. In embodiments in which the endoscope 10 is disposable, the power/HDMI cable 432, optical fibers 364, and irrigation line 434 may all be included as disposable components to ensure sterility or save on the costs of re-use.

A control wire 91 for button 90 is also shown in FIG. 85. As shown, the control wire 91 passes through an orifice in the sealing member 210. The control wire 91 is in communication with the handle PCB 430*a*. Also as shown in FIG. 85 the handle PCB 430*a* includes a handle PCB flex cable 430*e*. The handle PCB flex cable 430*e* connects to a handle PCB portion 430*f*, permitting PCB portion 430*f* to be oriented at an angle (e.g., perpendicular) to the rest of the handle PCB 430*a*. When assembled, the flex attached handle PCB portion 430*f* may be disposed between the two potentiometers 122 of the example rotation sensing assembly 150 (see FIG. 7).

In some embodiments, the handle PCB 430*a* may include an image or graphic processing unit 430*c*. Preferably, however, the image processing unit 430*c* may be located external to the endoscope 10. The image processing unit 430*b* may function as an electronic righting mechanism for the endoscope 10. The image processing unit 430*c* may receive the image captured by the image sensor 380 which is sent from the image sensor 380 to the handle PCB 430*a* via the flex cable 250. In a preferred embodiment, the image captured by the image sensor 380 is then transmitted to the image processing unit 430*c* external to the endoscope 10 via the power/HDMI cable 432. The image processing unit 430*c* may also receive a signal from the rotation sensing assembly 150. In some embodiments, an analog to digital converter 430*d* may be included on the handle PCB 430*a* to convert the signal from the rotation sensing assembly 150. The image processing unit 430*c* may use the signal from the rotation sensing assembly 150 to electronically "right" the image to a desired orientation. In some embodiments, image may be rotated by the image processing unit 430*c* so that the image is displayed as if it were captured from the user's point of view. In some embodiments, the image processing unit 430*c* may also correct for the effects of lens distortion.

Unless the orientation of an image displayed on a graphical user interface is first corrected, the displayed image may be disorienting to the user. By defining a direction according to the user's point of view, the image processing unit 430*c* may use data from the rotation sensing assembly 150 to automatically rotate images so that images correspond with the user's point of view.

Figure 86:
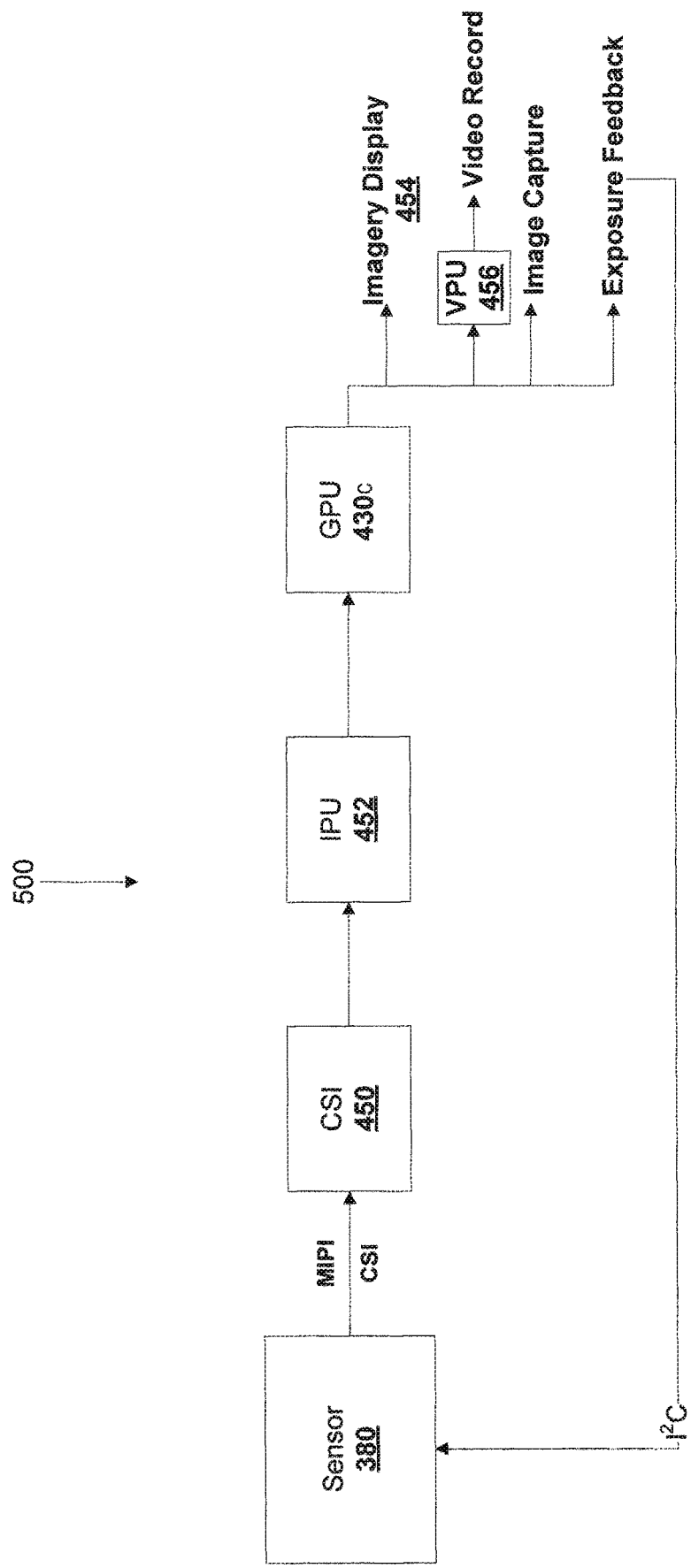
FIG. 86 shows a block diagram of an example image processing system.

FIG. 86 shows an example block diagram of an imaging system. As shown, the imaging system includes an image sensor 380 that captures an image. The image captured by the image sensor 380 may be passed via a camera serial interface 450 (for example a MIPI camera serial interface) to an image processing unit 452. The image processing unit 452 (IPU) may then move image frames to other hardware components in the imaging system. Other hardware components may include, but are not limited to, a memory device and a graphical processing unit 430*c* (GPU). The graphical processing unit 430*c* may correct any distortion caused by the lens assembly 354.

In some embodiments, the graphical processing unit 430*c* may correct this distortion by representing the image as a texture on a surface that has been loaded into the graphical processing unit 430*c*. This may cause the image to be adjusted or stretched in a manner which corrects and/or removes the distortion introduced by the lens assembly 354. In embodiments where the image is righted, the graphical processing unit 430*c* may then rotate the corrected image via input from a rotation sensing assembly 150 (see, for example, FIG. 7). For example, the measurement from a rotation sensing assembly 150 may be passed to the graphical processing unit 430*c* through an analog to digital converter 430*d* (see, for example, FIG. 85). The signal from the analog to digital converter 430*d* may then be used to rotate the image to its righted orientation. In some embodiments, a user may be able to toggle image righting, distortion correction, and/or various other image manipulations which may be performed on or off. Image righting will be further described later in the specification in relation to FIG. 87.

The processed image from the image processing unit 430*c* may then be displayed on a graphical user interface or display 454. In some embodiments, the processed image from the image processing unit 430*c* may be stored in a memory. In such embodiments, a user may capture images to be stored in memory for later recall by triggering a button 90, for example. Some embodiments may include a video processing unit 456 which may encode the frames from the image sensor 380 into a recordable video format. In such embodiments, encoded video may then be stored in memory. A user may command the endoscope to initiate and stop video capture via interaction with a button such as button 90 as described above.

In some embodiments, the image processing unit 430*c* may also subject a captured image to exposure feedback analysis. In specific embodiments, an image histogram may be created from all the pixels of the image. The image histogram may then be used to tune the image or tune the exposure of subsequent images received by the image chip or sensor 380. Such further processing by the image processing unit 430*c* may help to reduce blown-out white areas of the image or underexposed dark areas of the image. Other means of tuning an image or images, such as, for example, tone mapping, etc. may also be used.

Figure 87:
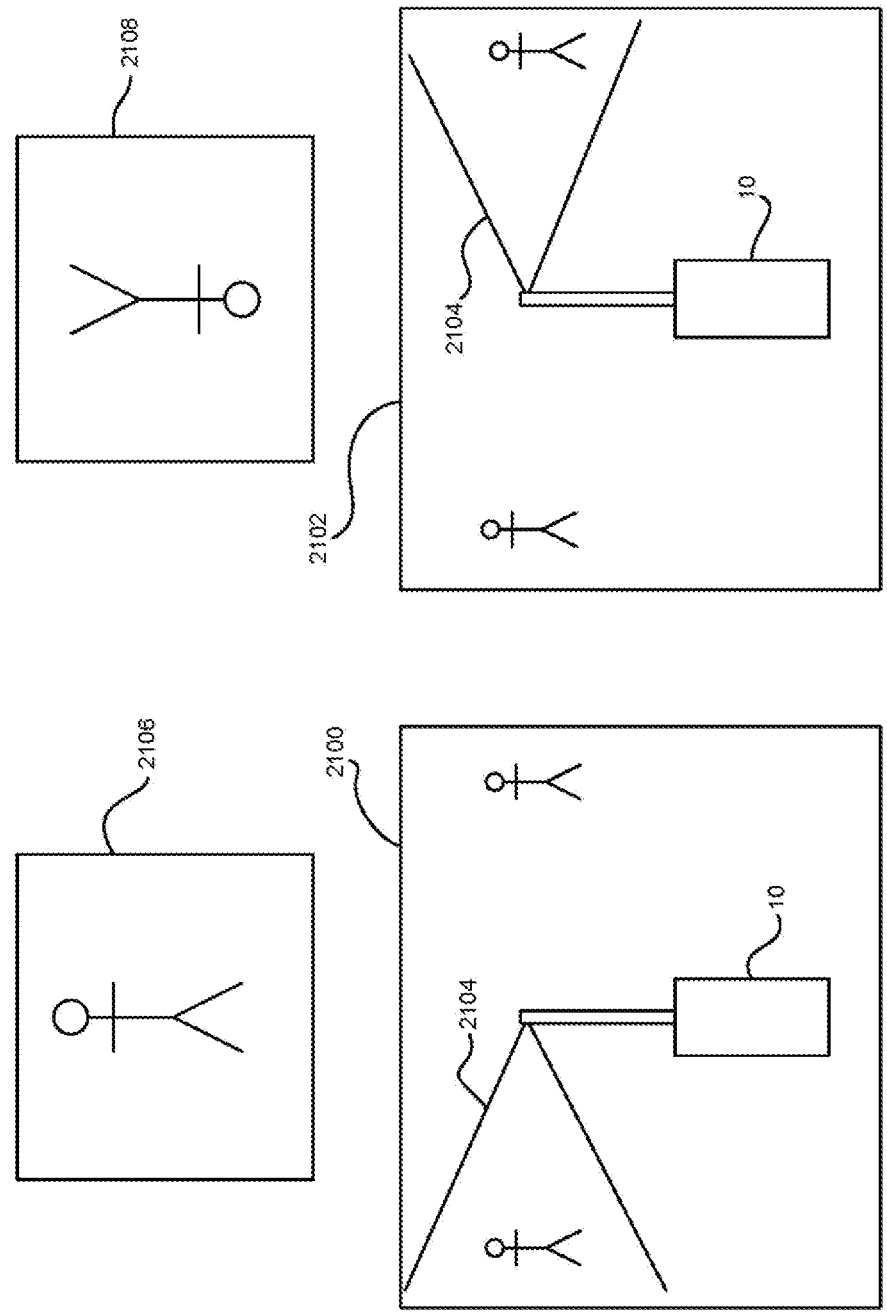
FIG. 87 depicts an example diagram illustrating how an image may be righted using input from a rotation sensing assembly.

FIG. 87 depicts an example diagram illustrating how an image may be righted using input from a rotation sensing assembly 150 (see, for example, FIG. 87). As shown, a first block 2100 and a second block 2102 are depicted. Within each block 2100, 2102 is an endoscope 10 having a field of view 2104. The field of view 2104 of the endoscope 10 in the first block 2100 is oriented approximately 180 degrees from the endoscope 10 in the second block 2102. This may be accomplished by rotating the distal end of the endoscope 10 relative to the proximal end of the endoscope 10. In conventional endoscopes 10, during rotation of the distal section relative to the proximal section, the image sensor does not rotate because the image sensor is housed in the proximal section. Thus, the endoscopes 10 shown in the first block 2100 and second block b would both capture image 2106.

In the various embodiments described herein where the image sensor 380 rotates with the distal end of the endoscope 2106, this would not be the case. The endoscope 10 shown in the first block 2100 would capture image 2106, while the same endoscope 10 rotated to the position shown in the second block 2102 would capture image 2108. This is so because as the image sensor rotates with the distal and of the endoscope 10, the image sensor will be cause to be upside-down. In this position, for example, the top of the image sensor will pick up what one accustomed to a conventional endoscope 10 would expect to be the bottom of the image.

In order to obviate the need for a user to acclimate to this, the image may be rotated in proportion to the degree of rotation of the distal end of the endoscope 10. Thus the image may always be displayed in a way which would be expected by a user accustomed to convention endoscopes 10. This may prevent any possible confusion which may be caused by a rotating image sensor. It may also facilitate user adoption of such an endoscope 10.

The illustrations provided by the drawings should be viewed as non-limiting examples of the inventions disclosed by this specification. The present disclosure is intended to embrace any alternatives, modifications and variances that may nevertheless encompass the novel features of the inventions disclosed herein.

The embodiments shown in the drawings are presented only to demonstrate certain examples of the disclosure. And the drawings are to be used only for illustrative purposes; as such, the size of some of the elements may be exaggerated and not drawn to a particular scale. Additionally, elements shown within the drawings that have the same reference numbers may be identical elements or may represent similar or analogous elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless otherwise specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are intended to distinguish between similar elements and not necessarily to describe a sequential or chronological order. It is to be understood that the terms so used are interchangeable under appropriate circumstances (unless clearly stated otherwise) and that the embodiments of the disclosure described herein are capable of operation in other sequences and/or arrangements than are described or illustrated herein.

What is claimed is:

1. An endoscope comprising:
   a proximal handle housing configured to house an electronic processing board for processing signals from an image sensor located at a distal end of a shaft of the endoscope;
   a distal handle housing configured to hold the electronic processing board in a position fixed with respect to the distal handle housing; and
   a magnetic rotary encoder connected to the electronic processing board wherein the proximal handle housing is rotatable with respect to the distal handle housing, and the rotary encoder is configured to provide a signal to an electronic processor representing the relative rotation of the proximal handle housing with respect to the distal handle housing.

2. The endoscope of claim 1, wherein the electronic processor is connected to a user interface displaying an image generated by the image sensor, and wherein a rotational orientation of the image is altered by a change in the relative rotation of the proximal handle housing with respect to the distal handle housing.

3. The endoscope of claim 1 further wherein the shaft is fixedly attached to the distal handle housing and the image sensor is part of a camera assembly located at the distal end of the shaft.

4. The endoscope of claim 3, wherein the camera assembly includes a lens adjacent to the image sensor.

5. The endoscope of claim 4, wherein the image sensor is a CMOS or a CCD device.

6. The endoscope of claim 1 wherein the electronic processing board receives image signals through a flex cable that extends through the shaft of the endoscope, and terminates at the image sensor located at a distal insertion end of the shaft.

7. An endoscope comprising:
   a distal insertion shaft comprising a liquid carrying conduit and a camera assembly is positioned within the liquid carrying conduit in a distal portion of the insertion shaft, the camera assembly includes a lens and an electronic image sensor; and
   a handle assembly comprising:
      a proximal housing section enclosing an electronic control board to receive image data from the camera assembly;
      a distal housing section comprising a pivot control apparatus to control movement of one or more pivot control cables connected to the camera assembly in the insertion shaft, the distal housing section interposed between the proximal housing section and the insertion shaft;
      a liquid port in fluid communication with the liquid carrying conduit of the insertion shaft:
      a first barrier positioned between the liquid carrying conduit of the insertion shaft and an internal housing of the handle assembly, the barrier configured to inhibit passage of liquid from the liquid carrying conduit to the housing of the handle assembly;
   wherein the first pass-through barrier permits passage of the one or more pivot control cables, a pivot control cable passage in the first pass-through barrier being configured to permit unrestricted proximal and distal movement of the one or more pivot control cables over a pre-determined distance; and
   a second pass-through barrier between the distal housing section and the proximal housing section permits passage of a communications cable from the camera assembly to the electronic control board, a communications cable passage in the second pass-through barrier being configured to provide a liquid seal between the distal housing section and the proximal housing section of the handle assembly.

8. The endoscope of claim 7, wherein the second pass-through barrier permits passage of an optical fiber bundle configured to provide illumination at a distal end of the insertion shaft, an optical fiber bundle passage in the second pass-through barrier being configured to provide a liquid seal between the distal housing section and the proximal housing section of the handle assembly.

9. The endoscope of claim 7, wherein the second pass-through barrier permits passage of a liquid carrying tube configured to pass liquid to or from the distal insertion shaft through the first pass-through barrier, the second pass-through barrier, and an end of the proximal housing section.

* * * * *